US010421751B2

(12) United States Patent
Aicher et al.

(10) Patent No.: US 10,421,751 B2
(45) Date of Patent: Sep. 24, 2019

(54) DIHYDRO-2H-BENZO[B][1,4]OXAZINE SULFONAMIDE AND RELATED COMPOUNDS FOR USE AS AGONISTS OF RORγ AND THE TREATMENT OF DISEASE

(71) Applicant: Lycera Corporation, Ann Arbor, MI (US)

(72) Inventors: Thomas Daniel Aicher, Ann Arbor, MI (US); Clarke B. Taylor, Ann Arbor, MI (US); Chad A. VanHuis, Hartland, MI (US)

(73) Assignee: Lycera Corporation, Ann Arbor, MI (US)

( * ) Notice: Subject to any disclaimer, the term of this patent is extended or adjusted under 35 U.S.C. 154(b) by 0 days.

(21) Appl. No.: 15/568,573

(22) PCT Filed: May 5, 2016

(86) PCT No.: PCT/US2016/030882
§ 371 (c)(1),
(2) Date: Oct. 23, 2017

(87) PCT Pub. No.: WO2016/179343
PCT Pub. Date: Nov. 10, 2016

(65) Prior Publication Data
US 2018/0111922 A1  Apr. 26, 2018

Related U.S. Application Data

(60) Provisional application No. 62/157,224, filed on May 5, 2015, provisional application No. 62/210,076, filed on Aug. 26, 2015.

(51) Int. Cl.
| | | |
|---|---|---|
| *A61P 35/00* | (2006.01) | |
| *C07D 413/06* | (2006.01) | |
| *A61P 35/02* | (2006.01) | |
| *C07D 413/12* | (2006.01) | |
| *C07D 401/12* | (2006.01) | |
| *C07D 401/06* | (2006.01) | |
| *C07D 401/04* | (2006.01) | |
| *C07D 413/14* | (2006.01) | |

(52) U.S. Cl.
CPC ............ *C07D 413/06* (2013.01); *A61P 35/00* (2018.01); *A61P 35/02* (2018.01); *C07D 401/04* (2013.01); *C07D 401/06* (2013.01); *C07D 401/12* (2013.01); *C07D 413/12* (2013.01); *C07D 413/14* (2013.01)

(58) Field of Classification Search
CPC ............................... C07D 413/06; A61P 35/00
IPC ............................... C07D 413/06; A61P 35/00
See application file for complete search history.

(56) References Cited

U.S. PATENT DOCUMENTS

| | | |
|---|---|---|
| 3,803,184 A | 4/1974 | Njimi et al. |
| 3,936,478 A | 2/1976 | Takeshita et al. |
| 4,952,235 A | 8/1990 | Andree et al. |
| 5,229,109 A | 7/1993 | Grimm et al. |
| 5,229,115 A | 7/1993 | Lynch |
| 5,583,152 A | 12/1996 | Bernstein et al. |
| 5,776,451 A | 7/1998 | Hsu et al. |
| 5,985,903 A | 11/1999 | Assmann et al. |
| 6,020,354 A | 2/2000 | Assmann et al. |
| 6,037,367 A | 3/2000 | Christensen, IV et al. |
| 6,160,001 A | 12/2000 | Assmann et al. |
| 6,172,092 B1 | 1/2001 | Assmann et al. |
| 6,180,643 B1 | 1/2001 | Zablocki et al. |
| 6,348,032 B1 | 2/2002 | Sperl et al. |
| 6,352,985 B1 | 3/2002 | Yamasaki et al. |
| 6,387,939 B1 | 5/2002 | Assmann et al. |
| 6,392,010 B1 | 5/2002 | Salvino et al. |
| 6,403,607 B1 | 6/2002 | Hidaka et al. |
| 6,440,973 B1 | 8/2002 | Zablocki et al. |
| 6,534,535 B1 | 3/2003 | Zhu et al. |
| 6,605,634 B2 | 8/2003 | Zablocki et al. |
| 6,638,960 B2 | 10/2003 | Assmann et al. |
| 6,683,091 B2 | 1/2004 | Asberom et al. |
| 6,828,344 B1 | 12/2004 | Seehra et al. |
| 7,084,176 B2 | 8/2006 | Morie et al. |
| 7,115,750 B1 | 10/2006 | Kato et al. |
| 7,138,401 B2 | 11/2006 | Kasibhatla et al. |
| 7,329,675 B2 | 2/2008 | Cox et al. |

(Continued)

FOREIGN PATENT DOCUMENTS

| | | |
|---|---|---|
| EP | 0882718 A1 | 12/1998 |
| EP | 1531848 A2 | 5/2005 |

(Continued)

OTHER PUBLICATIONS

International Search Report and Written Opinion for International Application No. PCT/US2015/017977 dated Jun. 23, 2015 (10 pages).
Zhang et al., "Increasing Human Th17 Differentiation Through Activation of Orphan Nuclear Receptor Retinoid Acid-Related Orphan Receptor γ (RORγ) by a Class of Aryl Amide Compounds," Molecular Pharmacology, vol. 82, pp. 583-590 (2012).
English Abstract JP6-250441 published 1994 (1 page).
English Abstract of JP2004307487A published 2004 (2 pages).
International Search Report and Written Opinion for PCT/US2011/059788 dated May 23, 2012 (23 pages).
International Search Report and Written Opinion for PCT/US2013/040085 dated Oct. 23, 2013 (9 pages).
Annunziato et al., "Type 17 T helper cells-origins, features and possible roles in rheumatic disease," 5 Nat. Rev. Rheumatol. 325-31 (2009).

(Continued)

*Primary Examiner* — Alexander R Pagano
*Assistant Examiner* — Ebenezer O Sackey
(74) *Attorney, Agent, or Firm* — Dechert LLP

(57) ABSTRACT

The invention provides dihydro-2H-benzo[b] [1,4]oxazine sulfonamide and related compounds, pharmaceutical compositions, methods of promoting RORγ activity, methods of increasing the amount of IL-17 in a subject, and methods of treating cancer and other medical disorders using such compounds.

26 Claims, No Drawings

(56) References Cited

U.S. PATENT DOCUMENTS

| | | |
|---|---|---|
| 7,420,059 B2 | 9/2008 | O'Connor et al. |
| 7,482,342 B2 | 1/2009 | D'Orchymont et al. |
| 7,569,571 B2 | 8/2009 | Dong et al. |
| 7,652,043 B2 | 1/2010 | Beachy et al. |
| 7,696,200 B2 | 4/2010 | Ackermann et al. |
| 7,713,996 B2 | 5/2010 | Ackermann et al. |
| 7,741,495 B2 | 6/2010 | Liou et al. |
| 7,799,933 B2 | 9/2010 | Ceccarelli et al. |
| 7,973,135 B2 | 7/2011 | Liik et al. |
| 7,993,638 B2 | 8/2011 | Cai et al. |
| 7,998,736 B2 | 8/2011 | Morgan et al. |
| 8,067,608 B2 | 11/2011 | Beachy et al. |
| 8,383,099 B2 | 2/2013 | Dudley et al. |
| 8,389,738 B2 | 3/2013 | Kousaka et al. |
| 8,389,739 B1 | 3/2013 | Thacher et al. |
| 8,541,185 B2 | 9/2013 | Oved et al. |
| 8,741,812 B2 | 6/2014 | Javitt |
| 9,095,583 B2 | 8/2015 | Karstens et al. |
| 9,266,827 B2 * | 2/2016 | Aicher .................. C07C 311/30 |
| 9,394,315 B2 | 7/2016 | Aicher et al. |
| 9,487,490 B2 | 11/2016 | Barr et al. |
| 9,512,111 B2 | 12/2016 | Glick et al. |
| 9,556,168 B2 | 1/2017 | Barr et al. |
| 9,603,838 B2 | 3/2017 | Karstens et al. |
| 9,657,033 B2 | 5/2017 | Aicher et al. |
| 9,663,502 B2 | 5/2017 | Aicher et al. |
| 9,663,522 B2 | 5/2017 | Barr et al. |
| 9,783,511 B2 | 10/2017 | Aicher et al. |
| 9,802,958 B2 | 10/2017 | Aicher et al. |
| 9,809,561 B2 | 10/2017 | Aicher et al. |
| 9,896,441 B2 * | 2/2018 | Aicher .................. C07D 413/14 |
| 10,208,061 B2 | 2/2019 | Aicher et al. |
| 10,221,146 B2 | 3/2019 | Aicher et al. |
| 2005/0037925 A1 | 2/2005 | Tsukamoto et al. |
| 2006/0004000 A1 | 1/2006 | D'Orchymont et al. |
| 2006/0100230 A1 | 5/2006 | Bischoff et al. |
| 2006/0111421 A1 | 5/2006 | Chadwick et al. |
| 2007/0010537 A1 | 1/2007 | Hamamura et al. |
| 2007/0010670 A1 | 1/2007 | Hirata et al. |
| 2007/0049556 A1 | 3/2007 | Zhang et al. |
| 2007/0060567 A1 | 3/2007 | Ackermann et al. |
| 2007/0154487 A1 | 7/2007 | Littman et al. |
| 2007/0185136 A1 | 8/2007 | Courtemanche et al. |
| 2007/0191603 A1 | 8/2007 | Ackermann et al. |
| 2007/0197782 A1 | 8/2007 | Clough et al. |
| 2007/0219257 A1 | 9/2007 | Beachy et al. |
| 2007/0232661 A1 | 10/2007 | Beachy et al. |
| 2007/0281922 A1 | 12/2007 | Liu et al. |
| 2008/0027002 A1 | 1/2008 | Liik et al. |
| 2008/0027100 A1 | 1/2008 | McCormick et al. |
| 2008/0058386 A1 | 3/2008 | Liou et al. |
| 2008/0153805 A1 | 6/2008 | Ceccarelli et al. |
| 2008/0199486 A1 | 8/2008 | Argon et al. |
| 2008/0305169 A1 | 12/2008 | Miki et al. |
| 2009/0005410 A1 | 1/2009 | Charvat et al. |
| 2009/0042851 A1 | 2/2009 | Despeyroux et al. |
| 2009/0075973 A1 | 3/2009 | Newcom et al. |
| 2009/0131523 A1 | 5/2009 | Yosef et al. |
| 2009/0247502 A1 | 10/2009 | Newcom et al. |
| 2009/0275586 A1 | 11/2009 | Govek et al. |
| 2010/0022515 A1 | 1/2010 | Alper et al. |
| 2010/0087376 A1 | 4/2010 | Kazantseva et al. |
| 2010/0130484 A1 | 5/2010 | Ackermann et al. |
| 2010/0234340 A1 | 9/2010 | Schunk et al. |
| 2010/0310533 A1 | 12/2010 | Yee |
| 2011/0053915 A1 | 3/2011 | Ivaschenko et al. |
| 2011/0112070 A1 | 5/2011 | Baldwin et al. |
| 2011/0118246 A1 | 5/2011 | Baldwin et al. |
| 2011/0130384 A1 | 6/2011 | Setoh et al. |
| 2011/0142814 A1 | 6/2011 | Zanin-Zhorov et al. |
| 2011/0151478 A1 | 6/2011 | Liik et al. |
| 2011/0178063 A1 | 7/2011 | Baldwin et al. |
| 2011/0229504 A1 | 9/2011 | Fritsche et al. |
| 2011/0236363 A1 | 9/2011 | Chang et al. |
| 2012/0135011 A1 | 5/2012 | Podack et al. |
| 2013/0039911 A1 | 2/2013 | Bedi et al. |
| 2013/0045191 A1 | 2/2013 | Weinschenk et al. |
| 2013/0102075 A1 | 4/2013 | Vera et al. |
| 2013/0102542 A1 | 4/2013 | Kazantseva et al. |
| 2014/0038942 A1 | 2/2014 | Karstens et al. |
| 2014/0088094 A1 | 3/2014 | Glick et al. |
| 2014/0186295 A1 | 7/2014 | Kupper et al. |
| 2014/0187504 A1 | 7/2014 | Chaturvedi |
| 2014/0187554 A1 | 7/2014 | Kamenecka et al. |
| 2014/0314795 A1 | 10/2014 | Riddell et al. |
| 2014/0343023 A1 | 11/2014 | Wolfrum et al. |
| 2015/0017120 A1 | 1/2015 | Wittrup et al. |
| 2015/0111877 A1 | 4/2015 | Aicher et al. |
| 2015/0126493 A1 | 5/2015 | Aicher et al. |
| 2015/0133437 A1 | 5/2015 | Aicher et al. |
| 2015/0191434 A1 | 7/2015 | Barr et al. |
| 2015/0210687 A1 | 7/2015 | Barr et al. |
| 2015/0218096 A1 | 8/2015 | Barr et al. |
| 2015/0218169 A1 | 8/2015 | Barr et al. |
| 2015/0297566 A1 | 10/2015 | Karstens et al. |
| 2016/0304476 A1 | 10/2016 | Aicher et al. |
| 2016/0304505 A1 | 10/2016 | Aicher et al. |
| 2016/0311787 A1 | 10/2016 | Aicher et al. |
| 2016/0318951 A1 | 11/2016 | Aicher et al. |
| 2017/0007686 A1 | 1/2017 | Glick et al. |
| 2017/0183331 A1 | 6/2017 | Aicher et al. |
| 2017/0190659 A1 | 7/2017 | Aicher et al. |
| 2017/0313722 A1 | 11/2017 | Aicher et al. |
| 2018/0030005 A1 | 2/2018 | Aicher et al. |
| 2018/0179224 A1 | 6/2018 | Aicher et al. |
| 2018/0208587 A1 | 7/2018 | Aicher et al. |
| 2018/0265502 A1 | 9/2018 | Aicher et al. |

FOREIGN PATENT DOCUMENTS

| | | |
|---|---|---|
| EP | 1768662 A2 | 4/2007 |
| EP | 1820515 A1 | 8/2007 |
| EP | 2038301 A2 | 3/2009 |
| EP | 2158327 A2 | 3/2010 |
| EP | 2181710 A1 | 5/2010 |
| EP | 2321407 A1 | 5/2011 |
| EP | 2462165 A1 | 6/2012 |
| EP | 2542590 A2 | 1/2013 |
| EP | 2547354 A2 | 1/2013 |
| EP | 2158327 B1 | 5/2013 |
| EP | 2649086 A1 | 10/2013 |
| EP | 2688594 A2 | 1/2014 |
| EP | 2689010 A1 | 1/2014 |
| EP | 2825197 A1 | 1/2015 |
| JP | 6-250441 A | 9/1994 |
| JP | 2000-511558 A | 9/2000 |
| JP | 2004307487 A | 11/2004 |
| JP | 2006-512357 A | 4/2006 |
| JP | 2013-541597 A | 11/2013 |
| JP | 2017-507950 A | 3/2017 |
| JP | 2018-515491 A | 6/2018 |
| WO | WO-92/13856 A1 | 8/1992 |
| WO | WO-97/01561 A1 | 1/1997 |
| WO | WO-97/48697 A1 | 12/1997 |
| WO | WO-98/22457 A1 | 5/1998 |
| WO | WO-00/17202 A1 | 3/2000 |
| WO | WO-01/012600 A1 | 2/2001 |
| WO | WO-2001/012186 A1 | 2/2001 |
| WO | WO-02/14361 A2 | 2/2002 |
| WO | WO-2002/058622 A2 | 8/2002 |
| WO | WO-02/100819 A1 | 12/2002 |
| WO | WO-03/014075 A2 | 2/2003 |
| WO | WO-03/104428 A2 | 12/2003 |
| WO | WO-2004/050631 A1 | 6/2004 |
| WO | WO-2004/056820 A1 | 7/2004 |
| WO | WO-2004/056830 A1 | 7/2004 |
| WO | WO-05/028434 A2 | 3/2005 |
| WO | WO-2005/030225 A2 | 4/2005 |
| WO | WO-2005/033048 A2 | 4/2005 |
| WO | WO-2005/033288 A2 | 4/2005 |
| WO | WO-2005/037834 A1 | 4/2005 |
| WO | WO-2005/058847 A1 | 6/2005 |
| WO | WO-2005/084208 A2 | 9/2005 |
| WO | WO-2005/120558 A2 | 12/2005 |

(56) References Cited

FOREIGN PATENT DOCUMENTS

| | | |
|---|---|---|
| WO | WO-2006/007486 A2 | 1/2006 |
| WO | WO-2006/057460 A1 | 6/2006 |
| WO | WO-2006/065495 A2 | 6/2006 |
| WO | WO-2006/115509 A2 | 11/2006 |
| WO | WO-2007/010259 A1 | 1/2007 |
| WO | WO-2007/024944 A1 | 3/2007 |
| WO | WO-2007/031429 A1 | 3/2007 |
| WO | WO-2007/093507 A1 | 8/2007 |
| WO | WO-2007/113337 A1 | 10/2007 |
| WO | WO-2007/125405 A2 | 11/2007 |
| WO | WO-2007/138998 A1 | 12/2007 |
| WO | WO-2008/003703 A1 | 1/2008 |
| WO | WO-2008/008923 A1 | 1/2008 |
| WO | WO-2008/045664 A2 | 4/2008 |
| WO | WO-2008/062740 A1 | 5/2008 |
| WO | WO-2008/074692 A1 | 6/2008 |
| WO | WO-2008/097428 A2 | 8/2008 |
| WO | WO-2008/150827 A1 | 12/2008 |
| WO | WO-2008/151200 A2 | 12/2008 |
| WO | WO-2009/032667 A1 | 3/2009 |
| WO | WO-2009/035997 A2 | 3/2009 |
| WO | WO-2009/077956 A2 | 6/2009 |
| WO | WO-2009/147187 A1 | 12/2009 |
| WO | WO-2009/149819 A1 | 12/2009 |
| WO | WO-2009/149820 A1 | 12/2009 |
| WO | WO-2009/157196 A1 | 12/2009 |
| WO | WO-2010/017827 A1 | 2/2010 |
| WO | WO-2010/030947 A1 | 3/2010 |
| WO | WO-2010/038901 A1 | 4/2010 |
| WO | WO-2010/057101 A2 | 5/2010 |
| WO | WO-2010/058023 A1 | 5/2010 |
| WO | WO-2010/059602 A2 | 5/2010 |
| WO | WO-2010/071853 A1 | 6/2010 |
| WO | WO-2010/102958 A1 | 9/2010 |
| WO | WO-2010/117425 A1 | 10/2010 |
| WO | WO-2010/123139 A1 | 10/2010 |
| WO | WO-2010/125082 A1 | 11/2010 |
| WO | WO-2011/017303 A1 | 2/2011 |
| WO | WO-2011/019634 A2 | 2/2011 |
| WO | WO-2011/059839 A1 | 5/2011 |
| WO | WO-2011/067364 A1 | 6/2011 |
| WO | WO-2011/067365 A1 | 6/2011 |
| WO | WO-2011/067366 A1 | 6/2011 |
| WO | WO-2011/109059 A1 | 9/2011 |
| WO | WO-2011/109789 A2 | 9/2011 |
| WO | WO-2011/113819 A2 | 9/2011 |
| WO | WO-2011/115892 A1 | 9/2011 |
| WO | WO-2012/020100 A2 | 2/2012 |
| WO | WO-2012/032065 A1 | 3/2012 |
| WO | WO-2012/032067 A1 | 3/2012 |
| WO | WO-2012/037108 A1 | 3/2012 |
| WO | WO-2012/064744 A2 | 5/2012 |
| WO | WO-2012/079000 A1 | 6/2012 |
| WO | WO-2012/127464 A2 | 9/2012 |
| WO | WO-2012/129394 A2 | 9/2012 |
| WO | WO-2012/129514 A1 | 9/2012 |
| WO | WO-2012/139775 A1 | 10/2012 |
| WO | WO-2012/129394 A9 | 11/2012 |
| WO | WO-2012/178108 A1 | 12/2012 |
| WO | WO-2013/045431 A1 | 4/2013 |
| WO | WO-2013/074916 A1 | 5/2013 |
| WO | WO-2013/135588 A1 | 9/2013 |
| WO | 2013169864 * | 11/2013 |
| WO | WO-2013/167136 A1 | 11/2013 |
| WO | WO-2013/169588 A1 | 11/2013 |
| WO | WO-2013/169704 A2 | 11/2013 |
| WO | WO-2013/169864 A2 | 11/2013 |
| WO | WO-2013/176740 A1 | 11/2013 |
| WO | WO-2014/028669 A1 | 2/2014 |
| WO | WO-2014/031174 A1 | 2/2014 |
| WO | WO-2014/095757 A1 | 6/2014 |
| WO | WO-2014/201378 A1 | 12/2014 |
| WO | WO-2014/201378 A9 | 1/2015 |
| WO | WO-2015/131035 A1 | 9/2015 |
| WO | WO-2015/171610 A2 | 11/2015 |
| WO | WO-2016/179343 A1 | 11/2016 |

OTHER PUBLICATIONS

Boaventura et al., "Human mucosal leishmaniasis: Neutrophils infiltrate areas of tissue damage that express high levels of Th17-related cytokines," 40 Eur. J. Immunol. 2830-36 (2010).

Buonocore et al., "Innate lymphoid cells drive interleukin-23-dependent innate intestinal pathology," 464 Nature 1371-75 (2010).

Eberl et al., "An essential function for the nuclear receptor RORγt in the generation of fetal lymphoid tissue inducer cells," 5(1) Nat. Immunol. 64-73 (2004).

Figueroa-Vega et al., "Increased Circulating Pro-Inflammatory Cytokines and Th17 Lymphocytes in Hashimoto's Thyroiditis," 95(2) J. Clin. Endocrinol. Metab. 953-62 (2010).

Gennaro (ed.), Remington: The Science and Practice of Pharmacy, 20th edition (2000).

He et al., "RORγt, a Novel Isoform of an Orphan Receptor, Negatively Regulates Fas Ligand Expression and IL-2 Production in T Cells," 9 Immunity 797-806 (1998).

Hirose et al., "RORγ: the third member of ROR/RZR orphan receptor subfamily that is highly expressed in skeletal muscle," 205 Biochem. Biophys. Res. Comm. 1976-83 (1994).

Hueber et al., "Cutting Edge: Mast Cells Express IL-17A in Rheumatoid Arthritis Synovium," 184 J. Immunol. 3336-40 (2010).

Ivanov et al., "The Orphan Nuclear Receptor RORγt Directs the Differentiation Program of Proinflammatory IL-17+ T Helper Cells," 126 *Cell* 1121-33 (2006).

Jia et al., "The T helper type 17/regulatory T cell imbalance in patients with acute Kawasaki disease," 162 Clin. Exp. Immunol. 131-37 (2010).

Jin et al., "Structural Basis for Hydroxycholesterols as Natural Ligands of Orphan Nuclear Receptor RORγ," *Mol. Endocrinol.* (2010) vol. 24, No. 5, pp. 923-929.

Kastelein et al., "Discovery and Biology of IL-23 and IL-27: Related but Functionally Distinct Regulators of Inflammation," 25 Annu. Rev. Immunol. 221-42 (2007).

Kurebayashi et al., "Selective LXXLL peptides antagonize transcriptional activation by the retinoid-related orphan receptor RORγ," 315 Biochem. Biophys. Res. Comm. 919-27 (2004).

Louten et al., "Development and function of TH17 cells in health and disease," 123(5) J. Allergy Clin. Immunol. 1004-11 (2009).

Miossec et al., "Interleukin-17 and Type 17 Helper T Cells," 361(9) New Eng. J. Med. 888-98 (2009).

Sun et al., "Requirement for RORγ in Thymocyte Survival and Lymphoid Organ Development," 288 Science 2369-72 (2000).

Sutton et al., "Interleukin-1 and IL-23 Induce Innate IL-17 Production from γδ T Cells, Amplifying Th17 Responses and Autoimmunity," 31 Immunity 331-41 (2009).

Wang et al., "Identification of SR1078, a Synthetic Agonist for the Orphan Nuclear Receptors RORα and RORγ," 5(11) ACS Chem. Biol. 1029-34 (2010).

Xie et al., "RORγt Recruits Steroid Receptor Coactivators to Ensure Thymocyte Survival," 175(6) J. Immunol. 3800-09 (2005).

Yang et al., "T Helper 17 Lineage Differentiation is programmed by Orphan Nuclear Receptors RORα and RORγ," 28 Immunity 29-39 (2008).

André et al., "Disruption of retinoid-related orphan receptor β changes circadian behaviour, causes retinal degeneration and leads to vacillans phenotype in mice," 17(14) The EMBO J. 3867-77 (1998).

Becker-André et al., "Identification of nuclear receptor mRNAs by RT-PCR amplification of conserved zinc-finger motif sequences," 194(3) Biochem. Biophys. Res. Comm. 1371-79 (1993).

Burris et al., "Targeting Orphan Nuclear Receptors for Treatment of Metabolic Diseases and Autoimmunity," 19(1) Chem. Biol. 51-59 (2012).

Cai, et al., "Pivotal Role of Dermal IL-17-Producing γδ T Cells in Skin Inflammation", Immunity (2011) vol. 35, pp. 596-610.

(56) References Cited

OTHER PUBLICATIONS

Carlberg et al., "RZRs, a new family of retinoid-related orphan receptors that function as both monomers and homodimers," 8 Mol. Endocrinol. 757-70 (1994).
D. van der Heijde, et al., "Secukinumab Provides Significant and Sustained Inhibition of Joint Structural Damage in a Phase III Study of Active Psoriatic Arthritis" Arthritis & Rheumatology Brief Report, Accepted Article DOI: 10.1002/art.39685, American College of Rheumatology, (2016) pp. 1-27.
Baeten, et al., "Secukinumab, an Interleukin-17A Inhibitor, in Ankylosing Spondylitis", The New England Journal of Medicine, (2015) vol. 373, pp. 2534-2548.
Dussault et al., "Orphan nuclear receptor RORα-deficient mice display the cerebellar defects of *staggerer*," 70 Mech. Develop. 147-53 (1998).
Giguère et al., "Isoform-specific amino-terminal domains dictate DNA-binding properties of RORα, a novel family of orphan hormone nuclear receptors," 8 Genes & Develop. 538-53 (1994).
Huh et al., "Small molecule inhibitors of RORγt: Targeting Th17 cells and other applications," 42 Eur. J. Immunol. 2232-2237 (2012).
Krueger, "A welcome surprise in psoriasis", Nature Medicine, (2012) vol. 18, No. 12, pp. 1750-1751.
Leonardi, et al., "Anti-Interleukin-17 Monoclonal Antibody Ixekizumab in Chronic Plaque Psoriasis", The New England Journal of Medicine, (2012) vol. 366, Iss. 13, pp. 1-10.
Martinez, "Th17-biased RORγt transgenic mice become susceptible to a viral model for multiple sclerosis", Brain, Behavior, and Immunity, (2014) vol. 43, pp. 86-97.
Medvedev et al., "Cloning of a cDNA encoding the murine orphan receptor RZR/RORγ and characterization of its response element," 181 Gene 199-206 (1996).
Nakajima, et al., "IL-17A as an Inducer for Th2 Immune Responses in Murine Atopic Dermatitis Models", Journal of Investigative Dermatology, (2014) vol. 134, pp. 2122-2130.
Ortiz et al., "TOR: a new orphan receptor expressed in the thymus that can modulate retinoid and thyroid hormone signals," 9 Mol. Endocrinol. 1679-91 (1995).
Papp, et al. "Brodalumab, an Anti-Interleukin-17-Receptor Antibody for Psoriasis", The New England Journal of Medicine, (2012) vol. 366, Iss. 13, 9 pgs.
Skepner, J. et al. "Pharmacologic Inhibition of RORγt Regulates Th17 Signature Gene Expression and Suppresses Cutaneous Inflammation In Vivo," downloaded from the Internet at http://www.jimmunol.org/cgi/doi/10.4049/jimmunol.1302190 on Feb. 17, 2014, published in final edited form in *J. Immunol.* (2014) vol. 192, No. 6, pp. 2564-2575.
Smith, "The Bench-to-Bedside Story of IL-17 and the Therapeutic Efficacy of its Targeting in Spondyloarthritis", Curr Rheumatol Rep. (2016) vol. 18, pp. 1-10.
Solt et al., "Action of RORs and their ligands in (patho)physiology," 23(12) Trends in Endocrinology and Metabolism. 619-627 (2012).
Tlustochowicz, et al. "Efficacy and Safety of Subcutaneous and Intravenous Loading Dose Regimens of Secukinumab in Patients with Active Rheumatoid Arthritis: Results from a Randomized Phase II Study" The Journal of Rheumatology, (2016) vol. 43, No. 3, pp. 495-503.
Villey et al., "RORγT, a thymus-specific isoform of the orphan nuclear receptor RORγ/TOR, is up-regulated by signaling through the pre-T cell receptor and binds to the TEA promoter," 29 Eur. J. Immunol. 4072-80 (1999).
Wiesenberg et al., "Transcriptional activation of the nuclear receptor RZRα by the pineal gland hormone melatonin and identification of CGP 52608 as a synthetic ligand," 23(3) Nucl. Acids Res. 327-33 (1995).
Xiao, et al., "Small-Molecule RORγt Antagonists Inhibit T Helper 17 Cell Transcriptional Network by Divergent Mechanisms", Immunity (2014) vol. 40, pp. 477-489.
Arisawa et al., "Development of Isomerization and Cycloisomerization with Use of a Ruthenium Hydride with N-Heterocyclic Carbene and its Application to the Synthesis of Heterocycles," 71 J. Org. Chem. 4255-61 (2006).
Berge et al., "Pharmaceutical salts," 66(1) J. Pharm. Sci. 1-19 (1977).
Bhagawanth et al., "Room-Temperature Pd-Catalyzed Amidation of Aryl Bromides Using tert-Butyl Carbamate," 74 J. Org. Chem. 4634-37 (2009).
Boger et al., "Regiocontrolled Nucleophilic Addition to Selectively Activated p-Quinone Diimines: Alternative Preparation of a Key Intermediate Employed in the Preparation of the CC-1065 Left-Hand Subunit," 55 J. Org. Chem. 1379-90 (1990).
Carroll et al., "Synthesis, Nicotinic Acetylcholine Receptor Binding, and Antinociceptive Properties of 2-exo-2-(2',3'-Disubstituted 5'-pyridinyl)-y-azabicyclo[2.2.1]heptanes: Epibatidine Analogues," 45 J. Med. Chem. 4755-61 (2002).
Chang et al., "7-Aroyl-aminoindoline-1-sulfonamides as a Novel Class of Potent Antitubulin Agents," 49 J. Med. Chem. 6656-59 (2006).
Colbon et al., "Double Arylation of Allyl Alcohol via a One-Pot Heck Arylation—Isomerization—Acylation Cascade," 13 Org. Lett. 5456-59 (2011).
De et al., Methods in Molecular Biology 1184, second edition, Human Press (2014).
Gould, "Salt selection for basic drugs," 33 Int'l J. Pharmaceutics 201-217 (1986).
Grasa et al., "Amination Reactions of Aryl Halides with Nitrogen-Containing Reagents Mediated by Palladium/Imidazolium Salt Systems," 66 J. Org. Chem. 7729-37 (2001).
Greene & Wuts, Protective Groups in Organic Synthesis, 2d Edition (1991).
Guimond et al., "Rhodium(III)-Catalyzed Isoquinolone Synthesis: The N—O Bond as a Handle for C—N Bond Formation and Catalyst Turnover," 132(20) J. Am. Chem. Soc. 6908-09 (2010).
Hanessian et al., "A versatile protocol for the stereocontrolled elaboration of vicinal secondary and tertiary centers of relevance to natural product synthesis," 52(6) J. Org. Chem. 1170-72 (1987).
Hauser et al., "Relative Ease of Cyclization of 2-, 3-, and 4-Aminopyridine Derivatives. Synthesis of Naphthyridines," 15 J. Org. Chem. 1224-32 (1950).
International Search Report and Written Opinion for PCT/US2013/039422 dated Oct. 11, 2013 (9 pages).
International Search Report and Written Opinion for PCT/US2013/039839 dated Oct. 18, 2013 (8 pages).
Ishikura et al., "An Efficient Synthesis of 3-Heteroarylpyridines via Diethyl-(3-pyridyl)-borane," Synthesis 936-38 (1984).
Jayashree et al., "Design and synthesis of 2-quinolones as antioxidants and antimicrobials: a rational approach," 19 Med. Chem. Res. 193-209 (2010).
Jiang et al., "Synthesis and Cytotoxicity Evaluation of Novel Indolylpyrimidines and Indolylpyrazines as Potential Antitumor Agents," 9 Bioorg. Med. Chem. 1149-54 (2001).
Li et al., "Chemical Libraries via Sequential C—H Functionalization of Phenols," 10 J. Comb. Chem. 170-74 (2008).
Li et al., "Synthesis and Resolution of a Novel Chiral Diamine Ligand and Application to Asymmetric Lithiation-Substitution," 2 Org. Lett. 875-78 (2000).
Liu et al., "1-Sulfonylindazoles as potent and selective 5-HT6 ligands," 19 Bioorg. Med. Chem. Lett. 2413-15 (2009).
Murase et al., "A New Concise Synthesis of Arcyriacyanin A and Its Unique Inhibitory Activity against a Panel of Human Cancer Cell Line," 48(1) Chem. Pharm. Bull. 81-84 (2000).
Ninomiya et al., "Phosphorous in Organic Synthesis—VII: Diphenyl Phosphorazidate (DPPA). A New Convenient Reagent for a Modified Curtius Reaction," 30 Tetrahedron 2151-57 (1975).
Nyrkova et al., "Synthesis of a New Heterocyclic System—3,4-Diazaphenoxazine," 1(9) J. Org. Chem. USSR, 1711-14, translating 1(9) Zh. Org. Khimii, 1688-91 (1965).
Santilli et al., "Synthesis of 5,6,7,8-Tetrahydro-5-oxopyrido[2,3-d]pyrimidine-6-carbonitriles and—6-carboxylic Acid Esters," 12 J. Het. Chem. 311-16 (1975).
Skraup, "Eine Synthese des Chinolins," 13 Berichte 2086-87 (1880).

(56) References Cited

OTHER PUBLICATIONS

Stefko et al., "General and Modular Synthesis of Isomeric 5-Substituted Pyridin-2-yl and 6-Substituted Pyridin-3-yl C-Ribonucleosides Bearing Diverse Alkyl, Aryl, Hetaryl, Amino, Carbamoyl, and Hydroxy Groups," 76 J. Org. Chem. 6619-35 (2011).
STN Columbus, pp. 1-40 (2011).
Takano et al., "A new synthesis of a steroid side chain via stereocontrolled protonation: synthesis of (-)-desmosterol," 14 J. Chem. Soc., Chem. Commun. 760-61 (1983).
van Heerden et al., "Dibutylboron triflate promoted conjugate addition of benzylic and allylic organocopper reagents to chiral α,β-unsaturated N-acyl imidazolidinones" 38(10) Tet. Lett. 182124 (1997).
Wang et al., "Synthesis of new carbon-11-labeled 7-aroyl-aminoindoline-1-sulfonamides as potential PET agents for imaging of tubulin polymerization in cancers," 51(1) J. Label. Compd. Radiopharm. 6-11 (2008).
Yeh et al., "Practical Cu-catalyzed amination of functionalized heteroaryl halides," 47(34) Tetrahedron Lett. 6011-16 (2006).
Zhu et al., "The Direct Formulation of Functionalized Alkyl(aryl)zinc halides by Oxidative Addition of Highly Reactive Zinc with Organic Halides and Their Reactions with Acid Chlorides, α,β-Unsaturated Ketones, and Allylic, Aryl, and Vinyl Halides," 56 J. Org. Chem. 1445-53 (1991).
International Search Report and Written Opinion for PCT/US2014/071663 dated Apr. 17, 2015 (6 pages).
International Search Report and Written Opinion for PCT/US2014/071671 dated Apr. 28, 2015 (10 pages).
International Search Report and Written Opinion for PCT/US2014/071656 dated Mar. 12, 2015 (8 pages).
Yang, T. et al. "Discovery of Tertiary Amine and Indole Derivatives as Potent RORγt Inverse Agonists," ACS Med. Chem. Lett. (2014) vol. 5, pp. 65-68.
Jun., C. H. "Adoptive T cell therapy for cancer in the clinic," J. Clin. Invest. (2007) vol. 117, No. 6, pp. 1466-1476.
Zhu, J. et al. "Differentiation of Effector CD4 T Cell Populations," Author manuscript available in PMC on Nov. 20, 2012, published in final edited form in Annu. Rev. Immunol. (2010) vol. 28, pp. 445-489.
Martin-Orozco, N. et al. "Th17 cells promote cytotoxic T cell activation in tumor immunity," Author manuscript available in PMC on Nov. 20, 2010, published in final edited form in Immunity (2009) vol. 31, pp. 787-798.
Pardoll, D. M. "The blockade of immune checkpoints in cancer immunotherapy," Nature Rev. Cancer (2012) vol. 12, pp. 252-264.
Restifo, N. P. et al." Adoptive immunotherapy for cancer: harnessing the T cell response," Nature Rev. Immunol. (2012) vol. 12, pp. 269-281.
Drug Discovery & Development "Lycera's Oral Immunotherapy May Have Anti-Cancer Activity," dated Nov. 7, 2014. (2 pages).
Lycera "Lycera Announces Research Showing Promising Anti-Cancer Activity of Novel, Oral Immunotherapy Candidates," Press release dated Feb. 9, 2015. (2 pages).
X. Hu et al. in Poster Presentation Entitled "Novel, Synthetic RORgamma Agonist Compounds as a Potential Anti-Cancer Approach" at Society for Immunotherapy of Cancer (SITC) Meeting 2014, Nov. 6-9, 2014.
Huang, Z. et al. "Retinoid-related orphan receptor γt is a potential therapeutic target for controlling inflammatory autoimmunity," Expert Opin. Ther. Targets (2007) vol. 11, No. 6, pp. 737-743.
Wang et al., "Modulation of Retinoic Acid Receptor-related Orphan Receptor α and γ Activity by 7-Oxygenated Sterol Ligands," J. Biol. Chem. (2010) vol. 285, No. 7, pp. 5013-5025.
Bai et al., "Sulfation of 25-hydroxycholesterol by SULT2B1b decreases cellular lipids via the LXR/SREBP-1c signaling pathway in human aortic endothelial cells," Atherosclerosis, vol. 214, pp. 350-356 (author's manuscript pp. 1-14) (2011).
Bensinger et al., "LXR signaling couples sterol metabolism to proliferation in the acquired immune response," Cell, vol. 134, pp. 97-111 (2008).

Brown et al., "Oxysterols and atherosclerosis," Atherosclerosis, vol. 142, pp. 1-28 (1999).
Chen et al., "Enzymatic reduction of oxysterols impairs LXR signaling in cultured cells and the livers of mice," Cell Metab., vol. 5, pp. 73-79 (2007).
Cheng et al.,"Increased cholesterol content in Gammadelta (γδ) T lymphocytes differentially regulates their activation," PLoS ONE 8, pp. 1-9 (2013).
Cook et al., "24-hydroxycholesterol sulfation by human cytosolic sulfotransferases: formation of monosulfates and disulfates, molecular modeling, sulfatase sensitivity, and inhibition of liver X receptor activation," Drug Metab. Dispos., vol. 37, pp. 2069-2078 (2009).
Hanyu et al.,"Cholesterol sulfate induces expression of the skin barrier protein filaggrin in normal human epidermal keratinocytes through induction of RORα," Biochem. Biophys. Res. Commun., vol. 428, pp. 99-104 (2012).
Hu et al., "Sterol metabolism controls $T_H17$ differentiation by generating endogenous RORγ agonists," Nature Chemical Biology, vol. 11, pp. 141-147 (2015).
Iida et al., "Tumor-Infiltrating CD4+Th17 Cells Produce IL-17 in Tumor Microenvironment and Promote Tumor Progression in Human Gastric Cancer," Oncology Reports, vol. 25, pp. 1271-1277 (2011).
Ikonen, "Cellular cholesterol trafficking and compartmentalization," Nat. Rev. Mol. Cell Biol., vol. 9, pp. 125-138 (2008).
Kallen et al.,"Crystal structure of the human RORα ligand binding domain in complex with cholesterol sulfate at 2.2 Å," J. Biol. Chem., vol. 279, pp. 14033-14038 (2004).
Kidani et al., "The sterol regulatory element binding proteins are essential for the metabolic programming of effector T cells and adaptive immunity," Nat. Immunol., vol. 14, pp. 489-499 (2013).
Liao et al., "Association Between Th17-Related Cytokines and Risk of Non-Small Cell Lung Cancer Among Patients With or Without Chronic Obstructive Pulmonary Disease," Cancer, pp. 3122-3129 (2015).
Ma et al., "25-Hydroxycholesterol-3-sulfate regulates macrophage lipid metabolism via the LXR/SREBP-1 signaling pathway," Am. J. Physiol. Endocrinol. Metab., vol. 295, pp. E1369-E1379 (2008).
Solt et al., "Identification of a selective RORγ ligand that suppresses $T_H17$ cells and stimulates T regulatory cells," ACS Chem. Biol., vol. 7, pp. 1515-1519 (2012).
Song et al., "Auto-oxidized cholesterol sulfates are antagonistic ligands of liver X receptors: implications for the development and treatment of atherosclerosis," Steroids, vol. 66, pp. 473-479 (2001).
Spann et al., "Regulated accumulation of desmosterol integrates macrophage lipid metabolism and inflammatory responses," Cell, vol. 151, pp. 138-152 (2012).
Spann et al., "Sterols and oxysterols in immune cell function," Nat. Immunol., vol. 14, pp. 893-900 (2013).
Wang et al., "A second class of nuclear receptors for oxysterols: Regulation of RORα and RORγ activity by 24S-hydroxycholesterol (cerebrosterol)," Biochim. Biophys. Acta, vol. 1801, pp. 917-923 (2010).
Yang et al., "Sterol intermediates from cholesterol biosynthetic pathway as liver X receptor ligands," J. Biol. Chem., vol. 281, pp. 27816-27826 (2006).
Arellano et al., "Clinical uses of GM-CSF, a critical appraisal and update," Biologics: Targets & Therapy, vol. 2, pp. 13-27 (2008).
Chang et al., "Synthetic RORγt Agonists Enhance Protective Immunity," ACS Chem. Biol., Just Accepted Manuscript—DOI: 10.1021/acschembio.5b00899—Publication Date (Web): Jan. 19, 2016, (30 pages).
Chen et al., "Th1-, Th2-, and Th17-associated cytokine expression in hypopharyngeal carcinoma and clinical significance," Eur Arch Otorhinolaryngol, DOI: 10.1007/s00405-015-3779-2, 8 pages, (2015).
Codarri et al., "RORγt drives production of the cytokine GM-CSF in helper T cells, which is essential for the effector phase of autoimmune neuroinflammation," Nature Immunology, vol. 12, pp. 560-568, (2011).
Gnerlich et al.,"Induction of Th17 Cells in the Tumor Microenvironment Improves Survival in a Murine Model of Pancreatic Cancer," The Journal of Immunology, vol. 185, pp. 4063-4071, (2010).
Hinrichs et al., "Type 17 $CD8_+$ T cells display enhanced antitumor immunity," Blood, vol. 114, pp. 596-599, (2009).

(56) References Cited

OTHER PUBLICATIONS

Hu et al. In "RORγ Agonists as a Novel Immunotherapy Approach for Cancer" in American Association for Cancer Research Annual Meeting in Philadelphia, Pennsylvania, Apr. 21, 2015, Poster Session: Novel Immunomodulators, Abstract No. 4273.
Kryczek et al.,"Phenotype, distribution, generation, and functional and clinical relevance of Th17 cells in the human tumor environments," *The American Society of Hematology*, vol. 114, pp. 1141-1149, (2009).
Ma et al., "Contribution of IL-17-producing γδ T cells to the efficacy of anticancer chemotherapy," *J. Exp. Med.*, vol. 208, pp. 491-503, (2011).
Munegowda et al., "Th17 and Th17-stimulated $CD8_+$ T cells play a distinct role in Th17-induced preventive and therapeutic antitumor immunity," *Cancer Immunol Immunother*, vol. 60, (2011), one page, Abstract only.
Muranski et al., "Tumor-specific Th17-polarized cells eradicate large established melanoma," *Blood*, vol. 112, pp. 362-373, (2008).
Nelson et al., "The Inducible Costimulator Augments Tc17 Cell Responses to Self and Tumor Tissue," *The Journal of Immunology*, vol. 194, pp. 1737-1747, (2015).
Nunez et al., "T helper type 17 cells contribute to anti-tumour immunity and promote the recruitment of T helper type 1 cells to the tumour," *Immunology*, vol. 139, pp. 61-71, (2012).
Soroosh et al., "Oxysterols are agonist ligands of RORγt and drive Th17 cell differentiation," PNAS, vol. 111, pp. 12163-12168, (2014).
International Search Report and Written Opinion for International Application No. PCT/US2015/029167 dated Jun. 13, 2017 (25 pages).
International Search Report and Written Opinion for International Application No. PCT/US2015/029240 dated Jan. 29, 2016 (14 pages).
International Search Report and Written Opinion for International Application No. PCT/US2016/030882 dated Jun. 6, 2016 (17 pages).
International Search Report and Written Opinion for International Application No. PCT/US2016/036889 dated Sep. 9, 2016 (17 pages).
Yang, S. M. and Murray, W. V. "Microwave assisted ring-opening of epoxides with N-biaryl sulfonamides in the synthesis of matrix metalloproteinase-9 inhibitors," *Tetrahedron Lett.* (2008) vol. 49, No. 5, pp. 835-839.
CAS Registry No. 1012413-39-6; STN Entry Date: Apr. 6, 2008; Chemical name: Benzenesulfonamide, N-[4-[(2-fluorophenyl)methoxy]phenyl]-N-methyl-.
CAS Registry No. 632292-33-2; STN Entry Date: Dec. 30, 2003; Chemical name: 2-[[1,2,3,4-tetrahydro-1-[(4-methylphenyl)sulfonyl]-6-quinolinyl]methyl]-1H-isoindole-1,3(2H)-dione.
Zhu, W. et al. "Potent 11β-Hydroxylase Inhibitors with Inverse Metabolic Stability in Human Plasma and Hepatic S9 Fractions to Promote Wound Healing," *J. Med. Chem.* (2014) vol. 57, No. 18, pp. 7811-7817.
Zhao, S.-H et al. "3,4-Dihydro-2H-benzo[1,4]oxazine Derivatives as $5-HT_6$ Receptor Antagonists," *Bioorg. Med. Chem. Lett.* (2007) vol. 17, pp. 3504-3507.
Tavares, F. X. et al. "Potent, Selective, and Orally Efficacious Antagonists of Melanin-Concentrating Hormone Receptor 1," *J. Med. Chem.* (2006) vol. 49, No. 24, pp. 7095-7107.
STN Chemical Structure Search Results (dated Jun. 5, 2015; 13 pages).
STN Chemical Structure Search Results (dated May 2, 2014; 10 pages).
STN Chemical Structure Search Results (dated May 2, 2014; 28 pages).
International Preliminary Report on Patentability for International Application No. PCT/US2015/029167 dated Jul. 4, 2017 (13 pages).
Garcia-Hernandez, M. et al. "Adoptive Transfer of Tumor-Specific Tc17 Effector T Cells Controls the Growth of B16 Melanoma in Mice," *J. Immunology.* (2010), vol. 184, No. 8, pp. 4215-4227.

\* cited by examiner

DIHYDRO-2H-BENZO[B][1,4]OXAZINE SULFONAMIDE AND RELATED COMPOUNDS FOR USE AS AGONISTS OF RORγ AND THE TREATMENT OF DISEASE

CROSS-REFERENCE TO RELATED APPLICATIONS

This application is the national stage of International (PCT) Patent Application Serial No. PCT/US2016/030882, filed May 5, 2016, which claims the benefit of and priority to U.S. Provisional Patent Application Ser. No. 62/157,224, filed May 5, 2015, and U.S. Provisional Patent Application Ser. No. 62/210,076, filed Aug. 26, 2015, the contents of each of which are hereby incorporated by reference in their entirety.

FIELD OF THE INVENTION

The invention provides dihydro-2H-benzo[b][1,4]oxazine sulfonamide and related compounds, methods of promoting RORγ activity and/or increasing the amount of IL-17 in a subject, and therapeutic uses of the dihydro-2H-benzo[b][1, 4]oxazine sulfonamide and related compounds, such as treating medical conditions in which activation of immune response is beneficial.

BACKGROUND

Retinoid-related orphan receptors (ROR) are reported to have an important role in numerous biological processes. See, for example, Dussault et al. in *Mech. Dev.* (1998) vol. 70, 147-153; and Andre et al. in *EMBO J.* (1998) vol. 17, 3867-3877. Scientific investigations relating to each of retinoid-related orphan receptors RORα, RORβ, and RORγ have been described in the literature. See, for example, Hirose et al. in *Biochem. Biophys. Res. Commun.* (1994) vol. 205, 1976-1983; Giguere et al. in *Genes. Dev.* (1994) vol. 8, 538-553; Medvedev et al. in *Gene* (1996) vol. 181, 199-206; Ortiz et al. in *Mol. Endocrinol.* (1995) vol. 9, 1679-1691; and A. M. Jetten in *Curr Drug Targets Inflamm Allergy* (2004) vol. 3, 395-412). Continuing research in this field is spurred by the promise of developing new therapeutic agents to treat medical disorders associated with retinoid-related orphan receptor activity.

RORγ has been reported to be expressed in high concentration in various tissues, such as thymus, kidney, liver, muscle, and certain fat tissue. See, for example, Hirose et al. in *Biochem. Biophys. Res. Commun.* (1994) vol. 205, 1976-1983; Medvedev et al. in *Gene* (1996) vol. 181, 199-206; Ortiz et al. in *Mol. Endocrinol.* (1995) vol. 9, 1679-1691; and He et al. in *Immunity* (1998) vol. 9, 797-806. Two isoforms of RORγ have been identified and are referred to as γ1 and γ2 (also referred to as RORγt). See, for example, He et al. in *Immunity* (1998) vol. 9, 797-806. Expression of the γ2 isoform has been reported to appear in, for example, double-positive thymocytes. See, for example, He et al. in *Immunity* (1998) vol. 9, 797-806; and Villey et al. in *Eur. J. Immunol.* (1999) vol. 29, 4072-4080. RORγt plays a critical role in regulating differentiation of Th17 cells, a subset of T helper lymphocytes. See, for example, Ivanov et al. in *Cell* (2006) vol. 126, 1121-1133. Th17 cells are important for recruiting tumor-killing cytotoxic CD8+ T cells and natural killer cells into the tumor microenvironment. The level of Th17 cells correlated positively with patient survival or slower disease progression in certain cancers. See, for example, Kryczek et al. in *Blood* (2009) vol 114, 1141-1149; and Sfanos et al. in *Clinical Cancer Research* (2008) vol 14, 3254-3261. Compounds capable of enhancing RORγt activity are thus contemplated to provide a therapeutic benefit in the treatment of cancer.

Cancer continues to be a significant health problem despite the substantial research efforts and scientific advances reported in the literature for treating this disease. Some of the most frequently diagnosed cancers include prostate cancer, breast cancer, and lung cancer. Prostate cancer is the most common form of cancer in men. Breast cancer remains a leading cause of death in women. Current treatment options for these cancers are not effective for all patients and/or can have substantial adverse side effects.

Accordingly, a need exists for improved treatments for cancer. The present invention addresses this need and provides other related advantages.

SUMMARY

The invention provides dihydro-2H-benzo[b][1,4]oxazine and related compounds, pharmaceutical compositions, methods of promoting RORγ activity and/or increasing the amount of IL-17 in a subject, and methods of treating various medical disorders using such compounds. In particular, one aspect of the invention provides a collection of dihydro-2H-benzo[b][1,4]oxazine sulfonamide and related compounds, such as a compound represented by Formula I:

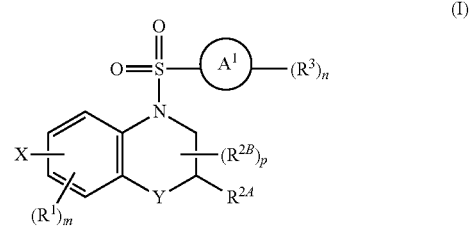

(I)

or a pharmaceutically acceptable salt thereof; wherein the variables are as defined in the detailed description. Another aspect of the invention provides a collection of compounds represented by Formula II:

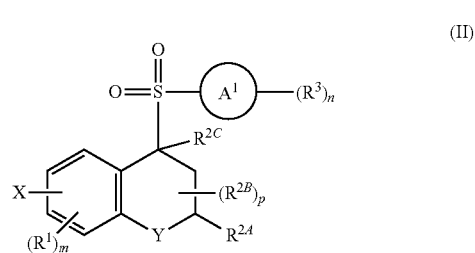

(II)

or a pharmaceutically acceptable salt thereof; wherein the variables are as defined in the detailed description. Further description of additional collections of dihydro-2H-benzo [b][1,4]oxazine sulfonamide and related compounds are described in the detailed description.

Another aspect of the invention provides a method of treating a subject suffering from a medical disorder. The method comprises administering to the subject a therapeutically effective amount of one or more dihydro-2H-benzo [b][1,4]oxazine sulfonamide or related compounds described herein, e.g., a compound of Formula I, I-A, I-B, II, II-A, II-B, or II-C. A large number of disorders can be treated using the dihydro-2H-benzo[b][1,4]oxazine sulfonamide and related compounds described herein. For example, the compounds described herein can be used to treat cancer, a bacterial infection, a fungal infection, or an immune deficiency disorder.

Another aspect of the invention provides a method of promoting the activity of RORγ. The method comprises exposing a RORγ to an effective amount of one or more dihydro-2H-benzo[b][1,4]oxazine sulfonamide or related compounds described herein, e.g., a compound of Formula I, I-A, I-B, II, II-A, II-B, or II-C, or a pharmaceutical composition described herein.

Another aspect of the invention provides a method of increasing the amount of IL-17 in a subject. The method comprises administering to a subject an effective amount of one or more dihydro-2H-benzo[b][1,4]oxazine sulfonamide or related compounds described herein, e.g., a compound of Formula I, I-A, I-B, II, II-A, II-B, or II-C, or a pharmaceutical composition described herein, to increase the amount of IL-17 in the subject.

DETAILED DESCRIPTION

The invention provides dihydro-2H-benzo[b][1,4]oxazine sulfonamide and related compounds, pharmaceutical compositions, methods of promoting RORγ activity and/or increasing the amount of IL-17 in a subject, and therapeutic uses of the dihydro-2H-benzo[b][1,4]oxazine sulfonamide and related compounds. The practice of the present invention employs, unless otherwise indicated, conventional techniques of organic chemistry, pharmacology, molecular biology (including recombinant techniques), cell biology, biochemistry, and immunology. Such techniques are explained in the literature, such as in "Comprehensive Organic Synthesis" (B. M. Trost & I. Fleming, eds., 1991-1992); "Handbook of experimental immunology" (D. M. Weir & C. C. Blackwell, eds.); "Current protocols in molecular biology" (F. M. Ausubel et al., eds., 1987, and periodic updates); and "Current protocols in immunology" (J. E. Coligan et al., eds., 1991), each of which is herein incorporated by reference in its entirety.

Various aspects of the invention are set forth below in sections; however, aspects of the invention described in one particular section are not to be limited to any particular section. Further, when a variable is not accompanied by a definition, the previous definition of the variable controls.

Definitions

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. If a chemical compound is referred to using both a chemical structure and a chemical name, and an ambiguity exists between the structure and the name, the structure predominates. These definitions apply regardless of whether a term is used by itself or in combination with other terms, unless otherwise indicated. Hence, the definition of "alkyl" applies to "alkyl" as well as the "alkyl" portions of "—O-alkyl" etc.

The term "alkyl" refers to a saturated straight or branched hydrocarbon, such as a straight or branched group of 1-12, 1-10, or 1-6 carbon atoms, referred to herein as $C_1$-$C_{12}$ alkyl, $C_1$-$C_{10}$ alkyl, and $C_1$-$C_6$ alkyl, respectively. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, octyl, etc.

The term "alkylene" refers to a diradical of an alkyl group. Exemplary alkylene groups include —CH$_2$—, —CH$_2$CH$_2$—, and —CH$_2$C(H)(CH$_3$)CH$_2$—. The term "—(C$_0$ alkylene)-" refers to a bond. Accordingly, the term "—(C$_{0-3}$ alkylene)-" encompasses a bond (i.e., C$_0$) and a —(C$_{1-3}$ alkylene) group.

The term "heteroalkylene" refers to an alkylene group in which one or more carbon atoms has been replaced by a heteroatom (e.g., N, O, or S). Exemplary heteroalkylene groups include —CH$_2$O—, —CH$_2$OCH$_2$—, and —CH$_2$CH$_2$O—. The heteroalkylene group may contain, for example, from 2-4, 2-6, or 2-8 atoms selected from the group consisting of carbon and a heteroatom (e.g., N, O, or S).

The term "cycloalkyl" refers to a monovalent saturated cyclic, bicyclic, or bridged cyclic (e.g., adamantyl) hydrocarbon group of 3-12, 3-8, 4-8, or 4-6 carbons, referred to herein, e.g., as "C$_3$-C$_6$ cycloalkyl," derived from a cycloalkane. Exemplary cycloalkyl groups include cyclohexyl, cyclopentyl, cyclobutyl, and cyclopropyl.

The term "cycloalkylene" refers to a diradical of a cycloalkyl group. Exemplary cycloalkylene groups include

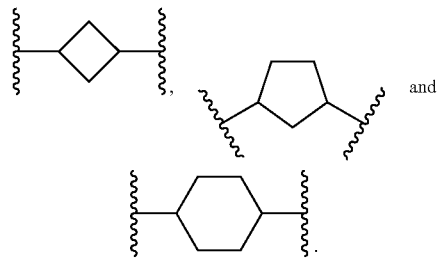

The term "haloalkyl" refers to an alkyl group that is substituted with at least one halogen. Exemplary haloalkyl groups include —CH$_2$F, —CHF$_2$, —CF$_3$, —CH$_2$CF$_3$, —CF$_2$CF$_3$, and the like. The term "fluoroalkyl" refers to an alkyl group that is substituted with at least one fluorine atom.

The term "hydroxyalkyl" refers to an alkyl group that is substituted with at least one hydroxyl. Exemplary hydroxyalkyl groups include —CH$_2$CH$_2$OH, —C(H)(OH)CH$_3$, —CH$_2$C(H)(OH)CH$_2$CH$_2$OH, and the like.

The term "aralkyl" refers to an alkyl group substituted with an aryl group. Exemplary aralkyl groups include

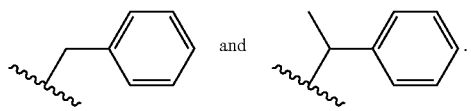

The term "heteroaralkyl" refers to an alkyl group substituted with a heteroaryl group.

The terms "alkenyl" and "alkynyl" are art-recognized and refer to unsaturated aliphatic groups analogous in length and possible substitution to the alkyls described above, but that contain at least one double or triple bond respectively.

The term "aryl" is art-recognized and refers to a carbocyclic aromatic group. Representative aryl groups include phenyl, naphthyl, anthracenyl, and the like. Unless specified otherwise, the aromatic ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —CO₂alkyl, carbonyl, carboxyl, alkylthio, sulfonyl, sulfonamido, sulfonamide, ketone, aldehyde, ester, heterocyclyl, aryl or heteroaryl moieties, —CF₃, —CN, or the like. The term "aryl" also includes polycyclic aromatic ring systems having two or more carbocyclic rings in which two or more carbons are common to two adjoining rings (the rings are "fused rings") wherein all of the fused rings are aromatic rings, e.g., in a naphthyl group.

The term "phenylene" refers to a multivalent radical (e.g., a divalent or trivalent radical) of benzene. To illustrate, a divalent valent radical of benzene is illustrated by the formula

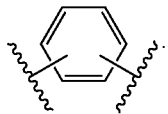

The term "partially unsaturated bicyclic carbocyclyl" refers to a bicyclic carbocyclic group that comprises at least one carbon-carbon double bond between ring carbon atoms and at least one ring in the bicyclic carbocyclic group is not aromatic. Representative examples of a partially unsaturated bicyclic carbocyclyl include, for example:

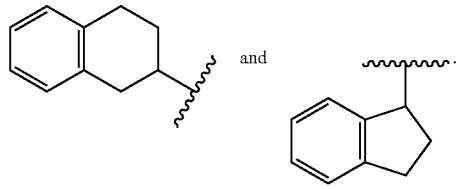 [SMILES: *C1CCc2ccccc2C1 ; *C1CCc2ccccc21]

The term "heteroaryl" is art-recognized and refers to aromatic groups that include at least one ring heteroatom. In certain instances, a heteroaryl group contains 1, 2, 3, or 4 ring heteroatoms (e.g., O, N, and S). Representative examples of heteroaryl groups include pyrrolyl, furanyl, thiophenyl, imidazolyl, oxazolyl, thiazolyl, triazolyl, pyrazolyl, pyridinyl, pyrazinyl, pyridazinyl and pyrimidinyl, and the like. Unless specified otherwise, the heteroaryl ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —CO₂alkyl, carbonyl, carboxyl, alkylthio, sulfonyl, sulfonamido, sulfonamide, ketone, aldehyde, ester, heterocyclyl, aryl or heteroaryl moieties, —CF₃, —CN, or the like. The term "heteroaryl" also includes polycyclic aromatic ring systems having two or more rings in which two or more ring atoms are common to two adjoining rings (the rings are "fused rings") wherein all of the fused rings are heteroaromatic, e.g., in a naphthyridinyl group. In certain embodiments, the heteroaryl is a 5-6 membered monoclic ring or a 9-10 membered bicyclic ring.

The term "heteroarylene" refers to a multi-valent (e.g., di-valent or trivalent) aromatic group that comprises at least one ring heteroatom. An exemplary "heteroarylene" is pyridinylene, which is a multi-valent radical of pyridine. For example, a divalent radical of pyridine is illustrated by the formula

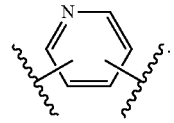

In certain embodiments, the "heteroarylene" is a divalant, 5-6 membered heteroaromatic group containing 1, 2, or 3 ring heteroatoms (e.g., O, N, or S).

The terms ortho, meta, and para are art-recognized and refer to 1,2-, 1,3- and 1,4-disubstituted benzenes, respectively. For example, the names 1,2-dimethylbenzene and ortho-dimethylbenzene are synonymous.

As used herein, the terms "heterocyclic" and "heterocyclyl" represent, for example, an aromatic or nonaromatic ring (e.g., a monocyclic or bicyclic ring) containing one or more heteroatoms. The heteroatoms can be the same or different from each other. Examples of heteratoms include, but are not limited to nitrogen, oxygen and sulfur. Aromatic and nonaromatic heterocyclic rings are well-known in the art. Some nonlimiting examples of aromatic heterocyclic rings include, but are not limited to, pyridine, pyrimidine, indole, purine, quinoline and isoquinoline. Nonlimiting examples of nonaromatic heterocyclic compounds include, but are not limited to, piperidine, piperazine, morpholine, pyrrolidine and pyrazolidine. Examples of oxygen containing heterocyclic rings include, but are not limited to, furan, oxirane, 2H-pyran, 4H-pyran, 2H-chromene, benzofuran, and 2,3-dihydrobenzo[b][1,4]dioxine. Examples of sulfur-containing heterocyclic rings include, but are not limited to, thiophene, benzothiophene, and parathiazine. Examples of nitrogen containing rings include, but are not limited to, pyrrole, pyrrolidine, pyrazole, pyrazolidine, imidazole, imidazoline, imidazolidine, pyridine, piperidine, pyrazine, piperazine, pyrimidine, indole, purine, benzimidazole, quinoline, isoquinoline, triazole, and triazine. Examples of heterocyclic rings containing two different heteroatoms include, but are not limited to, phenothiazine, morpholine, parathiazine, oxazine, oxazole, thiazine, and thiazole. The heterocyclic ring is optionally further substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —CO₂alkyl, carbonyl, carboxyl, alkylthio, sulfonyl, sulfonamido, sulfonamide, ketone, aldehyde, ester, heterocyclyl, aryl or heteroaryl moieties, —CF₃, —CN, or the like. In certain embodiments, the heterocyclyl group is a 3-7 membered ring that, unless specified otherwise, is substituted or unsubstituted.

The term "heterocycloalkyl" refers to a saturated heterocyclyl group having, for example, 3-7 ring atoms (e.g., O, N, or S).

The term "heterocycloalkylene" refers to a multi-valent (e.g., di-valent or trivalent) saturated heterocyclyl group having, for example, 3-7 ring atoms. An exemplary "heterocycloalkylene" is piperidinylene, which is a multi-valent radical of piperidine. In certain embodiments, the "heterocycloalkylene" is a divalent, 5-6 membered saturated heterocyclyl containing 1 or 2 ring heteroatoms (e.g., O, N, or S).

The term "partially unsaturated bicyclic heterocyclyl" refers to a bicyclic heterocyclic group that comprises at least one double bond between two ring atoms and at least one ring in the bicyclic heterocyclic group is not aromatic. Representative examples of a partially unsaturated bicyclic heterocyclyl include, for example:

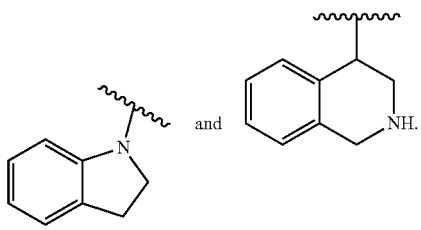 [SMILES: *N1CCc2ccccc21 ; *C1CNCc2ccccc21]

The term "partially unsaturated bicyclic oxo-heterocyclyl" refers to a bicyclic heterocyclic group that comprises at least one double bond between ring atoms, one oxo substituent, and at least one ring in the bicyclic heterocyclic group is not aromatic. Representative examples of a partially unsaturated bicyclic oxo-heterocyclyl include, for example:

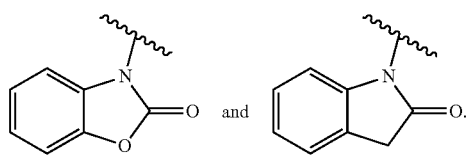 [SMILES: *n1c(=O)oc2ccccc21 ; "and" ; *N1C(=O)Cc2ccccc21]

The phrase "5-6 membered heterocyclic group containing at least one unsaturated carbon atom in the ring" refers to a 5-6 membered heterocyclic group containing at least one ring carbon atom where said carbon atom has a double bond to another atom, such as another atom in the heterocyclic ring or to an exocyclic oxygen atom such that the ring carbon atom is part of a C=O group. Exemplary 5-6 membered heterocyclic groups containing at least one unsaturated carbon atom in the ring include, for example:

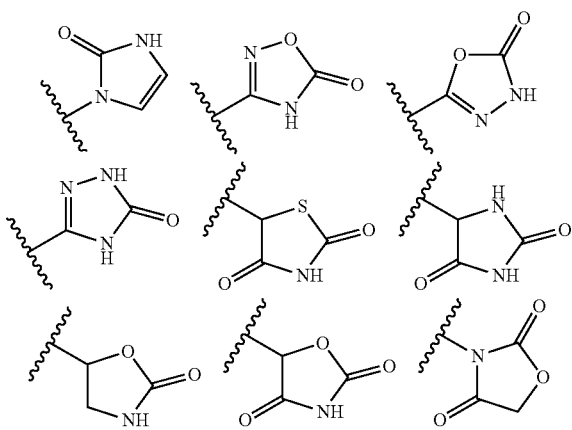

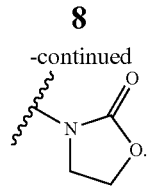

The terms "amine" and "amino" are art-recognized and refer to both unsubstituted and substituted amines, e.g., a moiety that may be represented by the general formulas:

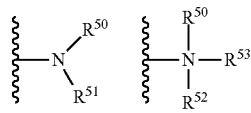

wherein $R^{50}$, $R^{51}$, $R^{52}$ and $R^{53}$ each independently represent a hydrogen, an alkyl, an alkenyl, $-(CH_2)_m-R^{61}$, or $R^{50}$ and $R^{51}$, taken together with the N atom to which they are attached complete a heterocycle having from 4 to 8 atoms in the ring structure; $R^{61}$ represents an aryl, a cycloalkyl, a cycloalkenyl, a heterocycle or a polycycle; and m is zero or an integer in the range of 1 to 8. In certain embodiments, only one of $R^{50}$ or $R^{51}$ may be a carbonyl, e.g., $R^{50}$, $R^{51}$ and the nitrogen together do not form an imide. In other embodiments, $R^{50}$ and $R^{51}$ (and optionally $R^{52}$) each independently represent a hydrogen, an alkyl, an alkenyl, or $-(CH_2)_m-R^{61}$.

The terms "alkoxyl" or "alkoxy" are art-recognized and refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, and $-O-(CH_2)_m-R^{61}$, where m and $R^{61}$ are described above.

The term "haloalkoxy" refers to an alkoxy group that is substituted with at least one halogen. Exemplary haloalkoxy groups include —OCH$_2$F, —OCHF$_2$, —OCF$_3$, —OCH$_2$CF$_3$, —OCF$_2$CF$_3$, and the like. The term "fluoroalkoxyl" refers to an alkoxy group substituted by at least one fluorine atom.

The term "oxo" is art-recognized and refers to a "=O" substituent. For example, a cyclopentane substituted with an oxo group is cyclopentanone.

The symbol "⌇" indicates a point of attachment.

The term "substituted" means that one or more hydrogens on the atoms of the designated group are replaced with a selection from the indicated group, provided that the atoms' normal valencies under the existing circumstances are not exceeded, and that the substitution results in a stable compound. Combinations of substituents and/or variables are permissible only if such combinations result in stable compounds. The terms "stable compound' or "stable structure" refer to a compound that is sufficiently robust to survive isolation to a useful degree of purity from a reaction mixture, and formulation into an efficacious therapeutic agent.

When any substituent or variable occurs more than one time in any constituent or the compound of the invention, its definition on each occurrence is independent of its definition at every other occurrence, unless otherwise indicated.

It should also be noted that any carbon as well as heteroatom with unsatisfied valences in the text, schemes, examples and tables herein is assumed to have the sufficient number of hydrogen atom(s) to satisfy the valences.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Nonlimiting examples of suitable solvates include ethanolates, methanolates, and the like. "Hydrate" is a solvate wherein the solvent molecule is $H_2O$.

Certain compounds contained in compositions of the present invention may exist in particular geometric or stereoisomeric forms. Further, certain compounds described herein may be optically active. The present invention contemplates all such compounds, including cis- and transisomers, R- and S-enantiomers, diastereomers, (D)-isomers, (L)-isomers, the racemic mixtures thereof, and other mixtures thereof, as falling within the scope of the invention. The compounds may contain one or more stereogenic centers. For example, asymmetric carbon atoms may be present in a substituent such as an alkyl group. All such isomers, as well as mixtures thereof, are intended to be included in this invention, such as, for example, racemic mixtures, single enantiomers, diastereomeric mixtures and individual diastereomers. Additional asymmetric centers may be present depending upon the nature of the various substituents on the molecule. Each such asymmetric center will independently produce two optical isomers, and it is intended that all of the possible optical isomers, diastereomers in mixtures, and pure or partially purified compounds are included within the ambit of this invention.

Diastereomeric mixtures can be separated into their individual diastereomers on the basis of their physical chemical differences by methods known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Alternatively, a particular enantiomer of a compound of the present invention may be prepared by asymmetric synthesis. Still further, where the molecule contains a basic functional group (such as amino) or an acidic functional group (such as carboxylic acid) diastereomeric salts are formed with an appropriate optically-active acid or base, followed by resolution of the diastereomers thus formed by fractional crystallization or chromatographic means known in the art, and subsequent recovery of the pure enantiomers.

Individual stereoisomers of the compounds of the invention may, for example, be substantially free of other isomers, or may be admixed, for example, as racemates or with all other, or other selected, stereoisomers. Chiral center(s) in a compound of the present invention can have the S or R configuration as defined by the IUPAC 1974 Recommendations. Further, to the extent a compound described herein may exist as a atropisomer (e.g., substituted biaryls), all forms of such atropisomer are considered part of this invention.

As used herein, the terms "subject" and "patient" are used interchangeable and refer to organisms to be treated by the methods of the present invention. Such organisms preferably include, but are not limited to, mammals (e.g., murines, simians, equines, bovines, porcines, canines, felines, and the like), and most preferably includes humans.

The term "$EC_{50}$" is art-recognized and refers to the concentration of a compound that is required to achieve 50% of the maximum possible activation of the target.

As used herein, the term "effective amount" refers to the amount of a compound sufficient to effect beneficial or desired results (e.g., a therapeutic, ameliorative, inhibitory or preventative result). An effective amount can be administered in one or more administrations, applications or dosages and is not intended to be limited to a particular formulation or administration route. As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "pharmaceutical composition" refers to the combination of an active agent with a carrier, inert or active, making the composition especially suitable for diagnostic or therapeutic use in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants, see e.g., Martin, Remington's Pharmaceutical Sciences, 15th Ed., Mack Publ. Co., Easton, Pa. [1975].

As used herein, the term "pharmaceutically acceptable salt" refers to any pharmaceutically acceptable salt (e.g., acid or base) of a compound of the present invention which, upon administration to a subject, is capable of providing a compound of this invention or an active metabolite or residue thereof. As is known to those of skill in the art, "salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metals (e.g., sodium) hydroxides, alkaline earth metals (e.g., magnesium), hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate (also known as toluenesulfonate), undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like. Further examples of salts include, but are not limited to: ascorbate, borate, nitrate, phosphate, salicylate, and sulfate. Further, acids which are generally considered suitable for the formation of pharmaceutically useful salts from basic pharmaceutical compounds are discussed, for example, by P. Stahl et al., Camille G. (eds.) *Handbook of Pharmaceutical Salts. Properties, Selection and Use*. (2002) Zurich: Wiley-VCH; S. Berge et al., *Journal of Pharmaceutical Sciences* (1977) 66(1) 1-19; P. Gould, *International J of Pharmaceutics* (1986) 33 201-217; Anderson et al., *The Practice of Medicinal Chemistry* (1996), Academic Press, New York; and in *The Orange Book* (Food & Drug Administration, Washington, D.C. on their website). These disclosures are incorporated herein by reference.

Additional exemplary basic salts include, but are not limited to: ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

In addition, when a compound of the invention contains both a basic moiety (such as, but not limited to, a pyridine or imidazole) and an acidic moiety (such as, but not limited to, a carboxylic acid) zwitterions ("inner salts") may be formed. Such acidic and basic salts used within the scope of the invention are pharmaceutically acceptable (i.e., non-toxic, physiologically acceptable) salts. Such salts of the compounds of the invention may be formed, for example, by reacting a compound of the invention with an amount of acid or base, such as an equivalent amount, in a medium such as one in which the salt precipitates or in an aqueous medium followed by lyophilization.

The present invention includes the compounds of the invention in all their isolated forms (such as any solvates, hydrates, stereoisomers, and tautomers thereof). Further, the invention includes compounds in which one or more of the atoms may be artificially enriched in a particular isotope having the same atomic number, but an atomic mass or mass number different from the atomic mass or mass number predominantly found in nature. The present invention is meant to include all suitable isotopic variations of the compounds of the invention. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds can be prepared without undue experimentation by conventional techniques known to those skilled in the art or by processes analogous to those described in the Schemes and Examples herein using appropriate isotopically-enriched reagents and/or intermediates.

Throughout the description, where compositions are described as having, including, or comprising specific components, or where processes and methods are described as having, including, or comprising specific steps, it is contemplated that, additionally, there are compositions of the present invention that consist essentially of, or consist of, the recited components, and that there are processes and methods according to the present invention that consist essentially of, or consist of, the recited processing steps.

The terms "a" and "an" as used herein mean "one or more" and include the plural unless the context is inappropriate.

The abbreviation "THF" is art-recognized and refers to tetrahydrofuran. The abbreviation "DCM" is art-recognized and refers to dichloromethane. The abbreviation "DMF" is art-recognized and refers to dimethylformamide. The abbreviation "DMA" is art-recognized and refers to dimethylacetamide. The abbreviation "EDTA" is art-recognized and refers to ethylenediaminetetraacetic acid. The abbreviation "TFA" is art-recognized and refers to trifluoroacetic acid. The abbreviation "Ts" is art-recognized and refers to tosylate. The abbreviation "TBS" is art-recognized and refers to tert-butyldimethylsilyl. The abbreviation "DMSO" is art-recognized and refers to dimethylsulfoxide. The abbreviation "Tf" is art-recognized and refers to triflate, or trifluoromethylsulfonate. The abbreviation "Pin" is art-recognized and refers to pinacolato.

As a general matter, compositions specifying a percentage are by weight unless otherwise specified.

I. Dihydro-2H-benzo[b][1,4]oxazine Sulfonamide and Related Compounds

The invention provides dihydro-2H-benzo[b][1,4]oxazine sulfonamide and related compounds. Exemplary compounds are described in the following sections, along with exemplary procedures for making the compounds. Additional exemplary compounds and synthetic procedures are described in the Examples.

One aspect of the invention provides a compound represented by Formula I:

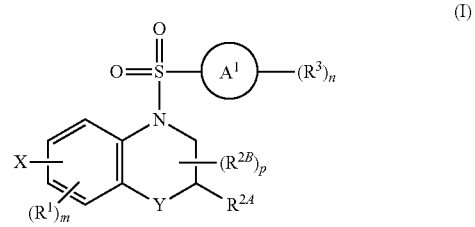

or a pharmaceutically acceptable salt thereof; wherein:

$A^1$ is phenylene, 5-6 membered heteroarylene, or $C_{3-6}$ heterocycloalkylene;

$R^1$ represents independently for each occurrence halogen, $C_{1-6}$ alkyl, $C_{1-6}$ haloalkyl, or $C_{3-6}$ cycloalkyl;

$R^{2A}$ is —($C_{1-6}$ alkylene)-$A^2$, -(2-6 membered heteroalkylene)-$A^2$, —($C_{0-3}$ alkylene)-($C_{3-6}$ cycloalkylene)-($C_{0-3}$ alkylene)-$A^2$, —O-$A^2$, —N($R^8$)-$A^2$, or -$A^2$; wherein $A^2$ is a 5-6 membered heterocyclic group containing at least one unsaturated carbon atom in the ring and the heterocyclic group being optionally substituted with 1, 2, or 3 substituents independently selected from the group consisting of $C_{1-6}$ alkyl, $C_{1-6}$ haloalkyl, $C_{3-6}$ cycloalkyl, halogen, $C_{1-6}$ alkoxy, $C_{1-6}$ haloalkoxy, oxo, —C(O)R$^9$, —CO$_2$R$^8$, —C(O)(N$^4$)(R$^5$), —N(R$^4$)C(O)(R$^9$), and —N(R$^4$)(R$^5$);

R$^{2B}$ represents independently for each occurrence $C_{1-6}$ alkyl or $C_{1-3}$ haloalkyl;

R$^3$ represents independently for each occurrence hydrogen, $C_{1-6}$ haloalkyl, halogen, hydroxyl, $C_{1-6}$ alkyl, $C_{3-6}$ cycloalkyl, $C_{1-6}$ alkoxy, $C_{1-6}$ haloalkoxy, —O—($C_{1-6}$ alkylene)-OH, or —O—($C_{1-6}$ alkylene)-CO$_2$R$^4$; or two vicinal occurrences of R$^3$ are taken together with intervening atoms to form a 4-6 membered ring;

R$^4$ and R$^5$ each represent independently for each occurrence hydrogen, $C_{1-6}$ alkyl, or $C_{3-6}$ cycloalkyl; or an occurrence of R$^4$ and R$^5$ attached to the same nitrogen atom are taken together with the nitrogen atom to which they are attached to form a 3-7 membered heterocyclic ring;

R$^6$ and R$^7$ each represent independently for each occurrence hydrogen or $C_{1-6}$ alkyl, or R$^6$ and R$^7$ are taken together with the carbon atom to which they are attached to form a 3-6 membered carbocyclic ring; or R$^6$ and R$^{2A}$ are taken together to form a bond;

R$^8$ represents independently for each occurrence hydrogen, $C_{1-6}$ alkyl, $C_{3-6}$ cycloalkyl, or aralkyl;

R$^9$ represents independently for each occurrence $C_{1-6}$ alkyl, $C_{3-6}$ cycloalkyl, or aralkyl;

X is one of the following:
(i) —($C_{2-6}$ alkenylene)-phenyl, —($C_{2-6}$ alkenylene)-heteroaryl, —($C_{1-6}$ alkylene)-phenyl, —($C_{1-6}$ alkylene)-heteroaryl, —($C_{1-6}$ alkylene)-(partially unsaturated bicyclic heterocyclyl), —($C_{1-6}$ alkylene)-(partially unsaturated bicyclic oxo-heterocyclyl), -(5-6 membered heterocycloalkylene)-phenyl, or —($C_{3-6}$ cycloalkylene)-phenyl, each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, $C_{1-6}$ haloalkoxy, hydroxyl, and cyano;
(ii) —($C_{2-6}$ alkenylene)-($C_{3-6}$ cycloalkyl),

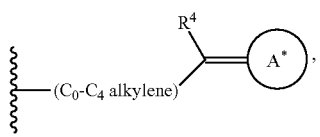

or an 8-10 membered, bicyclic partially saturated carbocyclyl, each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, $C_{1-6}$ haloalkoxy, hydroxyl, and cyano, wherein A* is a 5-8 membered, partially saturated carbocyclic or heterocyclic ring;

(iii) —($C_{1-6}$ alkylene)-Z$^1$ or —($C_{2-6}$ alkenylene)-Z$^1$, wherein Z$^1$ is —O-aralkyl, —O-heteroaralkyl, —O-phenyl, —O-heteroaryl, —O-(partially unsaturated bicyclic carbocyclyl), —O—($C_{1-6}$ alkylene)-($C_{3-6}$ cycloalkyl), —O—($C_{3-6}$ cycloalkyl), —N(R$^4$)-aralkyl, —N(R$^4$)-phenyl, —N(R$^4$)-(partially unsaturated bicyclic carbocyclyl), or —N(R$^4$)—($C_{1-6}$ alkylene)-($C_{3-6}$ cycloalkyl), each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, $C_{1-6}$ haloalkoxy, hydroxyl, and cyano; or (iv) —O-aralkyl, —O-heteroaralkyl, —O-phenyl, —O-heteroaryl, —O-(partially unsaturated bicyclic carbocyclyl), —O—($C_{1-6}$ alkylene)-($C_{3-6}$ cycloalkyl), —O—($C_{3-6}$ cycloalkyl), —N(R$^4$)-aralkyl, —N(R$^4$)-phenyl, —N(R$^4$)-(partially unsaturated bicyclic carbocyclyl), or —N(R$^4$)—($C_{1-6}$ alkylene)-($C_{3-6}$ cycloalkyl), each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, $C_{1-6}$ haloalkoxy, hydroxyl, and cyano;

Y is —C(R$^6$)(R$^7$)—, —O—, —C(O)—, or —S(O)$_p$—;

m and p each represent independently for each occurrence 0, 1, or 2; and n is 1, 2, or 3.

In certain embodiments, A$^1$ is phenylene or 5-6 membered heteroarylene.

In certain embodiments R$^1$ represents independently for each occurrence halogen or $C_{1-6}$ alkyl.

In certain embodiments, R$^3$ represents independently for each occurrence $C_{1-6}$ haloalkyl, halogen, $C_{1-6}$ alkyl, $C_{1-6}$ alkoxy, or —O—($C_{1-6}$ alkylene)-OH. In certain embodiments, R$^3$ is trifluoromethyl, fluoro, chloro, or methoxy. In certain embodiments, R$^3$ is trifluoromethyl.

In certain embodiments, -A$^1$-(R$^3$)$_n$ is

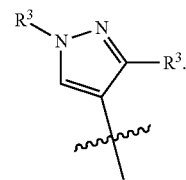

In certain embodiments, -A$^1$-(R$^3$)$_n$ is one of the following:

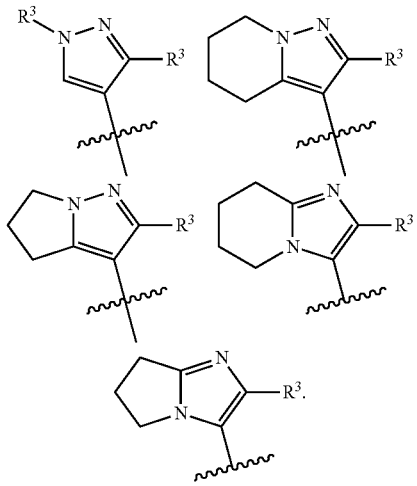

In certain embodiments, R$^{2A}$ is —($C_{1-6}$ alkylene)-A$^2$. In certain embodiments, R$^{2A}$ is —($C_{2-3}$ alkylene)-A$^2$. In certain embodiments, R$^{2A}$ is -(2-6 membered heteroalkylene)-A$^2$. In certain embodiments, R$^{2A}$ is —($C_{2-3}$ alkylene)-O-A$^2$. In certain embodiments, R$^{2A}$ is —O-A$^2$.

In certain embodiments, $A^2$ comprises at least two ring nitrogen atoms. In certain embodiments, $A^2$ comprises at least two ring nitrogen atoms, and at least one ring oxygen atom.

In certain embodiments, $A^2$ is a 5-6 membered heterocyclic group containing at least one ring carbon atom substituted by oxo and the heterocyclic group being optionally substituted by 1 or 2 substituents independently selected from the group consisting of $C_{1-6}$ alkyl, $C_{1-6}$ haloalkyl, $C_{3-6}$ cycloalkyl, halogen, $C_{1-6}$ alkoxy, $C_{1-6}$ haloalkoxy, oxo, —C(O)R$^9$, —CO$_2$R$^8$, —C(O)(N$^4$)(R$^5$), —N(R$^4$)C(O)(R$^9$), and —N(R$^4$)(R$^5$). In certain embodiments, $A^2$ is a 5-6 membered heterocyclic group containing (i) at least one ring carbon atom substituted by oxo and (ii) at least one double bond between two ring atoms, and the heterocyclic group being optionally substituted by 1 or 2 substituents independently selected from the group consisting of $C_{1-6}$ alkyl, $C_{1-6}$ haloalkyl, $C_{3-6}$ cycloalkyl, halogen, $C_{1-6}$ alkoxy, $C_{1-6}$ haloalkoxy, oxo, —C(O)R$^9$, —CO$_2$R$^8$, —C(O)(N$^4$)(R$^5$), —N(R$^4$)C(O)(R$^9$), and —N(R$^4$)(R$^5$). In certain embodiments, the heterocyclic group in $A^2$ is a 5-membered heterocyclic group.

In certain embodiments, $A^2$ is a 5-6 membered heteroaromatic group comprising at least two ring nitrogen atoms, at least one unsaturated carbon atom in the ring, and the heteroaromatic group being optionally substituted by 1 or 2 substituents independently selected from the group consisting of $C_{1-6}$ alkyl, $C_{1-6}$ haloalkyl, $C_{3-6}$ cycloalkyl, halogen, $C_{1-6}$ alkoxy, $C_{1-6}$ haloalkoxy, —C(O)R$^9$, —CO$_2$R$^8$, —C(O)(N$^4$)(R$^5$), —N(R$^4$)C(O)(R$^9$), and —N(R$^4$)(R$^5$). In certain embodiments, the heteroaromatic group in $A^2$ is a 5-membered heteroaromatic group.

In certain embodiments, $A^2$ is imidazolyl; pyrazolyl; 1,2,3-triazolyl; tetrazolyl; 1,2,4-oxadiazol-5(4H)-onyl; 1,3,4-oxadiazol-2(3H)-onyl; 1,3-dihydro-2H-imidazol-2-onyl; or 2,4-dihydro-3H-1,2,4-triazol-3-onyl; each of which is optionally substituted by 1, 2, or 3 substituents independently selected from the group consisting of $C_{1-6}$ alkyl, $C_{1-6}$ haloalkyl, $C_{3-6}$ cycloalkyl, halogen, $C_{1-6}$ alkoxy, $C_{1-6}$ haloalkoxy, —C(O)R$^9$, —CO$_2$R$^8$, —C(O)(N$^4$)(R$^5$), —N(R$^4$)C(O)(R$^9$), and —N(R$^4$)(R$^5$).

In certain embodiments, $A^2$ is imidazolyl; pyrazolyl; 1,2,3-triazolyl; tetrazolyl; 1,2,4-oxadiazol-5(4H)-onyl; 1,3,4-oxadiazol-2(3H)-onyl; 1,3-dihydro-2H-imidazol-2-onyl; or 2,4-dihydro-3H-1,2,4-triazol-3-onyl; each of which is optionally substituted by 1, 2, or 3 substituents independently selected from the group consisting of $C_{1-6}$ alkyl, $C_{1-6}$ haloalkyl, $C_{3-6}$ cycloalkyl, halogen, $C_{1-6}$ alkoxy, $C_{1-6}$ haloalkoxy, —C(O)R$^9$, and —CO$_2$R$^8$.

In certain embodiments, $A^2$ is one of the following:

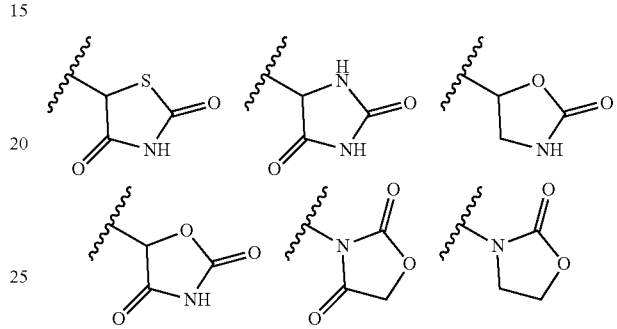

each of which is optionally substituted by 1, 2, or 3 substituents independently selected from the group consisting of $C_{1-6}$ alkyl, $C_{1-6}$ haloalkyl, $C_{3-6}$ cycloalkyl, halogen, $C_{1-6}$ alkoxy, $C_{1-6}$ haloalkoxy, —C(O)R$^9$, —CO$_2$R$^8$, and —C(O)(N$^4$)(R$^5$).

In certain embodiments, $A^2$ is oxazolidin-2-onyl; oxazolidine-2,4-dionyl; imidazolidine-2,4-dionyl; or thiazolidine-2,4-dionyl; each of which is optionally substituted by 1, 2, or 3 substituents independently selected from the group consisting of $C_{1-6}$ alkyl, $C_{1-6}$ haloalkyl, $C_{3-6}$ cycloalkyl, halogen, $C_{1-6}$ alkoxy, $C_{1-6}$ haloalkoxy, —C(O)R$^9$, —CO$_2$R$^8$, —C(O)(N$^4$)(R$^5$), —N(R$^4$)C(O)(R$^9$), and —N(R$^4$)(R$^5$).

In certain embodiments, $A^2$ is one of the following:

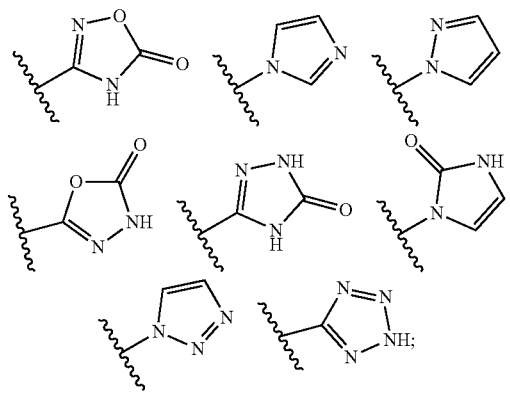

each of which is optionally substituted by 1, 2, or 3 substituents independently selected from the group consisting of $C_{1-6}$ alkyl, $C_{1-6}$ haloalkyl, $C_{3-6}$ cycloalkyl, halogen, $C_{1-6}$ alkoxy, $C_{1-6}$ haloalkoxy, —C(O)R$^9$, —CO$_2$R$^8$, and —C(O)(N$^4$)(R$^5$).

In certain embodiments, $R^{2B}$ is methyl.

In certain embodiments, X is —(C$_{2-6}$ alkenylene)-phenyl, —(C$_{2-6}$ alkenylene)-heteroaryl, —(C$_{1-6}$ alkylene)-phenyl, —(C$_{1-6}$ alkylene)-heteroaryl, —(C$_{1-6}$ alkylene)-(partially unsaturated bicyclic heterocyclyl), —(C$_{1-6}$ alkylene)-(partially unsaturated bicyclic oxo-heterocyclyl), or -(5-6 membered heterocycloalkylene)-phenyl, each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, and $C_{1-6}$ haloalkoxy. In certain embodiments, X is —(C$_{2-6}$ alkenylene)-phenyl, —(C$_{1-6}$ alkylene)-phenyl, or —(C$_{1-6}$ alkylene)-heteroaryl, each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, and $C_{1-6}$ haloalkoxy. In certain embodiments, X is —(C$_{2-6}$ alkenylene)-phenyl optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, and $C_{1-6}$ haloalkoxy.

In certain embodiments, X is —(C$_{1-6}$ alkylene)-Z$^1$ or —(C$_{2-6}$ alkenylene)-Z$^1$, wherein Z$^1$ is —O-aralkyl, —O-heteroaralkyl, —O-phenyl, —O-heteroaryl, —O-(partially unsaturated bicyclic carbocyclyl), —O—(C$_{1-6}$ alkylene)-(C$_{3-6}$ cycloalkyl), —O—(C$_{3-6}$ cycloalkyl), —N(R$^4$)-aralkyl, —N(R$^4$)-phenyl, —N(R$^4$)-(partially unsaturated bicyclic carbocyclyl), or —N(R$^4$)—(C$_{1-6}$ alkylene)-(C$_{3-6}$ cycloalkyl), each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, and $C_{1-6}$ haloalkoxy. In certain embodiments, X is —O-aralkyl, —O-heteroaralkyl, —O-phenyl, —O-heteroaryl, —O-(partially unsaturated bicyclic carbocyclyl), —O—($C_{1-6}$ alkylene)-($C_{3-6}$ cycloalkyl), —N($R^4$)-aralkyl, —N($R^4$)-phenyl, —N($R^4$)-(partially unsaturated bicyclic carbocyclyl), or —N($R^4$)—($C_{1-6}$ alkylene)-($C_{3-6}$ cycloalkyl), each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, and $C_{1-6}$ haloalkoxy. In certain embodiments, X is —O—($C_{1-6}$ alkylene)-phenyl or —N($R^4$)—($C_{1-6}$ alkylene)-phenyl, each of which is substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, and $C_{1-6}$ haloalkoxy. In certain embodiments, X is —O—($C_{1-6}$ alkylene)-phenyl or —N($R^4$)—($C_{1-6}$ alkylene)-phenyl, each of which is substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, and $C_{1-6}$ haloalkoxy, where at least one substituent is present at the ortho position on the phenyl group in variable X. In certain embodiments, X is —O—($C_{1-6}$ alkylene)-phenyl or —N($R^4$)—($C_{1-6}$ alkylene)-phenyl, each of which is substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, and $C_{1-6}$ haloalkoxy. In certain embodiments, X is —O-aralkyl or —N($R^4$)-aralkyl, each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, and $C_{1-6}$ haloalkoxy. In certain embodiments, X is —O-benzyl or —N($R^4$)-benzyl, each of which is substituted with 1 or 2 substituents independently selected from the group consisting of chloro, bromo, and fluoro.

In certain embodiments, Y is —C($R^6$)($R^7$)—. In certain embodiments, $R^6$ and $R^7$ are independently hydrogen or methyl.

In certain embodiments, Y is —C($R^6$)($R^7$)—, $R^6$ and $R^7$ are independently hydrogen or methyl, and X is attached at the 7-position of the 1,2,3,4-tetrahydroquinolinyl ring.

In certain embodiments, Y is —O—. In certain embodiments, X is attached at the 6-position of the 3,4-dihydro-2H-benzo[b][1,4]oxazinyl ring.

In certain embodiments, m is 0 or 1. In certain embodiments, p is 0. In certain embodiments, p is 1.

The definitions of variables in Formula I above encompass multiple chemical groups. The application contemplates embodiments where, for example, i) the definition of a variable is a single chemical group selected from those chemical groups set forth above, ii) the definition of a variable is a collection of two or more of the chemical groups selected from those set forth above, and iii) the compound is defined by a combination of variables in which the variables are defined by (i) or (ii), e.g., such as where A is phenylene and $R^3$ is selected from the group consisting of $C_{1-6}$ haloalkyl, halogen, hydroxyl, and $C_{1-6}$ alkyl.

Another aspect of the invention provides a compound represented by Formula I-A:

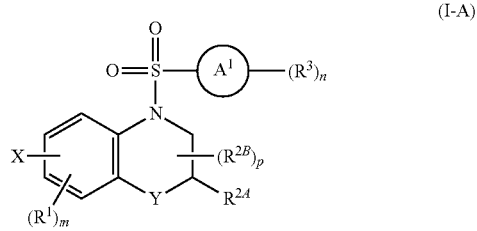

(I-A)

or a pharmaceutically acceptable salt thereof, wherein:
$A^1$ is phenylene or a 5-6 membered heteroarylene;
$R^1$ represents independently for each occurrence halogen, $C_{1-6}$ alkyl, or $C_{3-6}$ cycloalkyl;
$R^{2A}$ is —($C_{1-6}$ alkylene)-$A^2$, -(2-6 membered heteroalkylene)-$A^2$, or —O-$A^2$; wherein $A^2$ is a 5-6 membered heterocyclic group containing at least one unsaturated carbon atom and the heterocyclic group being optionally substituted with 1, 2, or 3 substituents independently selected from the group consisting of $C_{1-6}$ alkyl, $C_{1-6}$ haloalkyl, $C_{3-6}$ cycloalkyl, halogen, $C_{1-6}$ alkoxy, $C_{1-6}$ haloalkoxy, oxo, —C(O)$R^9$, —CO$_2$$R^8$, —C(O)(N$^4$)($R^5$), —N($R^4$)C(O)($R^9$), and —N($R^4$)($R^5$);
$R^{2B}$ represents independently for each occurrence $C_{1-6}$ alkyl or $C_{1-3}$ haloalkyl;
$R^3$ represents independently for each occurrence hydrogen, $C_{1-6}$ haloalkyl, halogen, hydroxyl, $C_{1-6}$ alkyl, $C_{3-6}$ cycloalkyl, $C_{1-6}$ alkoxy, $C_{1-6}$ haloalkoxy, or —O—($C_{1-6}$ alkylene)-OH; or two vicinal occurrences of $R^3$ are taken together with intervening atoms to form a 4-6 membered ring;
$R^4$ and $R^5$ each represent independently for each occurrence hydrogen, $C_{1-6}$ alkyl, or $C_{3-6}$ cycloalkyl; or an occurrence of $R^4$ and $R^5$ attached to the same nitrogen atom are taken together with the nitrogen atom to which they are attached to form a 3-7 membered heterocyclic ring;
$R^6$ and $R^7$ each represent independently for each occurrence hydrogen or $C_{1-6}$ alkyl, or $R^6$ and $R^7$ are taken together with the carbon atom to which they are attached to form a 3-6 membered carbocyclic ring;
$R^8$ represents independently for each occurrence hydrogen, $C_{1-6}$ alkyl, $C_{3-6}$ cycloalkyl, or aralkyl;
$R^9$ represents independently for each occurrence $C_{1-6}$ alkyl, $C_{3-6}$ cycloalkyl, or aralkyl;
X is one of the following:
  (i) —($C_{2-6}$ alkenylene)-phenyl, —($C_{2-6}$ alkenylene)-heteroaryl, —($C_{1-6}$ alkylene)-phenyl, —($C_{1-6}$ alkylene)-heteroaryl, —($C_{1-6}$ alkylene)-(partially unsaturated bicyclic heterocyclyl), —($C_{1-6}$ alkylene)-(partially unsaturated bicyclic oxo-heterocyclyl), or -(5-6 membered heterocycloalkylene)-phenyl, each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, and $C_{1-6}$ haloalkoxy;
  (ii) —($C_{1-6}$ alkylene)-$Z^1$ or —($C_{2-6}$ alkenylene)-$Z^1$, wherein $Z^1$ is —O-aralkyl, —O-heteroaralkyl, —O-phenyl, —O-heteroaryl, —O-(partially unsaturated bicyclic carbocyclyl), —O—($C_{1-6}$alkylene)-($C_{3-6}$ cycloalkyl), —O—($C_{3-6}$ cycloalkyl), —N($R^4$)-aralkyl, —N($R^4$)-phenyl, —N($R^4$)-(partially unsaturated bicyclic carbocyclyl), or —N($R^4$)—($C_{1-6}$ alkylene)-($C_{3-6}$ cycloalkyl), each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, and $C_{1-6}$ haloalkoxy; or
  (iii) —O-aralkyl, —O-heteroaralkyl, —O-phenyl, —O-heteroaryl, —O-(partially unsaturated bicyclic carbocyclyl), —O—($C_{1-6}$ alkylene)-($C_{3-6}$ cycloalkyl), —N($R^4$)-aralkyl, —N($R^4$)-phenyl, —N($R^4$)-(partially unsaturated bicyclic carbocyclyl), or —N($R^4$)—($C_{1-6}$ alkylene)-($C_{3-6}$ cycloalkyl), each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, and $C_{1-6}$ haloalkoxy;

Y is —C(R$^6$)(R$^7$)—, —O—, or —C(O)—;
m and p are independently 0, 1, or 2; and
n is 1, 2, or 3.

In certain embodiments, A$^1$ is phenylene. In certain embodiments, A$^1$ is a 5-6 membered heteroarylene.

In certain embodiments, n is 1. In certain embodiments, n is 1 or 2.

In certain embodiments, R$^3$ represents independently for each occurrence C$_{1-6}$ haloalkyl, halogen, C$_{1-6}$ alkyl, C$_{1-6}$ alkoxy, or —O—(C$_{1-6}$ alkylene)-OH. In certain embodiments, R$^3$ is trifluoromethyl, fluoro, chloro, or methoxy. In certain embodiments, R$^3$ is trifluoromethyl.

In certain embodiments, -A$^1$-(R$^3$)$_n$ is

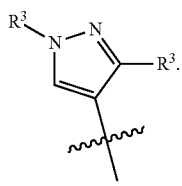

In certain embodiments, -A$^1$-(R$^3$)$_n$ is one of the following:

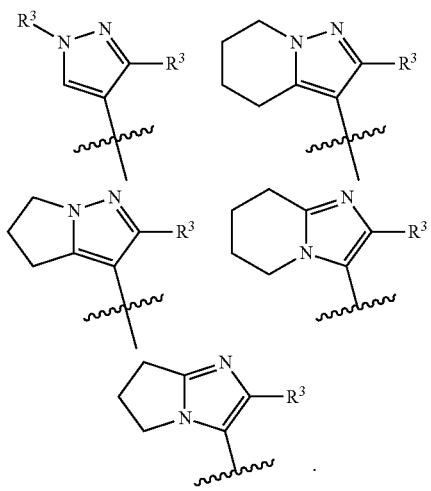

In certain embodiments, R$^{24}$ is —(C$_{1-6}$ alkylene)-A$^2$. In certain embodiments, R$^{24}$ is —(C$_{2-3}$ alkylene)-A$^2$. In certain embodiments, R$^{24}$ is -(2-6 membered heteroalkylene)-A$^2$. In certain embodiments, R$^{24}$ is —(C$_{2-3}$ alkylene)-O-A$^2$. In certain embodiments, R$^{24}$ is —O-A$^2$.

In certain embodiments, A$^2$ comprises at least two ring nitrogen atoms. In certain embodiments, A$^2$ comprises at least two ring nitrogen atoms, and at least one ring oxygen atom.

In certain embodiments, A$^2$ is a 5-6 membered heterocyclic group containing at least one ring carbon atom substituted by oxo and the heterocyclic group being optionally substituted by 1 or 2 substituents independently selected from the group consisting of C$_{1-6}$ alkyl, C$_{1-6}$ haloalkyl, C$_{3-6}$ cycloalkyl, halogen, C$_{1-6}$ alkoxy, C$_{1-6}$ haloalkoxy, oxo, —C(O)R$^9$, —CO$_2$R$^8$, —C(O)(N$^4$)(R$^5$), —N(R$^4$)C(O)(R$^9$), and —N(R$^4$)(R$^5$). In certain embodiments, A$^2$ is a 5-6 membered heterocyclic group containing (i) at least one ring carbon atom substituted by oxo and (ii) at least one double bond between two ring atoms, and the heterocyclic group being optionally substituted by 1 or 2 substituents independently selected from the group consisting of C$_{1-6}$ alkyl, C$_{1-6}$ haloalkyl, C$_{3-6}$ cycloalkyl, halogen, C$_{1-6}$ alkoxy, C$_{1-6}$ haloalkoxy, oxo, —C(O)R$^9$, —CO$_2$R$^8$, —C(O)(N$^4$)(R$^5$), —N(R$^4$)C(O)(R$^9$), and —N(R$^4$)(R$^5$). In certain embodiments, the heterocyclic group in A$^2$ is a 5-membered heterocyclic group.

In certain embodiments, A$^2$ is a 5-6 membered heteroaromatic group comprising at least two ring nitrogen atoms, at least one unsaturated carbon atom in the ring, and the heteroaromatic group being optionally substituted by 1 or 2 substituents independently selected from the group consisting of C$_{1-6}$ alkyl, C$_{1-6}$ haloalkyl, C$_{3-6}$ cycloalkyl, halogen, C$_{1-6}$ alkoxy, C$_{1-6}$ haloalkoxy, —C(O)R$^9$, —CO$_2$R$^8$, —C(O)(N$^4$)(R$^5$), —N(R$^4$)C(O)(R$^9$), and —N(R$^4$)(R$^5$). In certain embodiments, the heteroaromatic group in A$^2$ is a 5-membered heteroaromatic group.

In certain embodiments, A$^2$ is imidazolyl; pyrazolyl; 1,2,3-triazolyl; tetrazolyl; 1,2,4-oxadiazol-5(4H)-onyl; 1,3,4-oxadiazol-2(3H)-onyl; 1,3-dihydro-2H-imidazol-2-onyl; or 2,4-dihydro-3H-1,2,4-triazol-3-onyl; each of which is optionally substituted by 1, 2, or 3 substituents independently selected from the group consisting of C$_{1-6}$ alkyl, C$_{1-6}$ haloalkyl, C$_{3-6}$ cycloalkyl, halogen, C$_{1-6}$ alkoxy, C$_{1-6}$ haloalkoxy, —C(O)R$^9$, —CO$_2$R$^8$, —C(O)(N$^4$)(R$^5$), —N(R$^4$)C(O)(R$^9$), and —N(R$^4$)(R$^5$).

In certain embodiments, A$^2$ is imidazolyl; pyrazolyl; 1,2,3-triazolyl; tetrazolyl; 1,2,4-oxadiazol-5(4H)-onyl; 1,3,4-oxadiazol-2(3H)-onyl; 1,3-dihydro-2H-imidazol-2-onyl; or 2,4-dihydro-3H-1,2,4-triazol-3-onyl; each of which is optionally substituted by 1, 2, or 3 substituents independently selected from the group consisting of C$_{1-6}$ alkyl, C$_{1-6}$ haloalkyl, C$_{3-6}$ cycloalkyl, halogen, C$_{1-6}$ alkoxy, C$_{1-6}$ haloalkoxy, —C(O)R$^9$, and —CO$_2$R$^8$.

In certain embodiments, A$^2$ is one of the following:

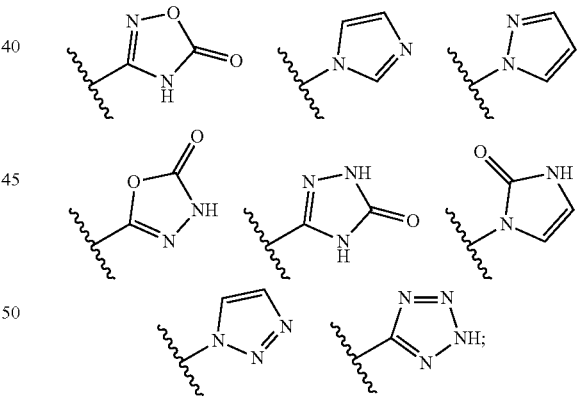

each of which is optionally substituted by 1, 2, or 3 substituents independently selected from the group consisting of C$_{1-6}$ alkyl, C$_{1-6}$ haloalkyl, C$_{3-6}$ cycloalkyl, halogen, C$_{1-6}$ alkoxy, C$_{1-6}$ haloalkoxy, —C(O)R$^9$, —CO$_2$R$^8$, and —C(O)(N$^4$)(R$^5$).

In certain embodiments, A$^2$ is oxazolidin-2-onyl; oxazolidine-2,4-dionyl; imidazolidine-2,4-dionyl; or thiazolidine-2,4-dionyl; each of which is optionally substituted by 1, 2, or 3 substituents independently selected from the group consisting of C$_{1-6}$ alkyl, C$_{1-6}$ haloalkyl, C$_{3-6}$ cycloalkyl, halogen, C$_{1-6}$ alkoxy, C$_{1-6}$ haloalkoxy, —C(O)R$^9$, —CO$_2$R$^8$, —C(O)(N$^4$)(R$^5$), —N(R$^4$)C(O)(R$^9$), and —N(R$^4$)(R$^5$).

In certain embodiments, A² is one of the following:

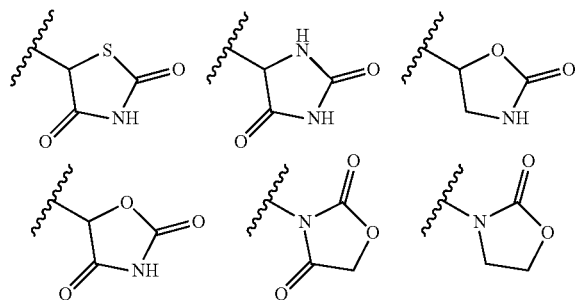

each of which is optionally substituted by 1, 2, or 3 substituents independently selected from the group consisting of C$_{1-6}$ alkyl, C$_{1-6}$ haloalkyl, C$_{3-6}$ cycloalkyl, halogen, C$_{1-6}$ alkoxy, C$_{1-6}$ haloalkoxy, —C(O)R⁹, —CO$_2$R⁸, and —C(O)(N⁴)(R⁵).

In certain embodiments, R$^{2B}$ is methyl.

In certain embodiments, X is —(C$_{2-6}$ alkenylene)-phenyl, —(C$_{2-6}$ alkenylene)-heteroaryl, —(C$_{1-6}$ alkylene)-phenyl, —(C$_{1-6}$ alkylene)-heteroaryl, —(C$_{1-6}$ alkylene)-(partially unsaturated bicyclic heterocyclyl), —(C$_{1-6}$ alkylene)-(partially unsaturated bicyclic oxo-heterocyclyl), or -(5-6 membered heterocycloalkylene)-phenyl, each of which is optionally substituted with 1, 2, or 3 substituents independently selected from the group consisting of halogen, C$_{1-6}$ haloalkyl, C$_{1-6}$ alkyl, C$_{3-6}$ cycloalkyl, C$_{1-6}$ alkoxy, and C$_{1-6}$ haloalkoxy. In certain embodiments, X is —(C$_{2-6}$ alkenylene)-phenyl, —(C$_{1-6}$ alkylene)-phenyl, or —(C$_{1-6}$ alkylene)-heteroaryl), each of which is optionally substituted with 1, 2, or 3 substituents independently selected from the group consisting of halogen, C$_{1-6}$ haloalkyl, C$_{1-6}$ alkyl, C$_{3-6}$ cycloalkyl, C$_{1-6}$ alkoxy, and C$_{1-6}$ haloalkoxy. In certain embodiments, X is —(C$_{2-6}$ alkenylene)-phenyl optionally substituted with 1, 2, or 3 substituents independently selected from the group consisting of halogen, C$_{1-6}$ haloalkyl, C$_{1-6}$ alkyl, C$_{3-6}$ cycloalkyl, C$_{1-6}$ alkoxy, and C$_{1-6}$ haloalkoxy.

In certain embodiments, X is —(C$_{1-6}$ alkylene)-Z¹ or —(C$_{2-6}$ alkenylene)-Z¹, wherein Z¹ is —O-aralkyl, —O-heteroaralkyl, —O-phenyl, —O-heteroaryl, —O-(partially unsaturated bicyclic carbocyclyl), —O—(C$_{1-6}$ alkylene)-(C$_{3-6}$ cycloalkyl), —O—(C$_{3-6}$ cycloalkyl), —N(R⁴)-aralkyl, —N(R⁴)-phenyl, —N(R⁴)-(partially unsaturated bicyclic carbocyclyl), or —N(R⁴)—(C$_{1-6}$ alkylene)-(C$_{3-6}$ cycloalkyl), each of which is optionally substituted with 1, 2, or 3 substituents independently selected from the group consisting of halogen, C$_{1-6}$ haloalkyl, C$_{1-6}$ alkyl, C$_{3-6}$ cycloalkyl, C$_{1-6}$ alkoxy, and C$_{1-6}$ haloalkoxy. In certain embodiments, X is —O-aralkyl, —O-heteroaralkyl, —O-phenyl, —O-heteroaryl, —O-(partially unsaturated bicyclic carbocyclyl), —O—(C$_{1-6}$ alkylene)-(C$_{3-6}$ cycloalkyl), —N(R⁴)-aralkyl, —N(R⁴)-phenyl, —N(R⁴)-(partially unsaturated bicyclic carbocyclyl), or —N(R⁴)—(C$_{1-6}$ alkylene)-(C$_{3-6}$ cycloalkyl), each of which is optionally substituted with 1, 2, or 3 substituents independently selected from the group consisting of halogen, C$_{1-6}$ haloalkyl, C$_{1-6}$ alkyl, C$_{3-6}$ cycloalkyl, C$_{1-6}$ alkoxy, and C$_{1-6}$ haloalkoxy. In certain embodiments, X is —O—(C$_{1-6}$ alkylene)-phenyl or —N(R⁴)—(C$_{1-6}$ alkylene)-phenyl, each of which is substituted with 1, 2, or 3 substituents independently selected from the group consisting of halogen, C$_{1-6}$ haloalkyl, C$_{1-6}$ alkyl, C$_{3-6}$ cycloalkyl, C$_{1-6}$ alkoxy, and C$_{1-6}$ haloalkoxy. In certain embodiments, X is —O—(C$_{1-6}$ alkylene)-phenyl or —N(R⁴)—(C$_{1-6}$ alkylene)-phenyl, each of which is substituted with 1, 2, or 3 substituents independently selected from the group consisting of halogen, C$_{1-6}$ haloalkyl, C$_{1-6}$ alkyl, C$_{3-6}$ cycloalkyl, C$_{1-6}$ alkoxy, and C$_{1-6}$ haloalkoxy, where at least one substituent is present at the ortho position on the phenyl group in variable X. In certain embodiments, X is —O—(C$_{1-6}$ alkylene)-phenyl or —N(R⁴)—(C$_{1-6}$ alkylene)-phenyl, each of which is substituted with 1, 2, or 3 substituents independently selected from the group consisting of halogen, C$_{1-6}$ haloalkyl, C$_{1-6}$ alkyl, C$_{3-6}$ cycloalkyl, C$_{1-6}$ alkoxy, and C$_{1-6}$ haloalkoxy. In certain embodiments, X is —O-aralkyl or —N(R⁴)-aralkyl, each of which is optionally substituted with 1, 2, or 3 substituents independently selected from the group consisting of halogen, C$_{1-6}$ haloalkyl, C$_{1-6}$ alkyl, C$_{3-6}$ cycloalkyl, C$_{1-6}$ alkoxy, and C$_{1-6}$ haloalkoxy. In certain embodiments, X is —O-benzyl or —N(R⁴)-benzyl, each of which is substituted with 1 or 2 substituents independently selected from the group consisting of chloro, bromo, and fluoro.

In certain embodiments, Y is —C(R⁶)(R⁷)—. In certain embodiments, R⁶ and R⁷ are independently hydrogen or methyl.

In certain embodiments, Y is —C(R⁶)(R⁷)—, R⁶ and R⁷ are independently hydrogen or methyl, and X is attached at the 7-position of the 1,2,3,4-tetrahydroquinolinyl ring.

In certain embodiments, Y is —O—. In certain embodiments, X is attached at the 6-position of the 3,4-dihydro-2H-benzo[b][1,4]oxazinyl ring.

In certain embodiments, m is 0 or 1. In certain embodiments, p is 0. In certain embodiments, p is 1.

The definitions of variables in Formula I-A above encompass multiple chemical groups. The application contemplates embodiments where, for example, i) the definition of a variable is a single chemical group selected from those chemical groups set forth above, ii) the definition of a variable is a collection of two or more of the chemical groups selected from those set forth above, and iii) the compound is defined by a combination of variables in which the variables are defined by (i) or (ii), e.g., such as where A is phenylene and R³ is selected from the group consisting of C$_{1-6}$ haloalkyl, halogen, hydroxyl, and C$_{1-6}$ alkyl.

Another aspect of the invention provides a compound represented by Formula I-B:

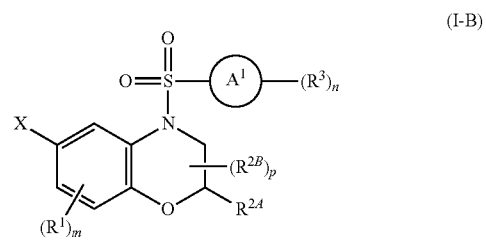

(I-B)

or a pharmaceutically acceptable salt thereof; wherein:
A¹ is phenylene or pyridinylene;
R¹ represents independently for each occurrence halogen, methyl, ethyl, or cyclopropyl;
R$^{2A}$ is —(C$_{1-6}$ alkylene)-A² or -(2-6 membered heteroalkylene)-A²; wherein A² is a 5-6 membered heterocyclic group containing at least one unsaturated carbon atom and the heterocyclic group being optionally substituted with 1, 2, or 3 substituents independently selected from the group consisting of $C_{1-6}$ alkyl, $C_{1-6}$ haloalkyl, $C_{3-6}$ cycloalkyl, halogen, $C_{1-6}$ alkoxy, $C_{1-6}$ haloalkoxy, oxo, and —$CO_2R^8$;

$R^{2B}$ is methyl or ethyl;

$R^3$ represents independently for each occurrence $C_{1-3}$ haloalkyl, halogen, $C_{1-3}$ alkyl, or —O—($C_{1-6}$ hydroxyalkyl);

$R^4$ and $R^5$ each represent independently for each occurrence hydrogen or methyl; or an occurrence of $R^4$ and $R^5$ attached to the same nitrogen atom are taken together with the nitrogen atom to which they are attached to form a 3-7 membered heterocyclic ring;

$R^8$ represents independently for each occurrence hydrogen or $C_{1-6}$ alkyl;

X is —($C_{2-6}$ alkenylene)-phenyl substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, and $C_{1-6}$ haloalkoxy;

m and p are independently 0 or 1; and n is 1 or 2.

In certain embodiments, $A^1$ is phenylene. In certain other embodiments, $A^1$ is pyridinylene.

In certain embodiments, $R^1$ is fluoro or methyl.

In certain embodiments, $R^{2A}$ is —($C_{1-6}$ alkylene)-$A^2$. In certain embodiments, $R^{2A}$ is —($C_{2-3}$ alkylene)-$A^2$. In certain embodiments, $R^{2A}$ is -(2-6 membered heteroalkylene)-$A^2$. In certain embodiments, $R^{2A}$ is further selected from —O-$A^2$.

In certain embodiments, $A^2$ comprises at least two ring nitrogen atoms. In certain embodiments, $A^2$ comprises at least two ring nitrogen atoms, and at least one ring oxygen atom.

In certain embodiments, $A^2$ is a 5-6 membered heterocyclic group containing at least one ring carbon atom substituted by oxo and the heterocyclic group being optionally substituted by 1 or 2 substituents independently selected from the group consisting of $C_{1-6}$ alkyl, $C_{1-6}$ haloalkyl, $C_{3-6}$ cycloalkyl, halogen, $C_{1-6}$ alkoxy, $C_{1-6}$ haloalkoxy, oxo, —C(O)$R^9$, —$CO_2R^8$, —C(O)($N^4$)($R^5$), —N($R^4$)C(O)($R^9$), and —N($R^4$)($R^5$). In certain embodiments, $A^2$ is a 5-6 membered heterocyclic group containing (i) at least one ring carbon atom substituted by oxo and (ii) at least one double bond between two ring atoms, and the heterocyclic group being optionally substituted by 1 or 2 substituents independently selected from the group consisting of $C_{1-6}$ alkyl, $C_{1-6}$ haloalkyl, $C_{3-6}$ cycloalkyl, halogen, $C_{1-6}$ alkoxy, $C_{1-6}$ haloalkoxy, oxo, —C(O)$R^9$, —$CO_2R^8$, —C(O)($N^4$)($R^5$), —N($R^4$)C(O)($R^9$), and —N($R^4$)($R^5$). In certain embodiments, the heterocyclic group in $A^2$ is a 5-membered heterocyclic group.

In certain embodiments, $A^2$ is a 5-6 membered heteroaromatic group comprising at least two ring nitrogen atoms, at least one unsaturated carbon atom in the ring, and the heteroaromatic group being optionally substituted by 1 or 2 substituents independently selected from the group consisting of $C_{1-6}$ alkyl, $C_{1-6}$ haloalkyl, $C_{3-6}$ cycloalkyl, halogen, $C_{1-6}$ alkoxy, $C_{1-6}$ haloalkoxy, —C(O)$R^9$, —$CO_2R^8$, —C(O)($N^4$)($R^5$), —N($R^4$)C(O)($R^9$), and —N($R^4$)($R^5$). In certain embodiments, the heteroaromatic group in $A^2$ is a 5-membered heteroaromatic group.

In certain embodiments, $A^2$ is imidazolyl; pyrazolyl; 1,2,3-triazolyl; tetrazolyl; 1,2,4-oxadiazol-5(4H)-onyl; 1,3,4-oxadiazol-2(3H)-onyl; 1,3-dihydro-2H-imidazol-2-onyl; or 2,4-dihydro-3H-1,2,4-triazol-3-onyl; each of which is optionally substituted by 1, 2, or 3 substituents independently selected from the group consisting of $C_{1-6}$ alkyl, $C_{1-6}$ haloalkyl, $C_{3-6}$ cycloalkyl, halogen, $C_{1-6}$ alkoxy, $C_{1-6}$ haloalkoxy, —C(O)$R^9$, —$CO_2R^8$, —C(O)($N^4$)($R^5$), —N($R^4$)C(O)($R^9$), and —N($R^4$)($R^5$).

In certain embodiments, $A^2$ is imidazolyl; pyrazolyl; 1,2,3-triazolyl; tetrazolyl; 1,2,4-oxadiazol-5(4H)-onyl; 1,3,4-oxadiazol-2(3H)-onyl; 1,3-dihydro-2H-imidazol-2-onyl; or 2,4-dihydro-3H-1,2,4-triazol-3-onyl; each of which is optionally substituted by 1, 2, or 3 substituents independently selected from the group consisting of $C_{1-6}$ alkyl, $C_{1-6}$ haloalkyl, $C_{3-6}$ cycloalkyl, halogen, $C_{1-6}$ alkoxy, $C_{1-6}$ haloalkoxy, —C(O)$R^9$, and —$CO_2R^8$.

In certain embodiments, $A^2$ is one of the following:

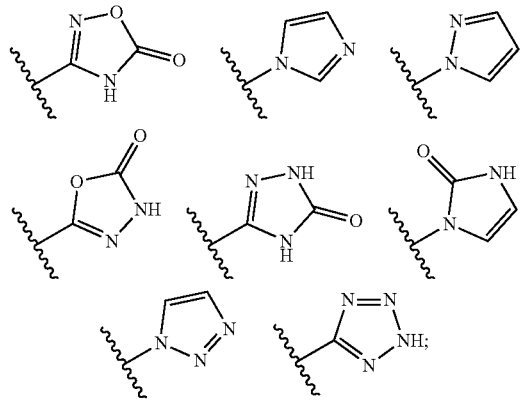

each of which is optionally substituted by 1, 2, or 3 substituents independently selected from the group consisting of $C_{1-6}$ alkyl, $C_{1-6}$ haloalkyl, $C_{3-6}$ cycloalkyl, halogen, $C_{1-6}$ alkoxy, $C_{1-6}$ haloalkoxy, —C(O)$R^9$, —$CO_2R^8$, and —C(O)($N^4$)($R^5$).

In certain embodiments, $A^2$ is oxazolidin-2-onyl; oxazolidine-2,4-dionyl; imidazolidine-2,4-dionyl; or thiazolidine-2,4-dionyl; each of which is optionally substituted by 1, 2, or 3 substituents independently selected from the group consisting of $C_{1-6}$ alkyl, $C_{1-6}$ haloalkyl, $C_{3-6}$ cycloalkyl, halogen, $C_{1-6}$ alkoxy, $C_{1-6}$ haloalkoxy, —C(O)$R^9$, —$CO_2R^8$, —C(O)($N^4$)($R^5$), —N($R^4$)C(O)($R^9$), and —N($R^4$)($R^5$).

In certain embodiments, $A^2$ is one of the following:

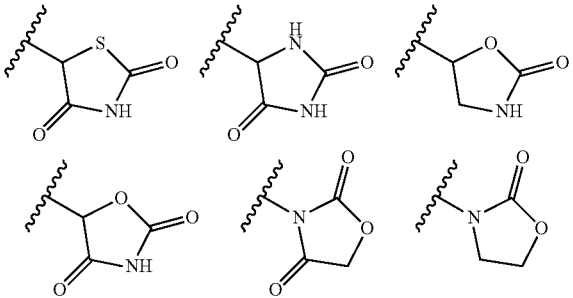

each of which is optionally substituted by 1, 2, or 3 substituents independently selected from the group consisting of $C_{1-6}$ alkyl, $C_{1-6}$ haloalkyl, $C_{3-6}$ cycloalkyl, halogen, $C_{1-6}$ alkoxy, $C_{1-6}$ haloalkoxy, —C(O)$R^9$, —$CO_2R^8$, and —C(O)($N^4$)($R^5$).

In certain embodiments, $R^3$ represents independently for each occurrence trifluoromethyl, halogen, or —O—($C_{1-6}$ hydroxyalkyl).

In certain embodiments, $R^4$ and $R^5$ are taken together with the nitrogen atom to which they are attached to form a 3-7 membered heterocyclic ring. In certain other embodiments, $R^4$ and $R^5$ each represent independently for each occurrence hydrogen or $C_{1-6}$ alkyl.

In certain embodiments, $R^8$ is hydrogen

In certain embodiments, X is —($C_{2-4}$ alkenylene)-phenyl substituted with 1, 2, or 3 substituents independently selected from the group consisting of halogen and $C_{1-6}$ haloalkyl. In certain embodiments, X is —($C_{2-4}$ alkenylene)-phenyl substituted with 1, 2, or 3 substituents independently selected from the group consisting of chloro, fluoro, and trifluoromethyl. In certain embodiments, X is —($C_{2-4}$ alkenylene)-phenyl substituted with 1 or 2 substituents independently selected from the group consisting of chloro, fluoro, and trifluoromethyl, and said substituents are located at the ortho positions of the phenyl group.

In certain embodiments, m and p are independently 0. In certain embodiments, n is 1.

The definitions of variables in Formula I-B above encompass multiple chemical groups. The application contemplates embodiments where, for example, i) the definition of a variable is a single chemical group selected from those chemical groups set forth above, ii) the definition of a variable is a collection of two or more of the chemical groups selected from those set forth above, and iii) the compound is defined by a combination of variables in which the variables are defined by (i) or (ii).

Another aspect of the invention provides a compound represented by Formula I-C:

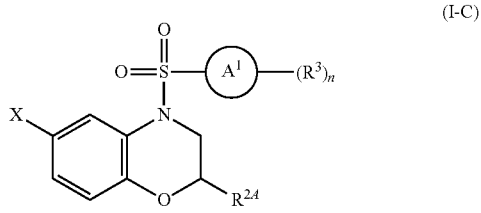

(I-C)

or a pharmaceutically acceptable salt thereof, wherein:
$A^1$ is phenylene or pyrazolylene;
$R^{2A}$ is -(2-6 membered heteroalkylene)-$A^2$; wherein $A^2$ is a 5-6 membered heterocyclic group containing at least one unsaturated carbon atom and the heterocyclic group being optionally substituted with 1, 2, or 3 substituents independently selected from the group consisting of $C_{1-3}$ alkyl, $C_{1-3}$ fluoroalkyl, chloro, fluoro, and oxo;
$R^3$ represents independently for each occurrence $C_{1-2}$ fluoroalkyl, chloro, fluoro, cyclopropyl, $C_{1-3}$ alkyl, $C_{1-2}$ alkoxy, or $C_{1-2}$ fluoroalkoxy;
X is —($C_{2-6}$ alkenylene)-phenyl wherein the phenyl is substituted with 1, 2, or 3 substituents independently selected from the group consisting of chloro, fluoro, $C_{1-2}$ fluoroalkyl, $C_{1-2}$ alkoxy, and $C_{1-2}$ fluoroalkoxy;
n is 1 or 2.

In certain embodiments, $A^1$ is phenylene. In certain embodiments, $A^1$ is phenylene; and $R^3$ represents independently for each occurrence $C_{1-2}$ fluoroalkyl, chloro, fluoro, $C_{1-2}$ alkoxy, or $C_{1-2}$ fluoroalkoxy.

In certain embodiments, $A^1$-$(R^3)_n$ is

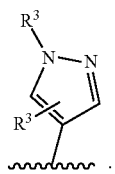

In certain embodiments, $R^{2A}$ is ($C_{2-3}$ alkylene)-O-$A^2$. In certain embodiments, $R^{2A}$ is —$(CH_2)_2$—O-$A^2$.

In certain embodiments, $R^3$ represents independently for each occurrence $C_{1-2}$ fluoroalkyl, chloro, fluoro, $C_{1-2}$ alkoxy, or $C_{1-2}$ fluoroalkoxy. In certain embodiments, $R^3$ represents independently for each occurrence $C_{1-2}$ fluoroalkyl, chloro, or fluoro. In certain embodiments, $R^3$ is —$CF_3$.

In certain embodiments, $A^2$ comprises at least two ring nitrogen atoms. In certain embodiments, $A^2$ comprises at least two ring nitrogen atoms, and at least one ring oxygen atom. In certain embodiments, $A^2$ is a 5-6 membered heterocyclic group containing at least one ring carbon atom substituted by oxo and the heterocyclic group being optionally substituted by 1 or 2 substituents independently selected from the group consisting of $C_{1-3}$ alkyl, $C_{1-3}$ fluoroalkyl, chloro, and fluoro. In certain embodiments, $A^2$ is a 5-6 membered heterocyclic group containing (i) at least one ring carbon atom substituted by oxo and (ii) at least one double bond between two ring atoms, and the heterocyclic group being optionally substituted by 1 or 2 substituents independently selected from the group consisting of $C_{1-3}$ alkyl, $C_{1-3}$ fluoroalkyl, chloro, and fluoro. In certain embodiments, the heterocyclic group in $A^2$ is a 5-membered heterocyclic group. In certain embodiments, $A^2$ is imidazolyl; pyrazolyl; 1,2,3-triazolyl; tetrazolyl; 1,2,4-oxadiazol-5(4H)-onyl; 1,3,4-oxadiazol-2(3H)-onyl; 1,3-dihydro-2H-imidazol-2-onyl; or 2,4-dihydro-3H-1,2,4-triazol-3-onyl; each of which is optionally substituted by 1, 2, or 3 substituents independently selected from the group consisting of $C_{1-3}$ alkyl, $C_{1-3}$ fluoroalkyl, chloro, and fluoro.

In certain embodiments, $A^2$ is one of the following:

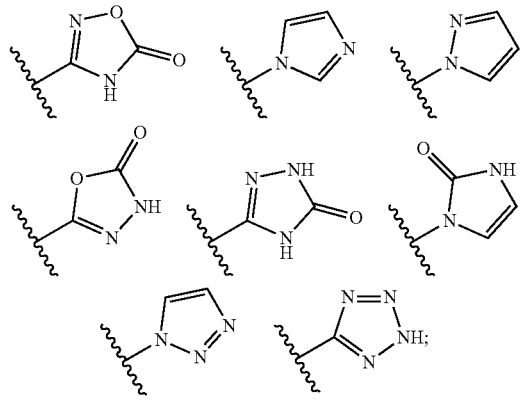

each of which is optionally substituted by 1, 2, or 3 substituents independently selected from the group consisting of $C_{1-3}$ alkyl and $C_{1-3}$ fluoroalkyl.

In certain embodiments, $A^2$ is H

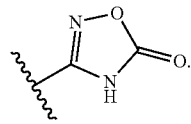

In certain embodiments, X is —($C_{2-4}$ alkenylene)-phenyl wherein the phenyl is substituted with 1, 2, or 3 substituents independently selected from the group consisting of chloro, fluoro, $C_{1-2}$ fluoroalkyl. In certain embodiments, X is —($C_{2-4}$ alkenylene)-phenyl wherein the phenyl is substituted with 1, 2, or 3 substituents independently selected from the group consisting of chloro, fluoro, and trifluoromethyl. In certain embodiments, X is —($C_{2-4}$ alkenylene)-phenyl substituted with 1 or 2 substituents independently selected from the group consisting of chloro, fluoro, and trifluoromethyl, and said substituents are located at the ortho positions of the phenyl group. In certain embodiments, X is —C(H)=C($CH_3$))-phenyl substituted with 1 or 2 substituents independently selected from the group consisting of chloro, fluoro, and trifluoromethyl, and said substituents are located at the ortho positions of the phenyl group.

The definitions of variables in Formula I-C above encompass multiple chemical groups. The application contemplates embodiments where, for example, i) the definition of a variable is a single chemical group selected from those chemical groups set forth above, ii) the definition of a variable is a collection of two or more of the chemical groups selected from those set forth above, and iii) the compound is defined by a combination of variables in which the variables are defined by (i) or (ii).

In certain other embodiments, the compound is a compound defined by one of the following formulae where variables X and Z are as defined in Table 1, or a pharmaceutically acceptable salt thereof.

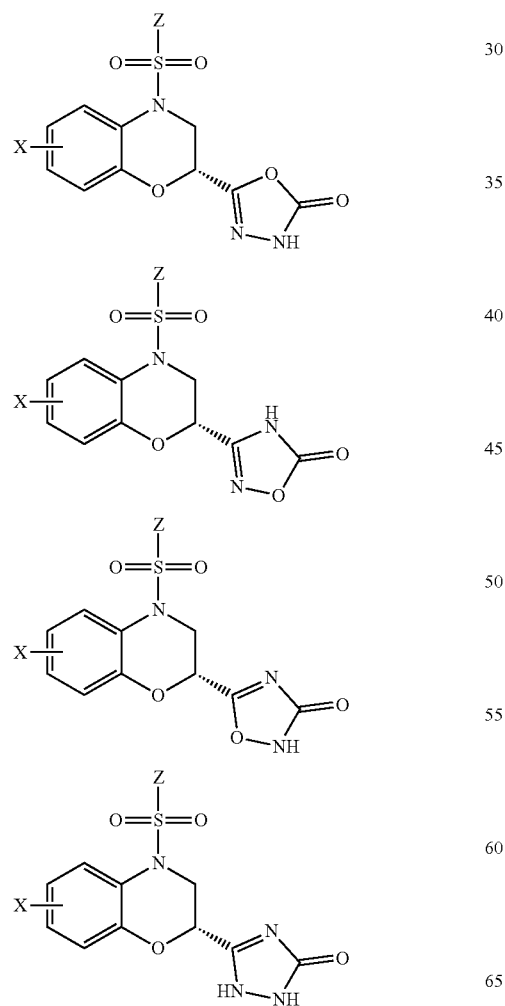

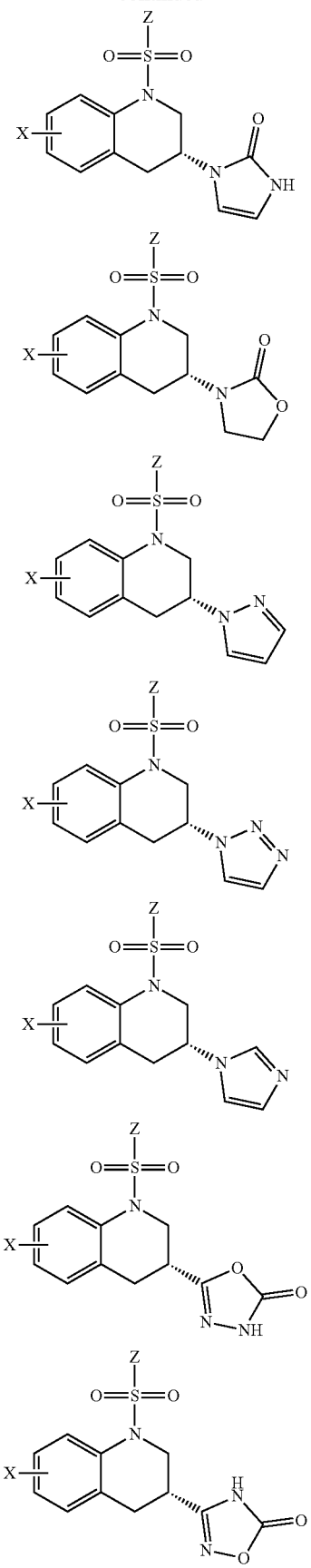

-continued
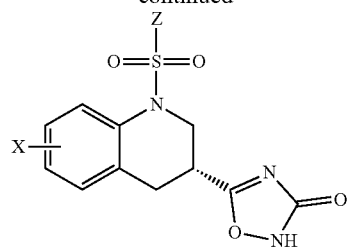
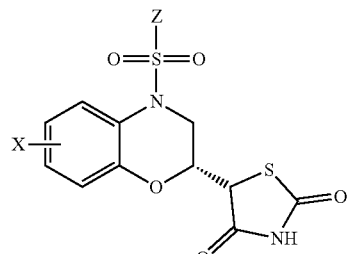
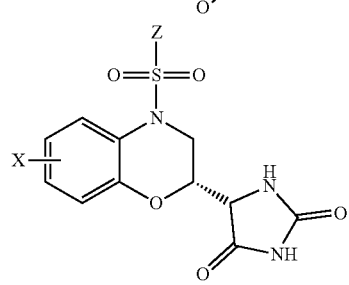
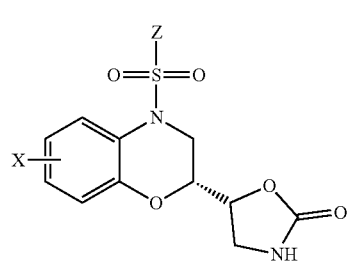
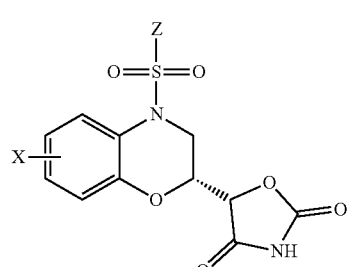
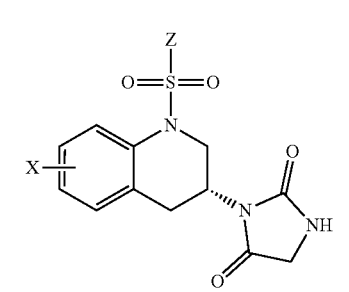
-continued
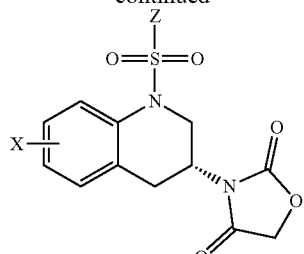
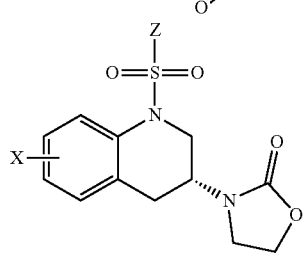
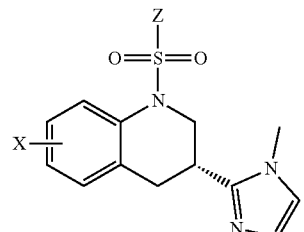
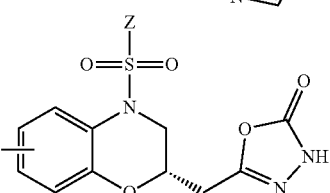
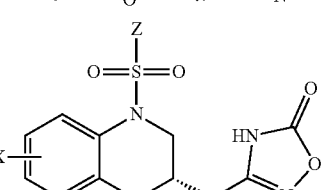
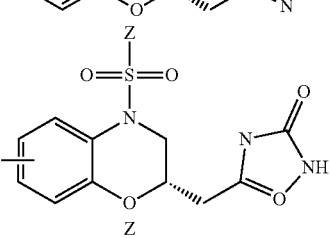
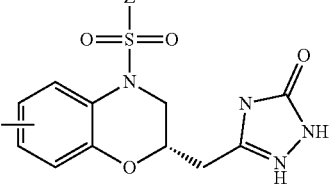
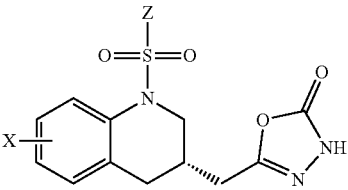

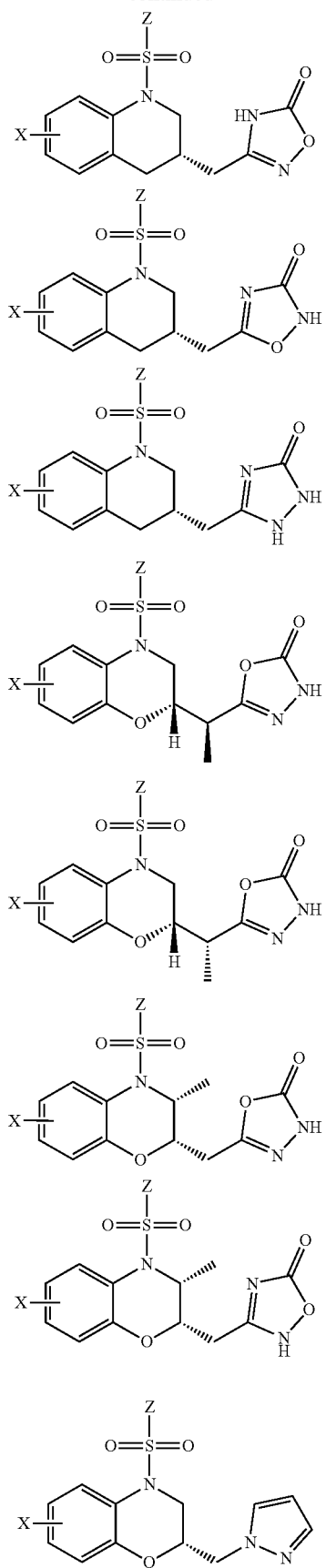
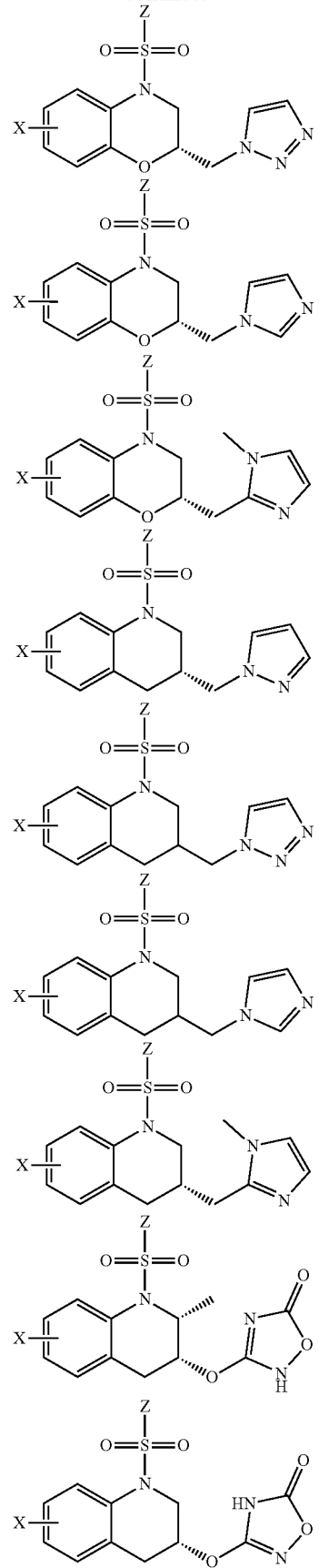

-continued
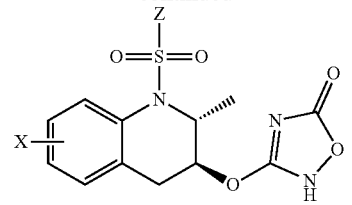
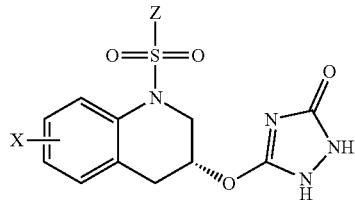
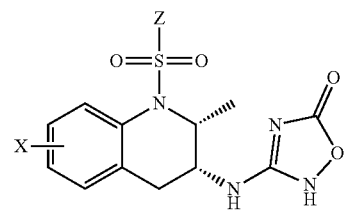
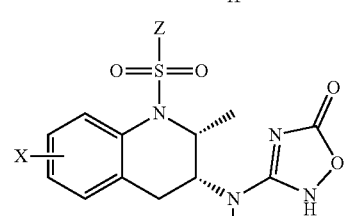
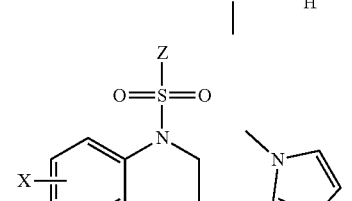
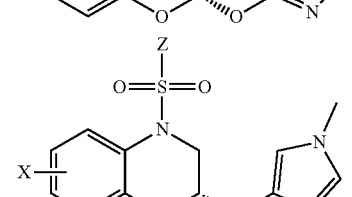
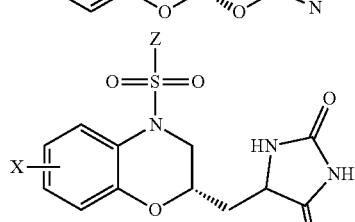
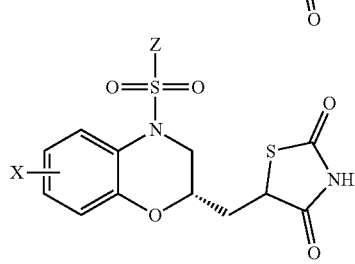
-continued
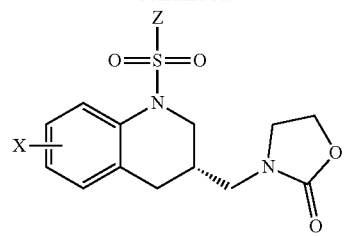
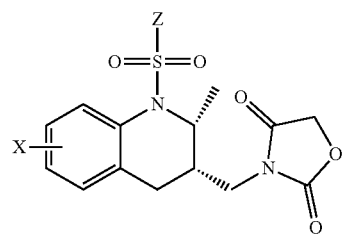
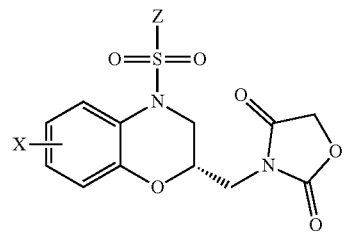
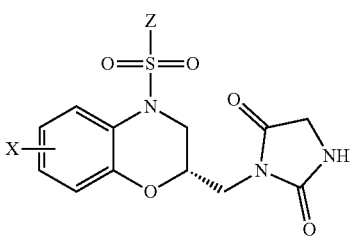
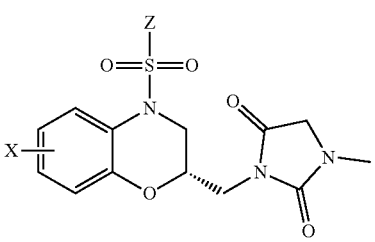
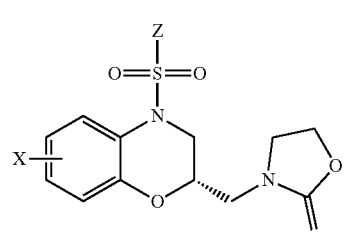
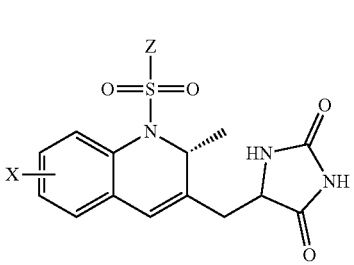

-continued
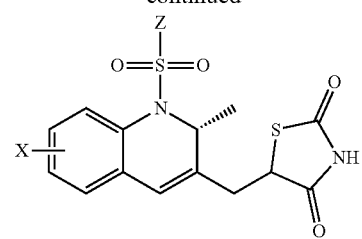
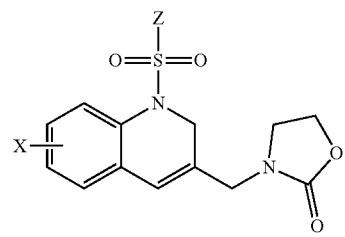
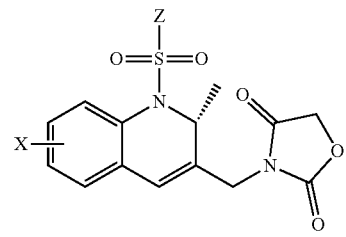
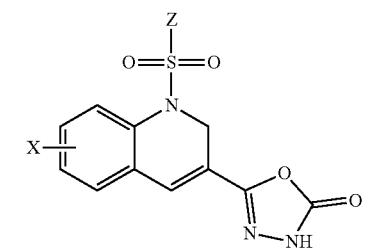
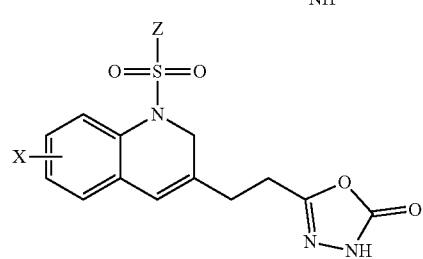
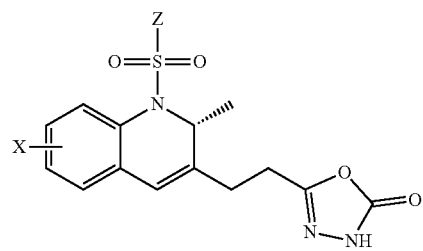
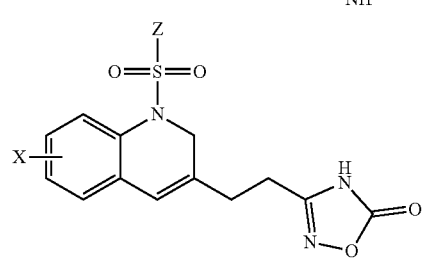
-continued
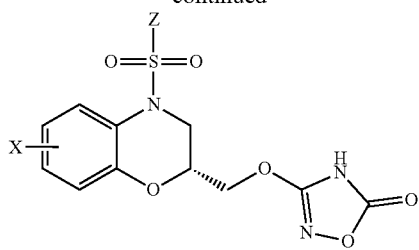
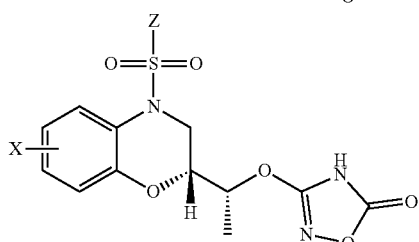
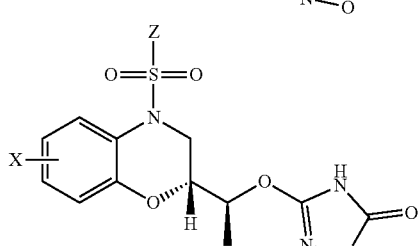
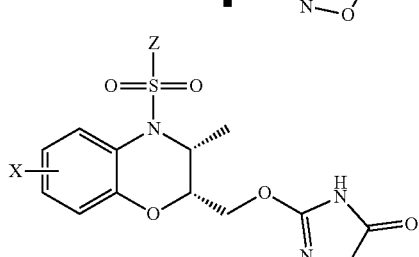
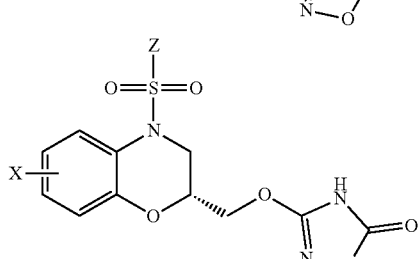
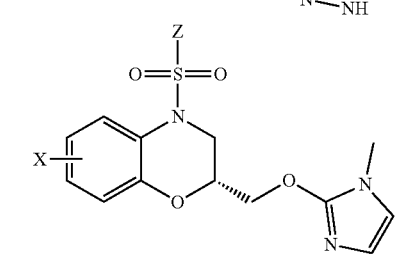
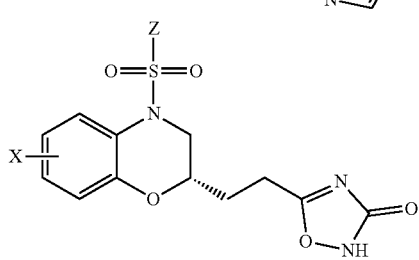

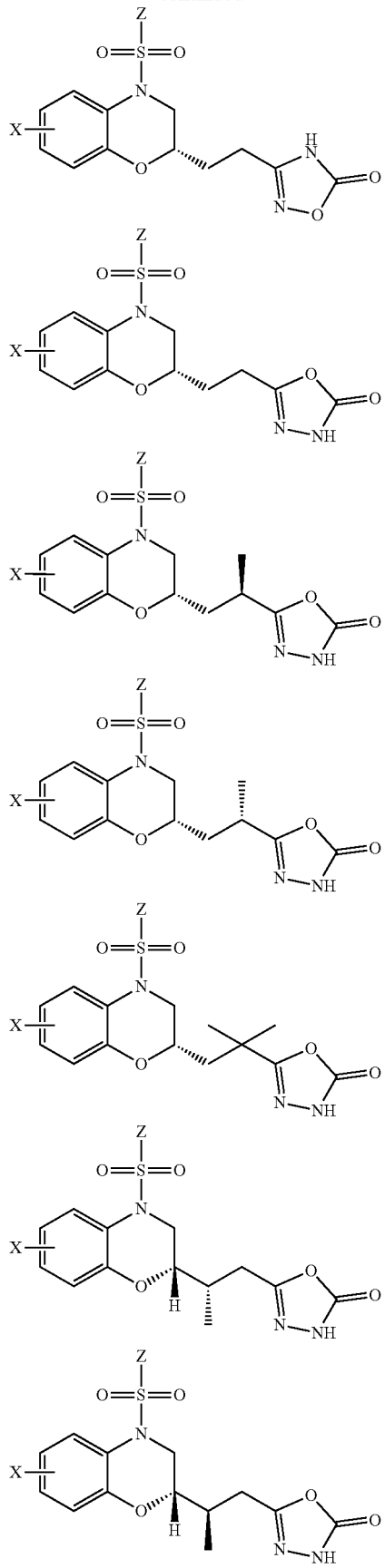
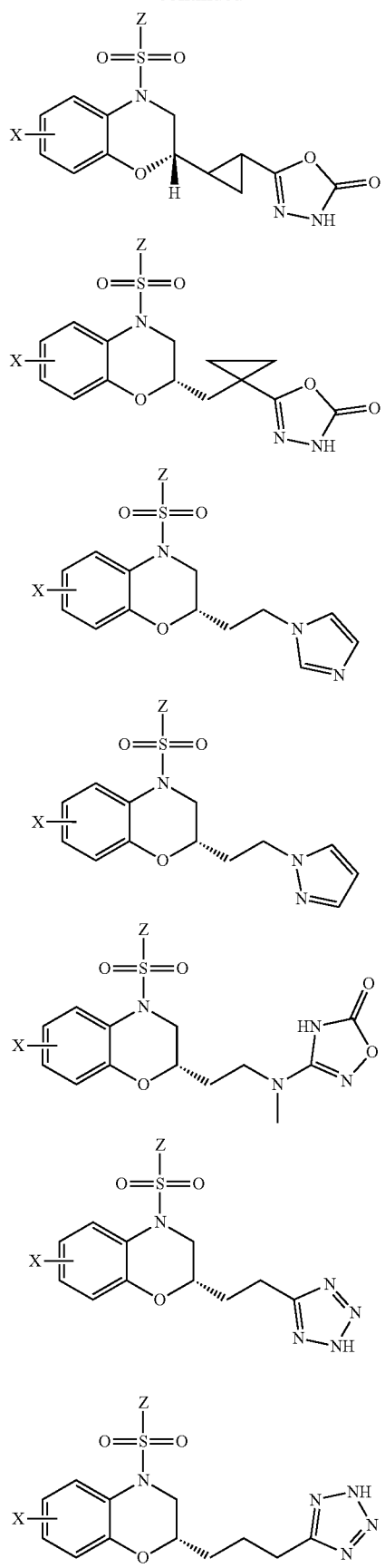

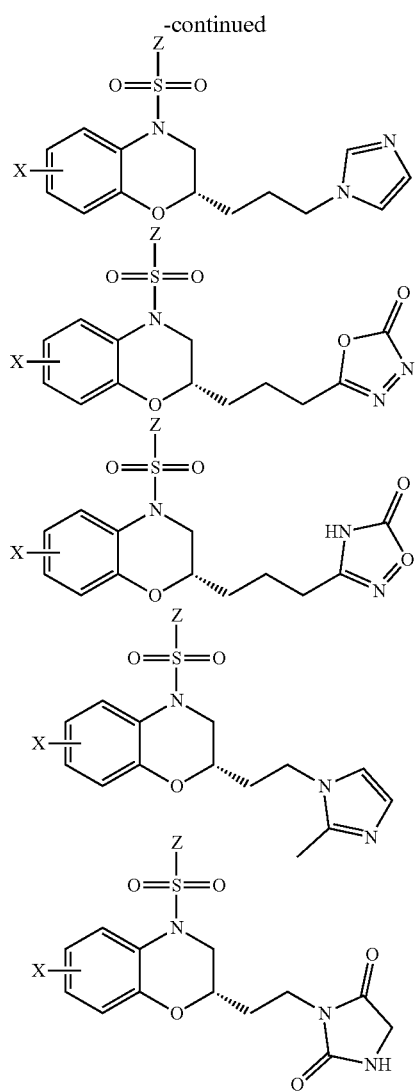
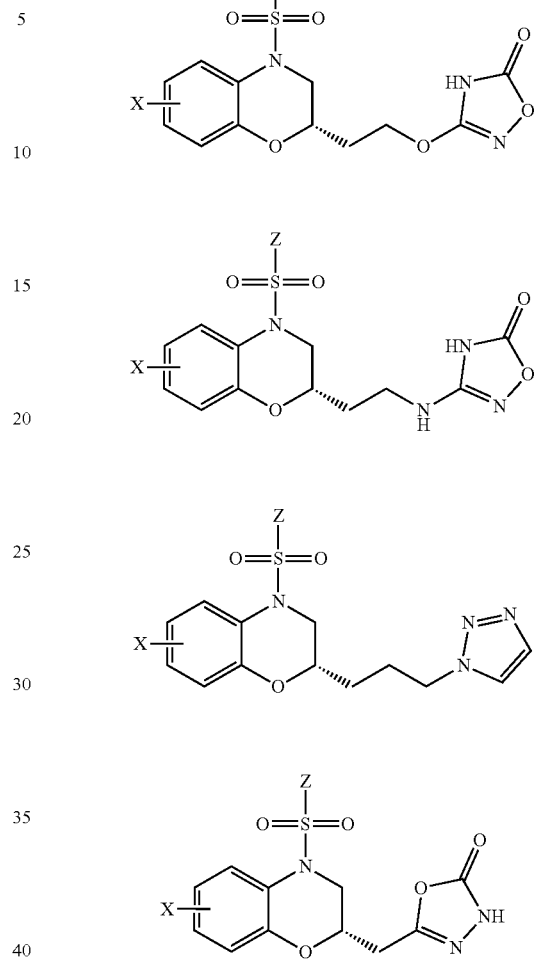
TABLE 1
| No. | X | Z |
|---|---|---|
| I-1 | 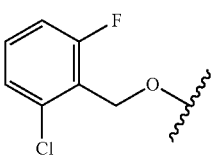 [SMILES: *OCc1c(F)cccc1Cl] | 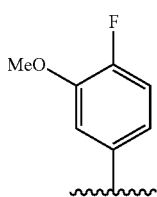 [SMILES: *c1ccc(F)c(OC)c1] |
| I-2 | 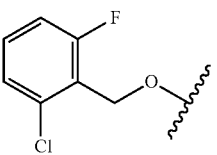 | 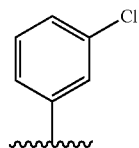 [SMILES: *c1cccc(Cl)c1] |

TABLE 1-continued
| No. | X | Z |
|---|---|---|
| I-3 | 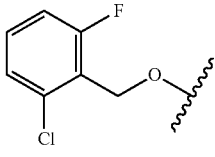 [SMILES: *OCc1c(F)cccc1Cl] | 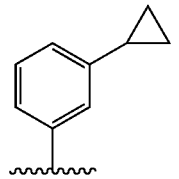 [SMILES: *c1cccc(C2CC2)c1] |
| I-4 | 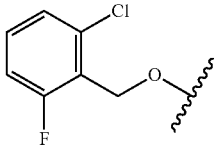 [SMILES: *OCc1c(F)cccc1Cl] | 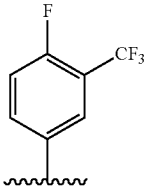 |
| I-5 | 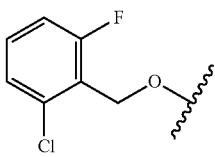 [SMILES: *OCc1c(F)cccc1Cl] | 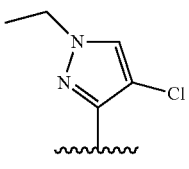 [SMILES: *c1nn(CC)cc1Cl] |
| I-6 | 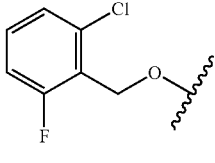 [SMILES: *OCc1c(F)cccc1Cl] | 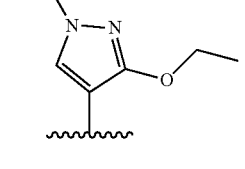 |
| I-7 | 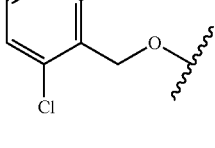 | 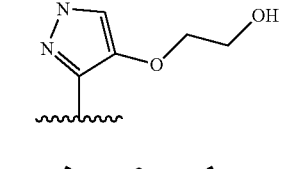 |
| I-8 | 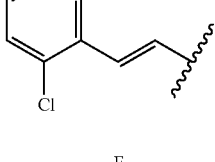 | 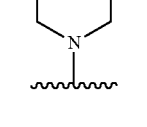 |
| I-9 | 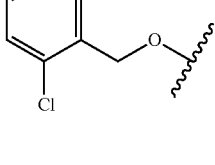 | 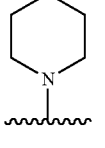 |
| I-10 | 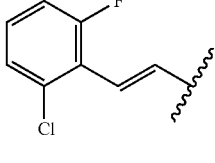 | 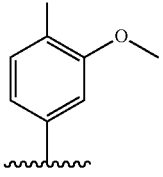 |

TABLE 1-continued

| No. | X | Z |
|---|---|---|
| I-11 | 2-chloro-6-fluorophenyl with propenyl linker | 4-fluoro-3-methoxyphenyl |
| I-12 | 3-chloropyridin-2-yl with vinyl linker | 1-ethyl-3-ethoxy-1H-pyrazol-4-yl |
| I-13 | 2,3-dihydro-1H-inden-1-yloxy | 4-fluoro-3-methoxyphenyl |
| I-14 | 2,3-dihydro-1H-inden-1-ylidene-methyl | 4-fluoro-3-methoxyphenyl |
| I-15 | 3,4-dihydronaphthalen-1(2H)-ylidene-methyl | 4-fluoro-3-methoxyphenyl |
| I-16 | 3-chloropyrazin-2-yl with vinyl linker | 4-fluoro-3-methoxyphenyl |
| I-17 | 2-chloro-6-(trifluoromethyl)phenyl with vinyl linker | 1-ethyl-4-(2-hydroxyethoxy)-1H-pyrazol-3-yl |
| I-18 | 2-(2-chloro-6-fluorophenyl)-2-methylcyclopropyl | 4-fluoro-3-methoxyphenyl |

TABLE 1-continued
| No. | X | Z |
|---|---|---|
| I-19 | 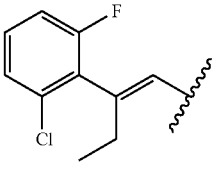 [SMILES: */C=C(\CC)c1c(F)cccc1Cl] | 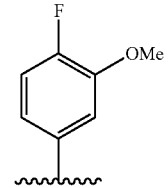 [SMILES: *c1ccc(F)c(OC)c1] |
| I-20 | 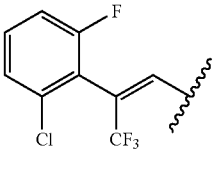 [SMILES: */C=C(/c1c(F)cccc1Cl)C(F)(F)F] | 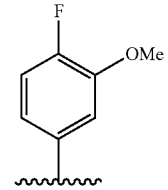 [SMILES: *c1ccc(F)c(OC)c1] |
| I-21 | 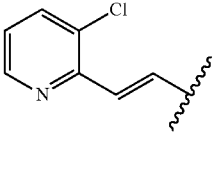 [SMILES: */C=C/c1ncccc1Cl] | 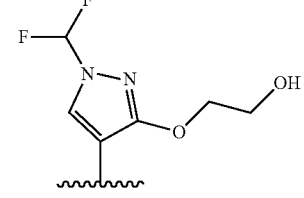 |
| I-22 | 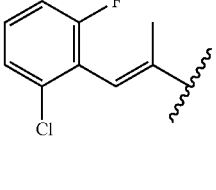 | 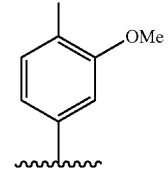 |
| I-23 | 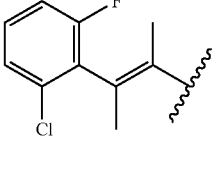 | 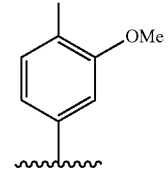 |
| I-24 | 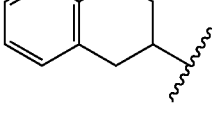 | 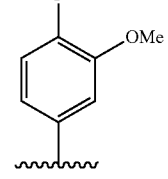 |
| I-25 | 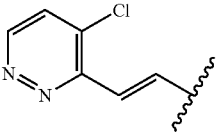 | 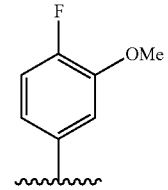 [SMILES: *c1ccc(F)c(OC)c1] |
| I-26 | 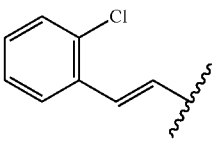 [SMILES: */C=C/c1ccccc1Cl] | 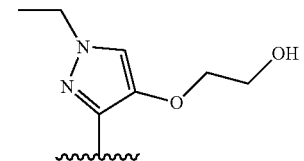 [SMILES: *c1nn(CC)cc1OCCO] |

TABLE 1-continued

| No. | X | Z |
|---|---|---|
| I-27 | 2,6-dichlorophenyl-CH=CH- | 1-ethyl-4-(2-hydroxyethoxy)-1H-pyrazol-3-yl |
| I-28 | 2-chloro-6-fluorophenyl-C(CF₃)=CH- | 4-fluoro-3-methoxyphenyl |
| I-29 | 2-fluoro-6-(trifluoromethyl)phenyl-CH=CH- | 4-fluoro-3-methoxyphenyl |
| I-30 | 3-chloropyridin-2-yl-CH=CH- | 1-ethyl-3-(2-hydroxyethoxy)-1H-pyrazol-4-yl |
| I-31 | 3-chloropyridin-2-yl-CH=CH- | 3-(difluoromethoxy)phenyl |
| I-32 | 3-chloropyridin-2-yl-CH=CH- | 1-cyclopropyl-3-(2-hydroxyethoxy)-1H-pyrazol-4-yl |
| I-33 | 3-chloropyridin-2-yl-C(CF₃)=CH- | 4-fluoro-3-methoxyphenyl |
| I-34 | 3-chloropyridin-2-yl-C(CF₃)=CH- | 1-ethyl-3-(2-hydroxyethoxy)-1H-pyrazol-4-yl |

TABLE 1-continued

| No. | X | Z |
|---|---|---|
| I-35 | 4-chloro-isoxazol-3-yl vinyl | 4-fluoro-3-methoxyphenyl |
| I-36 | 3-chloropyridin-2-yl vinyl | 1-ethyl-3-chloro-1H-pyrazol-4-yl |
| I-37 | 3-chloropyridin-2-yl (1-methyl)vinyl | 1-ethyl-3-chloro-1H-pyrazol-4-yl |
| I-38 | 2-chloro-6-fluorophenyl (1-methyl)vinyl | 5-chloro-2-(2-hydroxyethoxy)pyridin-3-yl |
| I-39 | 2-chloro-6-(trifluoromethyl)phenyl vinyl | 5-(trifluoromethyl)-2-(2-hydroxyethoxy)pyridin-3-yl |
| I-40 | 2-chloro-6-fluorophenyl (1-methyl)vinyl | 5-(trifluoromethyl)-2-ethoxypyridin-3-yl |
| I-41 | 3-chloro-6-fluoro(pyran) (1-methyl)vinyl | 5-(trifluoromethyl)-2-(dimethylamino)pyridin-3-yl |
| I-42 | 3-chloropyridin-2-yl (1-methyl)vinyl | 5-(trifluoromethyl)-2-(2-hydroxyethoxy)pyridin-3-yl |
| I-43 | 2-(trifluoromethyl)-6-chlorophenyl vinyl | 5-(trifluoromethyl)-2-(2-hydroxyethoxy)pyridin-3-yl |

TABLE 1-continued
| No. | X | Z |
|---|---|---|
| I-44 | 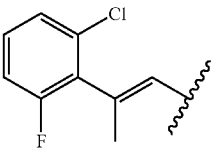 | 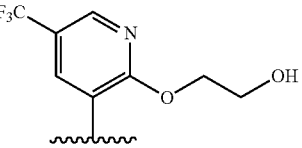 |
| I-45 | 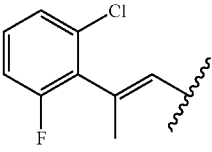 | 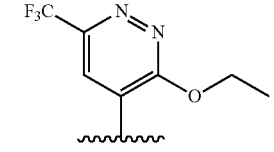 [SMILES: *c1cc(C(F)(F)F)nnc1OCC] |
| I-46 | 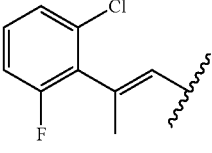 | 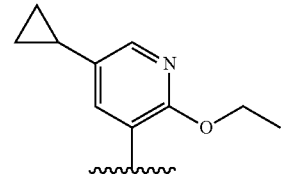 [SMILES: *c1cc(C2CC2)cnc1OCC] |
| I-47 | 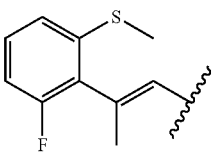 [SMILES: */C=C(\C)c1c(F)cccc1SC] | 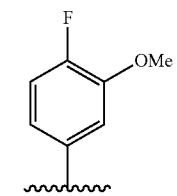 [SMILES: *c1ccc(F)c(OC)c1] |
| I-48 | 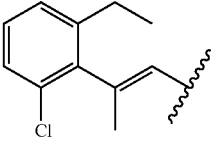 [SMILES: */C=C(\C)c1c(Cl)cccc1CC] | 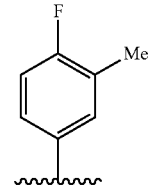 [SMILES: *c1ccc(F)c(C)c1] |
| I-49 | 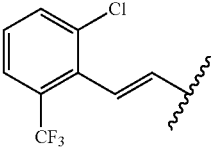 [SMILES: */C=C/c1c(Cl)cccc1C(F)(F)F] | 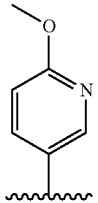 |
| I-50 | 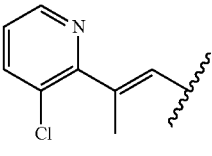 [SMILES: */C=C(\C)c1ncccc1Cl] | 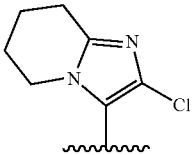 [SMILES: *c1c(Cl)nc2n1CCCC2] |
| I-51 | 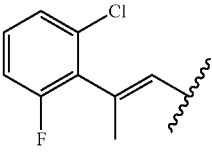 [SMILES: */C=C(\C)c1c(F)cccc1Cl] | 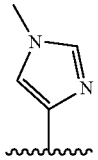 |

TABLE 1-continued

| No. | X | Z |
|---|---|---|
| I-52 | 2-Cl, 6-CF3 styryl | 1-methyl-imidazol-4-yl |
| I-53 | 2-Cl, 6-F benzyloxy | 5-methylpyridin-3-yl |
| I-54 | 2-Cl, 6-CF3 styryl | 5-methylpyridin-3-yl |
| I-55 | 2-CF3, 6-Cl styryl | 1-isopropyl-imidazol-4-yl |
| I-56 | 2-F, 6-Cl (1-methyl)styryl | 1-isopropyl-imidazol-4-yl |
| I-57 | 2-F, 6-Cl (1-methyl)styryl | oxazol-4-yl |
| I-58 | 2-CF3, 6-Cl styryl | oxazol-4-yl |
| I-59 | 2-Cl, 6-F benzyloxy | oxazol-4-yl |
| I-60 | 2-F, 6-Cl (1-methyl)styryl | 2-ethoxy-5,6,7,8-tetrahydroimidazo[1,2-a]pyridin-3-yl |

TABLE 1-continued
| No. | X | Z |
|---|---|---|
| I-61 | 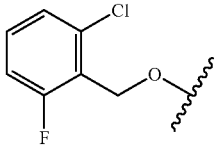 [SMILES: *OCc1c(F)cccc1Cl] | 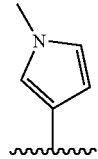 |
| I-62 | 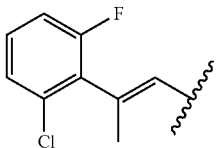 [SMILES: */C=C(\C)c1c(F)cccc1Cl] | 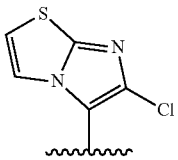 [SMILES: *c1c(Cl)nc2sccn12] |
| I-63 | 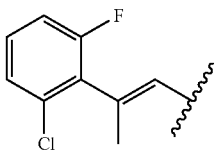 [SMILES: */C=C(\C)c1c(F)cccc1Cl] | 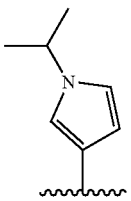 |
| I-64 | 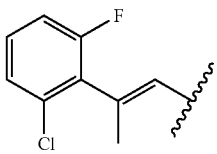 [SMILES: */C=C(\C)c1c(F)cccc1Cl] | 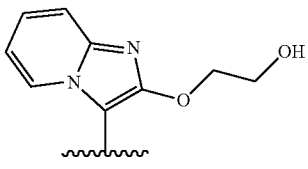 [SMILES: *c1c(OCCO)nc2ccccn12] |
| I-65 | 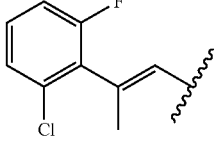 | 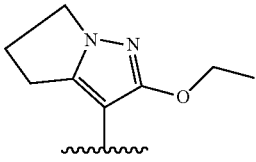 [SMILES: *c1c(OCC)nn2c1CCC2] |
| I-66 | 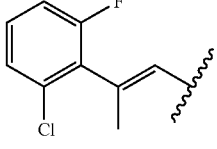 | 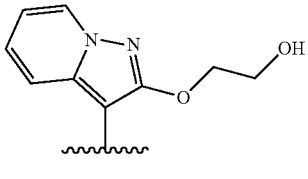 [SMILES: *c1c(OCCO)nn2ccccc12] |
| I-67 | 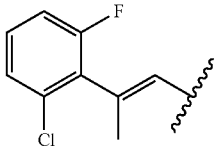 [SMILES: */C=C(\C)c1c(F)cccc1Cl] | 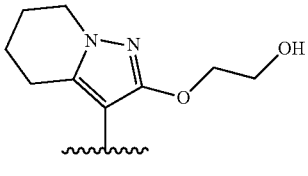 [SMILES: *c1c(OCCO)nn2c1CCCC2] |
| I-68 | 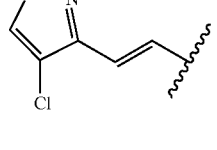 | 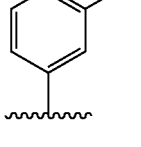 |
| I-69 | 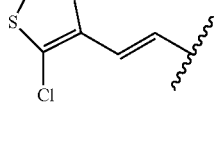 | 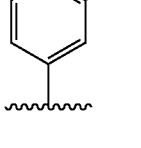 |

TABLE 1-continued

| No. | X | Z |
|---|---|---|
| I-70 | 5-chloro-oxazol-4-yl vinyl | 3-(trifluoromethyl)phenyl |
| I-71 | 2-chloro-6-fluorophenyl vinyl | 6-ethoxy-imidazo[2,1-b]thiazol-5-yl |
| I-72 | 4-chloro-isoxazol-5-yl vinyl | 3-(trifluoromethyl)phenyl |
| I-73 | 2-chloro-6-fluorophenyl 1-methylvinyl | 6-(2-hydroxyethoxy)-imidazo[2,1-b]thiazol-5-yl |
| I-74 | 3-chloropyrazin-2-yl vinyl | 3-(trifluoromethyl)phenyl |
| I-75 | 2-chloro-6-fluorophenyl vinyl | 3-(trifluoromethyl)phenyl |
| I-76 | 2-chloro-6-fluorophenyl ethyl | 3-(trifluoromethyl)phenyl |
| I-77 | 2,6-dichlorobenzyloxy | 3-fluoro-5-(trifluoromethyl)phenyl |
| I-78 | 4-chloropyridazin-3-yl vinyl | 3-fluoro-5-(trifluoromethyl)phenyl |

Another aspect of the invention provides a compound represented by Formula II:

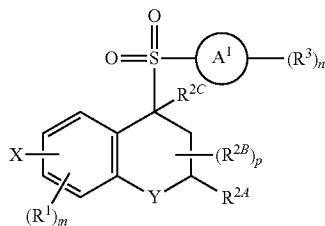

or a pharmaceutically acceptable salt thereof, wherein:

$A^1$ is phenyl, 5-6 membered heteroaryl, or $C_{3-6}$ heterocycloalkyl;

$R^1$ represents independently for each occurrence halogen, $C_{1-6}$ alkyl, $C_{1-6}$ haloalkyl, or $C_{3-6}$ cycloalkyl;

$R^{2A}$ is —($C_{1-6}$ alkylene)-$A^2$, -(2-6 membered heteroalkylene)-$A^2$, —($C_{0-3}$ alkylene)-($C_{3-6}$ cycloalkylene)-($C_{0-3}$ alkylene)-$A^2$, —O-$A^2$, —N($R^8$)-$A^2$, or -$A^2$; wherein $A^2$ is a 5-6 membered heterocyclic group containing at least one unsaturated carbon atom and the heterocyclic group being optionally substituted with 1, 2, or 3 substituents independently selected from the group consisting of $C_{1-6}$ alkyl, $C_{1-6}$ haloalkyl, $C_{3-6}$ cycloalkyl, halogen, $C_{1-6}$ alkoxy, $C_{1-6}$ haloalkoxy, oxo, —C(O)$R^9$, —CO$_2R^8$, —C(O)(N$^4$)($R^5$), —N($R^4$)C(O)($R^9$), and —N($R^4$)($R^5$);

$R^{2B}$ represents independently for each occurrence $C_{1-6}$ alkyl or $C_{1-3}$ haloalkyl;

$R^{2C}$ is hydrogen or $C_{1-6}$ alkyl;

$R^3$ represents independently for each occurrence hydrogen, $C_{1-6}$ haloalkyl, halogen, hydroxyl, $C_{1-6}$ alkyl, $C_{3-6}$ cycloalkyl, $C_{1-6}$ alkoxy, $C_{1-6}$ haloalkoxy, —O—($C_{1-6}$ alkylene)-OH, or —O—($C_{1-6}$ alkylene)-CO$_2R^4$; or two vicinal occurrences of $R^3$ are taken together with intervening atoms to form a 4-6 membered ring;

$R^4$ and $R^5$ each represent independently for each occurrence hydrogen, $C_{1-6}$ alkyl, or $C_{3-6}$ cycloalkyl; or an occurrence of $R^4$ and $R^5$ attached to the same nitrogen atom are taken together with the nitrogen atom to which they are attached to form a 3-7 membered heterocyclic ring;

$R^6$ and $R^7$ each represent independently for each occurrence hydrogen or $C_{1-6}$ alkyl, or $R^6$ and $R^7$ are taken together with the carbon atom to which they are attached to form a 3-6 membered carbocyclic ring; or $R^6$ and $R^{2A}$ are taken together to form a bond;

$R^8$ represents independently for each occurrence hydrogen, $C_{1-6}$ alkyl, $C_{3-6}$ cycloalkyl, or aralkyl;

$R^9$ represents independently for each occurrence $C_{1-6}$ alkyl, $C_{3-6}$ cycloalkyl, or aralkyl;

X is one of the following:

(i) —($C_{2-6}$ alkenylene)-phenyl, —($C_{2-6}$ alkenylene)-heteroaryl, —($C_{1-6}$ alkylene)-phenyl, —($C_{1-6}$ alkylene)-heteroaryl, —($C_{1-6}$ alkylene)-(partially unsaturated bicyclic heterocyclyl), —($C_{1-6}$ alkylene)-(partially unsaturated bicyclic oxo-heterocyclyl), -(5-6 membered heterocycloalkylene)-phenyl, or —($C_{3-6}$ cycloalkylene)-phenyl, each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, $C_{1-6}$ haloalkoxy, hydroxyl, and cyano;

(ii) —($C_{2-6}$ alkenylene)-($C_{3-6}$ cycloalkyl),

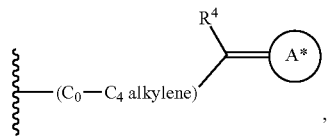

or an 8-10 membered, bicyclic partially saturated carbocyclyl, each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, $C_{1-6}$ haloalkoxy, hydroxyl, and cyano, wherein $A^*$ is a 5-8 membered, partially saturated carbocyclic or heterocyclic ring;

(iii) —($C_{1-6}$ alkylene)-$Z^1$ or —($C_{2-6}$ alkenylene)-$Z^1$, wherein $Z^1$ is —O-aralkyl, —O-heteroaralkyl, —O-phenyl, —O-heteroaryl, —O-(partially unsaturated bicyclic carbocyclyl), —O—($C_{1-6}$ alkylene)-($C_{3-6}$ cycloalkyl), —O—($C_{3-6}$ cycloalkyl), —N($R^4$)-aralkyl, —N($R^4$)-phenyl, —N($R^4$)-(partially unsaturated bicyclic carbocyclyl), or —N($R^4$)—($C_{1-6}$ alkylene)-($C_{3-6}$ cycloalkyl), each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, $C_{1-6}$ haloalkoxy, hydroxyl, and cyano; or (iv) —O-aralkyl, —O-heteroaralkyl, —O-phenyl, —O-heteroaryl, —O-(partially unsaturated bicyclic carbocyclyl), —O—($C_{1-6}$ alkylene)-($C_{3-6}$ cycloalkyl), —O—($C_{3-6}$ cycloalkyl), —N($R^4$)-aralkyl, —N($R^4$)-phenyl, —N($R^4$)-(partially unsaturated bicyclic carbocyclyl), or —N($R^4$)—($C_{1-6}$ alkylene)-($C_{3-6}$ cycloalkyl), each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, $C_{1-6}$ haloalkoxy, hydroxyl, and cyano;

Y is —C($R^6$)($R^7$)—, —O—, —C(O)—, or —S(O)$_p$—;

m and p each represent independently for each occurrence 0, 1, or 2; and n is 0, 1, 2, or 3.

In certain embodiments, $A^1$ is phenylene or 5-6 membered heteroarylene.

In certain embodiments $R^1$ represents independently for each occurrence halogen or $C_{1-6}$ alkyl.

In certain embodiments, $R^3$ represents independently for each occurrence $C_{1-6}$ haloalkyl, halogen, $C_{1-6}$ alkyl, $C_{1-6}$ alkoxy, or —O—($C_{1-6}$ alkylene)-OH. In certain embodiments, $R^3$ is trifluoromethyl, fluoro, chloro, or methoxy. In certain embodiments, $R^3$ is trifluoromethyl.

In certain embodiments, -$A^1$-($R^3$)$_n$ is

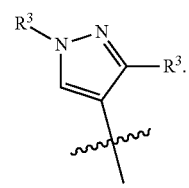

In certain embodiments, -A$^1$-(R$^3$)$_n$ is one of the following:

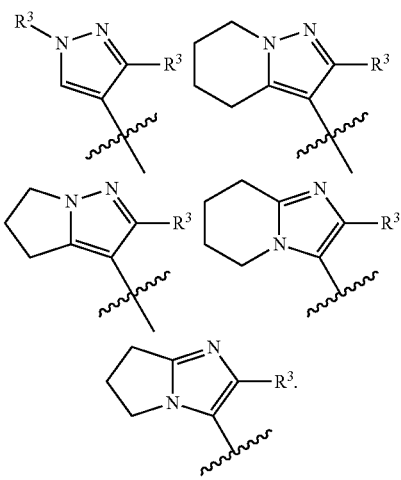

In certain embodiments, R$^{2A}$ is —(C$_{1-6}$ alkylene)-A$^2$. In certain embodiments, R$^{2A}$ is —(C$_{2-3}$ alkylene)-A$^2$. In certain embodiments, R$^{2A}$ is -(2-6 membered heteroalkylene)-A$^2$. In certain embodiments, R$^{2A}$ is —(C$_{2-3}$ alkylene)-O-A$^2$. In certain embodiments, R$^{2A}$ is —O-A$^2$.

In certain embodiments, A$^2$ comprises at least two ring nitrogen atoms. In certain embodiments, A$^2$ comprises at least two ring nitrogen atoms, and at least one ring oxygen atom.

In certain embodiments, A$^2$ is a 5-6 membered heterocyclic group containing at least one ring carbon atom substituted by oxo and the heterocyclic group being optionally substituted by 1 or 2 substituents independently selected from the group consisting of C$_{1-6}$ alkyl, C$_{1-6}$ haloalkyl, C$_{3-6}$ cycloalkyl, halogen, C$_{1-6}$ alkoxy, C$_{1-6}$ haloalkoxy, oxo, —C(O)R$^9$, —CO$_2$R$^8$, —C(O)(N$^4$)(R$^5$), —N(R$^4$)C(O)(R$^9$), and —N(R$^4$)(R$^5$). In certain embodiments, A$^2$ is a 5-6 membered heterocyclic group containing (i) at least one ring carbon atom substituted by oxo and (ii) at least one double bond between two ring atoms, and the heterocyclic group being optionally substituted by 1 or 2 substituents independently selected from the group consisting of C$_{1-6}$ alkyl, C$_{1-6}$ haloalkyl, C$_{3-6}$ cycloalkyl, halogen, C$_{1-6}$ alkoxy, C$_{1-6}$ haloalkoxy, oxo, —C(O)R$^9$, —CO$_2$R$^8$, —C(O)(N$^4$)(R$^5$), —N(R$^4$)C(O)(R$^9$), and —N(R$^4$)(R$^5$). In certain embodiments, the heterocyclic group in A$^2$ is a 5-membered heterocyclic group.

In certain embodiments, A$^2$ is a 5-6 membered heteroaromatic group comprising at least two ring nitrogen atoms, at least one unsaturated carbon atom in the ring, and the heteroaromatic group being optionally substituted by 1 or 2 substituents independently selected from the group consisting of C$_{1-6}$ alkyl, C$_{1-6}$ haloalkyl, C$_{3-6}$ cycloalkyl, halogen, C$_{1-6}$ alkoxy, C$_{1-6}$ haloalkoxy, —C(O)R$^9$, —CO$_2$R$^8$, —C(O)(N$^4$)(R$^5$), —N(R$^4$)C(O)(R$^9$), and —N(R$^4$)(R$^5$). In certain embodiments, the heteroaromatic group in A$^2$ is a 5-membered heteroaromatic group.

In certain embodiments, A$^2$ is imidazolyl; pyrazolyl; 1,2,3-triazolyl; tetrazolyl; 1,2,4-oxadiazol-5(4H)-onyl; 1,3,4-oxadiazol-2(3H)-onyl; 1,3-dihydro-2H-imidazol-2-onyl; or 2,4-dihydro-3H-1,2,4-triazol-3-onyl; each of which is optionally substituted by 1, 2, or 3 substituents independently selected from the group consisting of C$_{1-6}$ alkyl, C$_{1-6}$ haloalkyl, C$_{3-6}$ cycloalkyl, halogen, C$_{1-6}$ alkoxy, C$_{1-6}$ haloalkoxy, —C(O)R$^9$, —CO$_2$R$^8$, —C(O)(N$^4$)(R$^5$), —N(R$^4$)C(O)(R$^9$), and —N(R$^4$)(R$^5$).

In certain embodiments, A$^2$ is imidazolyl; pyrazolyl; 1,2,3-triazolyl; tetrazolyl; 1,2,4-oxadiazol-5(4H)-onyl; 1,3,4-oxadiazol-2(3H)-onyl; 1,3-dihydro-2H-imidazol-2-onyl; or 2,4-dihydro-3H-1,2,4-triazol-3-onyl; each of which is optionally substituted by 1, 2, or 3 substituents independently selected from the group consisting of C$_{1-6}$ alkyl, C$_{1-6}$ haloalkyl, C$_{3-6}$ cycloalkyl, halogen, C$_{1-6}$ alkoxy, C$_{1-6}$ haloalkoxy, —C(O)R$^9$, and —CO$_2$R$^8$.

In certain embodiments, A$^2$ is one of the following:

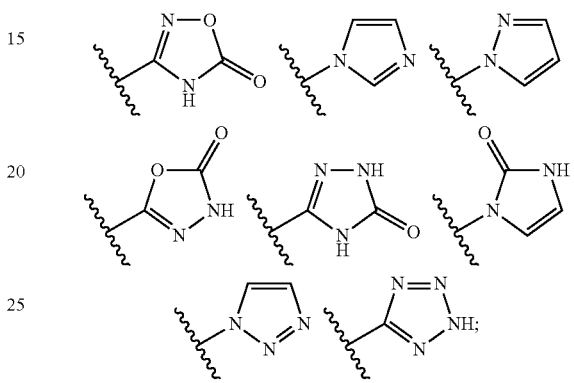

each of which is optionally substituted by 1, 2, or 3 substituents independently selected from the group consisting of C$_{1-6}$ alkyl, C$_{1-6}$ haloalkyl, C$_{3-6}$ cycloalkyl, halogen, C$_{1-6}$ alkoxy, C$_{1-6}$ haloalkoxy, —C(O)R$^9$, —CO$_2$R$^8$, and —C(O)(N$^4$)(R$^5$).

In certain embodiments, A$^2$ is oxazolidin-2-onyl; oxazolidine-2,4-dionyl; imidazolidine-2,4-dionyl; or thiazolidine-2,4-dionyl; each of which is optionally substituted by 1, 2, or 3 substituents independently selected from the group consisting of C$_{1-6}$ alkyl, C$_{1-6}$ haloalkyl, C$_{3-6}$ cycloalkyl, halogen, C$_{1-6}$ alkoxy, C$_{1-6}$ haloalkoxy, —C(O)R$^9$, —CO$_2$R$^8$, —C(O)(N$^4$)(R$^5$), —N(R$^4$)C(O)(R$^9$), and —N(R$^4$)(R$^5$).

In certain embodiments, A$^2$ is one of the following:

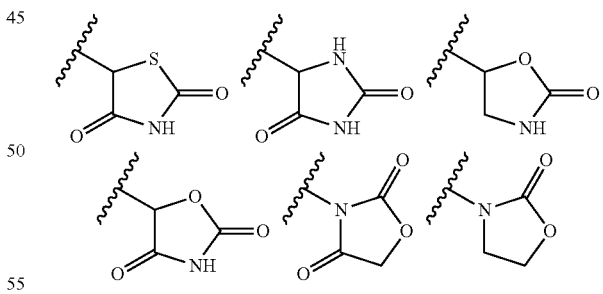

each of which is optionally substituted by 1, 2, or 3 substituents independently selected from the group consisting of C$_{1-6}$ alkyl, C$_{1-6}$ haloalkyl, C$_{3-6}$ cycloalkyl, halogen, C$_{1-6}$ alkoxy, C$_{1-6}$ haloalkoxy, —C(O)R$^9$, —CO$_2$R$^8$, and —C(O)(N$^4$)(R$^5$).

In certain embodiments, R$^{2B}$ is methyl.

In certain embodiments, X is —(C$_{2-6}$ alkenylene)-phenyl, —(C$_{2-6}$ alkenylene)-heteroaryl, —(C$_{1-6}$ alkylene)-phenyl, —(C$_{1-6}$ alkylene)-heteroaryl, —(C$_{1-6}$ alkylene)-(partially unsaturated bicyclic heterocyclyl), —(C$_{1-6}$ alkylene)-(partially unsaturated bicyclic oxo-heterocyclyl), or -(5-6 membered heterocycloalkylene)-phenyl, each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, and $C_{1-6}$ haloalkoxy. In certain embodiments, X is —($C_{2-6}$ alkenylene)-phenyl, —($C_{1-6}$ alkylene)-phenyl, or —($C_{1-6}$ alkylene)-heteroaryl), each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, and $C_{1-6}$ haloalkoxy. In certain embodiments, X is —($C_{2-6}$ alkenylene)-phenyl optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, and $C_{1-6}$ haloalkoxy.

In certain embodiments, X is —($C_{1-6}$ alkylene)-$Z^1$ or —($C_{2-6}$ alkenylene)-$Z^1$, wherein $Z^1$ is —O-aralkyl, —O-heteroaralkyl, —O-phenyl, —O-heteroaryl, —O-(partially unsaturated bicyclic carbocyclyl), —O—($C_{1-6}$ alkylene)-($C_{3-6}$ cycloalkyl), —O—($C_{3-6}$ cycloalkyl), —N($R^4$)-aralkyl, —N($R^4$)-phenyl, —N($R^4$)-(partially unsaturated bicyclic carbocyclyl), or —N($R^4$)—($C_{1-6}$ alkylene)-($C_{3-6}$ cycloalkyl), each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, and $C_{1-6}$ haloalkoxy. In certain embodiments, X is —O-aralkyl, —O-heteroaralkyl, —O-phenyl, —O-heteroaryl, —O-(partially unsaturated bicyclic carbocyclyl), —O—($C_{1-6}$ alkylene)-($C_{3-6}$ cycloalkyl), —N($R^4$)-aralkyl, —N($R^4$)-phenyl, —N($R^4$)-(partially unsaturated bicyclic carbocyclyl), or —N($R^4$)—($C_{1-6}$ alkylene)-($C_{3-6}$ cycloalkyl), each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, and $C_{1-6}$ haloalkoxy. In certain embodiments, X is —O—($C_{1-6}$ alkylene)-phenyl or —N($R^4$)—($C_{1-6}$ alkylene)-phenyl, each of which is substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, and $C_{1-6}$ haloalkoxy. In certain embodiments, X is —O—($C_{1-6}$ alkylene)-phenyl or —N($R^4$)—($C_{1-6}$ alkylene)-phenyl, each of which is substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, and $C_{1-6}$ haloalkoxy, where at least one substituent is present at the ortho position on the phenyl group in variable X. In certain embodiments, X is —O—($C_{1-6}$ alkylene)-phenyl or —N($R^4$)—($C_{1-6}$ alkylene)-phenyl, each of which is substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, and $C_{1-6}$ haloalkoxy. In certain embodiments, X is —O-aralkyl or —N($R^4$)-aralkyl, each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, and $C_{1-6}$ haloalkoxy. In certain embodiments, X is —O-benzyl or —N($R^4$)-benzyl, each of which is substituted with 1 or 2 substituents independently selected from the group consisting of chloro, bromo, and fluoro.

In certain embodiments, Y is —C($R^6$)($R^7$)—. In certain embodiments, $R^6$ and $R^7$ are independently hydrogen or methyl.

In certain embodiments, Y is —C($R^6$)($R^7$)—, $R^6$ and $R^7$ are independently hydrogen or methyl, and X is attached at the 7-position of the 1,2,3,4-tetrahydroquinolinyl ring.

In certain embodiments, Y is —O—. In certain embodiments, X is attached at the 6-position of the 3,4-dihydro-2H-benzo[b][1,4]oxazinyl ring.

In certain embodiments, m is 0 or 1. In certain embodiments, p is 0. In certain embodiments, p is 1.

The definitions of variables in Formula II above encompass multiple chemical groups. The application contemplates embodiments where, for example, i) the definition of a variable is a single chemical group selected from those chemical groups set forth above, ii) the definition of a variable is a collection of two or more of the chemical groups selected from those set forth above, and iii) the compound is defined by a combination of variables in which the variables are defined by (i) or (ii), e.g., such as where A is phenylene and $R^3$ is selected from the group consisting of $C_{1-6}$ haloalkyl, halogen, hydroxyl, and $C_{1-6}$ alkyl.

Another aspect of the invention provides a compound represented by Formula II-A:

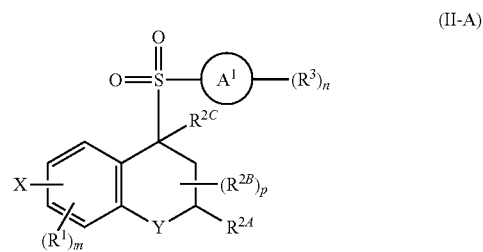

(II-A)

or a pharmaceutically acceptable salt thereof; wherein:

$A^1$ is phenylene or a 5-6 membered heteroarylene;

$R^1$ represents independently for each occurrence halogen, $C_{1-6}$ alkyl, or $C_{3-6}$ cycloalkyl;

$R^{2A}$ is —($C_{1-6}$ alkylene)-$A^2$, -(2-6 membered heteroalkylene)-$A^2$, or —O-$A^2$; wherein $A^2$ is a 5-6 membered heterocyclic group containing at least one unsaturated carbon atom and the heterocyclic group being optionally substituted with 1, 2, or 3 substituents independently selected from the group consisting of $C_{1-6}$ alkyl, $C_{1-6}$ haloalkyl, $C_{3-6}$ cycloalkyl, halogen, $C_{1-6}$ alkoxy, $C_{1-6}$ haloalkoxy, oxo, —C(O)$R^9$, —$CO_2R^8$, —C(O)($N^4$)($R^5$), —N($R^4$)C(O)($R^9$), and —N($R^4$)($R^5$);

$R^{2B}$ represents independently for each occurrence $C_{1-6}$ alkyl or $C_{1-3}$ haloalkyl;

$R^{2C}$ is hydrogen or $C_{1-6}$ alkyl;

$R^3$ represents independently for each occurrence hydrogen, $C_{1-6}$ haloalkyl, halogen, hydroxyl, $C_{1-6}$ alkyl, $C_{3-6}$ cycloalkyl, $C_{1-6}$ alkoxy, $C_{1-6}$ haloalkoxy, or —O—($C_{1-6}$ alkylene)-OH; or two vicinal occurrences of $R^3$ are taken together with intervening atoms to form a 4-6 membered ring;

$R^4$ and $R^5$ each represent independently for each occurrence hydrogen, $C_{1-6}$ alkyl, or $C_{3-6}$ cycloalkyl; or an occurrence of $R^4$ and $R^5$ attached to the same nitrogen atom are taken together with the nitrogen atom to which they are attached to form a 3-7 membered heterocyclic ring;

$R^6$ and $R^7$ each represent independently for each occurrence hydrogen or $C_{1-6}$ alkyl, or $R^6$ and $R^7$ are taken together with the carbon atom to which they are attached to form a 3-6 membered carbocyclic ring;

$R^8$ represents independently for each occurrence hydrogen, $C_{1-6}$ alkyl, $C_{3-6}$ cycloalkyl, or aralkyl;

$R^9$ represents independently for each occurrence $C_{1-6}$ alkyl, $C_{3-6}$ cycloalkyl, or aralkyl;

X is one of the following:
(i) —($C_{2-6}$ alkenylene)-phenyl, —($C_{2-6}$ alkenylene)-heteroaryl, —($C_{1-6}$ alkylene)-phenyl, —($C_{1-6}$ alkylene)-heteroaryl, —($C_{1-6}$ alkylene)-(partially unsaturated bicyclic heterocyclyl), —($C_{1-6}$ alkylene)-(partially unsaturated bicyclic oxo-heterocyclyl), -(5-6 membered heterocycloalkylene)-phenyl, or —($C_{3-6}$ cycloalkylene)-phenyl, each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, $C_{1-6}$ haloalkoxy, hydroxyl, and cyano;
(ii) —($C_{1-6}$ alkylene)-$Z^1$ or —($C_{2-6}$ alkenylene)-$Z^1$, wherein $Z^1$ is —O-aralkyl, —O-heteroaralkyl, —O-phenyl, —O-heteroaryl, —O-(partially unsaturated bicyclic carbocyclyl), —O—($C_{1-6}$ alkylene)-($C_{3-6}$ cycloalkyl), —O—($C_{3-6}$ cycloalkyl), —N($R^4$)-aralkyl, —N($R^4$)-phenyl, —N($R^4$)-(partially unsaturated bicyclic carbocyclyl), or —N($R^4$)—($C_{1-6}$ alkylene)-($C_{3-6}$ cycloalkyl), each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, $C_{1-6}$ haloalkoxy, hydroxyl, and cyano; or
(iii) —O-aralkyl, —O-heteroaralkyl, —O-phenyl, —O-heteroaryl, —O-(partially unsaturated bicyclic carbocyclyl), —O—($C_{1-6}$ alkylene)-($C_{3-6}$ cycloalkyl), —O—($C_{3-6}$ cycloalkyl), —N($R^4$)-aralkyl, —N($R^4$)-phenyl, —N($R^4$)-(partially unsaturated bicyclic carbocyclyl), or —N($R^4$)—($C_{1-6}$ alkylene)-($C_{3-6}$ cycloalkyl), each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, $C_{1-6}$ haloalkoxy, hydroxyl, and cyano;

Y is —C($R^6$)($R^7$)—, —O—, or —C(O)—;
m and p are independently 0, 1, or 2; and
n is 1, 2, or 3.

In certain embodiments, $A^1$ is phenylene. In certain embodiments, $A^1$ is a 5-6 membered heteroarylene.

In certain embodiments, n is 1. In certain embodiments, n is 1 or 2.

In certain embodiments, $R^3$ represents independently for each occurrence $C_{1-6}$ haloalkyl, halogen, $C_{1-6}$ alkyl, $C_{1-6}$ alkoxy, or —O—($C_{1-6}$ alkylene)-OH. In certain embodiments, $R^3$ is trifluoromethyl, fluoro, chloro, or methoxy. In certain embodiments, $R^3$ is trifluoromethyl.

In certain embodiments, -$A^1$-$(R^3)_n$ is

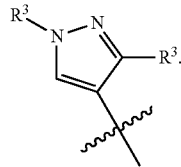

In certain embodiments, -$A^1$-$(R^3)_n$ is one of the following:

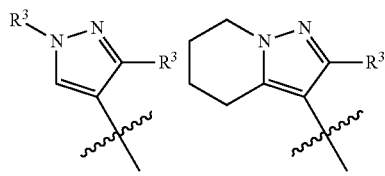

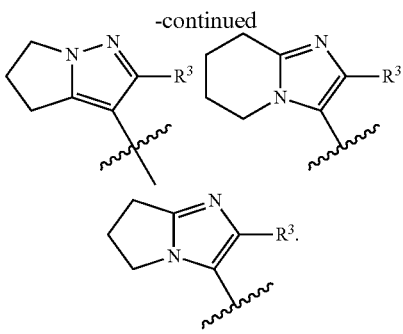

In certain embodiments, $R^{2A}$ is —($C_{1-6}$ alkylene)-$A^2$. In certain embodiments, $R^{2A}$ is —($C_{2-3}$ alkylene)-$A^2$. In certain embodiments, $R^{2A}$ is -(2-6 membered heteroalkylene)-$A^2$. In certain embodiments, $R^{2A}$ is —($C_{2-3}$ alkylene)-O-$A^2$. In certain embodiments, $R^{2A}$ is —O-$A^2$.

In certain embodiments, $A^2$ comprises at least two ring nitrogen atoms. In certain embodiments, $A^2$ comprises at least two ring nitrogen atoms, and at least one ring oxygen atom.

In certain embodiments, $A^2$ is a 5-6 membered heterocyclic group containing at least one ring carbon atom substituted by oxo and the heterocyclic group being optionally substituted by 1 or 2 substituents independently selected from the group consisting of $C_{1-6}$ alkyl, $C_{1-6}$ haloalkyl, $C_{3-6}$ cycloalkyl, halogen, $C_{1-6}$ alkoxy, $C_{1-6}$ haloalkoxy, oxo, —C(O)$R^9$, —CO$_2$$R^8$, —C(O)($N^4$)($R^5$), —N($R^4$)C(O)($R^9$), and —N($R^4$)($R^5$). In certain embodiments, $A^2$ is a 5-6 membered heterocyclic group containing (i) at least one ring carbon atom substituted by oxo and (ii) at least one double bond between two ring atoms, and the heterocyclic group being optionally substituted by 1 or 2 substituents independently selected from the group consisting of $C_{1-6}$ alkyl, $C_{1-6}$ haloalkyl, $C_{3-6}$ cycloalkyl, halogen, $C_{1-6}$ alkoxy, $C_{1-6}$ haloalkoxy, oxo, —C(O)$R^9$, —CO$_2$$R^8$, —C(O)($N^4$)($R^5$), —N($R^4$)C(O)($R^9$), and —N($R^4$)($R^5$). In certain embodiments, the heterocyclic group in $A^2$ is a 5-membered heterocyclic group.

In certain embodiments, $A^2$ is a 5-6 membered heteroaromatic group comprising at least two ring nitrogen atoms, at least one unsaturated carbon atom in the ring, and the heteroaromatic group being optionally substituted by 1 or 2 substituents independently selected from the group consisting of $C_{1-6}$ alkyl, $C_{1-6}$ haloalkyl, $C_{3-6}$ cycloalkyl, halogen, $C_{1-6}$ alkoxy, $C_{1-6}$ haloalkoxy, —C(O)$R^9$, —CO$_2$$R^8$, —C(O)($N^4$)($R^5$), —N($R^4$)C(O)($R^9$), and —N($R^4$)($R^5$). In certain embodiments, the heteroaromatic group in $A^2$ is a 5-membered heteroaromatic group.

In certain embodiments, $A^2$ is imidazolyl; pyrazolyl; 1,2,3-triazolyl; tetrazolyl; 1,2,4-oxadiazol-5(4H)-onyl; 1,3,4-oxadiazol-2(3H)-onyl; 1,3-dihydro-2H-imidazol-2-onyl; or 2,4-dihydro-3H-1,2,4-triazol-3-onyl; each of which is optionally substituted by 1, 2, or 3 substituents independently selected from the group consisting of $C_{1-6}$ alkyl, $C_{1-6}$ haloalkyl, $C_{3-6}$ cycloalkyl, halogen, $C_{1-6}$ alkoxy, $C_{1-6}$ haloalkoxy, —C(O)$R^9$, —CO$_2$$R^8$, —C(O)($N^4$)($R^5$), —N($R^4$)C(O)($R^9$), and —N($R^4$)($R^5$).

In certain embodiments, $A^2$ is imidazolyl; pyrazolyl; 1,2,3-triazolyl; tetrazolyl; 1,2,4-oxadiazol-5(4H)-onyl; 1,3,4-oxadiazol-2(3H)-onyl; 1,3-dihydro-2H-imidazol-2-onyl; or 2,4-dihydro-3H-1,2,4-triazol-3-onyl; each of which is optionally substituted by 1, 2, or 3 substituents independently selected from the group consisting of $C_{1-6}$ alkyl, $C_{1-6}$ haloalkyl, $C_{3-6}$ cycloalkyl, halogen, $C_{1-6}$ alkoxy, $C_{1-6}$ haloalkoxy, —C(O)$R^9$, and —CO$_2R^8$.

In certain embodiments, $A^2$ is one of the following:

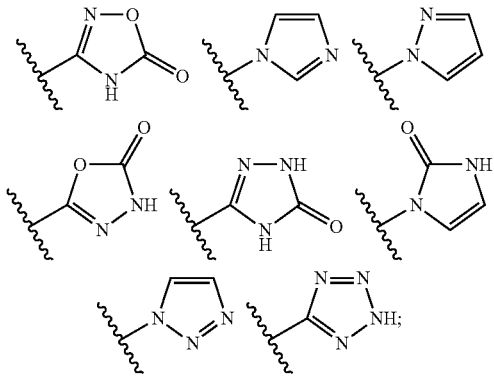

each of which is optionally substituted by 1, 2, or 3 substituents independently selected from the group consisting of $C_{1-6}$ alkyl, $C_{1-6}$ haloalkyl, $C_{3-6}$ cycloalkyl, halogen, $C_{1-6}$ alkoxy, $C_{1-6}$ haloalkoxy, —C(O)$R^9$, —CO$_2R^8$, and —C(O)($N^4$)($R^5$).

In certain embodiments, $A^2$ is oxazolidin-2-onyl; oxazolidine-2,4-dionyl; imidazolidine-2,4-dionyl; or thiazolidine-2,4-dionyl; each of which is optionally substituted by 1, 2, or 3 substituents independently selected from the group consisting of $C_{1-6}$ alkyl, $C_{1-6}$ haloalkyl, $C_{3-6}$ cycloalkyl, halogen, $C_{1-6}$ alkoxy, $C_{1-6}$ haloalkoxy, —C(O)$R^9$, —CO$_2R^8$, —C(O)($N^4$)($R^5$), —N($R^4$)C(O)($R^9$), and —N($R^4$)($R^5$).

In certain embodiments, $A^2$ is one of the following:

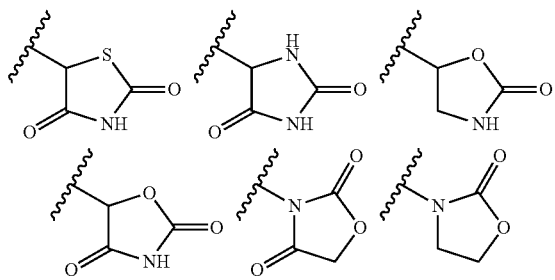

each of which is optionally substituted by 1, 2, or 3 substituents independently selected from the group consisting of $C_{1-6}$ alkyl, $C_{1-6}$ haloalkyl, $C_{3-6}$ cycloalkyl, halogen, $C_{1-6}$ alkoxy, $C_{1-6}$ haloalkoxy, —C(O)$R^9$, —CO$_2R^8$, and —C(O)($N^4$)($R^5$).

In certain embodiments, $R^{2B}$ is methyl.

In certain embodiments, X is —($C_{2-6}$ alkenylene)-phenyl, —($C_{2-6}$ alkenylene)-heteroaryl, —($C_{1-6}$ alkylene)-phenyl, —($C_{1-6}$ alkylene)-heteroaryl, —($C_{1-6}$ alkylene)-(partially unsaturated bicyclic heterocyclyl), —($C_{1-6}$ alkylene)-(partially unsaturated bicyclic oxo-heterocyclyl), or -(5-6 membered heterocycloalkylene)-phenyl, each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, and $C_{1-6}$ haloalkoxy. In certain embodiments, X is —($C_{2-6}$ alkenylene)-phenyl, —($C_{1-6}$ alkylene)-phenyl, or —($C_{1-6}$ alkylene)-heteroaryl), each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, and $C_{1-6}$ haloalkoxy. In certain embodiments, X is —($C_{2-6}$ alkenylene)-phenyl optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, and $C_{1-6}$ haloalkoxy.

In certain embodiments, X is —($C_{1-6}$ alkylene)-$Z^1$ or —($C_{2-6}$ alkenylene)-$Z^1$, wherein $Z^1$ is —O-aralkyl, —O-heteroaralkyl, —O-phenyl, —O-heteroaryl, —O-(partially unsaturated bicyclic carbocyclyl), —O—($C_{1-6}$ alkylene)-($C_{3-6}$ cycloalkyl), —O—($C_{3-6}$ cycloalkyl), —N($R^4$)-aralkyl, —N($R^4$)-phenyl, —N($R^4$)-(partially unsaturated bicyclic carbocyclyl), or —N($R^4$)—($C_{1-6}$ alkylene)-($C_{3-6}$ cycloalkyl), each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, and $C_{1-6}$ haloalkoxy. In certain embodiments, X is —O-aralkyl, —O-heteroaralkyl, —O-phenyl, —O-heteroaryl, —O-(partially unsaturated bicyclic carbocyclyl), —O—($C_{1-6}$ alkylene)-($C_{3-6}$ cycloalkyl), —N($R^4$)-aralkyl, —N($R^4$)-phenyl, —N($R^4$)-(partially unsaturated bicyclic carbocyclyl), or —N($R^4$)—($C_{1-6}$ alkylene)-($C_{3-6}$ cycloalkyl), each of which is optionally substituted with 1, 2 or 3 substituents independently selected from the group consisting of halogen, $C_{1-6}$ haloalkyl, $C_{1-6}$ alkyl, $C_{3-6}$ cycloalkyl, $C_{1-6}$ alkoxy, and $C_{1-6}$ haloalkoxy. In certain embodiments, X is —O—($C_{1-6}$ alkylene)-phenyl or —N($R^4$)—($C_{1-6}$ alkylene)-phenyl, each of which is substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, and $C_{1-6}$ haloalkoxy. In certain embodiments, X is —O—($C_{1-6}$ alkylene)-phenyl or —N($R^4$)—($C_{1-6}$ alkylene)-phenyl, each of which is substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, and $C_{1-6}$ haloalkoxy, where at least one substituent is present at the ortho position on the phenyl group in variable X. In certain embodiments, X is —O—($C_{1-6}$ alkylene)-phenyl or —N($R^4$)—($C_{1-6}$ alkylene)-phenyl, each of which is substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, and $C_{1-6}$ haloalkoxy. In certain embodiments, X is —O-aralkyl or —N($R^4$)-aralkyl, each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, and $C_{1-6}$ haloalkoxy. In certain embodiments, X is —O-benzyl or —N($R^4$)-benzyl, each of which is substituted with 1 or 2 substituents independently selected from the group consisting of chloro, bromo, and fluoro.

In certain embodiments, Y is —C($R^6$)($R^7$)—. In certain embodiments, $R^6$ and $R^7$ are independently hydrogen or methyl.

In certain embodiments, Y is —C($R^6$)($R^7$)—, $R^6$ and $R^7$ are independently hydrogen or methyl, and X is attached at the 7-position of the 1,2,3,4-tetrahydronaphthalenyl ring.

In certain embodiments, Y is —O—. In certain embodiments, X is attached at the 6-position of the chromanyl ring.

In certain embodiments, m is 0 or 1. In certain embodiments, p is 0. In certain embodiments, p is 1.

The definitions of variables in Formula II-A above encompass multiple chemical groups. The application contemplates embodiments where, for example, i) the definition of a variable is a single chemical group selected from those chemical groups set forth above, ii) the definition of a variable is a collection of two or more of the chemical groups selected from those set forth above, and iii) the compound is defined by a combination of variables in which the variables are defined by (i) or (ii), e.g., such as where A is phenylene and R³ is selected from the group consisting of $C_{1-6}$ haloalkyl, halogen, hydroxyl, and $C_{1-6}$ alkyl.

Another aspect of the invention provides a compound represented by Formula II-B:

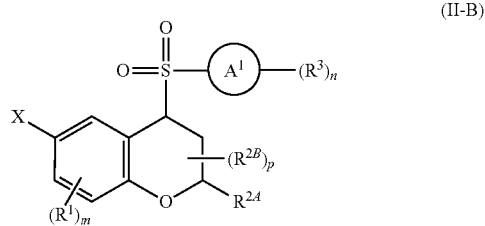

(II-B)

or a pharmaceutically acceptable salt thereof; wherein:

A is phenylene or pyridinylene;

$R^1$ represents independently for each occurrence halogen, methyl, ethyl, or cyclopropyl;

$R^{2A}$ is —($C_{1-6}$ alkylene)-$A^2$ or -(2-6 membered heteroalkylene)-$A^2$; wherein $A^2$ is a 5-6 membered heterocyclic group containing at least one unsaturated carbon atom and the heterocyclic group being optionally substituted with 1, 2, or 3 substituents independently selected from the group consisting of $C_{1-6}$ alkyl, $C_{1-6}$ haloalkyl, $C_{3-6}$ cycloalkyl, halogen, $C_{1-6}$ alkoxy, $C_{1-6}$ haloalkoxy, oxo, and —$CO_2R^8$;

$R^{2B}$ is methyl or ethyl;

$R^3$ represents independently for each occurrence $C_{1-3}$ haloalkyl, halogen, $C_{1-3}$ alkyl, or —O—($C_{1-6}$ hydroxyalkyl);

$R^4$ and $R^5$ each represent independently for each occurrence hydrogen or methyl; or an occurrence of $R^4$ and $R^5$ attached to the same nitrogen atom are taken together with the nitrogen atom to which they are attached to form a 3-7 membered heterocyclic ring;

$R^8$ represents independently for each occurrence hydrogen or $C_{1-6}$ alkyl;

X is —($C_{2-6}$ alkenylene)-phenyl substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, and $C_{1-6}$ haloalkoxy;

m and p are independently 0 or 1; and n is 1 or 2.

In certain embodiments, A is phenylene. In certain other embodiments, A is pyridinylene.

In certain embodiments, $R^1$ is fluoro or methyl.

In certain embodiments, $R^{2A}$ is —($C_{1-6}$ alkylene)-$A^2$. In certain embodiments, $R^{2A}$ is —($C_{2-3}$ alkylene)-$A^2$. In certain embodiments, $R^{2A}$ is -(2-6 membered heteroalkylene)-$A^2$.

In certain embodiments, $A^2$ comprises at least two ring nitrogen atoms. In certain embodiments, $A^2$ comprises at least two ring nitrogen atoms, and at least one ring oxygen atom.

In certain embodiments, $A^2$ is a 5-6 membered heterocyclic group containing at least one ring carbon atom substituted by oxo and the heterocyclic group being optionally substituted by 1 or 2 substituents independently selected from the group consisting of $C_{1-6}$ alkyl, $C_{1-6}$ haloalkyl, $C_{3-6}$ cycloalkyl, halogen, $C_{1-6}$ alkoxy, $C_{1-6}$ haloalkoxy, oxo, —C(O)$R^9$, —$CO_2R^8$, —C(O)($N^4$)($R^5$), —N($R^4$)C(O)($R^9$), and —N($R^4$)($R^5$). In certain embodiments, $A^2$ is a 5-6 membered heterocyclic group containing (i) at least one ring carbon atom substituted by oxo and (ii) at least one double bond between two ring atoms, and the heterocyclic group being optionally substituted by 1 or 2 substituents independently selected from the group consisting of $C_{1-6}$ alkyl, $C_{1-6}$ haloalkyl, $C_{3-6}$ cycloalkyl, halogen, $C_{1-6}$ alkoxy, $C_{1-6}$ haloalkoxy, oxo, —C(O)$R^9$, —$CO_2R^8$, —C(O)($N^4$)($R^5$), —N($R^4$)C(O)($R^9$), and —N($R^4$)($R^5$). In certain embodiments, the heterocyclic group in $A^2$ is a 5-membered heterocyclic group.

In certain embodiments, $A^2$ is a 5-6 membered heteroaromatic group comprising at least two ring nitrogen atoms, at least one unsaturated carbon atom in the ring, and the heteroaromatic group being optionally substituted by 1 or 2 substituents independently selected from the group consisting of $C_{1-6}$ alkyl, $C_{1-6}$ haloalkyl, $C_{3-6}$ cycloalkyl, halogen, $C_{1-6}$ alkoxy, $C_{1-6}$ haloalkoxy, —C(O)$R^9$, —$CO_2R^8$, —C(O)($N^4$)($R^5$), —N($R^4$)C(O)($R^9$), and —N($R^4$)($R^5$). In certain embodiments, the heteroaromatic group in $A^2$ is a 5-membered heteroaromatic group.

In certain embodiments, $A^2$ is imidazolyl; pyrazolyl; 1,2,3-triazolyl; tetrazolyl; 1,2,4-oxadiazol-5(4H)-onyl; 1,3,4-oxadiazol-2(3H)-onyl; 1,3-dihydro-2H-imidazol-2-onyl; or 2,4-dihydro-3H-1,2,4-triazol-3-onyl; each of which is optionally substituted by 1, 2, or 3 substituents independently selected from the group consisting of $C_{1-6}$ alkyl, $C_{1-6}$ haloalkyl, $C_{3-6}$ cycloalkyl, halogen, $C_{1-6}$ alkoxy, $C_{1-6}$ haloalkoxy, —C(O)$R^9$, —$CO_2R^8$, —C(O)($N^4$)($R^5$), —N($R^4$)C(O)($R^9$), and —N($R^4$)($R^5$).

In certain embodiments, $A^2$ is imidazolyl; pyrazolyl; 1,2,3-triazolyl; tetrazolyl; 1,2,4-oxadiazol-5(4H)-onyl; 1,3,4-oxadiazol-2(3H)-onyl; 1,3-dihydro-2H-imidazol-2-onyl; or 2,4-dihydro-3H-1,2,4-triazol-3-onyl; each of which is optionally substituted by 1, 2, or 3 substituents independently selected from the group consisting of $C_{1-6}$ alkyl, $C_{1-6}$ haloalkyl, $C_{3-6}$ cycloalkyl, halogen, $C_{1-6}$ alkoxy, $C_{1-6}$ haloalkoxy, —C(O)$R^9$, and —$CO_2R^8$.

In certain embodiments, $A^2$ is one of the following:

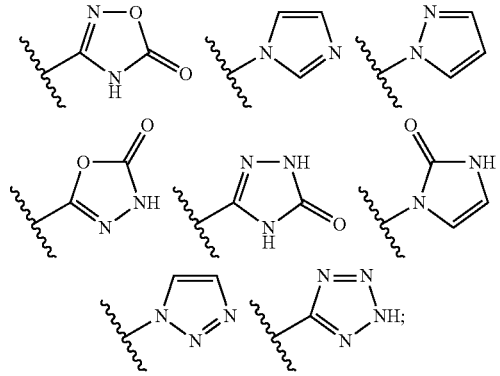

each of which is optionally substituted by 1, 2, or 3 substituents independently selected from the group consisting of $C_{1-6}$ alkyl, $C_{1-6}$ haloalkyl, $C_{3-6}$ cycloalkyl, halogen, $C_{1-6}$ alkoxy, $C_{1-6}$ haloalkoxy, —C(O)$R^9$, —$CO_2R^8$, and —C(O)($N^4$)($R^5$).

In certain embodiments, $A^2$ is oxazolidin-2-onyl; oxazolidine-2,4-dionyl; imidazolidine-2,4-dionyl; or thiazolidine-2,4-dionyl; each of which is optionally substituted by 1, 2, or 3 substituents independently selected from the group consisting of $C_{1-6}$ alkyl, $C_{1-6}$ haloalkyl, $C_{3-6}$ cycloalkyl, halogen, $C_{1-6}$ alkoxy, $C_{1-6}$ haloalkoxy, —C(O)$R^9$, —$CO_2R^8$, —C(O)($N^4$)($R^5$), —N($R^4$)C(O)($R^9$), and —N($R^4$)($R^5$).

In certain embodiments, A² is one of the following:

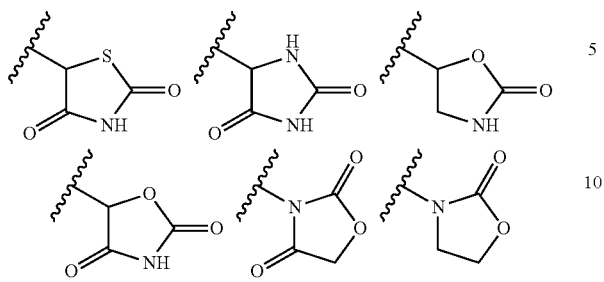

each of which is optionally substituted by 1, 2, or 3 substituents independently selected from the group consisting of $C_{1-6}$ alkyl, $C_{1-6}$ haloalkyl, $C_{3-6}$ cycloalkyl, halogen, $C_{1-6}$ alkoxy, $C_{1-6}$ haloalkoxy, —C(O)R⁹, —CO₂R⁸, and —C(O)(N⁴)(R⁵).

In certain embodiments, R³ represents independently for each occurrence trifluoromethyl, halogen, or —O—($C_{1-6}$ hydroxyalkyl).

In certain embodiments, R⁴ and R⁵ are taken together with the nitrogen atom to which they are attached to form a 3-7 membered heterocyclic ring. In certain other embodiments, R⁴ and R⁵ each represent independently for each occurrence hydrogen or $C_{1-6}$ alkyl.

In certain embodiments, R⁸ is hydrogen.

In certain embodiments, X is —($C_{2-4}$ alkenylene)-phenyl substituted with 1, 2, or 3 substituents independently selected from the group consisting of halogen and $C_{1-6}$ haloalkyl. In certain embodiments, X is —($C_{2-4}$ alkenylene)-phenyl substituted with 1, 2, or 3 substituents independently selected from the group consisting of chloro, fluoro, and trifluoromethyl. In certain embodiments, X is —($C_{2-4}$ alkenylene)-phenyl substituted with 1 or 2 substituents independently selected from the group consisting of chloro, fluoro, and trifluoromethyl, and said substituents are located at the ortho positions of the phenyl group.

In certain embodiments, m and p are independently 0. In certain embodiments, n is 1.

The definitions of variables in Formula II-B above encompass multiple chemical groups. The application contemplates embodiments where, for example, i) the definition of a variable is a single chemical group selected from those chemical groups set forth above, ii) the definition of a variable is a collection of two or more of the chemical groups selected from those set forth above, and iii) the compound is defined by a combination of variables in which the variables are defined by (i) or (ii).

In certain other embodiments, the compound is a compound defined by one of the following formulae where variables X and Z are as defined in Table 2, or a pharmaceutically acceptable salt thereof.

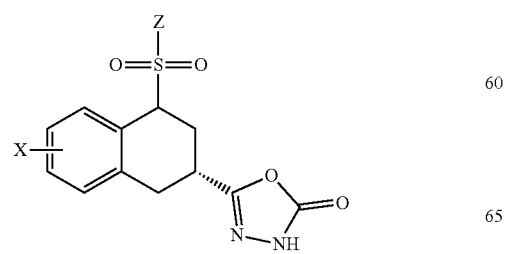

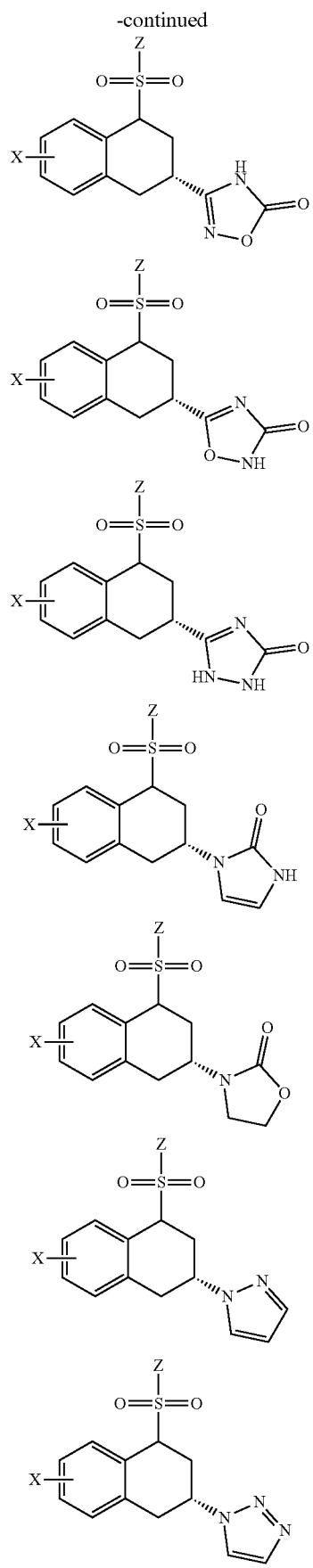

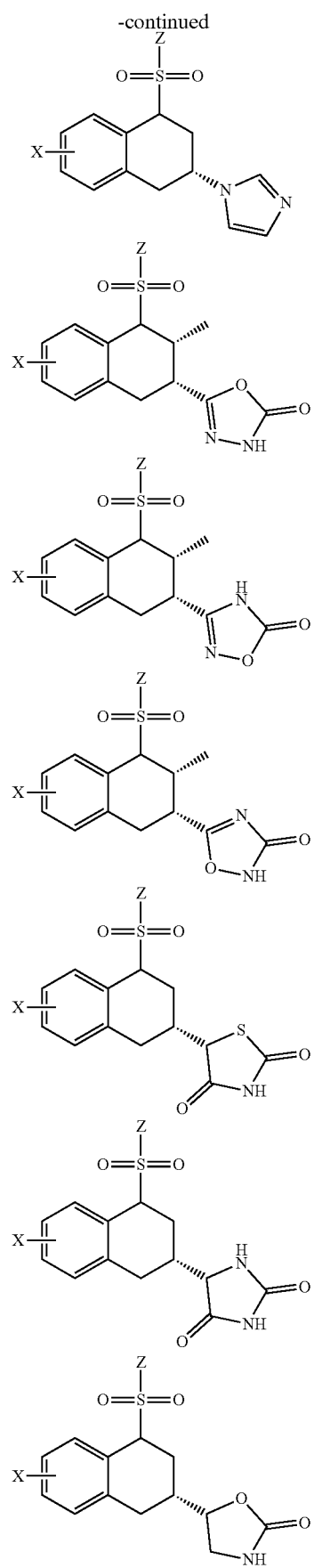
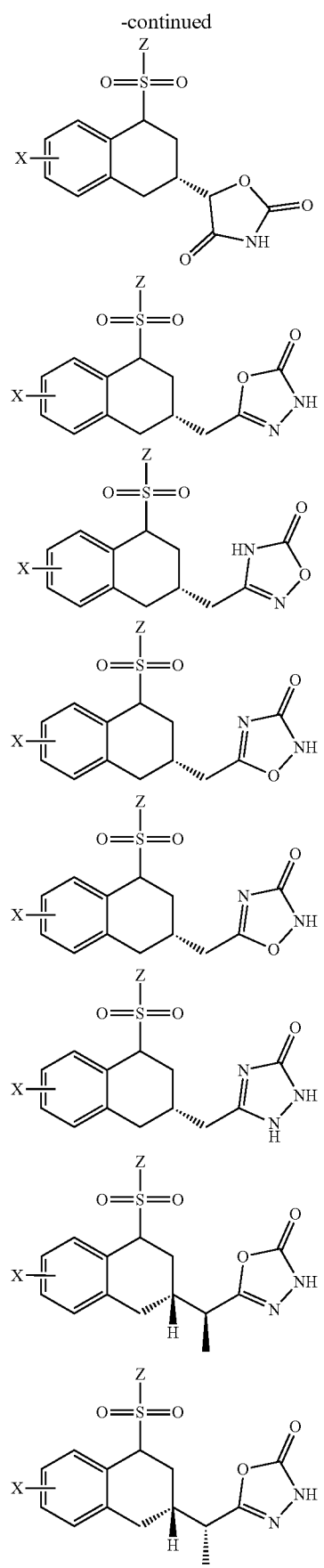

75
-continued
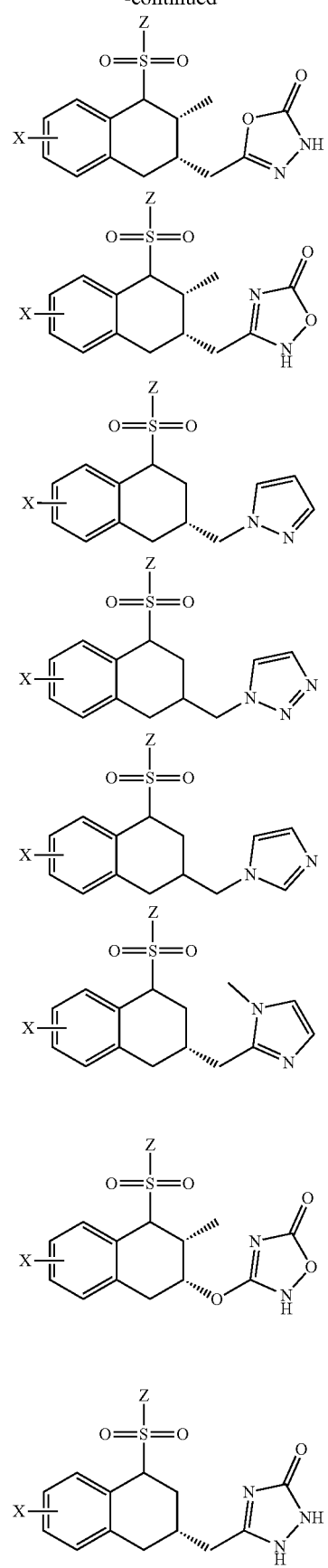
76
-continued
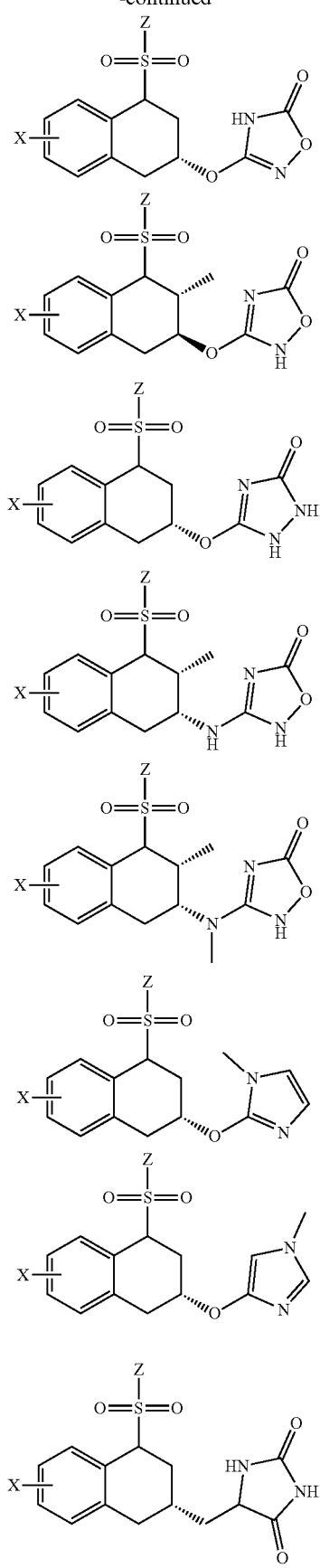

77
-continued
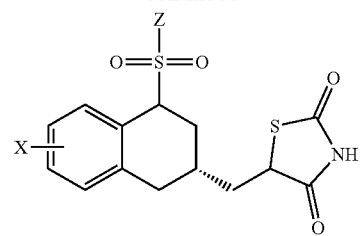
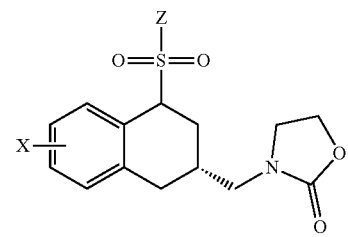
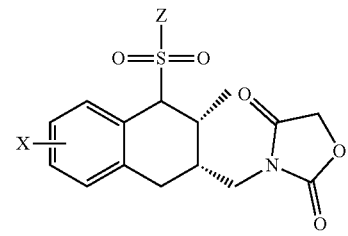
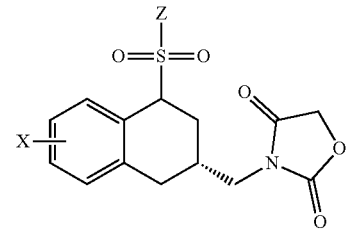
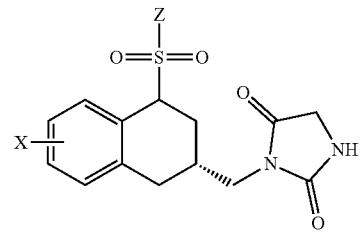
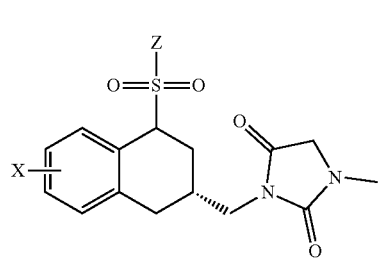
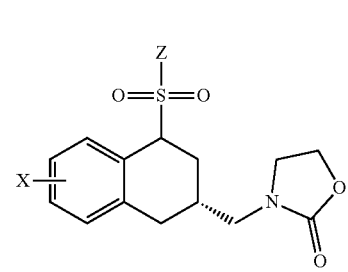
78
-continued
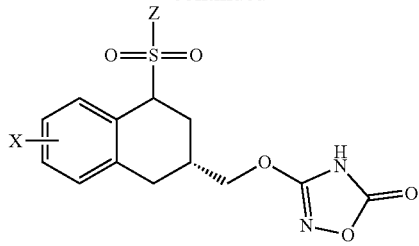
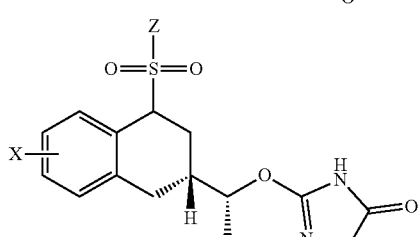
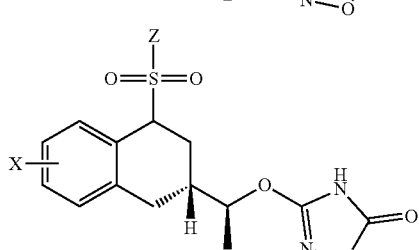
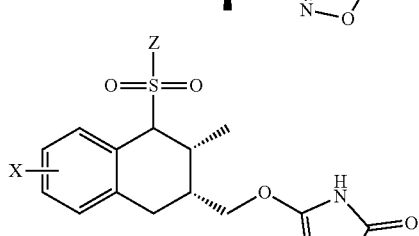
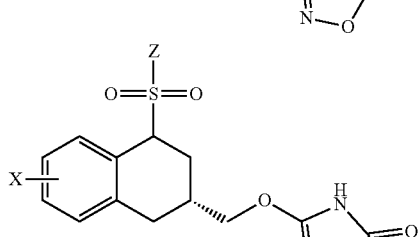
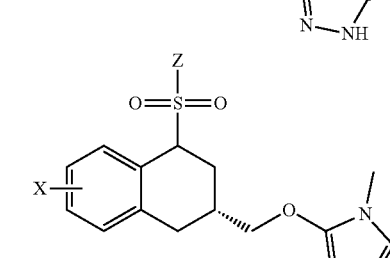
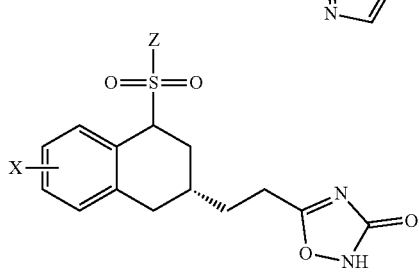

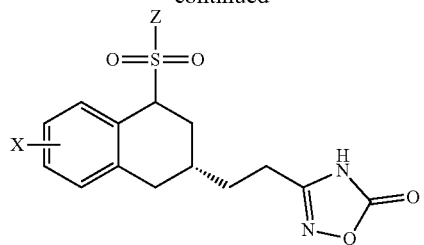
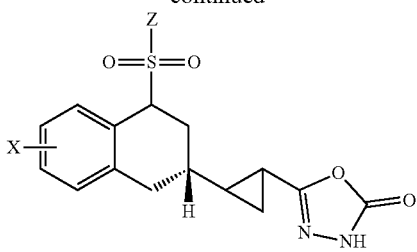
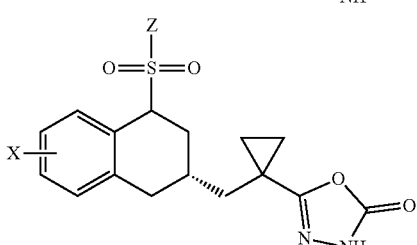
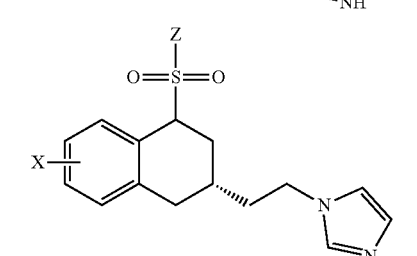
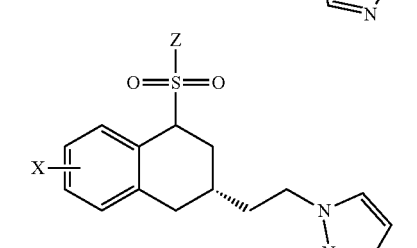
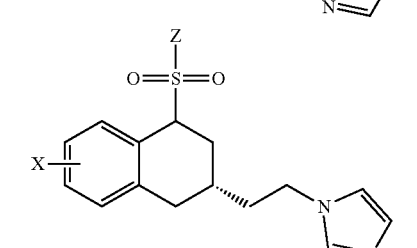
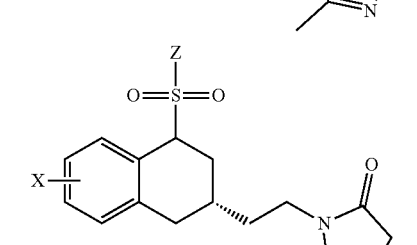
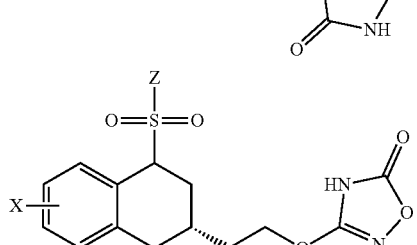

-continued
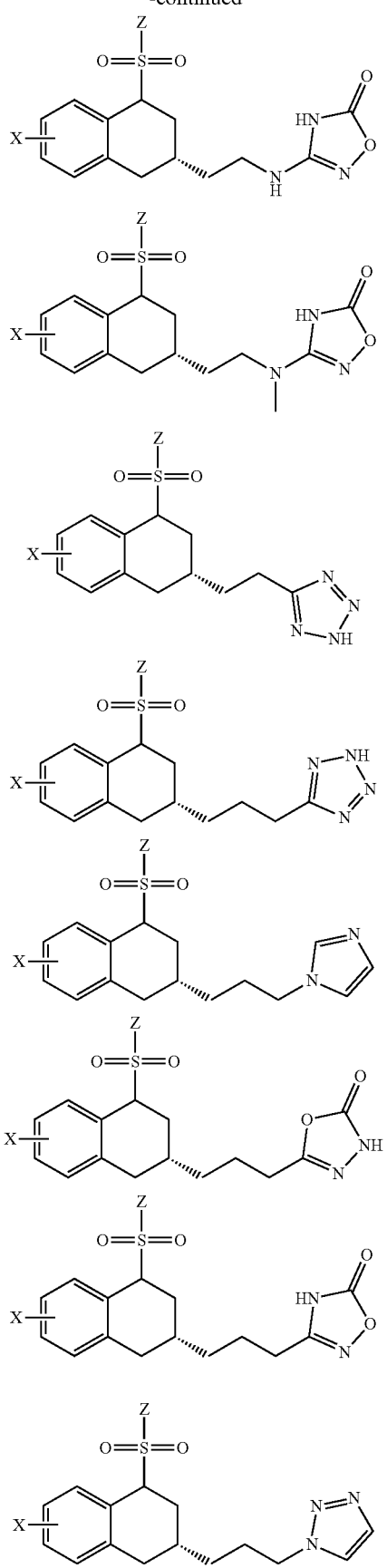
-continued
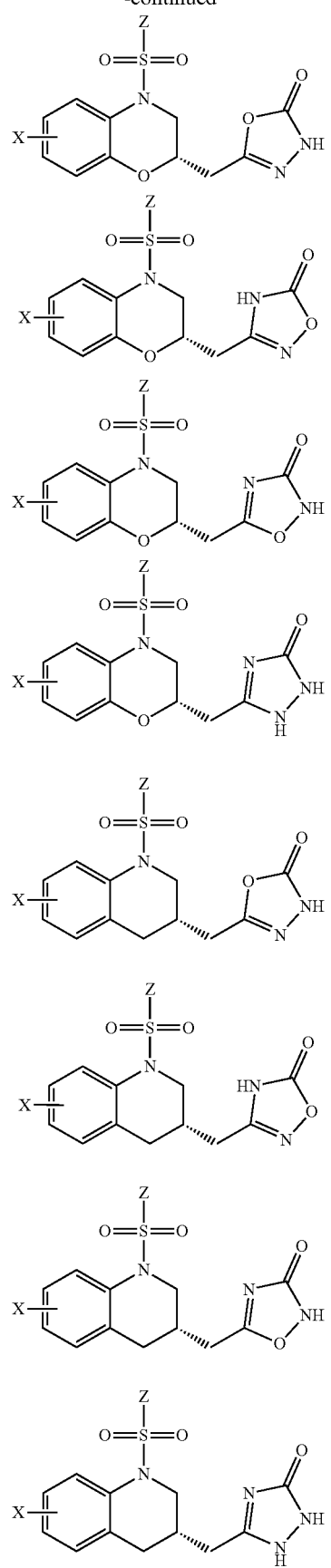

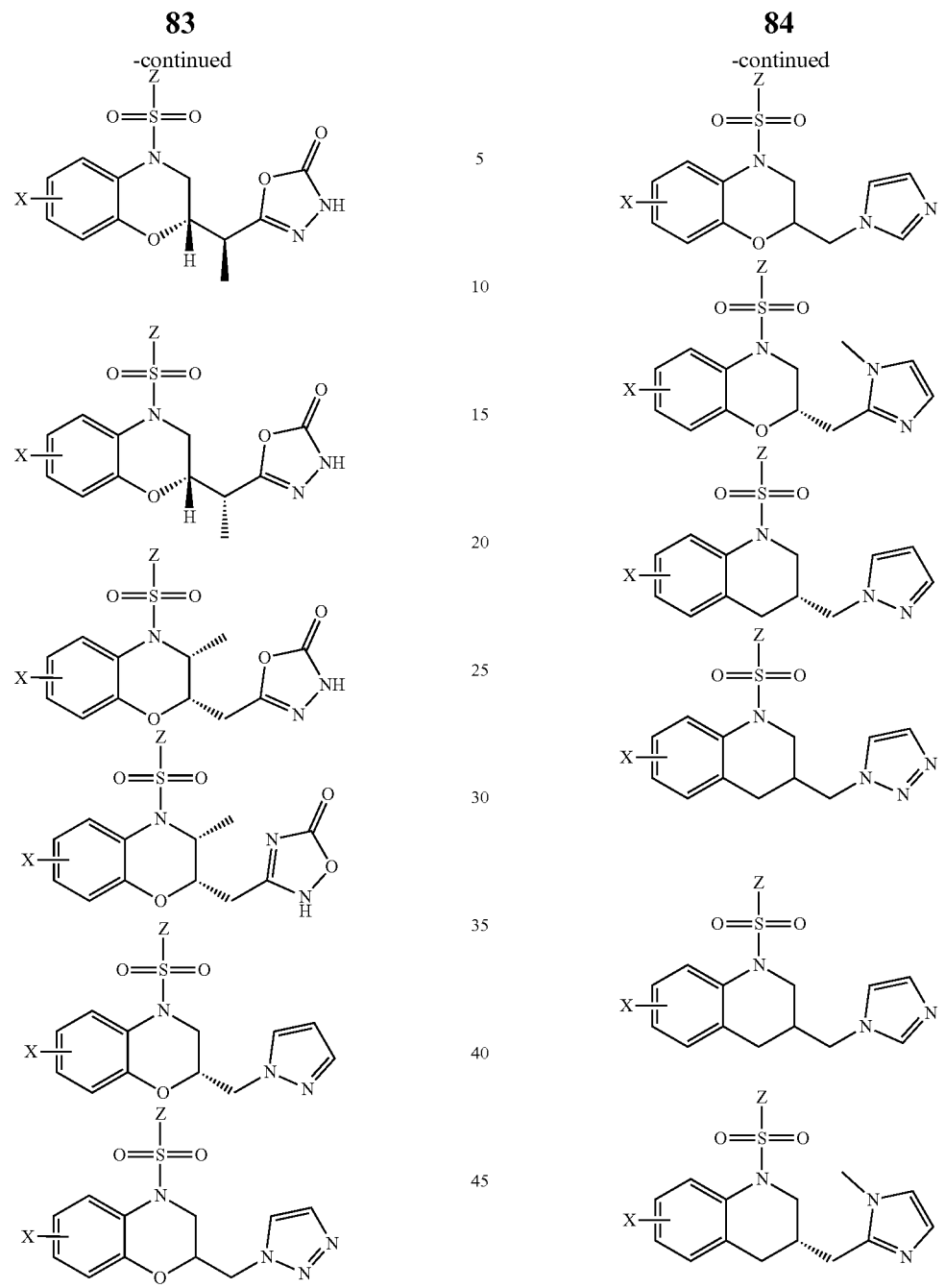
TABLE 2
| No. | X | Z |
|---|---|---|
| II-1 | | |
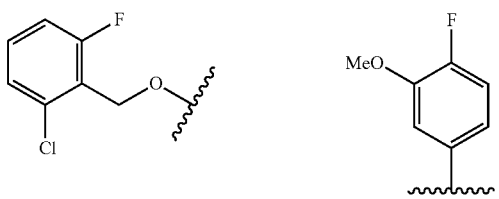

TABLE 2-continued
| No. | X | Z |
|---|---|---|
| II-2 | 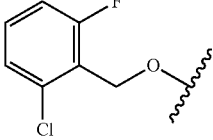 | 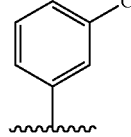 |
| II-3 | 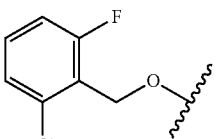 | 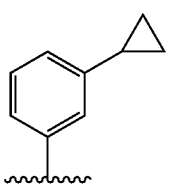 [SMILES: *c1cccc(C2CC2)c1] |
| II-4 | 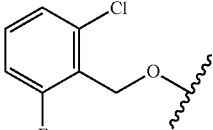 | 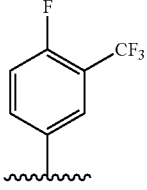 [SMILES: *c1ccc(F)c(C(F)(F)F)c1] |
| II-5 | 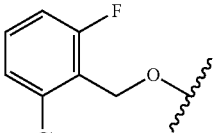 | 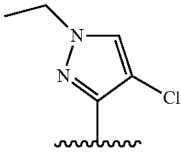 [SMILES: *c1nn(CC)cc1Cl] |
| II-6 | 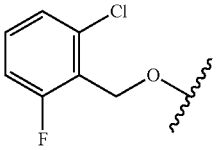 [SMILES: *OCc1c(F)cccc1Cl] | 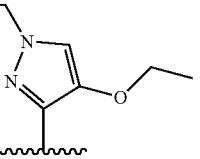 |
| II-7 | 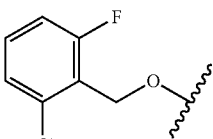 | 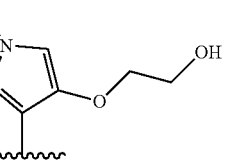 |
| II-8 | 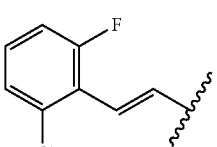 | 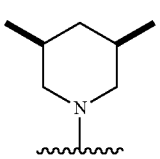 |
| II-9 | 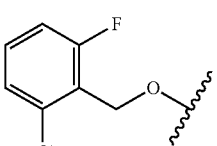 | 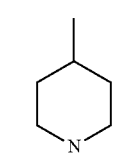 |
| II-10 | 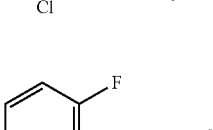 | 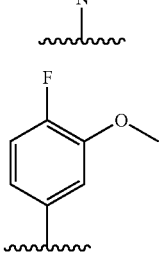 |

TABLE 2-continued
| No. | X | Z |
|---|---|---|
| II-11 | 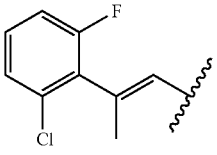 [SMILES: */C=C(\C)c1c(F)cccc1Cl] | 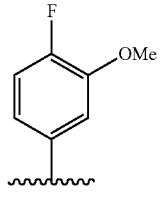 [SMILES: *c1ccc(F)c(OC)c1] |
| II-12 | 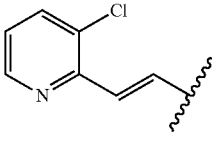 [SMILES: */C=C/c1ncccc1Cl] | 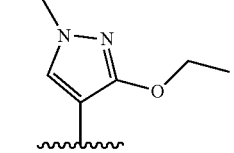 |
| II-13 | 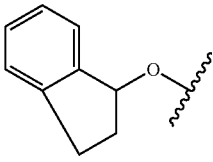 [SMILES: *OC1CCc2ccccc21] | 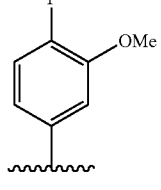 |
| II-14 | 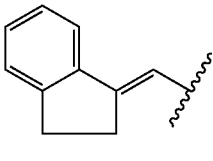 [SMILES: */C=C1\CCc2ccccc21] | 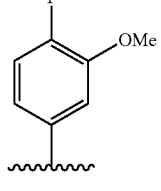 |
| II-15 | 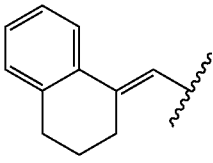 [SMILES: */C=C1\CCCc2ccccc21] | 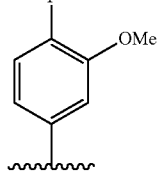 |
| II-16 | 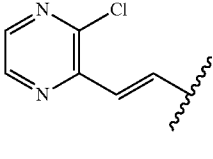 [SMILES: */C=C/c1nccnc1Cl] | 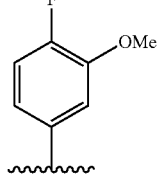 |
| II-17 | 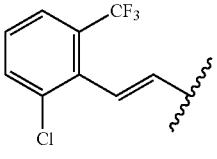 [SMILES: */C=C/c1c(Cl)cccc1C(F)(F)F] | 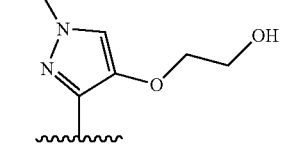 |
| II-18 | 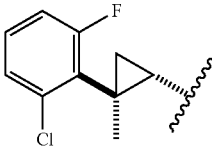 | 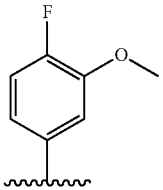 |

TABLE 2-continued

| No. | X | Z |
|---|---|---|
| II-19 | 2-chloro-6-fluorophenyl with ethyl-substituted vinyl linker | 4-fluoro-3-methoxyphenyl |
| II-20 | 2-chloro-6-fluorophenyl with CF₃-substituted vinyl linker | 4-fluoro-3-methoxyphenyl |
| II-21 | 3-chloropyridin-2-yl with vinyl linker | 1-(difluoromethyl)-3-(2-hydroxyethoxy)-1H-pyrazol-4-yl |
| II-22 | 2-chloro-6-fluorophenyl with methyl-substituted vinyl linker | 4-fluoro-3-methoxyphenyl |
| II-23 | 2-chloro-6-fluorophenyl with dimethyl-substituted vinyl linker | 4-fluoro-3-methoxyphenyl |
| II-24 | 1,2,3,4-tetrahydronaphthalen-2-yl | 4-fluoro-3-methoxyphenyl |
| II-25 | 4-chloropyridazin-3-yl with vinyl linker | 4-fluoro-3-methoxyphenyl |
| II-26 | 2-chlorophenyl with vinyl linker | 1-ethyl-4-(2-hydroxyethoxy)-1H-pyrazol-3-yl |

TABLE 2-continued

| No. | X | Z |
|---|---|---|
| II-27 | 2,6-dichlorophenyl-CH=CH- | 1-ethyl-4-(2-hydroxyethoxy)pyrazol-3-yl |
| II-28 | 2-chloro-6-fluoro-(1-CF₃)phenyl-C= | 4-fluoro-3-methoxyphenyl |
| II-29 | 2-fluoro-6-trifluoromethylphenyl-CH=CH- | 4-fluoro-3-methoxyphenyl |
| II-30 | 3-chloropyridin-2-yl-CH=CH- | 1-ethyl-3-(2-hydroxyethoxy)pyrazol-4-yl |
| II-31 | 3-chloropyridin-2-yl-CH=CH- | 3-(difluoromethoxy)phenyl |
| II-32 | 3-chloropyridin-2-yl-CH=CH- | 1-cyclopropyl-4-(2-hydroxyethoxy)pyrazol-3-yl |
| II-33 | 3-chloropyridin-2-yl-(1-CF₃)C= | 4-fluoro-3-methoxyphenyl |
| II-34 | 3-chloropyridin-2-yl-(1-CF₃)C= | 1-ethyl-3-(2-hydroxyethoxy)pyrazol-4-yl |

TABLE 2-continued

| No. | X | Z |
|---|---|---|
| II-35 | 4-chloroisoxazol-3-yl, vinyl linker | 4-fluoro-3-methoxyphenyl |
| II-36 | 3-chloropyridin-2-yl, vinyl linker | 1-ethyl-3-chloro-1H-pyrazol-4-yl |
| II-37 | 3-chloropyridin-2-yl, 1-methylvinyl linker | 1-ethyl-3-chloro-1H-pyrazol-4-yl |
| II-38 | 2-chloro-6-fluorophenyl, 1-methylvinyl linker | 5-chloro-2-(2-hydroxyethoxy)pyridin-3-yl |
| II-39 | 2-chloro-6-(trifluoromethyl)phenyl, vinyl linker | 5-(trifluoromethyl)-2-(2-hydroxyethoxy)pyridin-3-yl |
| II-40 | 2-chloro-6-fluorophenyl, 1-methylvinyl linker | 5-(trifluoromethyl)-2-ethoxypyridin-3-yl |
| II-41 | 2-chloro-6-fluorophenyl, 1-methylvinyl linker | 5-(trifluoromethyl)-2-(dimethylamino)pyridin-3-yl |
| II-42 | 3-chloropyridin-2-yl, 1-methylvinyl linker | 5-(trifluoromethyl)-2-(2-hydroxyethoxy)pyridin-3-yl |
| II-43 | 2-(trifluoromethyl)-6-chlorophenyl, vinyl linker | 5-(trifluoromethyl)-2-(2-hydroxyethoxy)pyridin-3-yl |

TABLE 2-continued

| No. | X | Z |
|---|---|---|
| II-44 | 2-Cl, 6-F phenyl with C(Me)=CH- | 5-CF₃, 2-(OCH₂CH₂OH) pyridin-3-yl |
| II-45 | 2-Cl, 6-F phenyl with C(Me)=CH- | 6-CF₃, 3-OEt pyridazin-4-yl |
| II-46 | 2-Cl, 6-F phenyl with C(Me)=CH- | 5-cyclopropyl, 2-OEt pyridin-3-yl |
| II-47 | 2-SMe, 6-F phenyl with C(Me)=CH- | 4-F, 3-OMe phenyl |
| II-48 | 2-Et, 6-Cl phenyl with C(Me)=CH- | 4-F, 3-Me phenyl |
| II-49 | 2-Cl, 6-CF₃ phenyl with CH=CH- | 6-OMe pyridin-3-yl |
| II-50 | 3-Cl pyridin-2-yl with C(Me)=CH- | 2-Cl-5,6,7,8-tetrahydro-[1,2,4]triazolo[1,5-a]pyridin-3-yl |
| II-51 | 2-Cl, 6-F phenyl with C(Me)=CH- | 1-methyl-1H-imidazol-4-yl |

TABLE 2-continued

| No. | X | Z |
|---|---|---|
| II-52 | 2-Cl, 6-CF3 phenyl-CH=CH- | 1-methyl-imidazol-4-yl |
| II-53 | 2-Cl, 6-F phenyl-CH2-O- | 5-methyl-pyridin-3-yl |
| II-54 | 2-Cl, 6-CF3 phenyl-CH=CH- | 5-methyl-pyridin-3-yl |
| II-55 | 2-CF3, 6-Cl phenyl-CH=CH- | 1-isopropyl-imidazol-4-yl |
| II-56 | 2-F, 6-Cl phenyl-C(CH3)=CH- | 1-isopropyl-imidazol-4-yl |
| II-57 | 2-F, 6-Cl phenyl-C(CH3)=CH- | oxazol-4-yl |
| II-58 | 2-CF3, 6-Cl phenyl-CH=CH- | oxazol-4-yl |
| II-59 | 2-Cl, 6-F phenyl-CH2-O- | oxazol-4-yl |
| II-60 | 2-F, 6-Cl phenyl-C(CH3)=CH- | 2-ethoxy-5,6,7,8-tetrahydroimidazo[1,2-a]pyridin-3-yl |

TABLE 2-continued

| No. | X | Z |
|---|---|---|
| II-61 | 2-chloro-6-fluorobenzyloxy | 1-methyl-1H-pyrrol-3-yl |
| II-62 | 1-(2-chloro-6-fluorophenyl)prop-1-en-2-yl | 6-chloroimidazo[2,1-b]thiazol-5-yl |
| II-63 | 1-(2-chloro-6-fluorophenyl)prop-1-en-2-yl | 1-isopropyl-1H-pyrrol-3-yl |
| II-64 | 1-(2-chloro-6-fluorophenyl)prop-1-en-2-yl | 2-(2-hydroxyethoxy)imidazo[1,2-a]pyridin-3-yl |
| II-65 | 1-(2-chloro-6-fluorophenyl)prop-1-en-2-yl | 2-ethoxy-5,6-dihydro-4H-pyrrolo[1,2-b]pyrazol-3-yl |
| II-66 | 1-(2-chloro-6-fluorophenyl)prop-1-en-2-yl | 2-(2-hydroxyethoxy)pyrazolo[1,5-a]pyridin-3-yl |
| II-67 | 1-(2-chloro-6-fluorophenyl)prop-1-en-2-yl | 2-(2-hydroxyethoxy)-4,5,6,7-tetrahydropyrazolo[1,5-a]pyridin-3-yl |
| II-68 | (E)-2-(4-chloroisoxazol-3-yl)vinyl | 3,5-bis(trifluoromethyl)phenyl (3-CF3, 5-CF3) |
| II-69 | (E)-2-(5-chlorothiazol-4-yl)vinyl | 3,5-bis(trifluoromethyl)phenyl |

TABLE 2-continued

| No. | X | Z |
|---|---|---|
| II-70 | 5-chloro-oxazol-4-yl vinyl | 3-(trifluoromethyl)phenyl |
| II-71 | 2-chloro-6-fluorophenyl vinyl | 6-ethoxyimidazo[2,1-b]thiazol-5-yl |
| II-72 | 4-chloro-isoxazol-5-yl vinyl | 3-(trifluoromethyl)phenyl |
| II-73 | 2-chloro-6-fluorophenyl 1-methylvinyl | 6-(2-hydroxyethoxy)imidazo[2,1-b]thiazol-5-yl |
| II-74 | 3-chloropyrazin-2-yl vinyl | 3-(trifluoromethyl)phenyl |
| II-75 | 2-chloro-6-fluorophenyl vinyl | 3-(trifluoromethyl)phenyl |
| II-76 | 2-chloro-6-fluorophenyl ethyl | 3-(trifluoromethyl)phenyl |
| II-77 | 2,6-dichlorobenzyloxy | 3-fluoro-5-(trifluoromethyl)phenyl |
| II-78 | 4-chloropyridazin-3-yl vinyl | 3-fluoro-5-(trifluoromethyl)phenyl |

Methods for preparing compounds described herein are illustrated in the following synthetic Schemes. The Schemes are given for the purpose of illustrating the invention, and are not intended to limit the scope or spirit of the invention. Starting materials shown in the Schemes can be obtained from commercial sources or be prepared based on procedures described in the literature.

The synthetic route illustrated in Scheme 1 is a general method for preparing substituted 1,2,3,4-tetrahydroquinoline compounds F and G. Reaction of aniline A with diethyl 2-(ethoxymethylene)malonate B followed by thermally induced cyclization with acid affords the substituted ethyl 4-oxo-1,4-dihydroquinoline-3-carboxylate C. Treatment of compound C with phosphoryl trichloride affords the ethyl 4-chloroquinoline-3-carboxylate D. Reduction of compound D with borane in pyridine (or by transition metal-mediated hydrogenation) affords the ethyl 1,2,3,4-tetrahydroquinoline-3-carboxylate E, which can be reacted with a sulfonyl chloride or sulfamoyl chloride to provide the substituted sulfonamide-tetrahydroquinoline F. The ester group of F can be hydrolyzed to afford the substituted 1,2,3,4-tetrahydroquinoline-3-carboxylic acid G. Compound G can be obtained in enanteriomerically enriched form by chiral separation techniques described in the literature for carboxylic acids.

The reaction procedures in Scheme 1 are contemplated to be amenable to preparing a wide variety of 3-substituted 1,2,3,4-tetrahydroquinoline compounds having different substituents at the R, X, and 3-positions. For example, numerous substituted anilines are known in the literature and/or are commercially available or readily prepared from nitroaromatic compounds. Furthermore, if a functional group on a molecule would not be amenable to a reaction condition described in Scheme 1, it is contemplated that the functional group can first be protected using standard protecting group chemistry and strategies, and then the protecting group is removed after completing the desired synthetic transformation. See, for example, Greene, T. W.; Wuts, P. G. M. *Protective Groups in Organic Synthesis*, 2$^{nd}$ ed.; Wiley: New York, 1991, for further description of protecting chemistry and strategies. For example, if X is OMe, the methyl moiety can be removed from F with boron tribromide to afford a 6- or 7-hydroxytetrahydroquinoline. The resulting compound can be subjected to either alkylation with halides or with a Mitsunobu reaction to afford a wide variety of OR groups as X. In other embodiments, the —OH may be converted to triflate and be subjected to Pd-mediated catalyzed reactions to afford a wide variety of carbon linked substituents. In certain other embodiments, the ester group in compound F can be converted to another functional group using standard functional group manipulation procedures known in the art. See, for example, "Comprehensive Organic Synthesis" (B. M. Trost & I. Fleming, eds., 1991-1992).

SCHEME 1.

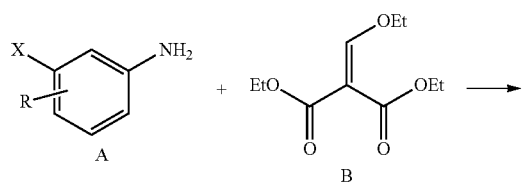

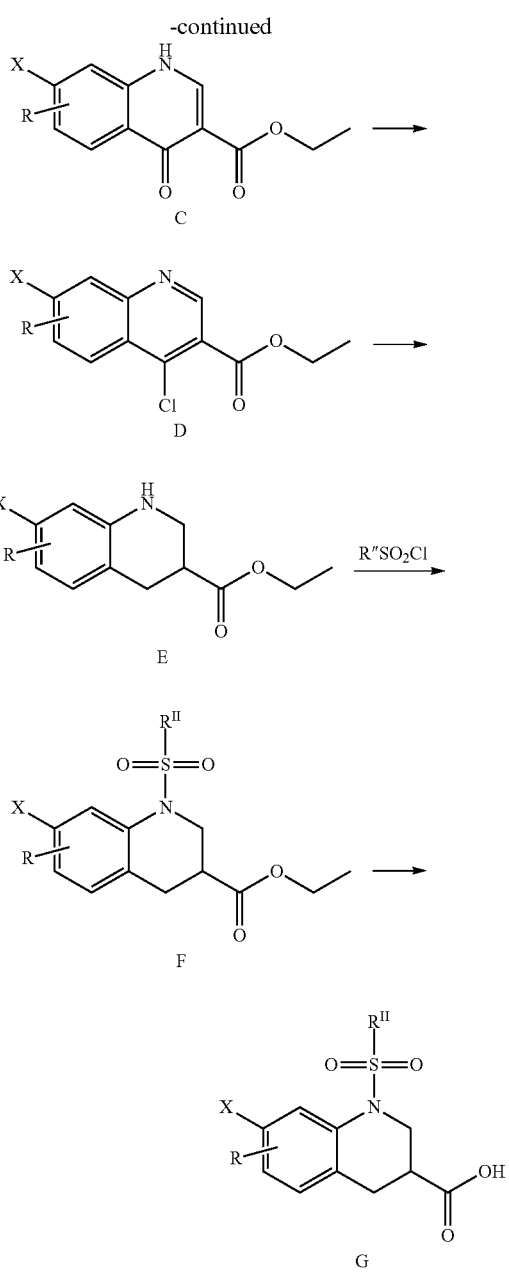

R may be, for example, hydrogen or a substituent, such as methyl or halogen;
X may be for example an O-alkylene-cycloalkyl; and
R″ may be an aromatic or heteroaromatic substituent.

Scheme 2 illustrates an alternative general method for preparing substituted 1,2,3,4-tetrahydroquinoline compound F. Condensation of a substituted 2-nitrobenzaldehyde A with diethyl malonate affords α-β-unsaturated diester B. Reduction of B with sodium borohydride affords diester C. Reduction of the nitro moiety of C with either metal-mediated hydrogenation or dissolving metal reduction procedures (e.g., Zn/AcOH or Fe in HCl) affords 2-oxo-1,2,3,4-tetrahydroquinoline-3-carboxylate D. Selective reduction of the 2-keto moiety of D affords ethyl 1,2,3,4-tetrahydroquinoline-3-carboxylate E. The ester group in E can be converted into additional functional groups via the methodology described above in connection with Scheme 1.

SCHEME 2.

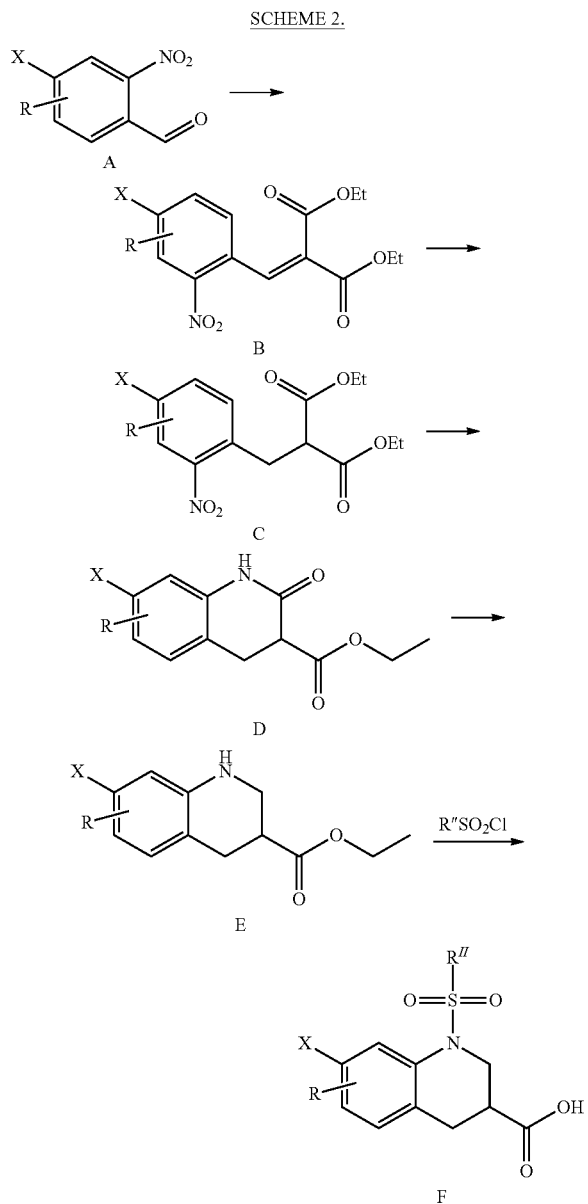

R may be, for example, hydrogen or a substituent, such as methyl or halogen;
X may be for example an O-alkylene-cycloalkyl; and
R" may be an aromatic or heteroaromatic substituent.

Scheme 3 illustrates a general method for preparing substituted (R)-2-alkyl-1-(aryl or heteroaryl sulfonyl)-1,2-dihydroquinoline-3-carboxylic acids D. A tandem Michael-aldol dehydration of a substituted N-(2-formylphenyl)(aryl or heteroaryl)sulfonamide A with a 3-substituted acrylaldehyde B catalyzed by (S)-diphenylprolinol triethyl silyl ether (see, for example, W. Wang et al. in *Org. Lett.* 9: 965-968, 2007; and A. Cordova et al. in *Adv. Synth. Catal.* 349: 827-832, 2007) affords substituted (R)-2-alkyl-1-(aryl or heteroaryl sulfonyl)-1,2-dihydroquinoline-3-carbaldehyde C. Oxidation (see, for example, Y. K. Bae et al. in *Synlett.* 24: 1848-1850, 2013; and S. J. Williams et al. in WO 2011/047432) of the aldehyde in C affords substituted (R)-2-alkyl-1-(aryl or heteroaryl sulfonyl)-1,2-dihydroquinoline-3-carboxylic acid D.

SCHEME 3.

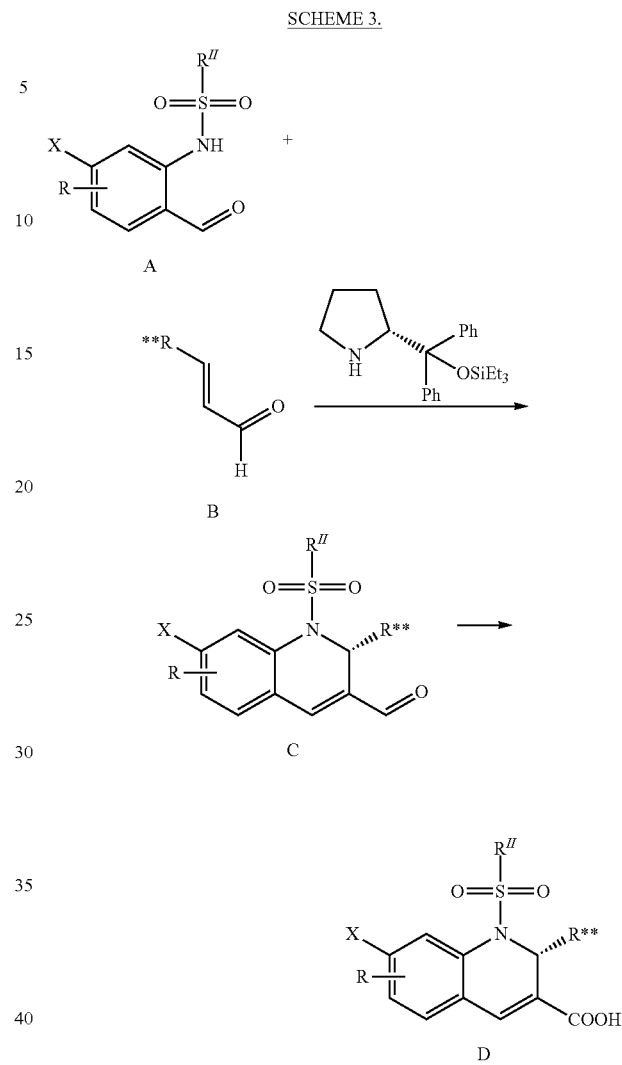

Scheme 4 illustrates a general method for preparing substituted (R)-(2-alkyl-1-(aryl or heteroaryl sulfonyl)-1,2-dihydroquinolin-3-yl)alkyl alcohol B. Reduction of aldehydein compound A with sodium borohydride in the presence of cerium (III) chloride (see, for example, Y. Hamada et al. in *Tetrahedron* 64: 11568-11579, 2008) yields compound B where R' is hydrogen. Addition of an alkyl magnesium or alkyl lithium halide in the presence of cerium (III) chloride affords the secondary alcohol B where R' is a lower alkyl (i.e., $C_{1-6}$ alkyl).

SCHEME 4.

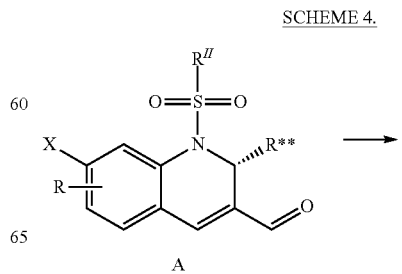

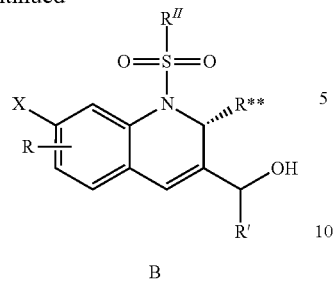

B

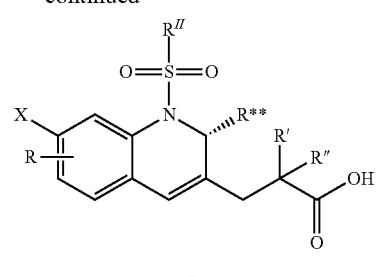

D

Scheme 5 illustrates a general procedure for preparing substituted (R)-3-(2-alkyl-1-(aryl or heteroaryl sulfonyl)-1,2-dihydroquinolin-3-yl)propanoic acid D. Treatment of allylic alcohol A with methane sulfonyl halide (or a tosyl halide or triflic anhydride may be used to activate the hydroxyl group, and alternatively the hydroxyl group may be converted to an allylic halide by methods known in the literature) affords compound B where the allylic hydroxyl is activated with a leaving group. When R' is the same as R", an ester of an appropriate substituted (or unsubstituted) acetic acid is converted to an anion with an appropriate base (e.g., LDA, lithium hexamethyldisilazide, etc.) and is alkylated with B to yield compound C. When R' is not the same as R", various chiral enolate chemistry methods from the literature may be used to provide a chiral acid. For example, the anion of an acyloxazolidinone may be be utilized. Removal of the alkyl ester of the chiral auxiliary with an appropriate base (e.g., potassium carbonate, lithium hydroxide in the presence of peroxide) or an acid (for tert-butyl esters) affords (R)-3-(2-alkyl-1-(aryl or heteroaryl sulfonyl)-1,2-dihydroquinolin-3-yl)propanoic acid D.

Scheme 6 illustrates a general procedure for preparing substituted (R)-(2-alkyl-1-(aryl or heteroarylsulfonyl)-1,2-dihydroquinolin-3-yl)alkylamines C and D. Mitsunobu reaction (see, for example, D. L. Hughes et al. in *Organic Reactions* 42: 1992) of allylic alcohol A with phthalamide affords substituted phthamide B. Treatment of compound B with hydrazine in an appropriate solvent (for example, ethanol or isopropanol; see, for example, H. Itoh et al. in *J. Org. Chem.* 43: 2320, 1978) affords (R)-(2-alkyl-1-(aryl or heteroarylsulfonyl)-1,2-dihydroquinolin-3-yl)alkylamine C. Reductive amination of the amine group in compound C (see, for example, C. A. Maryanoff et al. in *J. Org. Chem.* 61: 3849-3860, 1996) affords (R)-(2-alkyl-1-(aryl or heteroarylsulfonyl)-1,2-dihydroquinolin-3-yl)alkylamine D.

SCHEME 5.

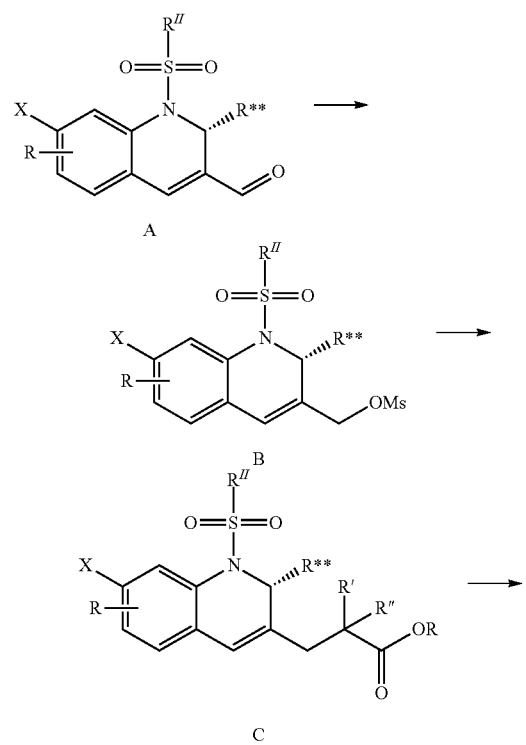

SCHEME 6.

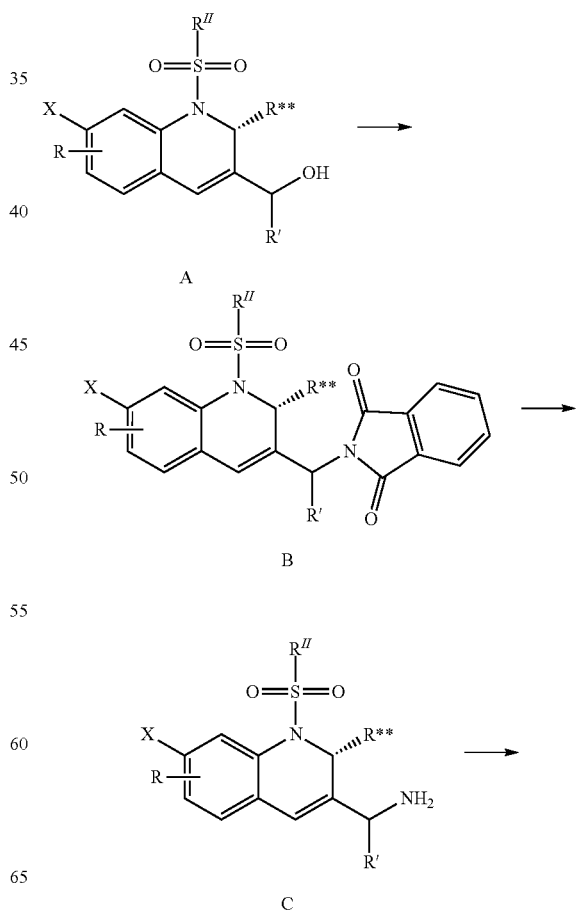

-continued

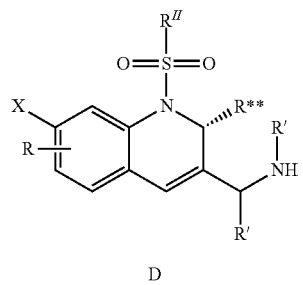

D

Scheme 7 illustrates a general procedure for preparing substituted (R)—N-((2-alkyl-1-(aryl or heteroarylsulfonyl)-1,2-dihydroquinolin-3-yl)alkyl)amide B, substituted (R)—N-((2-alkyl-1-(aryl or heteroarylsulfonyl)-1,2-dihydroquinolin-3-yl)alkyl)carbamate C, substituted (R)—N-((2-alkyl-1-(aryl or heteroarylsulfonyl)-1,2-dihydroquinolin-3-yl)alkyl)urea D (or substituted (R)—N-((2-alkyl-1-(aryl or heteroarylsulfonyl)-1,2-dihydroquinolin-3-yl)alkyl)thiourea), substituted (R)—N-((2-alkyl-1-(aryl or heteroarylsulfonyl)-1,2-dihydroquinolin-3-yl)alkyl)sulfonamide E, and substituted (R)—N-((2-alkyl-1-(aryl or heteroarylsulfonyl)-1,2-dihydroquinolin-3-yl)alkyl)sulfamide F. Reaction of substituted (R)-(2-alkyl-1-(aryl or heteroarylsulfonyl)-1,2-dihydroquinolin-3-yl)alkylamine A with an appropriate base and an acyl halide affords amide B. Alternatively, a coupling agent (e.g., a carbodiimide, PyBOP, treatment of the acid with a chloroformate to make a mixed anhydride, etc.) may be utilized to couple a wide variety of acids to form amide B. The amine A may also be coupled with a choroformate to afford compound C; with an isocyanate, carbamoyl choride, or isothiocyanate to afford D; with a sulfonyl halide to afford E; or with a sulfamoyl halide to afford F.

SCHEME 7.

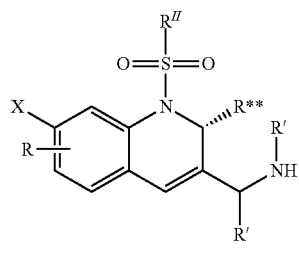

A

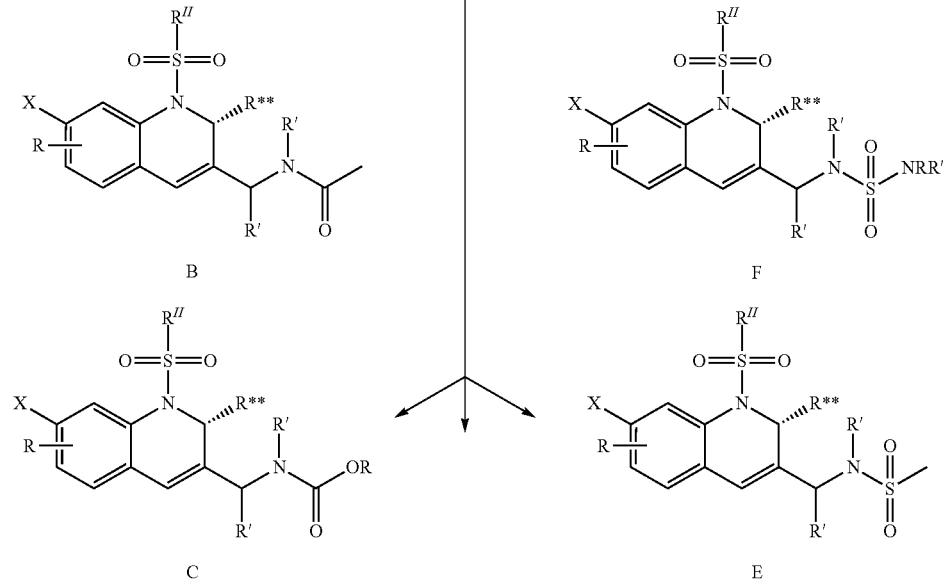

-continued

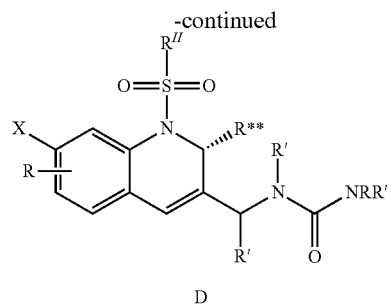

D

Scheme 8 illustrates a general method of preparing substituted cis-3-substituted-2-alkyl-1-(aryl or heteroarylsulfonyl)-1,2,3,4-tetrahydroquinoline B. Hydrogenation of the substituted (R)-2-alkyl-1-(aryl or heteroarylsulfonyl)-1,2-dihydroquinoline A prepared via the above methods in the presence of a catalyst affords the substituted cis-3-substituted-2-alkyl-1-(aryl or heteroarylsulfonyl)-1,2,3,4-tetrahydroquinoline B. The choice of the catalyst depends on the substituents X and R. In cases where dehalogenation or reductive removal of benzylic heteroatom is not an issue, Pd or Pt on carbon may be utilized. In other cases, Rh and/or a heterogeneous catalyst which does not reduce these functionalities is more appropriate per literature procedures for such reductions.

SCHEME 8.

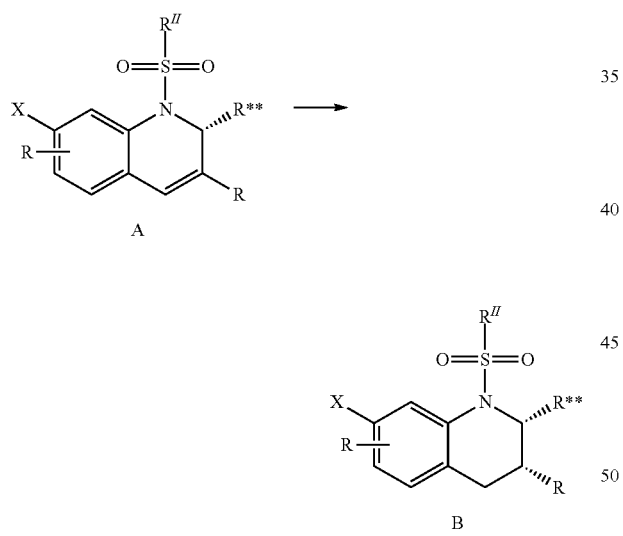

Scheme 9 illustrates an alternative general method to prepare substituted 3-substituted-1-(aryl or heteroarylsulfonyl)-1,2,3,4-tetrahydroquinoline E. A tandem reaction combining radical and ionic cyclization of halogenated aniline A and a substituted acrylate B affords substituted 3,4-dihydroquinolin-2-one C (see, for example, N. Jiao et al. in *Tetrahedron* 65: 1982-1987, 2009). Reduction of the amide group in C with a hydride (e.g., a borane or lithium aluminum hydride) affords substituted 1,2,3,4-tetrahydroquinoline D. Sulfonylation of D with a sulfonyl halide yields the substituted 3-substituted-1-(aryl or heteroarylsulfonyl)-1,2,3,4-tetrahydroquinoline E.

SCHEME 9.

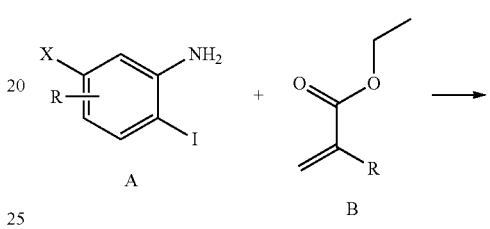

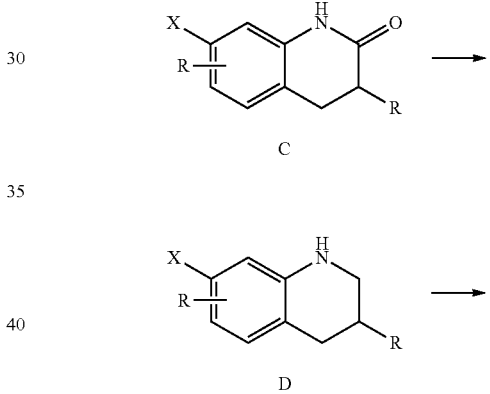

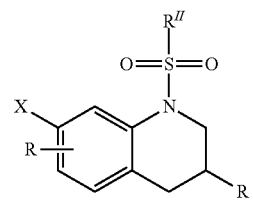

Scheme 10 illustrates an alternative general method to prepare chiral substituted 3-substituted-1-(aryl or heteroarylsulfonyl)-1,2,3,4-tetrahydroquinolines. Alkylation of an acylated oxazolidinedione B with 2-nitrobenzylic halide A affords with high diastereomeric excess the 3-arylpropionamide C. Reduction of C with dissolving metal conditions affords chiral substituted 3,4-dihydroquinolin-2-one D which can be elaborated to the substituted 3-substituted-1-(aryl or heteroarylsulfonyl)-1,2,3,4-tetrahydroquinolines E and F based on procedures described above.

SCHEME 10.

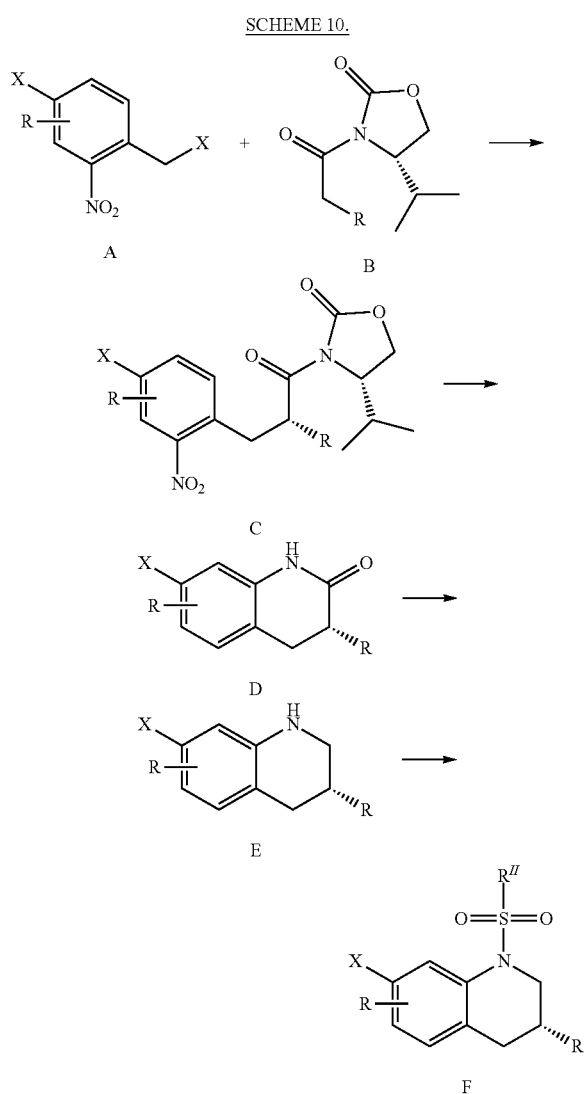

Scheme 11 illustrates an alternative general method of preparing substituted cis-2,3-disubstituted-1-(aryl or heteroarylsulfonyl)-1,2,3,4-tetrahydroquinoline E. Alkylation of (3-ketoester B with 2-nitrobenzylic halide A affords substituted 2-(2-nitrobenzyl)-3-ketoester C. Reduction of C affords substituted ethyl cis-2-alkyl-1,2,3,4-tetrahydroquinoline-3-carboxylate D (see, for example, R. A. Bunce et al. in *J. Heterocyclic Chem.* 44: 1059-1064, 2007). This material can be sulfonylated as described above to afford the substituted cis-2,3-disubstituted-1-(aryl or heteroarylsulfonyl)-1,2,3,4-tetrahydroquinoline E.

SCHEME 11.

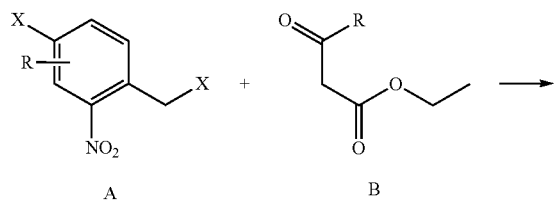

Scheme 12 illustrates a general method of preparing chiral substituted 1-(aryl or hetereoarylsulfonyl)-1,2,3,4-tetrahydroquinoline E substituted at the 3-position with an oxygen bearing group. Wittig reaction of 2-nitroaldehyde A forms α,β-unsaturated ester B, which is subjected to Os-catalyzed asymmetric dihydroxylation with the (DHQ)$_2$-PHAL ligand (see, for example, K. B. Sharpless et al. in *Chem. Rev.* 94: 2483-2547, 1994) followed by treatment of the diol with thionyl chloride to form cyclic sulfite C (see, for example, K. B. Sharpless et al. in *J. Am. Chem. Soc.* 110: 7538-7539, 1988). Sulfite C undergoes a one-pot cobalt chloride catalyzed reductive cyclization with sodium borohydride (see, for example, A. Sudalai et al. in *Organic Letters* 11: 803-806, 2009) to form the substituted chiral 3-hydroxy-1,2,3,4-tetrahydroquinoline D. This material is sulfonylated as described above to afford chiral substituted 1-(aryl or hetereoarylsulfonyl)-3-hydroxy-1,2,3,4-tetrahydroquinoline E. The pendant hydroxyl may be alkylated (for example with 2-chloroacetic acid). When using a different suitable ligand in the chiral osmylation, the enantiomers of C and then D and E can be produced. The hydroxyl group in compound E can be mesylated and displaced with azide, and reduced to afford access to a wide variety of chiral 3-aminosubsituted-1,2,3,4-tetrahydroquinolines. The opposite chirality at the hydroxyl position is available using the analogous sequence replacing with a suitable ligand for the chiral osmylation, may be mesylated and displaced with azide, which can be reduced to afford access to a wide variety of chiral 3-amino-subsituted-1,2,3,4-tetrahydroquinolines.

SCHEME 12.

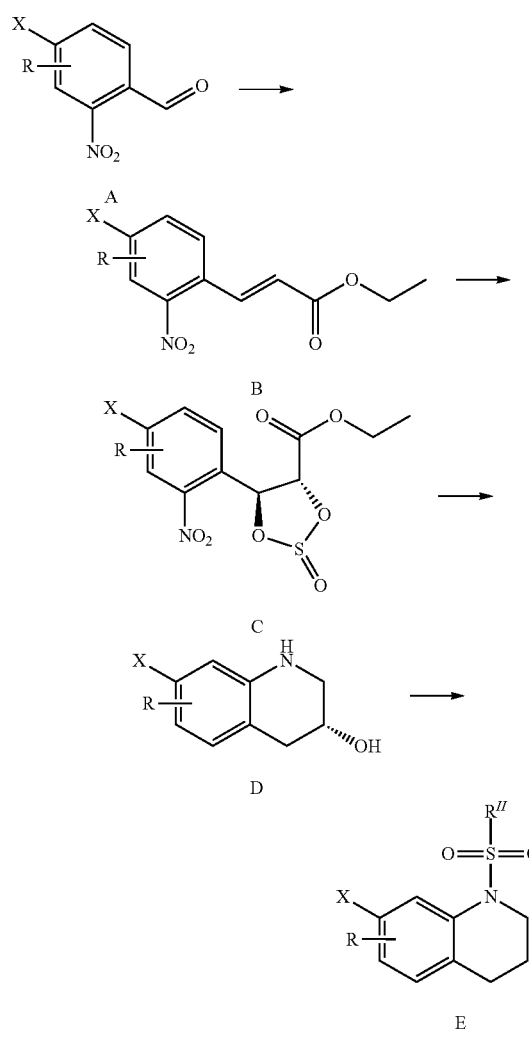

Scheme 13 illustrates a general method of forming substituted (E)-7-(2-aryl-alken-1-en-1-yl)-1-(aryl or heteroarylsulfonyl)-1,2,3,4-tetrahydroquinolines, substituted (E)-6-(2-aryl-alken-1-en-1-yl)-4-(aryl or heteroarylsulfonyl)-3,4-dihydro-2H-benzo[b][1,4]oxazines, and substituted (E)-N-alkyl-N-(3-(2-aryl-alken-1-en-1-yl)phenyl)(arene or heteroarene)sulfonamides. Copper(I)-catalyzed carboboration (see, for example, R. Alfaro et al. in *J. Am. Chem. Soc.* 134: 15165-15168, 2012) of an aryl-alkyne affords tri- and tetrasubstitued vinylboronates that are suitable for Pd-mediated stereoselective addition to the appropriate 7-halo or 7-triflate-1,2,3,4-tetrahydroquinoline (A=CRR'), or 6-halo or 6-triflate-3,4-dihydro-2H-benzo[b][1,4]oxazine (A=O) to afford the final product.

SCHEME 13.

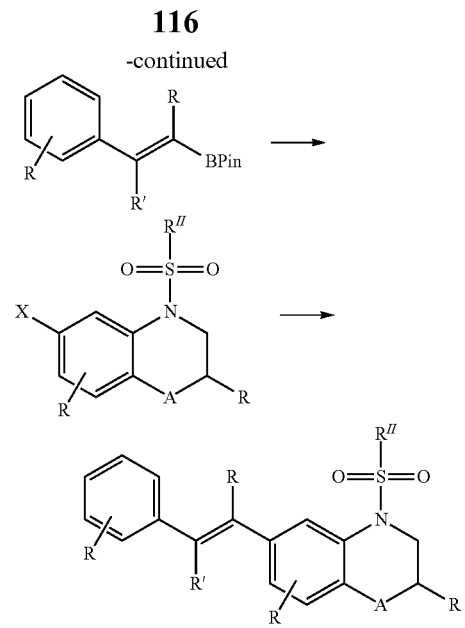

Scheme 14 illustrates a general method of forming chiral substituted 7-cyclopropyl-1-(aryl or heteroarylsulfonyl)-1,2,3,4-tetrahydroquinolines, 6-cyclopropyl-4-(aryl or heteroarylsulfonyl)-3,4-dihydro-2H-benzo[b][1,4]oxazines, or N-(3-cyclopropylphenyl)-N-alkyl(aryl or heteroaryl) sulfonamides C. A chiral cyclopropylboronic acid A (see, for example, M.-Z. Deng et al. in *Angew. Chem. Ed.* 37: 2845-2847, 1998) is added to the appropriate haloarene or triflate B (X is halogen or triflate) to afford compound C.

SCHEME 14.

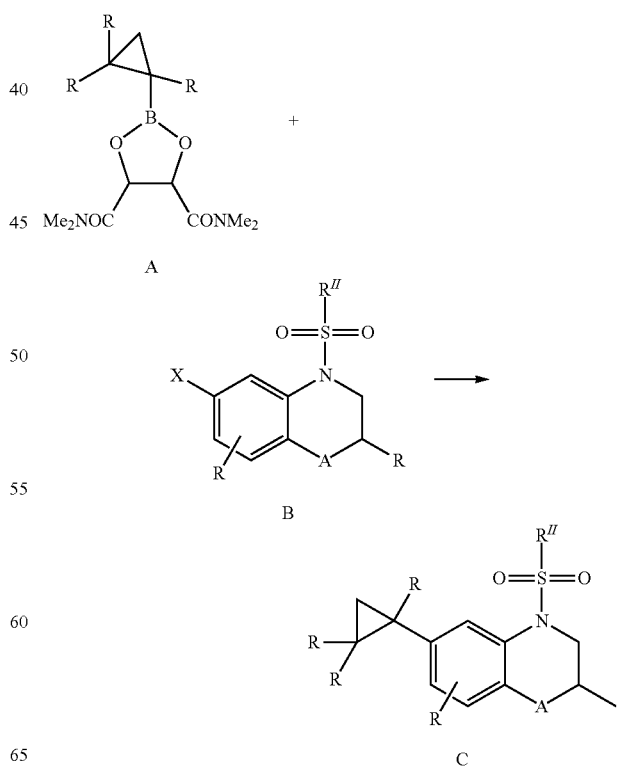

Scheme 15 illustrates a general method for preparing various substituted benzoxazine compounds. Reaction of aryl sulfonamide A with an epoxide provides benzoxazine B.

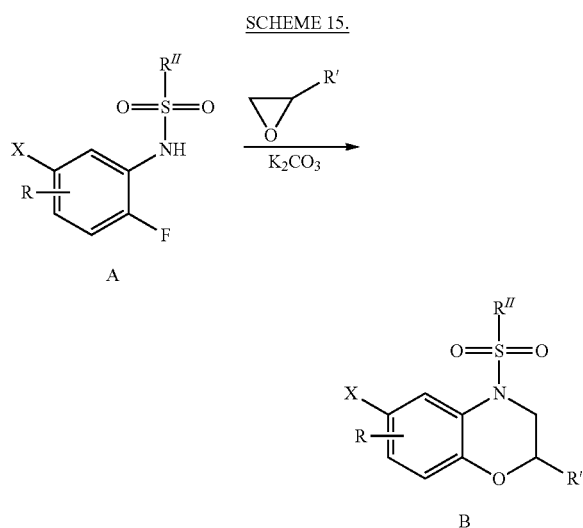

Scheme 16 illustrates another general method for preparing various substituted benzoxazine compounds. Reaction of 2-fluoro-nitrobenzene A with 2-hydroxyester B provides 2-O-arylacetic acid ester C. Reduction of the nitro moiety in C with a dissolving metal in an acid forms substituted benzoxazinone D. The amide group in benzoxazinone D can be reduced using, for example, lithium aluminum hydride (LiAlH₄) or a borane to provide benzoxazine E, which is treated with a sulfonyl halide and base to afford sulfonylated benzoxazine F.

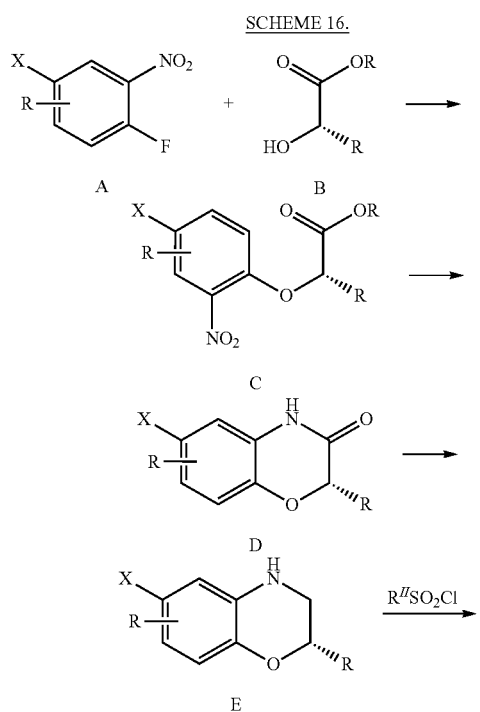

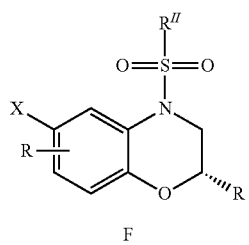

Scheme 17 illustrates a more specific example of a synthetic procedure generally illustrated in Scheme 16. Upon treatment with sodium nitrite in aqueous hydrochloric acid, D-glutamic acid A is cyclized to the carboxylic acid B. The carboxylic acid can be reduced to the alcohol with borane, and then the resulting hydroxyl group is protected (e.g., using a silyl or trityl moiety) to afford lactone C. Treatment of the lactone with LDA or LHDMS or another suitable base, followed by alkylation with an alkyl halide or alkyl triflate, affords diastereoselectively lactone D where Ry=H, and Rx is the alkyl moiety from the alkyl halide equivalent.

The other diastereomer of D where Ry and Rx are reversed can be prepared by treating lactone C with LDA and selectively protonating the enolate with saturated sodium sulfate which acts effectively as a very hindered proton source (see, for example, S. Takano et al. in *Chem Lett* 733 1982). This enolate can also be alkylated selectively with a second alkyl halide such that the product affords Rx as the second alkyl halide source and Ry is from the first alkylation reaction.

Deprotection of the ether in compound D, followed by oxidation of the resulting hydroxyl group affords substituted carboxylic acid E. Treatment of E with acid in methanol affords substituted diester F, which when treated with a 2-nitrophenol affords substituted ester G. Cyclization which occurs during a dissolving metal reduction of G affords the substituted benzoxazinone H. The amide group in benzoxazinone H can be selectively reduced using a borane to provide benzoxazine I, which is treated with a sulfonyl halide and base to afford the substituted sulfonylated benzoxazine J. If desired, the ester group in J can be converted to a heterocycle using methods illustrated herein, such as in Schemes below.

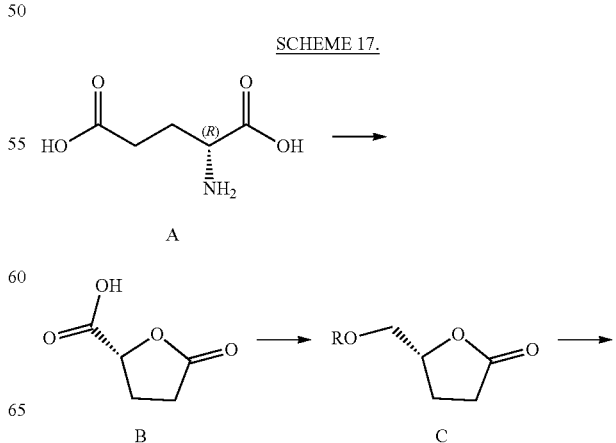

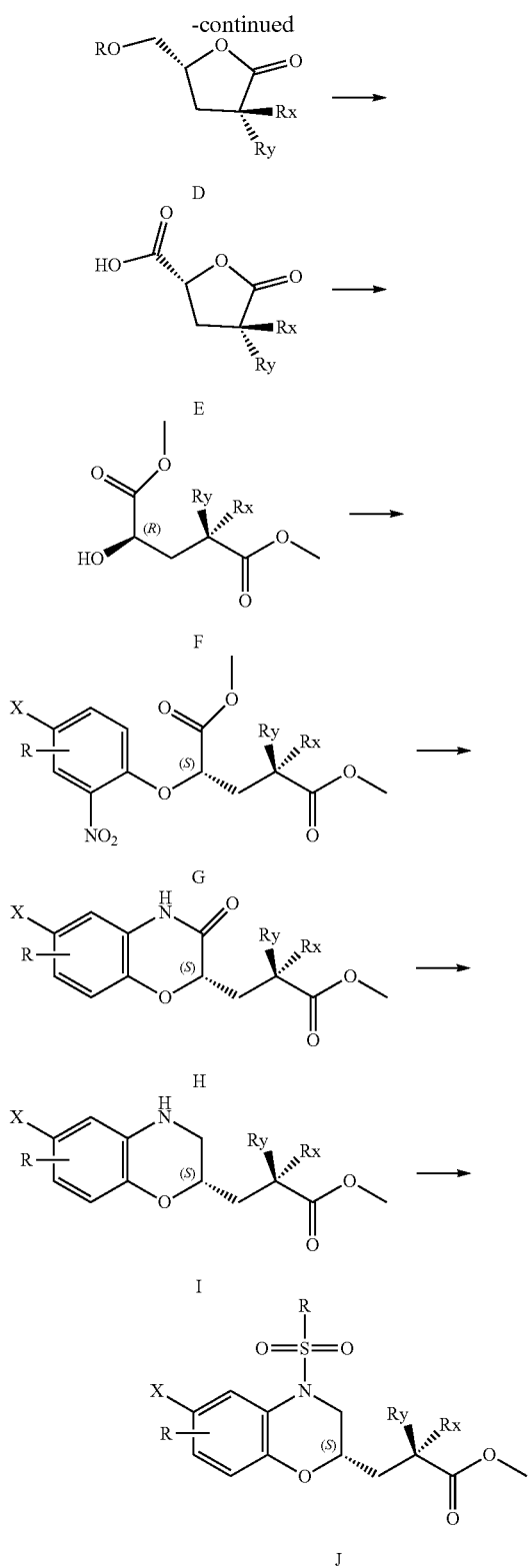

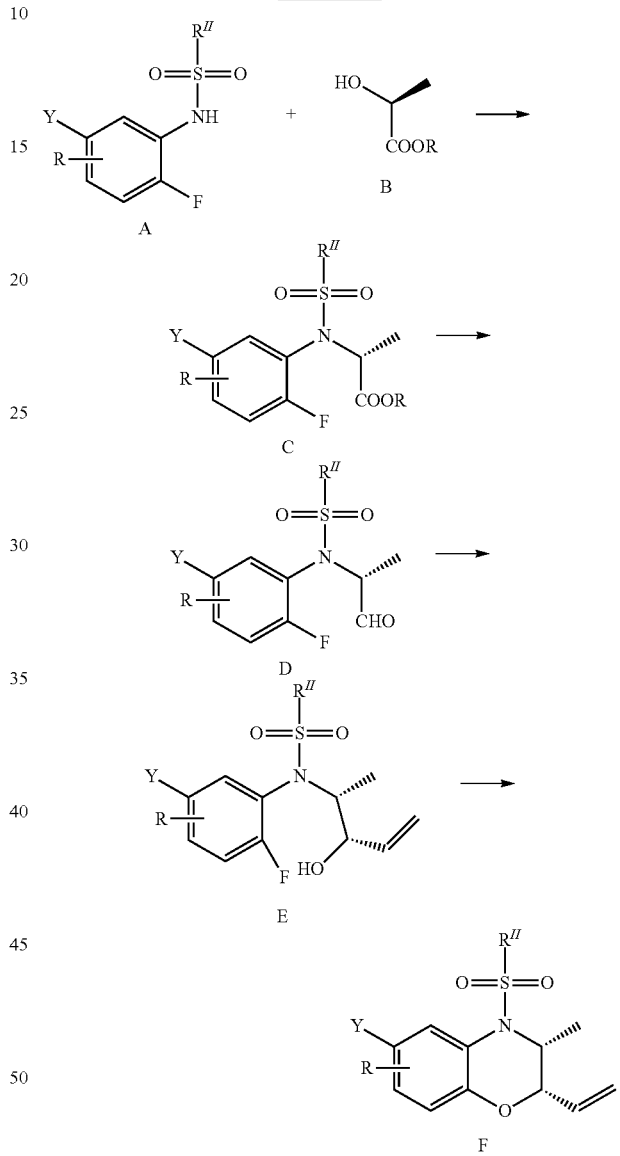

Treatment of compound E with base affords benzoxazine F. The vinyl moiety in F may be converted to other alkenes via olefin metathesis chemistry, and the resulting alkenes can be reduced to substituted alkanes, or can be oxidized to a hydroxyl group, a diol, a carboxylic acid, or other function group useful for the introduction of a heterocyclic group.

SCHEME 18.

Scheme 18 illustrates a general method for preparing various substituted benzoxazine compounds. Mitsunobu addition of sulfonamide A to chiral α-hydroxyester B affords O-aryl ether C. Treatment of compound C with DIBAL affords aldehyde D, to which vinyl magnesium bromide adds to form the anti-aminoalcohol E (see, for example, D. Gryko et al. in *Tetrahedron: Asymmetry* 8: 4059-4067, 1997).

Scheme 19 illustrates a general method for preparing chiral benzoxazines with a heterocycle as a component of $R^{2A}$. Literature reports by Link and Corey demonstrate that trichloroketones can be reliably stereospecifically reduced with a proline-based catalyst and boranes and then be displaced by phenols to afford substituted 2-phenoxycarboxylic acids (see, for example, *Tetrahedron Lett* 33: 3431-3434, 1992). There are a variety of methods to obtain trichloroketones (see for example, *Tetrahedron Lett* 33: 3435-3438, 1992), one of which is illustrated below. Treatment of an aldehyde A with trichloroacetic acid and sodium trichloroacetate in DMF affords racemic trichlorocarbinol B which can be oxidized with a chromate to afford trichloroketone C. After stereospecific reduction the chiral trichlorocarbinol D, in the presence of hydroxide, a substituted 2-nitrophenol opens a 1,1-dichloroepoxide formed in the reaction conditions to afford substituted 2-aryloxycarboxylic acid E. Esterification of E followed by a dissolving metal reduction affords substituted benzoxazinone G. The amide group in benzoxazinone G can be reduced using, for example, lithium aluminum hydride (LiAlH$_4$) or a borane to provide benzoxazine H, which is treated with a sulfonyl halide and base to afford substituted sulfonylated benzoxazine I.

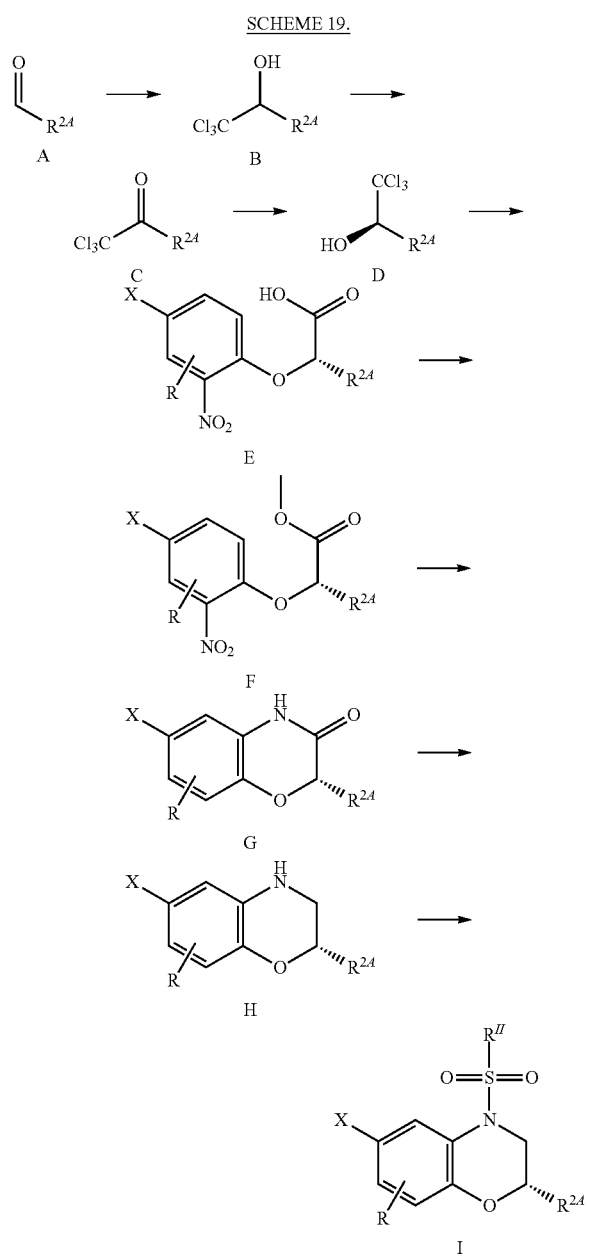

Scheme 20 illustrates a general method for preparing trisubstituted olefins in a stereocontrolled manner. Aldehyde A (where A as O, A'=N) can be prepared based on procedures in Scheme 19, by utilizing a substituted 4-hydroxy-3-nitrobenzaldehyde. Alternatively, aldehyde A can be prepared by formylating a THQ or benzoxazine where X is Br or OTf with Pd-mediated conditions; or by converting a bromide or triflate to the nitrile and reducing the nitrile to the aldehyde with DIBAL. This substituted aldehyde A can be reacted under Corey-Fuchs conditions (see, for example, *Tetrahedron Lett* 13: 3769-3772, 1972) with triphenyl phosphine and carbon tetrabromide to form dibromo-olefin B. The bromide trans- to the phenyl moiety of the benzoxazine or the tetrahydroquinoline can be selectively replaced with an aryl or alkyl group (see, for example, *Synlett* 5 737-739, 2000; *Tetrahedron* 64: 10250-1257; *Angew Chem Int* 51: 5718-5722; *Org Lett* 12: 2754-2757, 2010; and *Org Lett* 2797-3000, 2004) to form the bromo-substituted stilbene C in a stereoselective manner. Addition of a second R via a second Pd-mediated catalyzed reaction affords a trisubstituted olefin D with good stereocontrol.

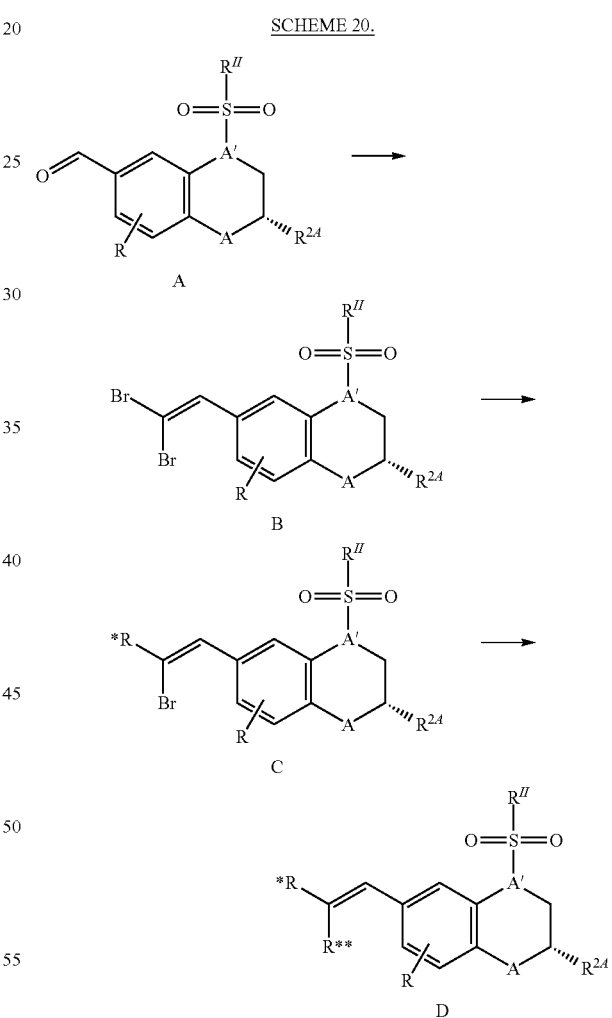

Scheme 21 illustrates a general method for preparing trifluoromethyl substituted olefin B in a stereocontrolled manner. It is a more specific example of the general procedure illustrated in Scheme 20. Copper or Pd— mediated addition of a CF$_3$ to bromo-substituted stilbene A can introduce the substituent with retention of stereochemistry using conditions described in, for example, *Adv Syn and Catalysis* 353: 3044-3048, 2011.

SCHEME 21.

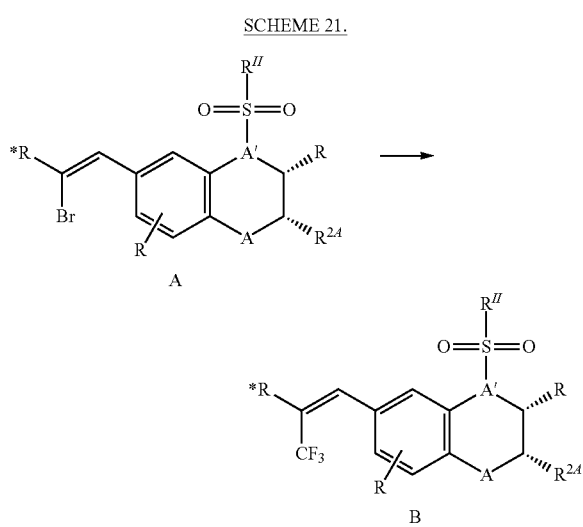

Scheme 22 illustrates an alternative general method for preparing disubstituted olefin D in a stereocontrolled manner. Copper-mediated addition of a bisboronate via the method of Hwanjong Jang et al. (see, for example, *J. Am. Chem. Soc.* 133: 7859-7871, 2011) to an acetylene A affords, in a stereospecific manner, vinyl boronate B. Palladium catalyzed coupling of the vinyl boronate to an aryl halide or aryl triflate C affords methyl-substituted olefin D.

SCHEME 22.

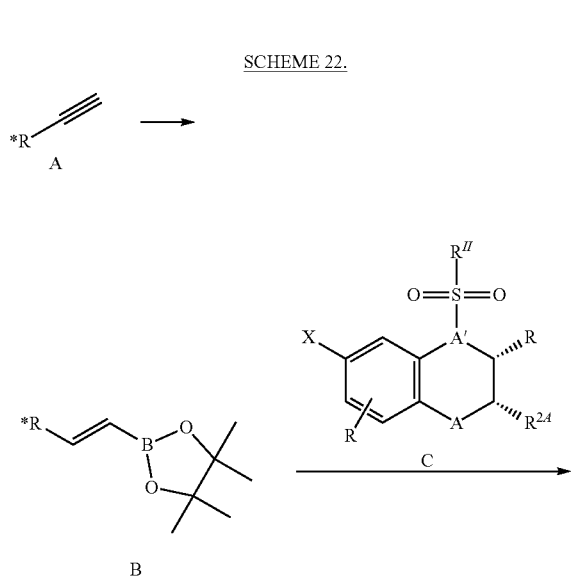

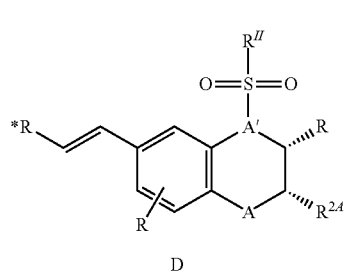

Scheme 23 illustrates another general method for preparing disubstituted olefins D in a stereocontrolled manner. Heck reaction of vinyl boronate A (see, for example, Andrew Lightfoot et al. in *Tetrahedron Lett.* 44: 7645-7648, 2003) with an aryl halide or aryl triflate B affords vinyl boronate C in a stereospecific manner. Palladium-catalyzed coupling of this boronate with an aryl or heteroaryl halide or triflate affords disubstituted olefin D.

SCHEME 23.

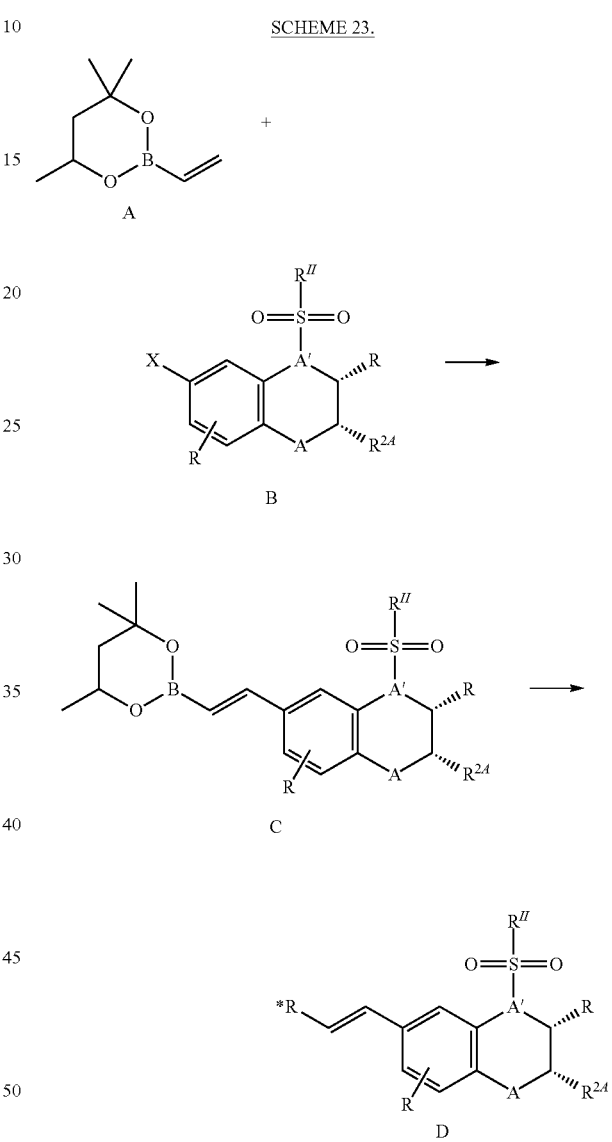

Scheme 24 illustrates a general method for preparing substituted 3-alkyoxy or 3-amino 1,2,4-oxadiazol-5(4H)-one D or 1,2,4-trizol-5(4H)-one E. Treatment of alcohol A (Q=O) or an amine (Q=NH or N-lower alkyl) affords thiocarbamate B. The thiocarbamate may be converted to 3-alkyoxy or 3-amino 1,2,4-oxadiazol-5(4H)-one D or 1,2,4-trizol-5(4H)-one E by treatment with hydroxylamine or hydrazine in the presence of a NaOH to facilitate the ring closure. Alternatively, sulfur may be alkyled and then the resulting compound reacted with hydroxylamine or hydrazine to obtain 3-alkyoxy or 3-amino 1,2,4-oxadiazol-5(4H)-one D or 1,2,4-trizol-5(4H)-one E.

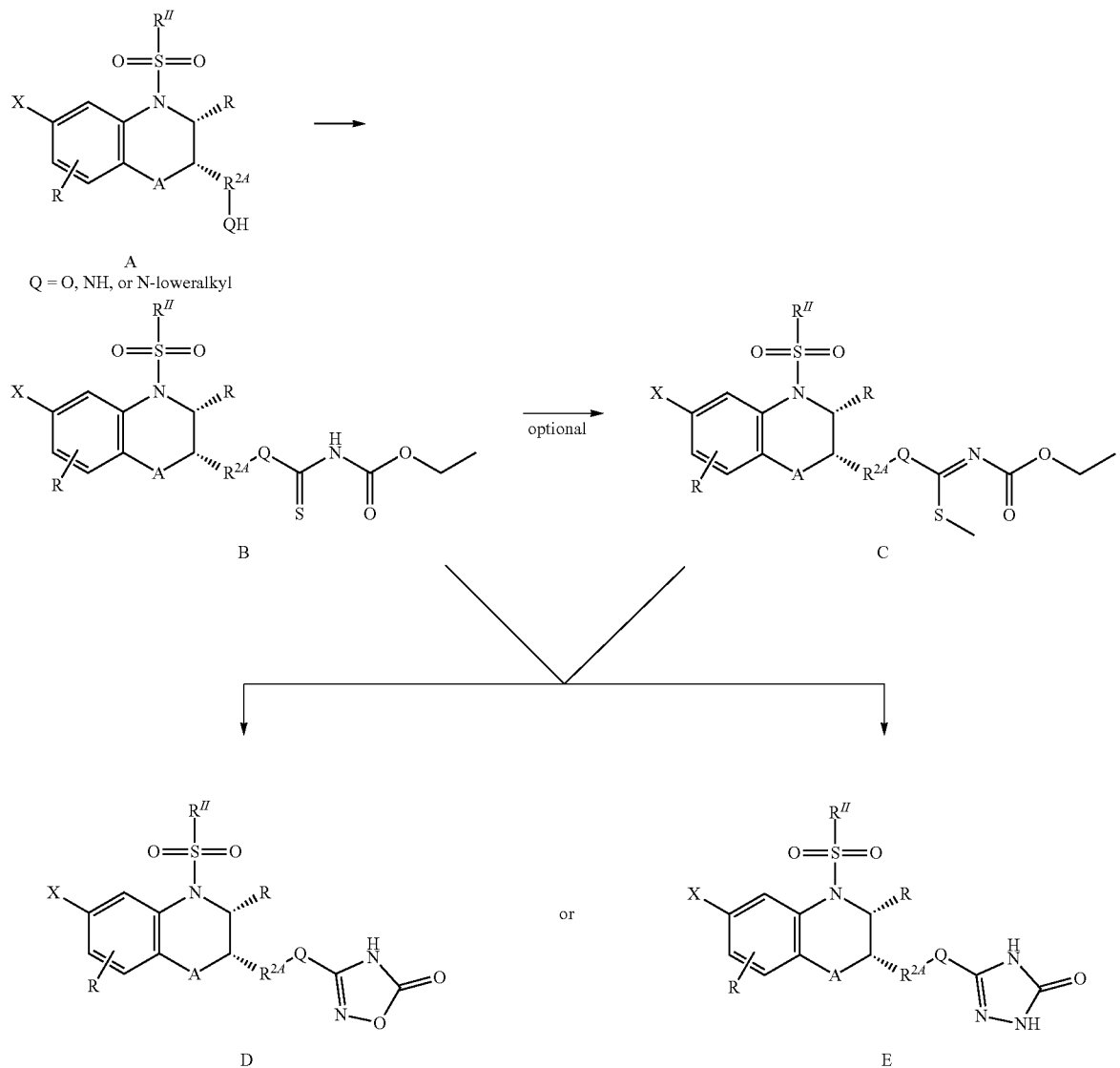
SCHEME 24.
Scheme 25 illustrates a general method for preparing substituted 1,3,4-oxadiazol-2(3H)-one C or 1,3,4-oxadiazole D. Treatment of ester A with hydrazine affords hydrazide B that upon treatment with triphosgene (or a synthetic equivalent such as dicarbonyl imidazole) or an acid chloride affords, after cyclization, the substituted 1,3,4-oxadiazol-2(3H)-one C or 1,3,4-oxadiazole D.
SCHEME 25.
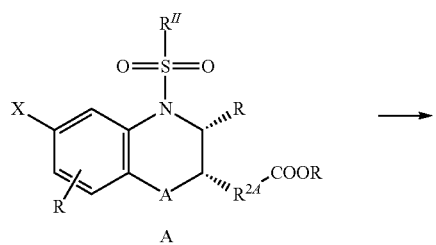

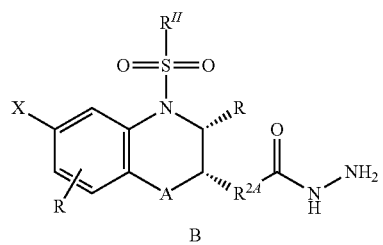
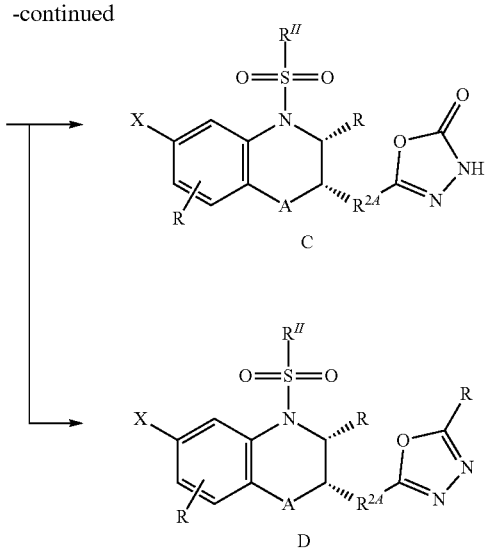

Scheme 26 illustrates a general method for preparing substituted 1,2,4-oxadiazol-5(4H)-one C or 1,2,4-oxadiazole D. Treatment of nitrile A (Q=O) with hydroxylamine affords substituted N-hydroxyaceimidamide B which upon treatment with triphosgene (or a synthetic equivalent such as dicarbonyl imidazole) or an acid chloride affords, after cyclization, substituted 1,2,4-oxadiazol-5(4H)-one C or 1,2,4-oxadiazole D.

Scheme 27 illustrates a general method for preparing substituted N-linked heterocycle C. Treatment of alcohol A with methanesulfonyl chloride or methane sulfonic anhydride affords mesylate B. The intermediate B can also be a tosylate, triflate, halide, etc. This intermediate is displaced with a heterocycle having an NH group (e.g., a substituted imidazole, pyrazole, triazole, etc) to afford N-linked heterocycle C.

SCHEME 26.

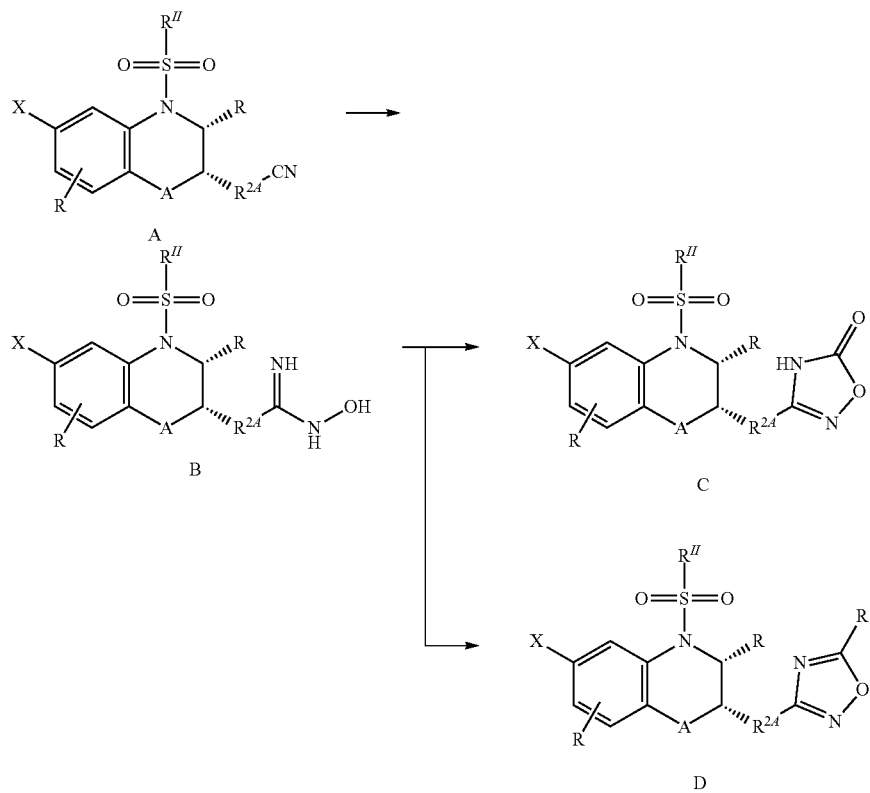

SCHEME 27.

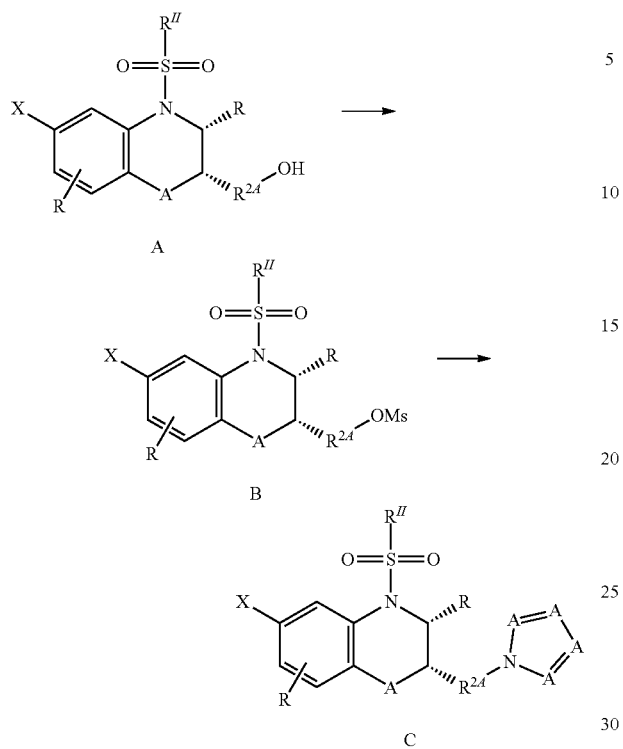

Scheme 28 illustrates an alternative general method for preparing substituted N-linked heterocycle B. Treatment of alcohol A with Mitsunobu conditions (e.g., triphenyl phosphine or its equivalent with diisopropyldiazodicarboxylate or its equivalent) with an acidic NH-substituted heterocycle (e.g., a substituted pyrrolidin-2,5-dione, 1-alkylimidazolin-2,4-dione, imidazoline-2,4-dione, oxazolidin-2,4-dione, or thiazolidine-2,4-dione) affords N-linked heterocycle B.

SCHEME 28.

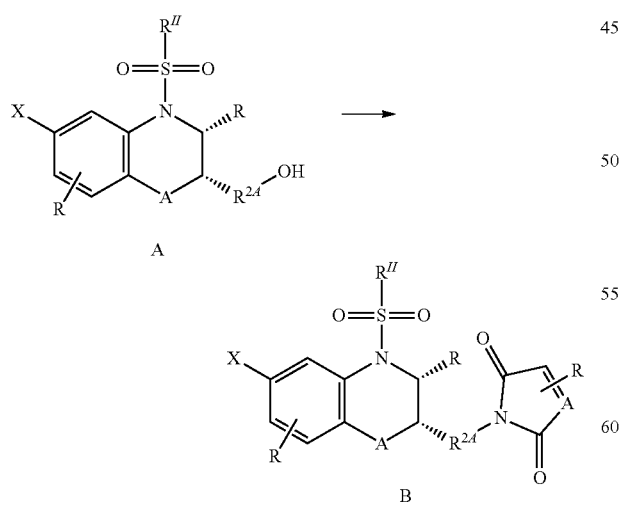

Scheme 29 illustrates a general method for preparing substituted C-linked heterocycle C. Treatment of alcohol A with methanesulfonyl chloride or methane sulfonic anhydride affords mesylate B. The intermediate B can also be a tosylate, triflate, halide, etc. This intermediate may be displaced by a carbanion of a variety of C-heterocycles (e.g., a substituted pyrrolidin-2-one, piperidin-2-one, thiazolidine-2,4-dione, imidazolidine-2,4-dione, or oxazolidin-2,4-dione) to afford C-linked heterocycle C.

SCHEME 29.

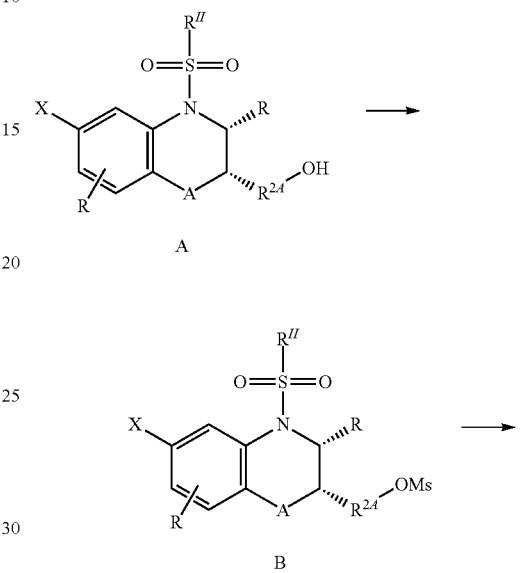

Scheme 30 illustrates a general method for preparing substituted (2S,4R)-2-substituted-4-(aryl or heteroaryl sulfonyl)chroman F. Treatment of benzylic halide A with mercaptan B affords thioether C. Oxidation of thioether C with meta-chloroperbenzoic acid or another oxidant affords sulfone D. Treatment of sulfone D with n-butyl lithium, tert-butoxide or another suitable base forms an anion which can be alkylated with an epoxide to afford alcohol E. Treatment of alcohol E with sodium hydride or another suitable base affords the chroman F.

SCHEME 30.

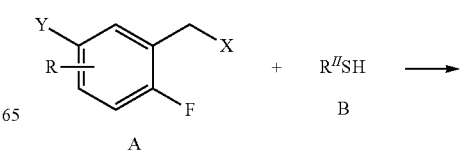

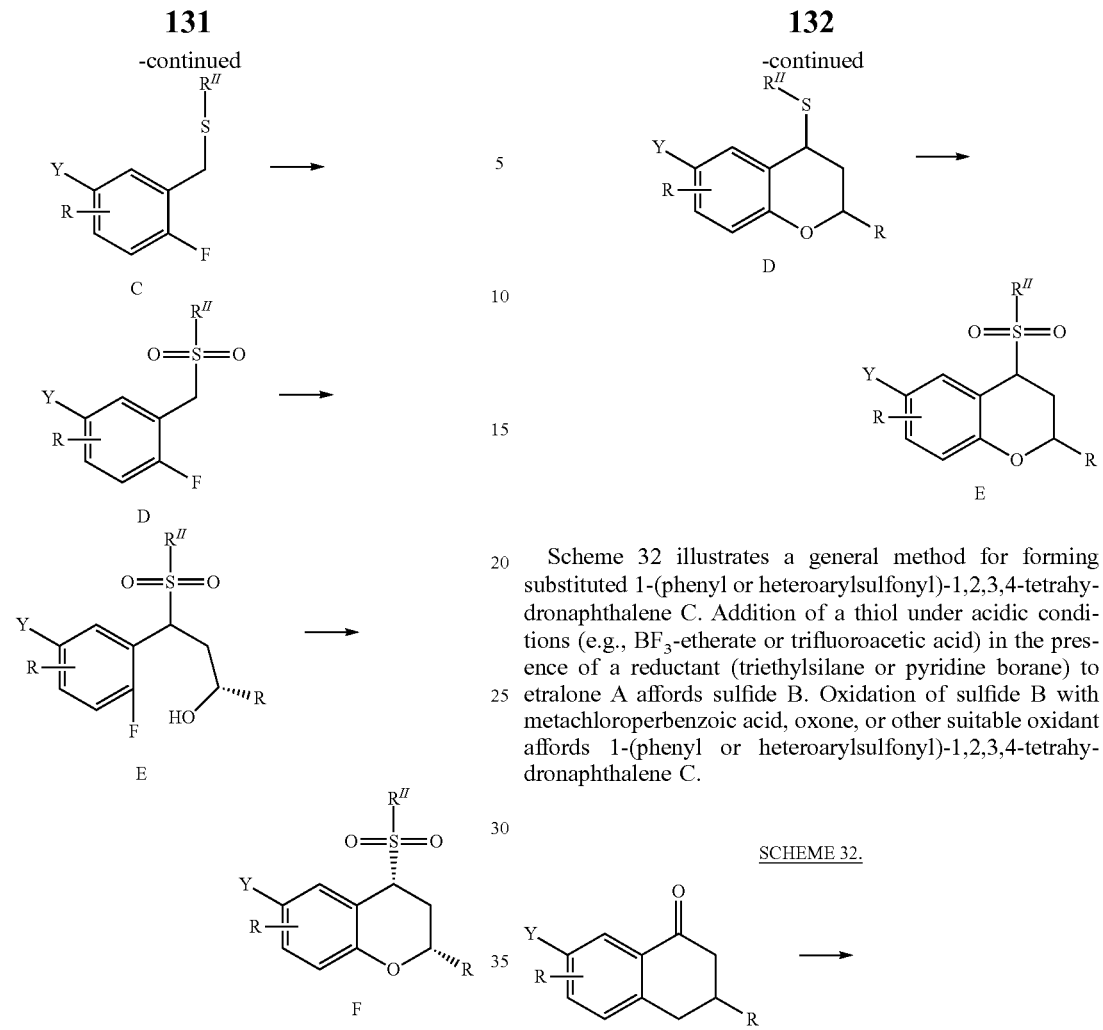

Scheme 32 illustrates a general method for forming substituted 1-(phenyl or heteroarylsulfonyl)-1,2,3,4-tetrahydronaphthalene C. Addition of a thiol under acidic conditions (e.g., $BF_3$-etherate or trifluoroacetic acid) in the presence of a reductant (triethylsilane or pyridine borane) to etralone A affords sulfide B. Oxidation of sulfide B with metachloroperbenzoic acid, oxone, or other suitable oxidant affords 1-(phenyl or heteroarylsulfonyl)-1,2,3,4-tetrahydronaphthalene C.

Scheme 31 illustrates another general method of forming substituted (benzyl or heteroarylalkyl sulfonyl)benzene E. Condensation of 2-hydroxyacetophenone A with aldehyde B catalyzed by pryrrolidine affords chromanone C. Addition of a thiol to chromanone C under acidic conditions (e.g., $BF_3$-etherate or trifluoroacetic acid) in the presence of a reductant (e.g., triethylsilane or pyridine borane) affords sulfide D. Oxidation of sulfide D with metachloroperbenzoic acid, oxone, or other suitable oxidant affords substituted (benzyl or heteroarylalkyl sulfonyl)benzene E.

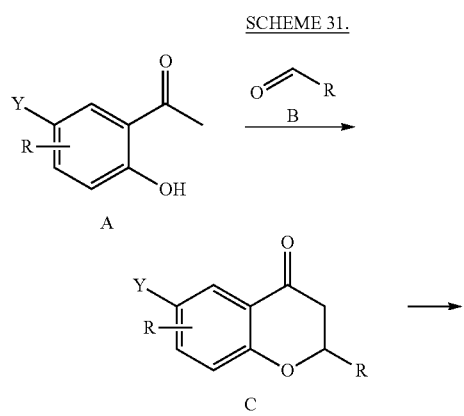

II. Therapeutic Applications of Dihydro-2H-benzo[b][1,4]oxazine Sulfonamide and Related Compounds It is contemplated that the dihydro-2H-benzo[b][1,4]oxazine sulfonamide and related compounds described herein, such as a compound of Formula I, I-A, I-B, II, II-A, II-B, II-C, or other compounds in Section I, provide therapeutic benefits to subjects suffering from a cancer, bacterial infection, fungal infection, or immune deficiency disorder.

Accordingly, one aspect of the invention provides a method of treating a disorder selected from the group consisting of cancer, bacterial infection, fungal infection, and immune deficiency disorder. The method comprises administering a therapeutically effective amount of a dihydro-2H-benzo[b][1,4]oxazine sulfonamide or related compound described herein, such as a compound of Formula I, I-A, I-B, II, II-A, II-B, II-C, or other compounds in Section I, to a subject in need thereof to ameliorate a symptom of the disorder. In certain embodiments, the particular compound of Formula I, I-A, I-B, II, II-A, II-B, or II-C is a compound defined by one of the embodiments described above.

In certain embodiments, the disorder is cancer. In certain embodiments, the cancer is a solid tumor or leukemia. In certain other embodiments, the cancer is colon cancer, pancreatic cancer, breast cancer, ovarian cancer, prostate cancer, squamous cell carcinoma, basal cell carcinoma, adenocarcinoma, sweat gland carcinoma, sebaceous gland carcinoma, lung cancer, leukemia, bladder cancer, stomach cancer, cervical cancer, testicular cancer, skin cancer, rectal cancer, thyroid cancer, kidney cancer, uterus cancer, espophagus cancer, liver cancer, an acoustic neuroma, oligodendroglioma, meningioma, neuroblastoma, or retinoblastoma. In certain other embodiments, the cancer is small cell lung cancer, non-small cell lung cancer, melanoma, cancer of the central nervous system tissue, brain cancer, Hodgkin's lymphoma, non-Hodgkin's lymphoma, cutaneous T-Cell lymphoma, cutaneous B-Cell lymphoma, or diffuse large B-Cell lymphoma. In certain other embodiments, the cancer is breast cancer, colon cancer, small-cell lung cancer, non-small cell lung cancer, prostate cancer, renal cancer, ovarian cancer, leukemia, melanoma, or cancer of the central nervous system tissue. In certain other embodiments, the cancer is colon cancer, small-cell lung cancer, non-small cell lung cancer, renal cancer, ovarian cancer, renal cancer, or melanoma.

Additional exemplary cancers include fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, Ewing's tumor, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, epithelial carcinoma, glioma, astrocytoma, medulloblastoma, and hemangioblastoma.

In certain embodiments, the cancer is a neuroblastoma, meningioma, hemangiopericytoma, multiple brain metastase, glioblastoma multiforms, glioblastoma, brain stem glioma, poor prognosis malignant brain tumor, malignant glioma, anaplastic astrocytoma, anaplastic oligodendroglioma, neuroendocrine tumor, rectal adeno carcinoma, Dukes C & D colorectal cancer, unresectable colorectal carcinoma, metastatic hepatocellular carcinoma, Kaposi's sarcoma, karotype acute myeloblastic leukemia, Hodgkin's lymphoma, non-Hodgkin's lymphoma, cutaneous T-Cell lymphoma, cutaneous B-Cell lymphoma, diffuse large B-Cell lymphoma, low grade follicular lymphoma, metastatic melanoma, localized melanoma, malignant mesothelioma, malignant pleural effusion mesothelioma syndrome, peritoneal carcinoma, papillary serous carcinoma, gynecologic sarcoma, soft tissue sarcoma, scelroderma, cutaneous vasculitis, Langerhans cell histiocytosis, leiomyosarcoma, fibrodysplasia ossificans progressive, hormone refractory prostate cancer, resected high-risk soft tissue sarcoma, unrescectable hepatocellular carcinoma, Waidenstrom's macroglobulinemia, smoldering myeloma, indolent myeloma, fallopian tube cancer, androgen independent prostate cancer, androgen dependent stage IV non-metastatic prostate cancer, hormone-insensitive prostate cancer, chemotherapy-insensitive prostate cancer, papillary thyroid carcinoma, follicular thyroid carcinoma, medullary thyroid carcinoma, or leiomyoma.

In certain embodiments, the disorder is a bacterial infection. The bacterial infection can be characterized according to classifications known in the art. For example, in certain embodiments, the bacterial infection is a gram-positive bacterial infection, such as a gram-positive cocci bacterial infection or a gram-positive bacilli bacterial infection. In other embodiments, the bacterial infection is a gram-negative bacterial infection, such as a gram-negative cocci bacterial infection or a gram-negative bacilli bacterial infection. The bacterial infection can also be characterized according to whether it is caused by anaerobic or aerobic bacteria. Accordingly, in certain embodiments, the bacterial infection is an anaerobic bacterial infection. In certain other embodiments, the bacterial infection is an aerobic bacterial infection.

A variety of bacteria are contemplated to be susceptible to the tetrahydroquinoline compounds. Representative bacteria include Staphylococci species, e.g., *S. aureus*; Enterococci species, e.g., *E. faecalis* and *E. faecium*; Streptococci species, e.g., *S. pyogenes* and *S. pneumoniae*; *Escherichia* species, e.g., *E. coli*, including enterotoxigenic, enteropathogenic, enteroinvasive, enterohemorrhagic and enteroaggregative *E. coli* strains; *Haemophilus* species, e.g., *H. influenza*; and *Moraxella* species, e.g., *M. catarrhalis*. Other examples include Mycobacteria species, e.g., *M. tuberculosis, M. avian-intracellulare, M. kansasii, M. bovis, M. africanum, M. genavense, M. leprae, M. xenopi, M. simiae, M. scrofulaceum, M. malmoense, M. celatum, M. abscessus, M. chelonae, M. szulgai, M. gordonae, M. haemophilum, M. fortuni* and *M. marinum*; Corynebacteria species, e.g., *C. diphtheriae; Vibrio* species, e.g., *V. cholerae; Campylobacter* species, e.g., *C. jejuni; Helicobacter* species, e.g., *H. pylori; Pseudomonas* species, e.g., *P. aeruginosa; Legionella* species, e.g., *L. pneumophila; Treponema* species, e.g., *T. pallidum; Borrelia* species, e.g., *B. burgdorferi; Listeria* species, e.g., *L. monocytogenes; Bacillus* species, e.g., *B. cereus; Bordatella* species, e.g., *B. pertussis; Clostridium* species, e.g., *C. perfringens, C. tetani, C. difficile* and *C. botulinum; Neisseria* species, e.g., *N. meningitidis* and *N. gonorrhoeae; Chlamydia* species, e.g., *C. psittaci, C. pneumoniae* and *C. trachomatis; Rickettsia* species, e.g., *R. rickettsii* and *R. prowazekii; Shigella* species, e.g., *S. sonnei; Salmonella* species, e.g., *S. typhimurium; Yersinia* species, e.g., *Y. enterocolitica* and *Y. pseudotuberculosis; Klebsiella* species, e.g., *K. pneumoniae; Mycoplasma* species, e.g., *M. pneumoniae*; and *Trypanosoma brucei*. In certain embodiments, the compounds described herein are used to treat a subject suffering from a bacterial infection selected from the group consisting of *S. aureus, E. faecalis, E. faecium, S. pyogenes, S. pneumonia*, and *P. aeruginosa*.

The antibacterial activity of compounds described herein may be evaluated using assays known in the art, such as the microbroth dilution minimum inhibition concentration (MIC) assay, as further described in National Committee for Clinical Laboratory Standards. Performance Standards for Antimicrobial Susceptibility Testing; Fourteenth Informational Supplement. NCCLS document M100-S14 {ISBN 1-56238-516-X}. This assay may be used to determine the minimum concentration of a compound necessary to prevent visible bacterial growth in a solution. In general, the drug to be tested is serially diluted into wells, and aliquots of liquid bacterial culture are added. This mixture is incubated under appropriate conditions, and then tested for growth of the bacteria. Compounds with low or no antibiotic activity (a high MIC) will allow growth at high concentrations of compound, while compounds with high antibiotic activity will allow bacterial growth only at lower concentrations (a low MIC).

The assay uses stock bacterial culture conditions appropriate for the chosen strain of bacteria. Stock cultures from the permanent stock culture collection can be stored as frozen suspensions at −70° C. Cultures may be suspended in 10% skim milk (BD) prior to snap freezing in dry ice/ethanol and then placed in a −70° C. freezer. Cultures may be maintained on Tryptic Soy Agar containing 5% Sheep Blood at room temperature (20° C.), and each culture may be recovered from frozen form and transferred an additional time before MIC testing. Fresh plates are inoculated the day before testing, incubated overnight, and checked to confirm purity and identity.

The identity and purity of the cultures recovered from the stock culture can be confirmed to rule out the possibility of contamination. The identity of the strains may be confirmed by standard microbiological methods (See, e.g., Murray et al., Manual of Clinical Microbiology, Eighth Edition. ASM Press {ISBN 1-55581-255-4}). In general, cultures are streaked onto appropriate agar plates for visualization of purity, expected colony morphology, and hemolytic patterns. Gram stains can also be utilized. The identities are confirmed using a MicroScan WalkAway 40 SI Instrument (Dade Behring, West Sacramento, Calif.). This device utilizes an automated incubator, reader, and computer to assess for identification purposes the biochemical reactions carried out by each organism. The MicroScan WalkAway can also be used to determine a preliminary MIC, which may be confirmed using the method described below.

Frozen stock cultures may be used as the initial source of organisms for performing microbroth dilution minimum inhibition concentration (MIC) testing. Stock cultures are passed on their standard growth medium for at least 1 growth cycle (18-24 hours) prior to their use. Most bacteria may be prepared directly from agar plates in 10 mL aliquots of the appropriate broth medium. Bacterial cultures are adjusted to the opacity of a 0.5 McFarland Standard (optical density value of 0.28-0.33 on a Perkin-Elmer Lambda EZ150 Spectrophotometer, Wellesley, Mass., set at a wavelength of 600 nm). The adjusted cultures are then diluted 400 fold (0.25 mL inoculum+100 mL broth) in growth media to produce a starting suspension of approximately 5×10$^5$ colony forming units (CFU)/mL. Most bacterial strains may be tested in cation adjusted Mueller Hinton Broth (CAMHB).

Test compounds ("drugs") are solubilized in a solvent suitable for the assay, such as DMSO. Drug stock solutions may be prepared on the day of testing. Microbroth dilution stock plates may be prepared in two dilution series, 64 to 0.06 μg drug/mL and 0.25 to 0.00025 μg drug/mL. For the high concentration series, 200 μL of stock solution (2 mg/mL) is added to duplicate rows of a 96-well microtiter plate. This is used as the first well in the dilution series. Serial two-fold decremental dilutions are made using a BioMek FX robot (Beckman Coulter Inc., Fullerton, Calif.) with 10 of the remaining 11 wells, each of which will contain 100 μL of the appropriate solvent/diluent. Row 12 contains solvent/diluent only and serves as the control. For the first well of the low concentration series, 200 μL of an 8 μg/mL stock are added to duplicate rows of a 96-well plate. Serial two-fold dilutions are made as described above.

Daughter 96-well plates may be spotted (3.2 μL/well) from the stock plates listed above using the BioMek FX robot and used immediately or frozen at −70° C. until use. Aerobic organisms are inoculated (100 μL volumes) into the thawed plates using the BioMek FX robot. The inoculated plates are be placed in stacks and covered with an empty plate. These plates are then incubated for 16 to 24 hours in ambient atmosphere according to CLSI guidelines (National Committee for Clinical Laboratory Standards, Methods for Dilution, Antimicrobial Tests for Bacteria that Grow Aerobically; Approved Standard-Sixth Edition. NCCLS document M7-A6 {ISBN 1-56238-486-4}).

After inoculation and incubation, the degree of bacterial growth can be estimated visually with the aid of a Test Reading Mirror (Dynex Technologies 220 16) in a darkened room with a single light shining directly through the top of the microbroth tray. The MIC is the lowest concentration of drug that prevents macroscopically visible growth under the conditions of the test.

In certain embodiments, the disorder is a fungal infection. Exemplary fungi that may be treated include, for example, *Acremonium*, *Absidia* (e.g., *Absidia corymbifera*), *Alternaria*, *Aspergillus* (e.g., *Aspergillus clavatus*, *Aspergillus flavus*, *Aspergillus fumigatus*, *Aspergillus nidulans*, *Aspergillus niger*, *Aspergillus terreus*, and *Aspergillus versicolor*), *Aureobasidium*, *Basidiobolus*, *Blastomyces* (e.g., *Blastomyces dermatitidis*), *Candida* (e.g., *Candida albicans*, *Candida glabrata*, *Candida guilliermondii*, *Candida kefyr*, *Candida krusei*, *Candida lusitaniae*, *Candida parapsilosis*, *Candida pseudotropicalis*, *Candida stellatoidea*, *Candida tropicalis*, *Candida utilis*, *Candida lipolytica*, *Candidafamata* and *Candida rugosa*), *Cephalosporium*, *Chaetomium*, *Chrysosporium*, *Cladosporium* (e.g., *Cladosporium carrionii* and *Cladosporium trichloides*), *Coccidioides* (e.g., *Coccidioides immitis*), *Conidiobolus*, *Coprinus*, *Corynespora*, *Cryptococcus* (e.g., *Cryptococcus neoformans*), *Curvularia*, *Cunninghamella* (e.g., *Cunninghamella elegans*), *Exophiala* (e.g., *Exophiala dermatitidis* and *Exophiala spinifera*), *Epidermophyton* (e.g., *Epidermophyton floccosum*), *Fonsecaea* (e.g., *Fonsecaea pedrosoi*), *Fusarium* (e.g., *Fusarium solani*), *Geotrichum* (e.g., *Geotrichum candiddum* and *Geotrichum clavatum*), *Hendersonula*, *Histoplasma*, *Leptosphaeria*, *Loboa*, *Madurella*, *Malassezia* (e.g., *Malassezia furfur*), *Microsporum* (e.g., *Microsporum canis* and *Microsporum gypseum*), *Mycocentrospora*, *Mucor*, *Neotestudina*, *Paecilomyces*, *Paracoccidioides* (e.g., *Paracoccidioides brasiliensis*), *Penicillium* (e.g., *Penicillium marneffei*), *Phialophora*, *Pneumocystis* (e.g., *Pneumocystis carinii*), *Pseudallescheria* (e.g., *Pseudallescheria boydii*), *Rhinosporidium*, *Rhizomucor*, *Rhizopus* (e.g., *Rhizopus microsporus* var. *rhizopodiformis* and *Rhizopus oryzae*), *Saccharomyces* (e.g., *Saccharomyces cerevisiae*), *Scopulariopsis*, *Sporothrix* (e.g., *Sporothrix schenckii*), *Trichophyton* (e.g., *Trichophyton mentagrophytes* and *Trichophyton rubrum*), *Trichosporon* (e.g., *Trichosporon asahii*, *Trichosporon beigelii* and *Trichosporon cutaneum*), and *Wangiella*.

In certain embodiments, the disorder is an immune deficiency disorder. Exemplary immune deficiency disorders include, for example, a human immunodeficiency viral infection, a patient with a deficient immune system due to chemotherapy, or a patient recovering from surgery who has a deficient immune system.

In certain embodiments, the subject is a human.

Another aspect of the invention provides for the use of a compound described herein (such as a compound of Formula I, I-A, I-B, II, II-A, II-B, II-C, or other compounds in Section I) in the manufacture of a medicament. In certain embodiments, the medicament is for treating a disorder described herein, such as cancer.

Another aspect of the invention provides for the use of a compound described herein (such as a compound of Formula I, I-A, I-B, II, II-A, II-B, II-C, or other compounds in Section I) for treating a medical disorder, such a medical disorder described herein (e.g., cancer).

Further, it is contemplated that dihydro-2H-benzo[b][1,4]oxazine sulfonamide and related compounds described herein, such as a compound of Formula I, I-A, I-B, II, II-A, II-B, II-C, or other compounds in Section I, can promote the activity of RORγ. Accordingly, another aspect of the invention provides a method of promoting the activity of RORγ. The method comprises exposing a RORγ to an effective amount of a dihydro-2H-benzo[b][1,4]oxazine sulfonamide or related compound described herein, such as a compound of Formula I, I-A, I-B, II, II-A, II-B, II-C, or other compounds in Section I, to promote RORγ activity. In certain embodiments, the particular compound of Formula I, I-A, I-B, II, II-A, II-B, or II-C is the compound defined by one of the embodiments described above. Promoting the activity of RORγ means to increase the activity of RORγ. In certain embodiments, exposing a RORγ to an effective amount of a dihydro-2H-benzo[b][1,4]oxazine sulfonamide or related compound described herein (such as a compound of Formula I, I-A, I-B, II, II-A, II-B, II-C, or other compounds in Section I) results in an increase in RORγ activity of at least 5%, 10%, 20%, or 50% relative to the activity of RORγ under substantially the same conditions but without the presence of the dihydro-2H-benzo[b][1,4]oxazine sulfonamide or related compound.

Further, it is contemplated that dihydro-2H-benzo[b][1,4]oxazine sulfonamide and related compounds described herein, such as a compound of Formula I, I-A, I-B, II, II-A, II-B, II-C, or other compounds in Section I, can increase the amount of interleukin-17 (IL-17) in a subject. IL-17 is a cytokine that affects numerous biological functions. Accordingly, another aspect of the invention provides a method of increasing the amount of IL-17 in a subject. The method comprises administering to a subject an effective amount of a dihydro-2H-benzo[b][1,4]oxazine sulfonamide or related compound described herein, such as a compound of Formula I, I-A, I-B, II, II-A, II-B, II-C, or other compounds in Section I, to increase the amount of IL-17 in the subject. In certain embodiments, the particular compound of Formula I, I-A, I-B, II, II-A, II-B, or II-C is the compound defined by one of the embodiments described above.

In certain embodiments, the subject is a human. In certain embodiments, administering the compound increases the amount of IL-17 produced by Th-17 cells in the subject. A change in the amount of IL-17 produced by, for example, Th-17 cells can be measured using procedures described in the literature, such as an ELISA assay or intracellular staining assay.

Further, it is contemplated that dihydro-2H-benzo[b][1,4]oxazine sulfonamide and related compounds described herein, such as a compound of Formula I, I-A, I-B, II, II-A, II-B, II-C, or other compounds in Section I, may increase the synthesis of IL-17 in a subject. Accordingly, another aspect of the invention provides a method of increasing the synthesis of IL-17 in a subject. The method comprises administering to a subject an effective amount of a compound described herein, e.g., a compound of Formula I, I-A, I-B, II, II-A, II-B, II-C or other compounds in Section I, to increase the synthesis of IL-17 in the subject. In certain embodiments, the particular compound of Formula I, I-A, I-B, II, II-A, II-B, or II-C is a compound defined by one of the embodiments described above.

Adoptive Cellular Therapy

RORγ agonist compounds described herein may also be used in adoptive cellular therapy to treat various medical disorders, such as cancer, bacterial infections, fungal infections, and immune disorders. Cells, e.g., lymphocyte cells or dendritic cells, are exposed ex vivo to an RORγ agonist compound herein, and then the treated cells are administered to a patient. In adoptive cellular transfer, cells are obtained from a source (typically the patient in need of treatment), cultured ex vivo with an agent, and then the resulting cells are administered to the patient in need of therapy. The culturing typically subjects the cells to conditions whereby the cells increase in number (i.e., expansion) and/or acquire features providing improved therapeutic benefit. General features of the adoptive cellular therapy methods and compositions are described below, along with more specific embodiments of the lymphocyte cells, dendritic cells, and procedures for isolating and culturing cells.

Accordingly, one aspect of the invention provides a method of delivering to a patient a RORγ agonist treated cell selected from the group consisting of a lymphocyte cell and dendritic cell. The method comprises administering to a patient in need thereof a pharmaceutical composition comprising said cell that has been exposed ex vivo to an agonist of RORγ described herein, such as a compound of Formula I, I-A, I-B, II, II-A, II-B, or II-C. The method may further comprise a culturing step. In such embodiments, the method further comprises culturing a cell (i.e., the lymphocyte cell or dendritic cell) with an agonist of RORγ to provide the cell that has been exposed ex vivo to the agonist of RORγ. The culturing may comprise exposing the cell to a cytokine (e.g., IL-13, IL-2, IL-6, IL-7, IL-10, IL-12, IL-15, IL-18, IL-21, IL-23, or transforming growth factor beta). During the culturing step, the cell may be exposed to an antigen associated with a medical disorder. Although not to be bound by theory, cells having an receptor specific to an antigen associated with a medical disorder can provide a more effective therapy than cells lacking such a receptor. Accordingly, in certain embodiments, the culturing step comprises exposing the cell to an antigen associated with a medical disorder. The antigen may be an antigen presenting cell. Alternatively, the antigen may comprise cancer tissue. Further, as described below, the cell may be genetically altered to express a receptor specific to an antigen associated with a medical disorder.

The cell may be autologous or allogenic. Autologous cells are cells obtained from the patient whom will receive the cell exposed ex vivo to an agonist of RORγ. As such, in certain embodiments, the method may further comprise obtaining a cell from said patient, for use in the culturing step. Alternatively, the cells may be allogenic, i.e., obtained from a subject that produces cells allogenic to cells of the patient. In such embodiments, the method may further comprise obtaining a cell from a subject that produces cells allogenic to lymphocyte cells of the patient, for use in the culturing step.

In certain embodiments, the cell is a lymphocyte cell. Lymphocyte cells can be obtained from human or animal tissues according to procedures described in the literature. In certain embodiments, the lymphocyte cell is obtained from blood, cancer tissue, bone marrow, the spleen, a lymph node, or the thymus. In certain other embodiments, the lymphocyte cell is obtained from a population of peripheral blood mononuclear cells, such as human peripheral blood mononuclear cells. In certain other embodiments, the lymphocyte cell is obtained from a lymph node in proximity to a tumor or site of infection. In certain other embodiments, the lymphocyte cell is obtained from cancer tissue. In yet other embodiments, the lymphocyte cell is a tumor-infiltrating-lymphocyte cell.

Cells can be characterized according to the presence of a receptor for an antigen specific for a medical disorder. In certain embodiments, the cell expresses a receptor for an antigen specific for a medical disorder. As indicate above, such cells may provide more effective therapies for treating disease since the cells are more likely to target tissue specific to the disease to be treated. In certain embodiments, the medical disorder is a cancer, bacterial infection, fungal infection, or immune disorder. In yet other embodiments, the cell may express a receptor that, while not specific for a medical disorder, has utility in enhancing cell efficacy in treating the disorder.

Various types of lymphocyte cells have been described in the literature for use in adoptive cellular transfer. In certain embodiments, the lymphocyte cell is a T cell. In certain other embodiments, the lymphocyte cell is a $CD8^+$ T cell, $CD4^+$ T cell, or $T_H17$ cell. In certain other embodiments, the lymphocyte cell is a $CD8^+$ T cell, $CD4^+$ T cell, or a combination thereof. In certain other embodiments, the lymphocyte cell is a natural killer cell. In certain other embodiments, the lymphocyte cell is a Tc17 cell, natural killer T cell, or γδ T cell. In yet other embodiments, the lymphocyte cell is a genetically altered lymphocyte cell.

Cells may be administered to the patient according to procedures described in the literature. In certain embodiments, the administering comprises injecting into the patient the pharmaceutical composition. The injecting may be intravenous injection or injection directly into diseased tissue, such as a tumor. In yet other embodiments, the injecting may be subcutaneous injection into the patient.

The therapeutic method embraces combination therapies, such as administering (i) an agent that enhances the efficacy of the cell exposed to the agonist of RORγ and/or (ii) an agent having independent efficacy in treating the target medical disorder.

Another aspect of the invention provides a method of preparing a population of cells that have been exposed ex vivo to an agonist of RORγ described herein, where the cells are lymphocyte cells and/or dendritic cells. The method comprises exposing a population of cells selected from the group consisting of lymphocyte cells and dendritic cells ex vivo to an agonist of RORγ described herein to thereby provide said population of cells that have been exposed ex vivo to an agonist of RORγ. The population of cells may be used in therapeutic methods described herein. The exposing step may comprise culturing a population of cells with the agonist of RORγ for a duration of time sufficient to increase the number of cells in the population. The culturing may comprise exposing the cell to a cytokine (e.g., IL-13, IL-2, IL-6, IL-7, IL-10, IL-12, IL-15, IL-18, IL-21, IL-23, or transforming growth factor beta). Further during the culturing step, the cell may optionally be exposed to an antigen associated with a medical disorder. Accordingly, in certain embodiments, the culturing step comprises exposing the cell to an antigen associated with a medical disorder. The antigen may be an antigen presenting cell. Alternatively, the antigen may comprise cancer tissue. The cell may be autologous or allogenic. Autologous cells are cells obtained from the patient whom will receive the cell exposed ex vivo to an agonist of RORγ. As such, in certain embodiments, the method may further comprise obtaining a cell (i.e., a lymphocyte or dendritic cell) from said patient for use in the culturing step. Alternatively, the cells may be allogenic, i.e., obtained from subject that produces cells allogenic to cells of the patient. In such embodiments, the method may further comprise obtaining a cell from a subject that produces cells allogenic to cells of the patient, for use in the culturing step. In certain embodiments, the cell is a lymphocyte cell. Lymphocyte cells can be obtained from human or animal tissues according to procedures described in the literature. In certain embodiments, the lymphocyte cell is obtained from blood, cancer tissue, bone marrow, the spleen, a lymph node, or the thymus. In certain other embodiments, the lymphocyte cell is obtained from a population of peripheral blood mononuclear cells, such as human peripheral blood mononuclear cells. In certain other embodiments, the lymphocyte cell is obtained from a lymph node in proximity to a tumor or site of infection. In certain other embodiments, the lymphocyte cell is obtained from cancer tissue. In yet other embodiments, the lymphocyte cell is a tumor-infiltrating-lymphocyte cell.

Cells can be characterized according to the presence of a receptor for an antigen specific for a medical disorder. In certain embodiments, the cell expresses a receptor for an antigen specific for a medical disorder. As indicated above, such cells may provide more effective therapies for treating disease since the cells is more likely to target tissue specific to the disease to be treated. In certain embodiments, the medical disorder is a cancer, bacterial infection, fungal infection, or immune disorder. In yet other embodiments, the cell may express a receptor that, while not specific for a medical disorder, has utility in enhancing cell efficacy in treating the disorder.

As described above, various types of lymphocyte cells have been described in the literature for use in adoptive cellular transfer. In certain embodiments, the lymphocyte cell is a T cell. In certain other embodiments, the lymphocyte cell is a $CD8^+$ T cell, $CD4^+$ T cell, or $T_H17$ cell. In certain other embodiments, the lymphocyte cell is a $CD8^+$ T cell, $CD4^+$ T cell, or a combination thereof. In certain other embodiments, the lymphocyte cell is a natural killer cell. In certain other embodiments, the lymphocyte cell is a Tc17, natural killer T cell, or γδ T cell. In yet other embodiments, the lymphocyte cell is a genetically altered lymphocyte cell.

Another aspect of the invention provides a method of treating a medical disorder. The method comprises administering to a patient in need thereof a cell that has been exposed ex vivo to an agonist of RORγ described herein to treat the medical disorder, wherein the cell is a lymphocyte cell or dendritic cell. The medical disorder can be, for example, a cancer, bacterial infection, fungal infection, or immune disorder. Additional exemplary medical disorders are described above, and in certain embodiments, the medical disorder is a cancer selected from the group consisting of a solid tumor, lymphoma, and leukemia. In certain other embodiments, the medical disorder is a cancer selected from the group consisting of ovarian cancer, melanoma, colorectal cancer, lung cancer, breast cancer, prostate cancer, pancreatic cancer, renal cell carcinoma, leukemia, a B-cell lymphoma, and non-Hodgkin lymphoma.

Another aspect of the invention provides a population of lymphocyte cells that have been exposed ex vivo to an agonist of RORγ described herein. The population may be characterized by the presence and/or quantity of particular types of cells in the population. For example, in certain embodiments, the population comprises one or more of the following: T cells and natural killer cells. In certain other embodiments, a majority of lymphocyte cells in the population are T cells. In certain other embodiments, a majority of lymphocyte cells in the population are CD8$^+$ T cells, CD4$^+$ T cells, T$_H$17 cells, or a combination thereof. In yet other embodiments, a majority of lymphocyte cells in the population are natural killer cells. In yet other embodiments, a single type of lymphocyte cell (e.g., a T cell, CD8$^+$ T cell, CD4$^+$ T cell, T$_H$17 cell, Tc17 cell, natural killer T cell, or γδ T cell) comprises at least 60%, 70% 80%, 90% or 95% of the cells in the population. In yet other embodiments, the population is characterized by: (i) a majority of lymphocyte cells in the population are T cells, (ii) a majority of lymphocyte cells in the population are CD8$^+$ T cells, CD4$^+$ T cells, T$_H$17 cells, or a combination thereof, (iii) a majority of lymphocyte cells in the population are Tc17 cells, (iv) a majority of lymphocyte cells in the population are natural killer cells, or (v) a majority of lymphocyte cells in the population are natural killer T cells, γδ T cells, or a combination thereof. In yet other embodiments, a majority of lymphocyte cells in the population are CD8$^+$ T cells, CD4$^+$ T cells, or a combination thereof. In yet other embodiments, the population is characterized by a majority of lymphocyte cells in the population are Tc17 cells, CD4$^+$ Th0 T lymphocyte cells, Th17-polarized CD4+T lymphocyte cells, CD8+ Tc17 T lymphocyte cells, or a combination thereof.

In each of the above aspects and embodiments, lymphocyte cells may be characterized according to whether they are a tumor infiltrating lymphocyte, naïve T lymphocyte, memory T lymphocyte, effector T lymphocyte, CD8$^+$ T cell, CD4$^+$ T cell, CD4$^+$/CD8$^+$ double positive T lymphocyte, CD28$^+$CD8$^+$ T cell, or T$_H$17 cell. CD8$^+$ T cells can be separated into naïve CD8$^+$ T cells, memory CD8$^+$ T cells, and effector CD8$^+$ T cells, according to cell surface antigens characteristic to each type of cell. Whether a cell or cell population is positive for a particular cell surface marker can be determined by flow cytometry using staining with a specific antibody for the surface marker and an isotype matched control antibody. A cell population negative for a marker refers to the absence of significant staining of the cell population with the specific antibody above the isotype control, and positive refers to uniform staining of the cell population above the isotype control. For instance, CD4$^+$ T helper cells can be sorted into naïve, central memory, and effector cells by identifying cell populations that have cell surface antigens. In certain embodiments, central memory CD4$^+$ T cells are CD62L positive and CD45RO positive. In certain embodiments, effector CD4$^+$ T cells are CD62L and CD45RO negative. In yet other embodiments, the lymphocyte cell is a Th1 cell, Tc1 cell, Th0 cell, or Tc0 cell. In certain embodiments, the lymphocyte cell is a CD8$^+$ T cell, which is optionally further characterized according to the whether the CD8$^+$ T cell is a naïve CD8$^+$ T cell, a memory CD8$^+$ T cell, or an effector CD8$^+$ T cell. In certain embodiments, the lymphocyte cell is a memory CD8$^+$ T cell, which may be further characterized according to whether the cell is CD62L positive or CD45RO positive. In certain other embodiments, the lymphocyte cell is an effector CD8$^+$ T cell, which may be further characterized according to whether the cell is CD62L negative or CD45RO negative. In yet other embodiments, the lymphocyte cell is a CD4+Th0 T lymphocyte, Th17-polarized CD4+T lymphocyte, or CD8+Tc17 T lymphocyte. In still other embodiments, the lymphocyte cell is a memory T cell present in CD62L+ or CD62L− subsets of CD8+ peripheral blood lymphocytes. In certain embodiments, the central memory T cells may be CD45RO+, CD62L+, CD8+ T cells. In certain embodiments, effector T cells are negative for CD62L, CCR7, CD28, and CD127, and positive for granzyme B and perforin.

T cells can be characterized according to identity of a T cell receptor located on the surface of the T cell. The T cell receptor is a disulfide-linked membrane-anchored heterodimer that normally consists of highly variable alpha (c) and beta (β) chains expressed as part of a complex with the invariant CD3 chain molecules. T cells expressing this receptor are referred to as α:β (or αβ) T cells. A minority of T cells express an alternate receptor, formed by variable gamma (γ) and delta (δ) chains, and such T cells are referred as γδ T cells. One subtype of T cells is natural killer T (NKT) cells. NKT cells are a heterogeneous group of T cells that share properties of both T cells and natural killer NK cells. Many NKT cells recognize the non-polymorphic CD1d molecule, an antigen-presenting molecule that binds self- and foreign lipids and glycolipids. Other subtypes of T cells include, for example, CD8$^+$ T cells, CD4$^+$ T cells, Tc17 cells, natural killer T cells, and γδ T cells. Still other subtypes of T cells include, for example, CD4$^-$CD8$^-$ T cells and CD28$^+$ CD8$^+$ T cells.

Preferably the lymphocyte cell comprises a receptor specific for an antigen of a medical condition. The receptor can be the endogenous lymphocyte cell receptor, i.e., the antigen-specific lymphocyte cell receptor that is endogenous (i.e., native to) the lymphocyte. In such instances, the lymphocyte comprising the endogenous lymphocyte cell receptor can be a lymphocyte cell that was isolated from the patient, which is known to express the particular medical condition-specific antigen. Alternatively, the lymphocyte comprising the endogenous lymphocyte cell receptor can be a lymphocyte cell that was isolated from a subject that produces allogenic lymphocyte cells (i.e., lymphocyte cells that are histocompatible with the patient that will receive the lymphocyte cells). In certain embodiments, the subject from which lymphocyte cells are obtained may be immunized prior to obtaining the lymphocyte cells, so that the lymphocyte cells to be administered to the patient will have specificity for the medical disorder to be treated.

The antigen of a disease recognized by the endogenous lymphocyte cell receptor can be any antigen which is characteristic of the disease. For example, the antigen may be, for example, a tumor antigen, such as gp100, MART-1, TRP-1, TRP-2, tyrosinase, NY-ESO-1, MAGE-1, or MAGE-3.

Lymphocyte cells may also be characterized according to the presence of a phenotypic marker of activation for tumor reactivity, such as the presence of 4-1BBL. Populations of lymphocyte cells enriched for such a phenotypic marker may provide therapeutic advantages. Lymphocyte cells may also be characterized according to the level of expression of the RORγ. In certain embodiments, the lymphocyte cell may be induced to express or engineered to express RORγ, thereby increasing the amount of RORγ.

The lymphocyte cell may be a genetically modified lymphocyte cell, such as a genetically modified lymphocyte cell described in, for example, International Patent Application Publication No. WO 2012/129514, which is hereby incorporated by reference. Genetic modification of the lymphocyte may improve the efficacy of therapy by promoting the viability and/or function of transferred lymphocyte cells, provide a genetic marker to permit selection and/or evaluation of in vivo survival or migration, or may incorporate functions that improve the safety of immunotherapy, for example, by making the cell susceptible to negative selection in vivo. The lymphocyte may be genetically modified so that the lymphocyte cell expresses certain proteins, such as a survival cytokine (e.g., granulocyte-macrophage colony-stimulating factor) and/or receptor for an antigen (e.g., a tumor antigen).

Accordingly, in embodiments, lymphocyte cells are modified with chimeric antigen receptors (CAR). The CARs may comprise a single-chain antibody fragment (scFv) that is derived from the variable heavy (VH) and variable light (VL) chains of a monoclonal antibody (mAb) linked to the TCR CD3$^+$ chain that mediates T-cell activation and cytotoxicity. Costimulatory signals can also be provided through the CAR by fusing the costimulatory domain of CD28 or 4-1 BB to the CD3$^+$ chain. CARs are specific for cell surface molecules independent from HLA, thus overcoming the limitations of TCR-recognition including HLA-restriction and low levels of HLA-expression on tumor cells.

III. Combination Therapy

Another aspect of the invention provides for combination therapy. Dihydro-2H-benzo[b][1,4]oxazine sulfonamide and related compounds (e.g., a compound of Formula I, I-A, I-B, II, II-A, II-B, II-C, or other compounds in Section I) or their pharmaceutically acceptable salts may be used in combination with additional therapeutic agents to treat medical disorders, such as a cancer, bacterial infection, fungal infection, and immune deficiency disorder.

Exemplary therapeutic agents that may be used as part of a combination therapy in treating cancer, include, for example, mitomycin, tretinoin, ribomustin, gemcitabine, vincristine, etoposide, cladribine, mitobronitol, methotrexate, doxorubicin, carboquone, pentostatin, nitracrine, zinostatin, cetrorelix, letrozole, raltitrexed, daunorubicin, fadrozole, fotemustine, thymalfasin, sobuzoxane, nedaplatin, cytarabine, bicalutamide, vinorelbine, vesnarinone, aminoglutethimide, amsacrine, proglumide, elliptinium acetate, ketanserin, doxifluridine, etretinate, isotretinoin, streptozocin, nimustine, vindesine, flutamide, drogenil, butocin, carmofur, razoxane, sizofilan, carboplatin, mitolactol, tegafur, ifosfamide, prednimustine, picibanil, levamisole, teniposide, improsulfan, enocitabine, lisuride, oxymetholone, tamoxifen, progesterone, mepitiostane, epitiostanol, formestane, interferon-alpha, interferon-2 alpha, interferon-beta, interferon-gamma, colony stimulating factor-1, colony stimulating factor-2, denileukin diftitox, interleukin-2, and leutinizing hormone releasing factor.

An additional class of agents that may be used as part of a combination therapy in treating cancer is immune checkpoint inhibitors (also referred to as immune checkpoint blockers). Immune checkpoint inhibitors are a class of therapeutic agents that have the effect of blocking immune checkpoints. See, for example, Pardoll in *Nature Reviews Cancer* (2012) vol. 12, pages 252-264. Exemplary immune checkpoint inhibitors include agents that inhibit one or more of (i) cytotoxic T-lymphocyte-associated antigen 4 (CTLA4), (ii) programmed cell death protein 1 (PD1), (iii) PDL1, (iv) LAB3, (v) B7-H3, (vi) B7-H4, and (vii) TIM3. The CTLA4 inhibitor Ipilumumab has been approved by the United States Food and Drug Administration for treating melanoma.

Yet other agents that may be used as part of a combination therapy in treating cancer are monoclonal antibody agents that target non-checkpoint targets (e.g., herceptin) and non-cytoxic agents (e.g., tyrosine-kinase inhibitors).

Exemplary therapeutic agents that may be used as part of a combination therapy in treating a bacterial infection, include, for example, amoxicillin, azithromycin, cefazolin, ceftriaxone, cefuroxime, cephalexin, ciprofloxacin, clindamycin, doxycycline, levofloxacin, linezolid, metronidazole, moxifloxacin, and penicillin.

Exemplary therapeutic agents that may be used as part of a combination therapy in treating a fungal infection, include, for example, 2-phenylphenol; 8-hydroxyquinoline sulfate; acibenzolar-S-methyl; aldimorph; amidoflumet; ampropylfos; ampropylfos-potassium; andoprim; anilazine; azaconazole; azoxystrobin; benalaxyl; benodanil; benomyl; benthiavalicarb-isopropyl; benzamacril; benzamacril-isobutyl; bilanafos; binapacryl; biphenyl; bitertanol; blasticidin-S; bromuconazole; butylamine; calcium polysulphide; capsimycin; captafol; captan; carbendazim; carboxin; carpropamid; carvone; chinomethionat; chlobenthiazone; chlorfenazole; chloroneb; chlorothalonil; chlozolinate; clozylacon; cyazofamid; cyflufenamid; cymoxanil; cyproconazole; cyprodinil; cyprofuram; Dagger G; debacarb; dichlofluanid; dichlone; dichlorophen; diclocymet; diclomezine; dicloran; diethofencarb; difenoconazole; diflumetorim; dimethirimol; dimethomorph; dimoxystrobin; diniconazole; diniconazole-M; dinocap; diphenylamine; dipyrithione; ditalimfos; dithianon; dodine; drazoxolon; edifenphos; epoxiconazole; ethaboxam; ethirimol; etridiazole; famoxadone; fenamidone; fenapanil; fenarimol; fenbuconazole; fenfuram; fenhexamid; fenitropan; fenoxanil; fenpiclonil; fenpropidin; fenpropimorph; ferbam; fluazinam; flubenzimine; fludioxonil; flumetover; flumorph; fluoromide; fluoxastrobin; fluquinconazole; flurprimidol; flusilazole; flusulphamide, hexaconazole; hymexazole; imazalil; imibenconazole; iminoctadine triacetate; iminoctadine tris (albesil); iodocarb; ipconazole; iprobenfos; iprodione; iprovalicarb; irumamycin; isoprothiolane; isovaledione; kasugamycin; kresoxim-methyl; oxyfenthiin; paclobutrazole; pefurazoate; penconazole; pencycuron; phosdiphen; phthalide; picoxystrobin; piperalin; polyoxins; polyoxorim; probenazole; prochloraz; procymidone; propamocarb; propanosine-sodium; propiconazole; propineb; proquinazid; prothioconazole; pyraclostrobin; pyrazophos; pyrifenox; pyrimethanil; pyroquilon; pyroxyfur; pyrrolenitrine; tetraconazole; thiabendazole; thicyofen; thifluzamide; thiophanate-methyl; thiram; tioxymid; tricyclazole; tridemorph; trifloxystrobin; triflumizole; triforine; triticonazole; uniconazole; validamycin A; vinclozolin; zineb; ziram; and zoxamide.

The amount of dihydro-2H-benzo[b][1,4]oxazine sulfonamide or related compound (e.g., a compound of Formula I, I-A, I-B, II, II-A, II-B, II-C, or other compounds in Section I) and additional therapeutic agent and the relative timing of administration may be selected in order to achieve a desired combined therapeutic effect. For example, when administering a combination therapy to a patient in need of such administration, the therapeutic agents in the combination, or a pharmaceutical composition or compositions comprising the therapeutic agents, may be administered in any order such as, for example, sequentially, concurrently, together, simultaneously and the like. Further, for example, a dihydro-2H-benzo[b][1,4]oxazine sulfonamide or related compound (e.g., a compound of any one of Formula I, I-A, I-B, II, II-A, II-B, II-C, or other compounds in Section I) may be administered during a time when the additional therapeutic agent(s) exerts its prophylactic or therapeutic effect, or vice versa.

The doses and dosage regimen of the active ingredients used in the combination therapy may be determined by an attending clinician. In certain embodiments, the dihydro- 2H-benzo[b][1,4]oxazine sulfonamide or related compound (e.g., a compound of any one of Formula I, I-A, I-B, II, II-A, II-B, II-C, or other compounds in Section I) and the additional therapeutic agent(s) are administered in doses commonly employed when such agents are used as monotherapy for treating the disorder. In other embodiments, the dihydro-2H-benzo[b][1,4]oxazine sulfonamide or related compound (e.g., a compound of any one of Formula I, I-A, I-B, II, II-A, II-B, II-C, or other compounds in Section I) and the additional therapeutic agent(s) are administered in doses lower than the doses commonly employed when such agents are used as monotherapy for treating the disorder. In certain embodiments, the dihydro-2H-benzo[b][1,4]oxazine sulfonamide or related compound (e.g., a compound of any one of Formula I, I-A, I-B, II, II-A, II-B, II-C, or other compounds in Section I) and the additional therapeutic agent(s) are present in the same composition, which is suitable for oral administration.

In certain embodiments, the dihydro-2H-benzo[b][1,4] oxazine sulfonamide or related compound (e.g., a compound of any one of Formula I, I-A, I-B, II, II-A, II-B, II-C, or other compounds in Section I) and the additional therapeutic agent(s) may act additively or synergistically. A synergistic combination may allow the use of lower dosages of one or more agents and/or less frequent administration of one or more agents of a combination therapy. A lower dosage or less frequent administration of one or more agents may lower toxicity of the therapy without reducing the efficacy of the therapy.

Another aspect of this invention is a kit comprising a therapeutically effective amount of the dihydro-2H-benzo[b][1,4]oxazine sulfonamide or related compound (e.g., a compound of any one of Formula I, I-A, I-B, II, II-A, II-B, II-C, or other compounds in Section I), a pharmaceutically acceptable carrier, vehicle or diluent, and optionally at least one additional therapeutic agent listed above.

IV. Pharmaceutical Compositions and Dosing Considerations

As indicated above, the invention provides pharmaceutical compositions, which comprise a therapeutically-effective amount of one or more of the compounds described above, formulated together with one or more pharmaceutically acceptable carriers (additives) and/or diluents. The pharmaceutical compositions may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

The phrase "therapeutically-effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the present invention comprises an excipient selected from the group consisting of cyclodextrins, celluloses, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules, trouches and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrastemal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracistemally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Preferably, the compounds are administered at about 0.01 mg/kg to about 200 mg/kg, more preferably at about 0.1 mg/kg to about 100 mg/kg, even more preferably at about 0.5 mg/kg to about 50 mg/kg. When the compounds described herein are co-administered with another agent (e.g., as sensitizing agents), the effective amount may be less than when the agent is used alone.

If desired, the effective daily dose of the active compound may be administered as two, three, four, five, six or more sub-doses administered separately at appropriate intervals throughout the day, optionally, in unit dosage forms. Preferred dosing is one administration per day.

The invention further provides a unit dosage form (such as a tablet or capsule) comprising a dihydro-2H-benzo[b][1,4]oxazine sulfonamide or related compound described herein in a therapeutically effective amount for the treatment of a medical disorder described herein.

EXAMPLES

The invention now being generally described, will be more readily understood by reference to the following examples, which are included merely for purposes of illustration of certain aspects and embodiments of the present invention, and are not intended to limit the invention. Starting materials described herein can be obtained from commercial sources or may be readily prepared from commercially available materials using transformations known to those of skill in the art.

Example 1—Synthesis of (S,E)-5-(2-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)ethyl)-1,3,4-oxadiazol-2(3H)-one

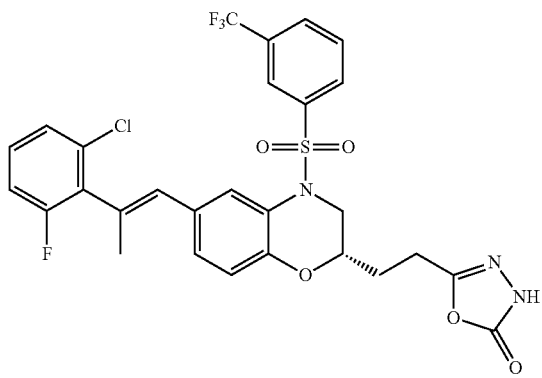 [SMILES: C/C(=C\c1ccc2c(c1)N(S(=O)(=O)c1cccc(C(F)(F)F)c1)C[C@H](CCc1n[nH]c(=O)o1)O2)c1c(F)cccc1Cl]

Part I—Synthesis of dimethyl (R)-2-hydroxypentanedioate

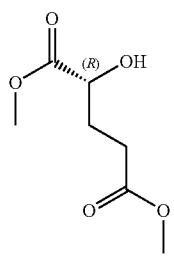

To a mixture of (2R)-5-oxotetrahydro-2-furancarboxylic acid (25 g, 192 mmol) in methanol (300 mL) was added concentrated hydrochloric acid (0.5 mL) and the mixture was refluxed overnight then cooled to ambient temperature. Excess solid sodium bicarbonate (4 g) was added slowly and the mixture was slurried for 20 minutes. Then, the mixture was filtered and concentrated to obtain dimethyl (R)-2-hydroxypentanedioate (34.7 g, 100%).

Part II—Synthesis of dimethyl (S)-2-(4-bromo-2-nitrophenoxy)pentanedioate

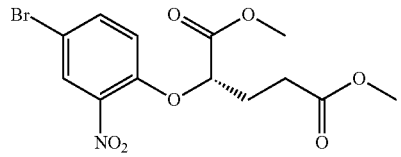 [SMILES: COC(=O)CC[C@H](Oc1ccc(Br)cc1[N+](=O)[O-])C(=O)OC]

To a solution of dimethyl (R)-2-hydroxypentanedioate (33.8 g, 192 mmol), 4-bromo-2-nitrophenol (50.2 g, 230 mmol), and triphenylphosphine (60.4 g, 230 mmol) in dichloromethane (300 mL) with activated molecular sieves at 0° C. was added a solution of diisopropyl azodicarboxylate (45.4 mL, 230 mmol) in dichloromethane (50 mL) dropwise. This mixture was stirred at 0° C. for 20 minutes, then at ambient temperature overnight. The resulting mixture was concentrated and the triphenylphosphine oxide removed by filtration through a large pad of silica gel, eluting with dichloromethane (~6 L). The eluted material was a mixture of the intended product and a small amount of residual phenol. According, the eluted material was redissolved in ethyl acetate, washed four times with 1M sodium hydroxide, then washed with brine, dried ($Na_2SO_4$), and concentrated to yield dimethyl (S)-2-(4-bromo-2-nitrophenoxy)pentanedioate (62.84 g, 87%) as a clear oil.

Part III—Synthesis of methyl (S)-3-(6-bromo-3-oxo-3,4-dihydro-2H-benzo[b][1,4]oxazin-2-yl)propanoate

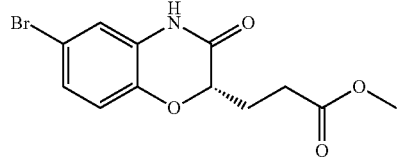 [SMILES: COC(=O)CC[C@@H]1Oc2ccc(Br)cc2NC1=O]

A flask equipped with a mechanical stirrer was charged with dimethyl (S)-2-(4-bromo-2-nitrophenoxy)pentanedioate (62.84 g, 167 mmol) and acetic acid (500 mL), followed by powdered iron (46.7 g, 835 mmol) at ambient temperature. The reaction mixture was heated to 60° C. for 2 hours, and then filtered hot through a pad of celite, washing with ethyl acetate (900 mL). The filtrates were combined and washed three times with water, washed with brine, dried ($Na_2SO_4$) and concentrated to yield methyl (S)-3-(6-bromo-3-oxo-3,4-dihydro-2H-benzo[b][1,4]oxazin-2-yl)propanoate (48.06 g, 92%) as a white solid.

Part IV—Synthesis of methyl (S)-3-(6-bromo-3,4-dihydro-2H-benzo[b][1,4]oxazin-2-yl)propanoate

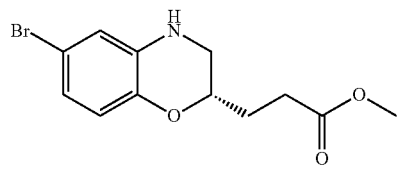 [SMILES: COC(=O)CC[C@H]1CNc2cc(Br)ccc2O1]

To methyl (S)-3-(6-bromo-3-oxo-3,4-dihydro-2H-benzo[b][1,4]oxazin-2-yl)propanoate (24.46 g, 77.9 mmol) in anhydrous tetrahydrofuran (200 mL) at 0° C. was added borane-methyl sulfide complex (19.5 mL, 195 mmol) dropwise. This mixture was heated to 50° C. for 1 hour. Then, the reaction mixture was cooled to 0° C., then carefully quenched by adding methanol (150 mL). The resulting mixture was re-heated to 60° C. for 60 minutes, then cooled and concentrated. The resulting residue was partitioned between water and ethyl acetate. The organic layer was washed with brine, dried (Na$_2$SO$_4$) and concentrated. The crude product was purified by column chromatography eluting with a gradient of 5-50% ethyl acetate in hexanes to yield methyl (S)-3-(6-bromo-3,4-dihydro-2H-benzo[b][1,4]oxazin-2-yl)propanoate (17.97 g, 77%) as a white solid.

Part V—Synthesis of (S)-methyl 3-(6-bromo-4-((3-(trifluoromethyl)phenyl)sulfonyl)-3,4-dihydro-2H-benzo[b][1,4]oxazin-2-yl)propanoate

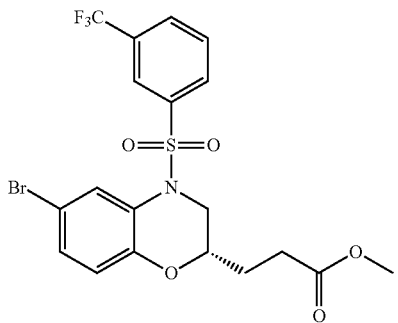 [SMILES: COC(=O)CC[C@H]1CN(S(=O)(=O)c2cccc(C(F)(F)F)c2)c2cc(Br)ccc2O1]

To a solution of (S)-3-(6-bromo-3,4-dihydro-2H-benzo[b][1,4]oxazin-2-yl)propanoate (10.0 g, 33.3 mmol) in pyridine (60 mL) was added 3-(trifluoromethyl)-benzenesulfonyl chloride (8.96 g, 36.6 mmol). The mixture was heated at 50° C. for four hours, then the mixture was cooled and concentrated. The resulting residue was partitioned between ethyl acetate and 1N HCl. The organic layer was washed twice with 1N HCl, then washed with brine, and dried (Na$_2$SO$_4$). Activated charcoal was added, slurried, then filtered through celite. The filtrate was concentrated onto a small amount of silica gel and the residue was purified via MPLC eluting with a gradient of ethyl acetate in hexanes. The major UV active component was concentrated to afford (S)-methyl 3-(6-bromo-4-((3-(trifluoromethyl)phenyl)sulfonyl)-3,4-dihydro-2H-benzo[b][1,4]oxazin-2-yl)propanoate (14.75 g, 87%).

Part VI—Synthesis of 1-chloro-2-ethynyl-3-fluorobenzene

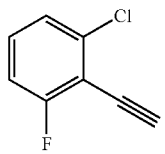

2-Chloro-6-fluorobenzaldehyde (2.00 g, 12.61 mmol) was dissolved in methanol (84 mL), and dimethyl (diazomethyl) phosphonate (2.39 mL, 15.77 mmol) was added followed by potassium carbonate (4.36 g, 31.53 mmol). The reaction mixture was stirred at room temperature overnight. Then, the crude mixture was diluted with methyl tert-butyl ether, washed with water, washed with brine, dried (Na$_2$SO$_4$), and concentrated to afford 1-chloro-2-ethynyl-3-fluorobenzene (1.83 g, 94%). $^1$H-NMR (400 MHz, DMSO-d$_6$) δ 7.45 (m, 2H), 7.32 (t, 1H), 4.86 (s, 1H).

Part VII—Synthesis of (E)-2-(2-(2-chloro-6-fluorophenyl)prop-1-en-1-yl)-4,4,5,5-tetramethyl-1,3,2-dioxaborolane

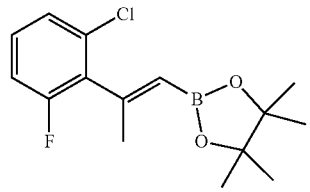 [SMILES: C/C(=C\B1OC(C)(C)C(C)(C)O1)c1c(F)cccc1Cl]

Bis(pinacolato)diborane (5.82 g, 22.92 mmol), copper (I) chloride (0.21 g, 2.08 mmol), and 4,5-bis(diphenylphosphino)-9,9-dimethylxanthene (1.21 g, 2.08 mmol) were suspended in THF (208 mL) and the mixture was degassed with nitrogen, and stirred for five minutes. A solution of sodium tert-butoxide (2.202 g, 22.92 mmol) in the minimum amount of THF was added, and the mixture stirred for an additional five minutes. 1-Chloro-2-ethynyl-3-fluorobenzene (3.22 g, 20.83 mmol) and methyl iodide (11.83 g, 83.33 mmol) were added to the reaction mixture, and the resulting mixture was stirred at room temperature overnight. Then, the crude product mixture was concentrated onto silica gel and purified by MPLC eluting with a gradient of 0-5% ethyl acetate in hexanes to afford (E)-2-(2-(2-chloro-6-fluorophenyl)prop-1-en-1-yl)-4,4,5,5-tetramethyl-1,3,2-dioxaborolane (2.41 g, 39%). $^1$H-NMR (400 MHz, DMSO-d$_6$) δ 7.31 (m, 2H), 7.20 (t, 1H), 5.18 (s, 1H), 2.15 (s, 3H), 1.23 (s, 12H).

Part VIII—Synthesis of (S,E)-methyl 3-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)propanoate

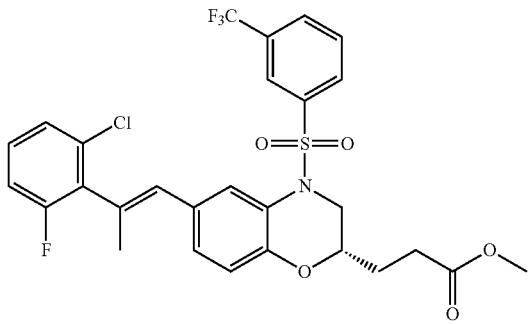 [SMILES: COC(=O)CC[C@H]1CN(S(=O)(=O)c2cccc(C(F)(F)F)c2)c2cc(/C=C(\C)c3c(F)cccc3Cl)ccc2O1]

A mixture of (S)-methyl 3-(6-bromo-4-((3-(trifluoromethyl)phenyl)sulfonyl)-3,4-dihydro-2H-benzo[b][1,4]oxazin-2-yl)propanoate (7.46 g, 14.7 mmol), (E)-2-(2-(2-chloro-6-fluorophenyl)prop-1-en-1-yl)-4,4,5,5-tetramethyl-1,3,2-dioxaborolane (6.09 g, 20.5 mmol), potassium carbonate (2.84 g, 20.5 mmol) in dioxane (80 mL) and water (20 mL) was degassed and was placed under an atomsphere of nitrogen. [1,1'-Bis(diphenylphosphino)ferrocene]dichloropalladium(II), complex with dichloromethane (1.12 g, 1.47 mmol) was added to the mixture and the mixture was heated to 70° C. for five hours. Toluene (100 mL) and a 20% solution of sodium bisulfite in water (50 mL) were added to the reaction mixture and the resulting mixture was stirred at 60° C. for an additional fifteen minutes. Then, the mixture was cooled and subsequently diluted with toluene (150 mL). The organic layer was washed with a 20% aqueous solution of sodium bisulfite, water, then brine. The organic solution was dried (Na$_2$SO$_4$), and activated charcoal was added. The resulting mixture was slurried, and filtered through a pad of celite. The filtrate was concentrated onto a small amount of silica gel and the residue was purified by MPLC eluting with a gradient of 0-30% ethyl acetate in hexanes to afford (S,E)-methyl 3-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)propanoate (8.31 g, 94%).

Part IX—Synthesis of (S,E)-5-(2-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)ethyl)-1,3,4-oxadiazol-2(3H)-one

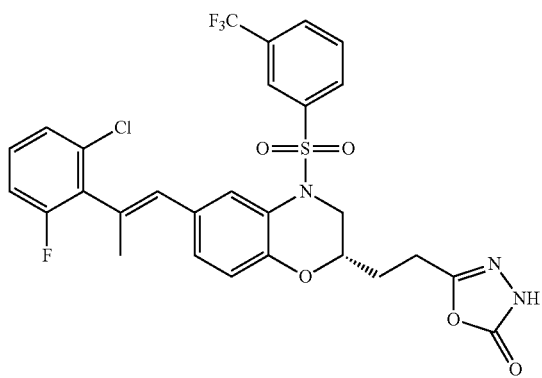 [SMILES: C/C(=C\c1ccc2c(c1)N(S(=O)(=O)c1cccc(C(F)(F)F)c1)C[C@H](CCc1n[nH]c(=O)o1)O2)c1c(F)cccc1Cl]

A solution of (S,E)-methyl 3-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)propanoate (70 mg, 0.117 mmol) and hydrazine (37.5 mg, 1.17 mmol) in methanol (2 mL) was heated to 50° C. for two hours. After allowing to cool, the mixture was concentrated to afford (S,E)-3-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)propanehydrazide which was used without purification. To a solution of this hydrazide in THF (2 mL) at 0° C. was added diisopropylethylamine (30 mg, 0.23 mmol) followed by triphosgene (20 mg, 0.058 mmol). This mixture was stirred at 0° C. for ten minutes, and at room temperature for two hours. The mixture was partitioned between ethyl acetate and water, washed with brine, dried (Na$_2$SO$_4$), and concentrated onto silica gel. The product was purified by MPLC eluting with a gradient of ethyl acetate in hexanes to afford (S,E)-5-(2-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)ethyl)-1,3,4-oxadiazol-2(3H)-one (35 mg, 48%) as a white solid. $^1$H-NMR (400 MHz, DMSO-d$_6$) δ 12.04 (s, 1H), 8.07 (m, 2H), 7.97 (s, 1H), 7.84 (d, 1H, J=8.1 Hz), 7.67 (d, 1H, J=1.7 Hz), 7.37 (m, 2H), 7.25 (m, 1H), 7.10 (m, 1H), 6.84 (d, 1H, J=8.4 Hz), 6.36 (s, 1H), 4.40 (dd, 1H, J1=14.1 Hz, J2=0.9 Hz), 3.53 (m, 1H), 3.4 (m, 2H), 2.63 (m, 2H), 2.07 (s, 3H), 1.95 (m, 1H), 1.80 (m, 1H). (ES, m/z): (M+Na)$^+$ 645.97, 647.95.

Example 2—Synthesis of (S,E)-2-(2-(2H-tetrazol-5-yl)ethyl)-6-(2-(2-chloro-6-fluorophenyl)prop-1-en-1-yl)-4-((3-(trifluoromethyl)phenyl)sulfonyl)-3,4-dihydro-2H-benzo[b][1,4]oxazine

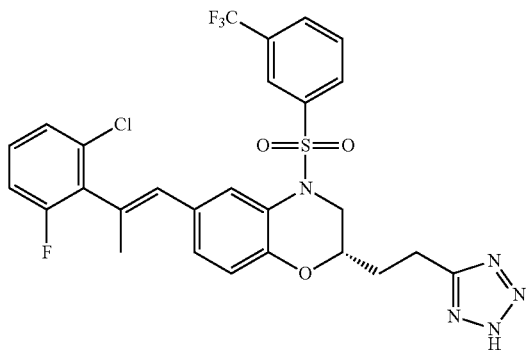 [SMILES: C/C(=C\c1ccc2c(c1)N(S(=O)(=O)c1cccc(C(F)(F)F)c1)C[C@H](CCc1nn[nH]n1)O2)c1c(F)cccc1Cl]

Part I—Synthesis of (R)-3-(4-bromo-2-nitrophenoxy)dihydrofuran-2(3H)-one

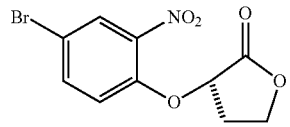

4-Bromo-2-nitrophenol (3 g, 13.76 mmol), (3R)-3-hydroxytetrahydrofuran-2-one (1.405 g, 13.76 mmol), and triphenylphosphine (4.33 g, 16.51 mmol) were suspended in dichloromethane (36 mL), and diisopropylazodicarboxylate (3.25 mL, 16.5 mmol) was added dropwise. The reaction mixture was stirred at room temperature for one hour, washed with water, dried (Na$_2$SO$_4$), and concentrated onto silica gel. The residue on the silica gel was purified by MPLC (2 columns: first, dichloromethane; second, a gradient of EtOAc/hexanes) affording (R)-3-(4-bromo-2-nitrophenoxy)dihydrofuran-2(3H)-one as a white solid (1.93 g, 46%). $^1$H-NMR (400 MHz, DMSO-d$_6$) δ 8.12 (s, 1H), 7.86 (d, 1H), 7.47 (d, 1H), 5.55 (t, 1H), 4.42 (m, 1H), 4.26 (m, 1H), 2.75 (m, 1H), 2.30 (m, 1H).

Part II—Synthesis of (S)-6-bromo-2-(2-hydroxyethyl)-2H-benzo[b][1,4]oxazin-3(4H)-one

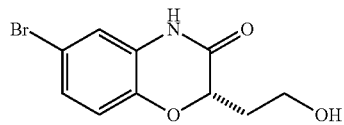

(R)-3-(4-Bromo-2-nitrophenoxy)dihydrofuran-2(3H)-one (1.93 g, 6.39 mmol) was dissolved in acetic acid and powdered iron (1.784 g, 31.95 mmol) was added. The resulting mixture was heated to 70° C. for two hours. Then, the resulting suspension was filtered through a pad of celite, and the pad was washed with ethyl acetate. The combined filtrates were partitioned between ethyl acetate and water, and the organic phase was washed a second time with water, washed with brine, and concentrated to provide a residue. The residue was purified via MPLC eluting with a gradient of 15-70% ethyl acetate in hexanes to afford (S)-6-bromo-2-(2-hydroxyethyl)-2H-benzo[b][1,4]oxazin-3(4H)-one as a white solid (1.32 g, 76%). $^1$H-NMR (400 MHz, DMSO-$d_6$) δ 10.73 (bs, 1H), 7.04 (d, 1H), 6.98 (s, 1H), 6.90 (d, 1H), 4.62 (m, 2H), 3.53 (m, 2H), 1.91 (m, 1H), 1.88 (m, 1H).

Part III—Synthesis of (S)-2-(6-bromo-3,4-dihydro-2H-benzo[b][1,4]oxazin-2-yl)ethan-1-ol

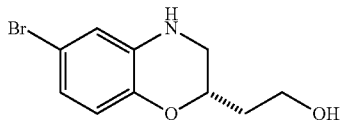 [SMILES: OCC[C@H]1CNc2cc(Br)ccc2O1]

(S)-6-Bromo-2-(2-hydroxyethyl)-2H-benzo[b][1,4]oxazin-3(4H)-one (1.32 g, 4.85 mmol) was dissolved in anhydrous THF (49 mL) under nitrogen at ambient temperature and borane-dimethylsulfide complex (1.47 g, 19.41 mmol) was added dropwise. The reaction mixture was heated to reflux for 90 minutes. Then, the reaction vessel containing the reaction mixture was cooled in an ice bath and subsequently methanol was added to the reaction mixture to quench the reaction. The resulting solution was heated to reflux for 20 minutes, and then concentrated to provide a residue. The residue was partitioned between ethyl acetate and water, washed with brine, dried (Na$_2$SO$_4$), and concentrated to provide crude product. The crude product was purified by MPLC eluting with a gradient of 15-70% ethyl acetate in hexanes to afford (S)-2-(6-bromo-3,4-dihydro-2H-benzo[b][1,4]oxazin-2-yl)ethan-1-ol (1.05 g, 84%).

Part IV—Synthesis of (S)-6-bromo-2-(2-((tert-butyldimethylsilyl)oxy)ethyl)-3,4-dihydro-2H-benzo[b][1,4]oxazine

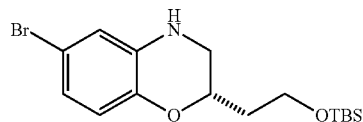 [SMILES: CC(C)(C)[Si](C)(C)OCC[C@H]1CNc2cc(Br)ccc2O1]

(S)-2-(6-Bromo-3,4-dihydro-2H-benzo[b][1,4]oxazin-2-yl)ethan-1-ol (0.28 g, 1.085 mmol), tert-butyldimethylchlorosilane (0.196 g, 1.302 mmol), and imidazole (0.148 g, 2.17 mmol) were dissolved in DMF (4 mL), and the reaction mixture was stirred at room temperature overnight. Next, the reaction mixture was partitioned between water and ethyl acetate, and the organic layer was washed twice more with water, washed with brine, dried (Na$_2$SO$_4$), and concentrated onto silica gel. The residue on the silica gel was purified by MPLC eluting with a gradient of 5-30% ethyl acetate in hexanes to afford (S)-6-bromo-2-(2-((tert-butyldimethylsilyl)oxy)ethyl)-3,4-dihydro-2H-benzo[b][1,4]oxazine (0.19 g, 47%). $^1$H-NMR (400 MHz, DMSO-$d_6$) δ 6.66 (s, 1H), 6.52 (s, 2H), 6.06 (bs, 1H), 4.02 (q, 1H), 3.72 (m, 2H), 3.33 (m, 1H), 2.94 (m, 1H), 1.70 (q, 2H), 0.82 (s, 9H), 0.01 (s, 6H).

Part V—Synthesis of (S)-2-(6-bromo-4-((3-(trifluoromethyl)phenyl)sulfonyl)-3,4-dihydro-2H-benzo[b][1,4]oxazin-2-yl)ethan-1-ol

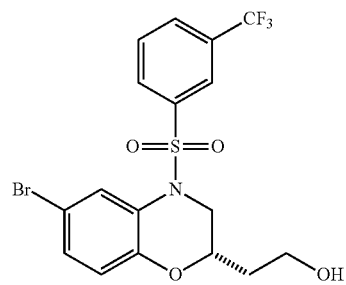

(S)-6-Bromo-2-(2-((tert-butyldimethylsilyl)oxy)ethyl)-3,4-dihydro-2H-benzo[b][1,4]oxazine (1.04 g, 2.79 mmol), 3-(trifluoromethyl)benzenesulfonyl chloride (1.025 g, 4.19 mmol), and potassium carbonate (0.772 g, 5.586 mmol) were suspended in acetone (28 mL), and the mixture was shaken at room temperature for 18 hours. Then, the crude material was filtered, and the filtrate was concentrated onto silica gel and purified by chromatography delivering (S)-2-(6-bromo-4-((3-(trifluoromethyl)phenyl)sulfonyl)-3,4-dihydro-2H-benzo[b][1,4]oxazin-2-yl)ethan-1-ol (1.61 g, 99%). It is noted that the silyl protecting group did not hydrolyze immediately, but after several days at room temperature formation of the alcohol was observed. $^1$H-NMR (400 MHz, DMSO-$d_6$) δ 8.11 (d, 1H), 7.95 (m, 2H), 7.84 (t, 1H), 7.78 (s, 1H), 7.25 (d, 1H), 6.80 (d, 1H), 4.56 (s, 1H), 3.39 (d, 1H), 3.41 (m, 3H), 3.28 (m, 1H), 1.63 (m, 2H).

Part VI—Synthesis of (S)-2-(6-Bromo-4-((3-(trifluoromethyl)phenyl)sulfonyl)-3,4-dihydro-2H-benzo[b][1,4]oxazin-2-yl)ethyl 4-methylbenzenesulfonate

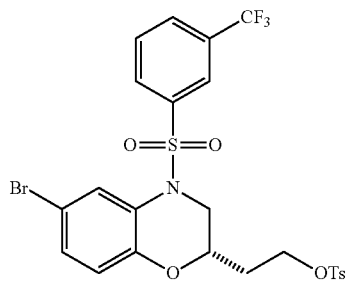 [SMILES: Cc1ccc(S(=O)(=O)OCC[C@H]2CN(S(=O)(=O)c3cccc(C(F)(F)F)c3)c3cc(Br)ccc3O2)cc1]

(S)-2-(6-Bromo-4-((3-(trifluoromethyl)phenyl)sulfonyl)-3,4-dihydro-2H-benzo[b][1,4]oxazin-2-yl)ethan-1-ol (0.13 g, 0.28 mmol) was dissolved in dichloromethane (6 mL) and triethylamine (0.058 mL, 0.42 mmol) was added followed by tosyl chloride (56 mg, 0.293 mmol). The reaction mixture was stirred at room temperature overnight. Then, additional tosyl chloride (56 mg, 0.293 mmol) and triethylamine (0.060 mL) were added, and the reaction mixture was stirred for one additional day. Then, the crude solution was washed with dilute HCl, washed with brine, dried (Na$_2$SO$_4$), and concentrated onto silica gel for purification by chromatography to afford (S)-2-(6-bromo-4-((3-(trifluoromethyl)phenyl)sulfonyl)-3,4-dihydro-2H-benzo[b][1,4]oxazin-2-yl) ethyl 4-methylbenzenesulfonate as a white solid (0.14 g, 81%). ¹H-NMR (400 MHz, DMSO-d₆) δ 8.12 (d, 1H), 7.98 (m, 2H), 7.87 (t, 1H), 7.76 (s, 1H), 7.59 (d, 2H), 7.33 (d, 2H), 7.24 (dd, 1H), 6.54 (d, 1H), 4.33 (dd, 1H), 4.08 (m, 1H), 4.00 (m, 1H), 3.24 (m, 2H), 2.32 (s, 3H), 1.97 (m, 1H), 1.70 (m, 1H).

Part VII—Synthesis of (S)-3-(6-bromo-4-((3-(trifluoromethyl)phenyl)sulfonyl)-3,4-dihydro-2H-benzo[b][1,4]oxazin-2-yl)propanenitrile

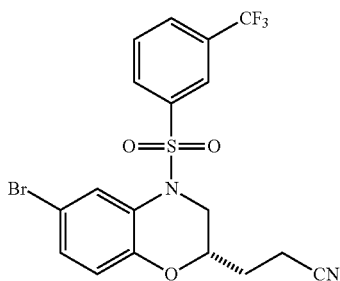 [SMILES: N#CCC[C@H]1CN(S(=O)(=O)c2cccc(C(F)(F)F)c2)c2cc(Br)ccc2O1]

(S)-2-(6-Bromo-4-((3-(trifluoromethyl)phenyl)sulfonyl)-3,4-dihydro-2H-benzo[b][1,4]oxazin-2-yl)ethyl 4-methylbenzenesulfonate (0.14 g, 0.226 mmol) was dissolved in DMSO (1 mL) and potassium cyanide (0.016 g, 0.248 mmol) was added. After one hour, additional potassium cyanide (17 mg) was added, and stirring was continued overnight. Then, the crude material was then partitioned between water and ethyl acetate. The organic phase was washed a second time, then washed with brine, dried (Na₂SO₄), and concentrated to afford (S)-3-(6-bromo-4-((3-(trifluoromethyl)phenyl)sulfonyl)-3,4-dihydro-2H-benzo[b][1,4]oxazin-2-yl)propanenitrile (0.09 g, 84%). ¹H-NMR (400 MHz, DMSO-d₆) δ 8.09 (d, 1H), 8.00 (m, 2H), 7.84 (t, 1H), 7.78 (s, 1H), 7.27 (d, 1H), 6.82 (d, 1H), 4.40 (d, 1H), 3.37 (m, 2H), 2.56 (m, 2H), 1.92 (m, 1H), 1.72 (m, 1H).

Part VIII—Synthesis of (S,E)-3-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)propanenitrile

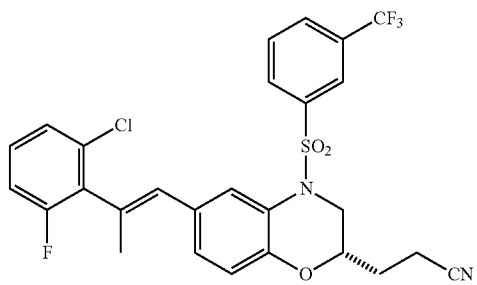 [SMILES: C/C(=C\c1ccc2c(c1)N(S(=O)(=O)c1cccc(C(F)(F)F)c1)C[C@H](CCC#N)O2)c1c(F)cccc1Cl]

(S)-3-(6-Bromo-4-((3-(trifluoromethyl)phenyl)sulfonyl)-3,4-dihydro-2H-benzo[b][1,4]oxazin-2-yl)propanenitrile (40 mg, 0.084 mmol), (E)-2-(2-(2-chloro-6-fluorophenyl)prop-1-en-1-yl)-4,4,5,5-tetramethyl-1,3,2-dioxaborolane (25 mg, 0.084 mmol), THF (3 mL), and sodium hydroxide (10 mg, 0.252 mmol) were combined in a vial, and the mixture was degassed by bubbling nitrogen. Tetrakis(triphenylphosphine)palladium (10 mg, 0.008 mmol) was added to the reaction mixture, and the resulting mixture was shaken at 70° C. overnight. Then, the crude mixture was partitioned between water and ethyl acetate. The organic phase was then washed with brine, dried (Na₂SO₄), and concentrated onto silica gel and purified by chromatography to afford (S,E)-3-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)propanenitrile as a yellow oil (31 mg, 65%). ¹H-NMR (400 MHz, DMSO-d₆) δ 8.03 (m, 3H), 7.82 (m, 2H), 7.67 (s, 1H), 7.35 (m, 4H), 7.11 (d, 1H), 6.89 (d, 1H), 6.38 (s, 1H), 4.42 (d, 1H), 3.40 (m, 3H), 2.60 (m, 3H), 2.07 (s, 3H), 1.96 (m, 2H), 1.78 (m, 2H), 1.20 (m, 2H), 1.02 (s, 3H).

Part XI—Synthesis of (S,E)-2-(2-(2H-tetrazol-5-yl)ethyl)-6-(2-(2-chloro-6-fluorophenyl)prop-1-en-1-yl)-4-((3-(trifluoromethyl)phenyl)sulfonyl)-3,4-dihydro-2H-benzo[b][1,4]oxazine

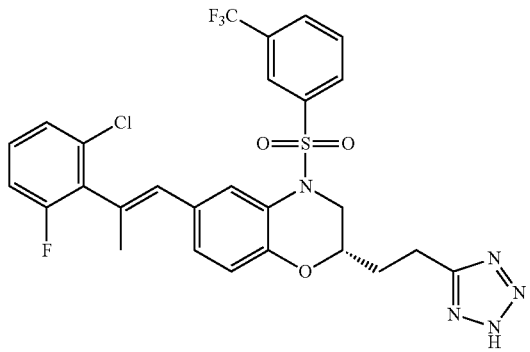 [SMILES: C/C(=C\c1ccc2c(c1)N(S(=O)(=O)c1cccc(C(F)(F)F)c1)C[C@H](CCc1nn[nH]n1)O2)c1c(F)cccc1Cl]

In a reaction tube were combined (S,E)-3-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)propanenitrile (110 mg, 0.195 mmol), dibutyltin oxide (4.8 mg, 0.019 mmol) and trimethylsilyl azide (44.9 mmol, 0.389 mmol) in anhydrous dimethoxyethane (2 mL). The tube was sealed and the mixture was heated at 140° C. for two hours, then cooled, and concentrated. The residue was first purified by MPLC eluting with a gradient of ethyl acetate and hexanes. The fractions containing the major UV active component were concentrated and the residue was further purified by reverse phase HPLC to afford of (S,E)-2-(2-(2H-tetrazol-5-yl)ethyl)-6-(2-(2-chloro-6-fluorophenyl)prop-1-en-1-yl)-4-((3-(trifluoromethyl)phenyl)sulfonyl)-3,4-dihydro-2H-benzo[b][1,4]oxazine (15 mg, 12%). ¹H-NMR (400 MHz, DMSO-d₆) δ 8.05 (m, 2H), 7.97 (s, 1H), 7.82 (m, 1H). 7.67 (s, 1H), 7.38 (m, 2H), 7.25 (m, 1H), 7.14 (m, 1H), 6.84 (m, 1H), 6.38 (s, 1H), 4.42 (m, 1H), 3.60 (m, 1H), 3.45 (m, 2H), 3.0 (m, 2H), 2.1 (s, 3H), 1.98 (m, 2H). (ES, m/z): (M−H)⁻ 606.32, 608.30.

Example 3—Synthesis of (R,E)-3-((7-(2-(2-chloro-6-fluorophenyl)prop-1-en-1-yl)-1-((3-(trifluoromethyl)phenyl)sulfonyl)-1,2,3,4-tetrahydroquinolin-3-yl)oxy)-1,2,4-oxadiazol-5(4H)-one

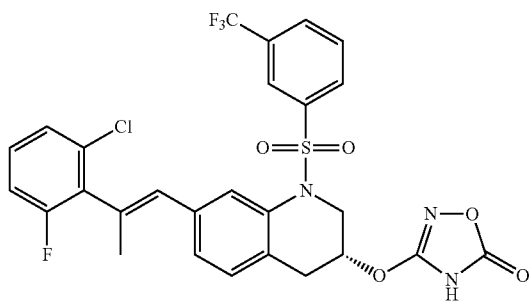 [SMILES: C/C(=C\c1ccc2c(c1)N(S(=O)(=O)c1cccc(C(F)(F)F)c1)C[C@H](Oc1noc(=O)[nH]1)C2)c1c(F)cccc1Cl]

Part I—Synthesis of (E)-ethyl 3-(4-methoxy-2-nitrophenyl)acrylate

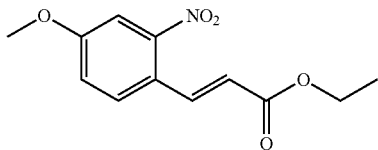 [SMILES: CCOC(=O)/C=C/c1ccc(OC)cc1[N+](=O)[O-]]

A mixture of 1-iodo-4-methoxy-2-nitrobenzene (279 mg, 1.00 mmol), palladium acetate (11.2 mg, 0.05 mmol), triethylamine (202 mg, 2.00 mmol), and ethyl acrylate (110 mg, 1.10 mmol) was heated to reflux for five hours. Then, the mixture was cooled, concentrated and diluted with ethyl acetate. The resulting organic mixture was washed with water, then brine, dried (Na$_2$SO$_4$) and concentrated. The resulting residue was purified via MPLC eluting with 3:1 hexane:ethyl acetate to afford (E)-ethyl 3-(4-methoxy-2-nitrophenyl)acrylate (201 mg, 80%) as a yellow solid.

Part II—Synthesis of (2R,3S)-ethyl 2,3-dihydroxy-3-(4-methoxy-2-nitrophenyl)propanoate

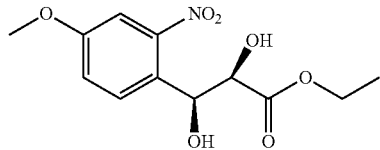 [SMILES: CCOC(=O)[C@H](O)[C@@H](O)c1ccc(OC)cc1[N+](=O)[O-]]

To a solution of (E)-ethyl 3-(4-methoxy-2-nitrophenyl) acrylate (5 g, 19.90 mmol) in tert-butanol/water (1:1) (150 mL) was added methanesulfonamide (2 g, 21.03 mmol) followed by the addition of AD-mix-α (16.4 g, 21.05 mmol) in several portions at 0° C. The reaction mixture was stirred overnight at room temperature and then quenched by the addition of saturated aqueous NaHSO$_3$ (200 mL). The resulting mixture was extracted three times with ethyl acetate, and the combined organic layers were concentrated. The resulting residue was purified via MPLC eluting with ethyl acetate/petroleum ether (4:1). Concentration of the major UV active component afforded (2R,3S)-ethyl 2,3-dihydroxy-3-(4-methoxy-2-nitrophenyl)propanoate (4.95 g, 87%) as a yellow solid.

Part III—Synthesis of (4R,5S)-ethyl 5-(4-methoxy-2-nitrophenyl)-1,3,2-dioxathiolane-4-carboxylate 2-oxide

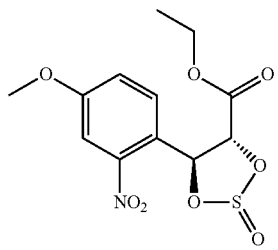

To a stirred solution of ethyl (2R,3S)-2,3-dihydroxy-3-(4-methoxy-2-nitrophenyl)propanoate (5 g, 17.53 mmol) and triethylamine (5.3 g, 52.38 mmol) in dichloromethane (150 mL) at 0° C. was added thionyl chloride (2.7 g, 22.69 mmol) dropwise. The mixture was stirred for 1 hour, and then quenched by the addition of water. The resulting mixture was extracted three times with dichloromethane. The combined organic layers were dried (Na$_2$SO$_4$) and concentrated. The resulting residue was purified via MPLC eluting with a gradient of ethyl acetate/petroleum ether (1:10-1:2). Concentration of the major UV active component afforded (4R,5S)-ethyl 5-(4-methoxy-2-nitrophenyl)-1,3,2-dioxathiolane-4-carboxylate 2-oxide (5.2 g, 90%) as a yellow oil.

Part IV—Synthesis of (R)-7-methoxy-1,2,3,4-tetrahydroquinolin-3-ol

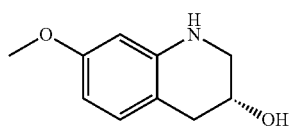

To a solution of (4R,5S)-ethyl 5-(4-methoxy-2-nitrophenyl)-1,3,2-dioxathiolane-4-carboxylate 2-oxide (1.5 g, 4.53 mmol) in 190 proof ethanol (60 mL) at 0° C. was added cobalt (II) chloride hexahydrate (213 mg, 0.90 mmol) followed by the addition of sodium borohydride (1.33 g, 36.1 mmol). The mixture was stirred overnight at room temperature. Then, the mixture was poured into ice water (100 mL), and extracted four times with ethyl acetate. The combined organic layers were concentrated and the resulting residue was purified via MPLC eluting with ethyl acetate/petroleum ether (1:1) to afford (R)-7-methoxy-1,2,3,4-tetrahydroquinolin-3-ol (550 mg, 68%) as a yellow solid.

Part V—Synthesis of (R)-7-methoxy-1-((3-(trifluoromethyl)phenyl)sulfonyl)-1,2,3,4-tetrahydroquinolin-3-ol

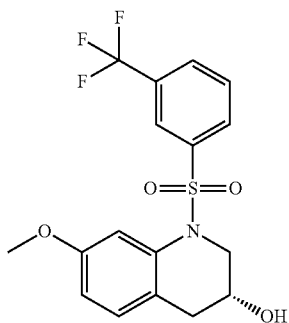 [SMILES: COc1ccc2c(c1)N(S(=O)(=O)c1cccc(C(F)(F)F)c1)C[C@H](O)C2]

To a room temperature solution of (R)-7-methoxy-1,2,3,4-tetrahydroquinolin-3-ol (400 mg, 2.23 mmol) in dichloromethane (12 mL) and pyridine (12 mL) was added 3-(trifluoromethyl)benzene-1-sulfonyl chloride (600 mg, 2.45 mmol). This mixture was stirred for two hours, diluted with dichloromethane and washed twice with 1M hydrogen chloride. The organic layer was dried (Na$_2$SO$_4$) and concentrated to afford (R)-7-methoxy-1-((3-(trifluoromethyl)phenyl)sulfonyl)-1,2,3,4-tetrahydroquinolin-3-ol (650 mg, 75%) as a colorless oil.

Part VI—Synthesis of (R)-1-((3-(trifluoromethyl)phenyl)sulfonyl)-1,2,3,4-tetrahydroquinoline-3,7-diol

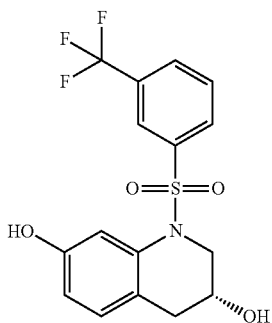 [SMILES: O=S(=O)(c1cccc(C(F)(F)F)c1)N1C[C@H](O)Cc2ccc(O)cc21]

To a solution of (R)-7-methoxy-1-((3-(trifluoromethyl)phenyl)sulfonyl)-1,2,3,4-tetrahydroquinolin-3-ol (1.1 g, 2.84 mmol) in dichloromethane (20 mL) at −78° C. was added boron tribromide (11.2 g, 44.7 mmol) dropwise. The reaction mixture was allowed to warm to room temperature and was stirred for two hours. Then, the reaction was quenched by adding water to the reaction mixture, and the resulting mixture was extracted twice with dichloromethane. The combined organic layers were dried (Na$_2$SO$_4$) and concentrated. The resulting residue was purified via MPLC eluting with petroleum ether:ethyl acetate (1:1). Concentration of the major UV active component afforded (R)-1-((3-(trifluoromethyl)phenyl)sulfonyl)-1,2,3,4-tetrahydroquinoline-3,7-diol (900 mg, 85%) as a colorless oil.

Part VII—Synthesis of (R)-3-hydroxy-1-((3-(trifluoromethyl)phenyl)sulfonyl)-1,2,3,4-tetrahydroquinolin-7-yl trifluoromethanesulfonate

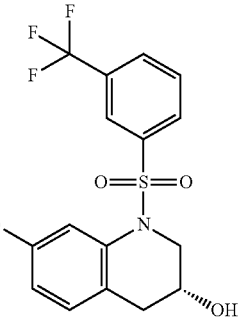

To a stirred solution of (R)-1-((3-(trifluoromethyl)phenyl)sulfonyl)-1,2,3,4-tetrahydroquinoline-3,7-diol (800 mg, 2.14 mmol) and pyridine (676 mg, 8.55 mmol) in dichloromethane (70 mL) was added a solution of trifluoromethanesulfonic anhydride (847 mg, 3.00 mmol) in dichloromethane (5 mL) dropwise. The reaction mixture was stirred for two hours at room temperature. Then, the reaction mixture was diluted with water. The resulting mixture was extracted with dichloromethane. The organic layer was washed with water, then brine, and concentrated. The resulting residue was purified via MPLC eluting with ethyl acetate/petroleum ether (1:10-1:3) to afford (R)-3-hydroxy-1-((3-(trifluoromethyl)phenyl)sulfonyl)-1,2,3,4-tetrahydroquinolin-7-yl trifluoromethanesulfonate (950 mg, 88%) as a yellow oil.

Part VIII—Synthesis of (R,E)-7-(2-(2-chloro-6-fluorophenyl)prop-1-en-1-yl)-1-((3-(trifluoromethyl)phenyl)sulfonyl)-1,2,3,4-tetrahydroquinolin-3-ol

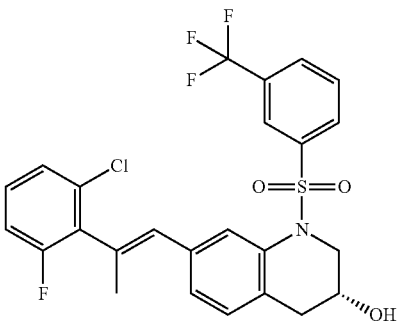 [SMILES: C/C(=C\c1ccc2c(c1)N(S(=O)(=O)c1cccc(C(F)(F)F)c1)C[C@H](O)C2)c1c(F)cccc1Cl]

To a flask, which was purged and maintained with an inert atmosphere of nitrogen, was placed a solution of (R)-3-hydroxy-1-((3-(trifluoromethyl)phenyl)sulfonyl)-1,2,3,4-tetrahydroquinolin-7-yl trifluoromethanesulfonate (400 mg, 0.79 mmol) in toluene (12 mL), ethanol (4 mL), water (2 mL), 2-[(1E)-2-(2-chloro-6-fluorophenyl)prop-1-en-1-yl]-4,4,5,5-tetramethyl-1,3,2-dioxaborolane (258 mg, 0.87 mmol), and potassium acetate (232 mg, 2.36 mmol). Tetrakis (triphenylphosphane) palladium (91 mg, 0.08 mmol) was added to the reaction mixture and the mixture was stirred for three hours at 90° C. Then, the reaction mixture was cooled and was extracted three times with ethyl acetate. The organic layers were combined and concentrated. The resulting residue was purified via MPLC eluting with ethyl acetate/petroleum ether (1:10-2:1) to afford (R,E)-7-(2-(2-chloro-6-fluorophenyl)prop-1-en-1-yl)-1-((3-(trifluoromethyl)phenyl)sulfonyl)-1,2,3,4-tetrahydroquinolin-3-ol (215 mg, 52%) as a yellow oil. ¹H-NMR (300 MHz, CD₃OD) δ 7.93-8.05 (m, 3H), 7.70-7.76 (m, 2H), 7.26-7.35 (m, 2H), 7.09-7.17 (m, 3H), 6.39 (s, 1H), 4.11 (m, 1H), 3.92 (m, 1H), 3.61-3.38 (m, 1H), 2.76 (m, 1H), 2.46 (m, 1H), 2.12 (s, 3H). (ES, m/z): (M+H)⁺ 526.

Part IX—Synthesis of ethyl N-([[(3R)-7-[(1E)-2-(2-chloro-6-fluorophenyl)prop-1-en-1-yl]-1-[[3-(trifluoromethyl)benzene]sulfonyl]-1,2,3,4-tetrahydroquinolin-3-yl]oxy]methanethioyl)carbamate

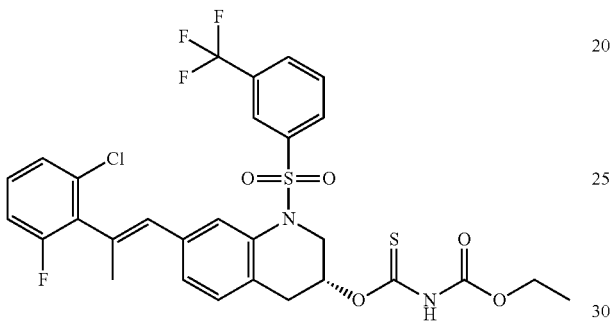

To a room temperature solution of (R,E)-7-(2-(2-chloro-6-fluorophenyl)prop-1-en-1-yl)-1-((3-(trifluoromethyl)phenyl)sulfonyl)-1,2,3,4-tetrahydroquinolin-3-ol (250 mg, 0.48 mmol) in chloroform (10 mL) was added ethyl N-carbothioylcarbamate (0.56 mL, 4.8 mmol). The solution was stirred for two days at 60° C. and concentrated. The resulting residue was purified by MPLC eluting with a gradient of ethyl acetate/petroleum ether (0-25%) to afford ethyl N-([[(3R)-7-[(1E)-2-(2-chloro-6-fluorophenyl)prop-1-en-1-yl]-1-[[3-(trifluoromethyl)benzene]sulfonyl]-1,2,3,4-tetrahydroquinolin-3-yl]oxy]methanethioyl)carbamate (250 mg, 80%) as a yellow oil.

Part X—Synthesis of (R,E)-3-((7-(2-(2-chloro-6-fluorophenyl)prop-1-en-1-yl)-1-((3-(trifluoromethyl)phenyl)sulfonyl)-1,2,3,4-tetrahydroquinolin-3-yl)oxy)-1,2,4-oxadiazol-5(4H)-one

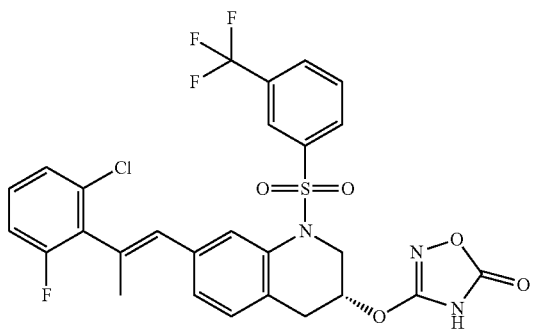 [SMILES: C/C(=C\c1ccc2c(c1)N(S(=O)(=O)c1cccc(C(F)(F)F)c1)C[C@H](Oc1noc(=O)[nH]1)C2)c1c(F)cccc1Cl]

A mixture of hydroxylamine hydrochloride (59.2 mg, 0.858 mmol) and lithium hydroxide monohydrate (20.4 mg, 0.49 mmol) in ethanol (5 mL) was stirred for thirty minutes at 40° C. To this solution was added ethyl N-([[(3R)-7-[(1E)-2-(2-chloro-6-fluorophenyl)prop-1-en-1-yl]-1-[[3-(trifluoromethyl)benzene]sulfonyl]-1,2,3,4-tetrahydroquinolin-3-yl]oxy]methanethioyl)carbamate (80 mg, 0.12 mmol) in ethanol (2 mL) dropwise with stirring and the mixture was stirred overnight at 40° C. Then, the mixture was concentrated and the resulting residue was purified by Prep-HPLC eluting with a gradient of 60% to 72% acetonitrile in water with 0.05% TFA to afford (R,E)-3-((7-(2-(2-chloro-6-fluorophenyl)prop-1-en-1-yl)-1-((3-(trifluoromethyl)phenyl)sulfonyl)-1,2,3,4-tetrahydroquinolin-3-yl)oxy)-1,2,4-oxadiazol-5(4H)-one (30 mg, 41%) as a white solid. ¹H-NMR (300 MHz, CD₃OD) δ 8.02 (d, J=9 Hz, 1H), 7.95 (m, 2H), 7.75 (t, J=7.5 Hz, 1H), 7.58 (s, 1H), 7.27 (m, 2H), 7.05-7.17 (m, 3H), 6.35 (s, 1H), 5.11 (m, 1H), 4.16-4.30 (m, 2H), 2.85 (d, J=6 Hz, 2H), 2.06 (s, 3H). (ES, m/z): (M+H)⁺ 508.

Example 4—Synthesis of (R,E)-3-((7-(2-(2-chloro-6-fluorophenyl)prop-1-en-1-yl)-1-((3-(trifluoromethyl)phenyl)sulfonyl)-1,2,3,4-tetrahydroquinolin-3-yl)oxy)-1H-1,2,4-triazol-5(4H)-one

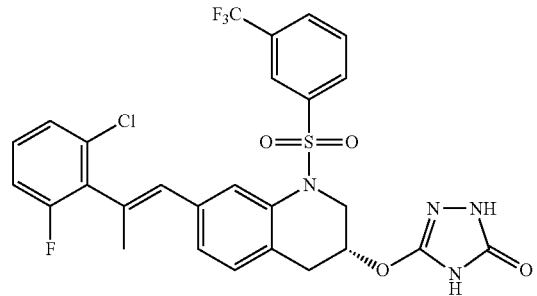 [SMILES: C/C(=C\c1ccc2c(c1)N(S(=O)(=O)c1cccc(C(F)(F)F)c1)C[C@H](Oc1n[nH]c(=O)[nH]1)C2)c1c(F)cccc1Cl]

To a mixture of ethyl N-([[(3R)-7-[(1E)-2-(2-chloro-6-fluorophenyl)prop-1-en-1-yl]-1-[[3-(trifluoromethyl)benzene]sulfonyl]-1,2,3,4-tetrahydroquinolin-3-yl]oxy]methanethioyl)carbamate (370 mg, 0.56 mmol), methanol (10 mL), and potassium hydroxide (3.16 mg, 0.06 mmol) was added a solution of hydrazine hydrate (31 mg, 0.6 mmol) in methanol (3 mL) dropwise with stirring at 0° C. The solution was stirred for five hours at room temperature and then concentrated. The resulting residue was purified by Prep-HPLC eluting with a gradient of 50-67% acetonitrile in water with 0.05% TFA to afford (R,E)-3-((7-(2-(2-chloro-6-fluorophenyl)prop-1-en-1-yl)-1-((3-(trifluoromethyl)phenyl)sulfonyl)-1,2,3,4-tetrahydroquinolin-3-yl)oxy)-1H-1,2,4-triazol-5(4H)-one as a white solid. ¹H-NMR (300 MHz, CDCl₃) δ 8.11 (s, 1H), 7.91 (s, 1H), 7.84 (s, 1H), 7.71 (s, 1H), 7.66 (s, 1H), 7.26-7.17 (m, 3H), 7.10-7.02 (m, 2H), 6.42 (s, 1H), 4.97 (s, 1H), 4.28 (s, 1H), 4.21 (s, 1H), 2.94 (s, 1H), 2.76 (s, 1H), 2.17 (s, 3H), 1.27 (s, 1H). (ES, m/z): (M−100)⁺ 508.

Example 5—Synthesis of (2R,3S)-3-((1H-imidazol-1-yl)methyl)-7-((E)-2-(2-chloro-6-fluorophenyl)prop-1-en-1-yl)-2-methyl-1-((3-(trifluoromethyl)phenyl)sulfonyl)-1,2,3,4-tetrahydroquinoline

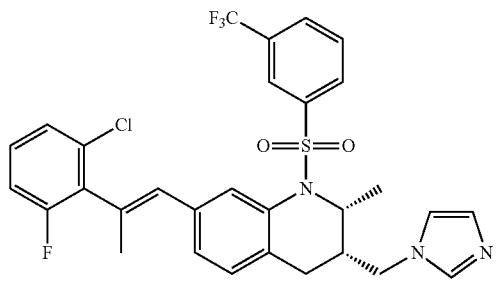 [SMILES: C/C(=C\c1ccc2c(c1)N(S(=O)(=O)c1cccc(C(F)(F)F)c1)[C@H](C)[C@H](Cn1ccnc1)C2)c1c(F)cccc1Cl]

Part I—Synthesis of (R)-methyl 3-(3-(trifluoromethyl)phenylsulfonamido)butanoate

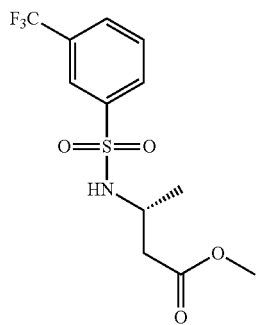 [SMILES: COC(=O)C[C@@H](C)NS(=O)(=O)c1cccc(C(F)(F)F)c1]

To a mixture of methyl (3R)-3-aminobutanoate hydrochloride (6.10 g, 39.7 mmol) and 3-(trifluoromethyl)benzenesulfonyl chloride (10.69 g, 43.7 mmol) in methylene chloride (100 mL) was added diisopropylethylamine (14.4 g, 111 mmol). The mixture was stirred overnight, then partitioned between dichloromethane and saturated ammonium chloride. The organic layer was washed with saturated sodium bicarbonate, then brine, and dried (Na$_2$SO$_4$) then concentrated. The resulting residue was purified by MPLC eluting with a gradient of 9:1 to 3:2 hexane:ethyl acetate to afford (R)-methyl 3-(3-(trifluoromethyl)phenylsulfonamido)butanoate (9.23 g, 71%) as a clear oil. $^1$H-NMR (400 MHz, DMSO-d$_6$) δ 8.03 (m, 3H), 7.83 (t, 1H), 3.55 (q, 1H), 3.42 (s, 3H), 2.36 (d, 2H), 0.93 (d, 3H). (MS, m/z): (M+Na)$^+$ 348.18.

Part II—Synthesis of (2R,3R)-methyl 2-(2,4-dibromobenzyl)-3-(3-(trifluoromethyl)phenyl-sulfonamido)butanoate

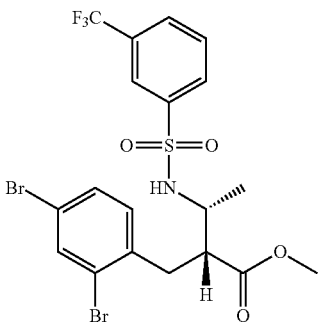 [SMILES: COC(=O)[C@H](Cc1ccc(Br)cc1Br)[C@@H](C)NS(=O)(=O)c1cccc(C(F)(F)F)c1]

To a 1M solution of lithium hexamethylsilazide in THF (75.2 mL, 75.2 mmol) at −78° C. was added a solution of (R)-methyl 3-(3-(trifluoromethyl)phenylsulfonamido)butanoate (11.65 g, 35.8 mmol) in THF (300 mL) dropwise. After completion of the addition, the mixture was stirred an additional thirty minutes allowing the mixture's temperature to rise to −40° C. Then, the mixture was cooled again at −78° C., and then a solution of 2,4-dibromo-1-(bromomethyl)benzene in THF (60 mL) was added dropwise. The cooling bath was removed from the reaction vessel and the reaction mixture was allowed to warm to room temperature. Next, the reaction was quenched by addition of saturated ammonium chloride to the reaction mixture, and the resulting mixture was partitioned between ethyl acetate and water. The organic layer was isolated and washed with brine, dried (Na$_2$SO$_4$), and concentrated. The resulting residue was purified by MPLC eluting with a gradient of ethyl acetate and hexanes to afford (2R,3R)-methyl 2-(2,4-dibromobenzyl)-3-(3-(trifluoromethyl)phenyl-sulfonamido)butanoate (12.14 g, 59%) as a white solid. $^1$H-NMR (400 MHz, DMSO-d$_6$) δ 8.11 (m, 3H), 8.02 (d, 1H), 7.84 (t, 1H), 7.79 (m, 1H), 7.47 (dd, 1H), 7.08 (d, 1H), 3.60 (m, 1H), 3.37 (s, 3H), 2.84 (m, 2H), 2.78 (m, 1H), 0.92 (d, 3H).

Part III—Synthesis of (2R,3R)-methyl 7-bromo-2-methyl-1-((3-(trifluoromethyl)-phenyl)sulfonyl)-1,2,3,4-tetrahydroquinoline-3-carboxylate

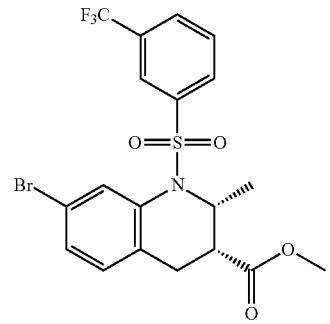 [SMILES: COC(=O)[C@@H]1Cc2ccc(Br)cc2N(S(=O)(=O)c2cccc(C(F)(F)F)c2)[C@@H]1C]

A mixture of (2R,3R)-methyl 2-(2,4-dibromobenzyl)-3-(3-(trifluoromethyl)phenyl-sulfonamido)butanoate (4.63 g, 8.08 mmol), copper (I) iodide (0.62 g, 3.23 mmol), N,N'-dimethylethylenediamine (0.71 g, 8.08 mmol) and potassium phosphate (5.14 g, 24.2 mmol) in toluene (80 mL) was heated at reflux overnight. Then, the reaction mixture was cooled and partitioned between ethyl acetate and saturated aqueous ammonium chloride. The organic layer was washed with brine, dried (Na$_2$SO$_4$) and concentrated. The resulting residue was purified by MPLC eluting with a gradient of hexanes and ethyl acetate to afford (2R,3R)-methyl 7-bromo-2-methyl-1-((3-(trifluoromethyl)-phenyl)sulfonyl)-1,2,3,4-tetrahydroquinoline-3-carboxylate (3.23 g, 81%). Note: This material contained some (2R,3R)-methyl 7-iodo-2-methyl-1-((3-(trifluoromethyl)-phenyl)sulfonyl)-1,2,3,4-tetrahydroquinoline-3-carboxylate and was used without further purification in the next step of the synthetic procedure. $^1$H-NMR (400 MHz, DMSO-d$_6$) δ 8.11 (d, 1H), 7.90 (m, 2H), 7.83 (t, 1H), 7.78 (s, 1H), 7.36 (d, 1H), 7.18 (d, 1H), 4.73 (m, 1H), 3.61 (s, 3H), 2.75 (m, 2H), 2.24 (m, 1H), 0.91 (d, 1H).

Part IV—Synthesis of (2R,3R)-methyl 7-((E)-2-(2-chloro-6-fluorophenyl)prop-1-en-1-yl)-2-methyl-1-((3-(trifluoromethyl)phenyl)sulfonyl)-1,2,3,4-tetrahydroquinoline-3-carboxylate

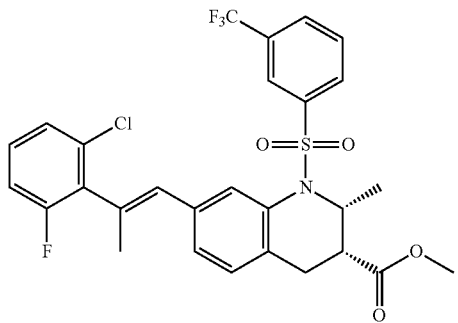 [SMILES: COC(=O)[C@@H]1Cc2ccc(/C=C(\C)c3c(F)cccc3Cl)cc2N(S(=O)(=O)c2cccc(C(F)(F)F)c2)[C@@H]1C]

To a degassed mixture of ((2R,3R)-methyl 7-bromo-2-methyl-1-((3-(trifluoromethyl)-phenyl)sulfonyl)-1,2,3,4-tetrahydroquinoline-3-carboxylate (3.23 g, 6.56 mmol), potassium carbonate (1.36 g, 9.84 mmol), (E)-2-(2-(2-chloro-6-fluorophenyl)prop-1-en-1-yl)-4,4,5,5-tetramethyl-1,3,2-dioxaborolane (2.14 g, 7.22 mmol), dioxane (24 mL) and water (6 mL) was added [1,1'-bis(diphenylphosphino)ferrocene]dichloropalladium(II), complex with dichloromethane (0.54 g, 0.66 mmol). The mixture was heated to 70° C. for five hours. Then, the mixture was cooled, and partitioned between ethyl acetate and water. The organic layer was washed with brine, dried (Na$_2$SO$_4$), and concentrated. The resulting residue was purified by MPLC eluting with a gradient of 0-50% ethyl acetate in hexanes to afford (2R,3R)-methyl 7-((E)-2-(2-chloro-6-fluorophenyl)prop-1-en-1-yl)-2-methyl-1-((3-(trifluoromethyl)phenyl)sulfonyl)-1,2,3,4-tetrahydroquinoline-3-carboxylate (2.69 g, 70%). $^1$H-NMR (400 MHz, DMSO-d$_6$) δ 8.11 (m, 1H), 7.90 (m, 4H), 7.64 (s, 1H), 7.38 (m, 2H), 7.26 (m, 2H), 7.19 (m, 1H), 6.41 (s, 1H), 4.80 (m, 1H), 4.00 (q, 1H), 3.64 (s, 3H), 3.62 (s, 1H), 3.53 (s, 2H), 2.80 (m, 3H), 2.35 (m, 2H), 2.11 (s, 3H), 1.97 (s, 2H), 1.15 (t, 2H), 0.98 (dd, 5H). (MS, m/z): (M+Na)$^+$ 604.2.

Part V—Synthesis of ((2R,3R)-7-((E)-2-(2-chloro-6-fluorophenyl)prop-1-en-1-yl)-2-methyl-1-((3-(trifluoromethyl)phenyl)sulfonyl)-1,2,3,4-tetrahydroquinolin-3-yl)methanol

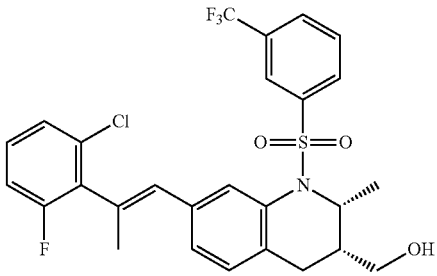 [SMILES: C/C(=C\c1ccc2c(c1)N(S(=O)(=O)c1cccc(C(F)(F)F)c1)[C@H](C)[C@H](CO)C2)c1c(F)cccc1Cl]

To a 1M solution of lithium aluminum hydride (5.08 mL, 5.08 mmol) was added dropwise a solution of (2R,3R)-methyl 7-((E)-2-(2-chloro-6-fluorophenyl)prop-1-en-1-yl)-2-methyl-1-((3-(trifluoromethyl)phenyl)sulfonyl)-1,2,3,4-tetrahydroquinoline-3-carboxylate (2.69 g, 4.62 mmol) in THF (46 mL). The mixture was stirred for three hours at room temperature, and then the reaction was quenched slowly by adding sodium sulfate decahydrate (3 g) to the reaction mixture. The resulting mixture was stirred for an additional hour, and then filtered. The filtrate was concentrated and the residue was purified by MPLC eluting with a gradient of hexanes and ethyl acetate. Concentration of the major UV active component afforded a residue which was further purified by MPLC eluting with a gradient of 0-5% methanol in dichloromethane to afford ((2R,3R)-7-((E)-2-(2-chloro-6-fluorophenyl)prop-1-en-1-yl)-2-methyl-1-((3-(trifluoromethyl)phenyl)sulfonyl)-1,2,3,4-tetrahydroquinolin-3-yl)methanol (0.91 g, 36%). $^1$H-NMR (400 MHz, DMSO-d$_6$) δ 8.07 (d, 1H), 7.93 (d, 1H), 7.80 (m, 2H), 7.69 (s, 1H), 7.38 (m, 2H), 7.27 (m, 1H), 7.14 (m, 2H), 6.40 (s, 1H), 4.70 (m, 2H), 3.27 (m, 1H), 3.19 (m, 1H), 2.27 (m, 1H), 2.10 (s, 3H), 1.59 (m, 1H), 0.98 (d, 3H). (ES, m/z): (M+K)$^+$ 592.14.

Part VI—Synthesis of ((2R,3R)-7-((E)-2-(2-chloro-6-fluorophenyl)prop-1-en-1-yl)-2-methyl-1-((3-(trifluoromethyl)phenyl)sulfonyl)-1,2,3,4-tetrahydroquinolin-3-yl)methyl methanesulfonate

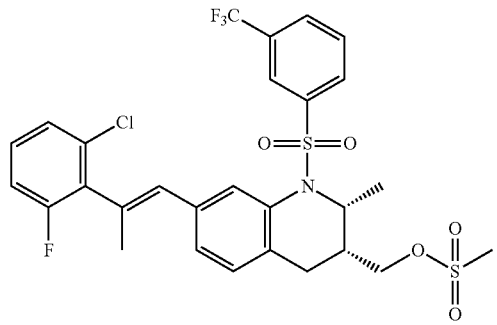 [SMILES: C/C(=C\c1ccc2c(c1)N(S(=O)(=O)c1cccc(C(F)(F)F)c1)[C@H](C)[C@H](COS(C)(=O)=O)C2)c1c(F)cccc1Cl]

To a solution of ((2R,3R)-7-((E)-2-(2-chloro-6-fluorophenyl)prop-1-en-1-yl)-2-methyl-1-((3-(trifluoromethyl)phenyl)sulfonyl)-1,2,3,4-tetrahydroquinolin-3-yl)methanol (0.91 g g, 1.64 mmol) and triethylamine (0.28 g, 2.79 mmol) in dichloromethane (8 mL) was added methanesulfonyl chloride. The mixture was stirred overnight at room temperature, and then washed with aqueous citric acid, brine, dried (Na$_2$SO$_4$), and concentrated. The resulting residue was purified via MPLC eluting with petroleum ether:ethyl acetate (1:1). Concentration of the major UV active component afforded ((2R,3R)-7-((E)-2-(2-chloro-6-fluorophenyl)prop-1-en-1-yl)-2-methyl-1-((3-(trifluoromethyl)phenyl)sulfonyl)-1,2,3,4-tetrahydroquinolin-3-yl)methyl methanesulfonate (0.98 g, 94%). $^1$H-NMR (400 MHz, DMSO-d$_6$) δ 8.08 (d, 1H), 7.93 (d, 1H), 7.83 (m, 2H), 7.69 (s, 1H), 7.38 (m, 2H), 7.28 (m, 1H), 7.19 (m, 2H), 6.42 (s, 1H), 4.66 (m, 1H), 4.10 (d, 2H), 3.18 (s, 3H), 2.63 (dd, 1H), 2.45 (m, 1H), 2.12 (s, 3H), 1.92 (m, 1H), 1.01 (d, 3H).

Part V—Synthesis of (2R,3S)-3-((1H-imidazol-1-yl)methyl)-7-((E)-2-(2-chloro-6-fluorophenyl)prop-1-en-1-yl)-2-methyl-1-((3-(trifluoromethyl)phenyl)sulfonyl)-1,2,3,4-tetrahydroquinoline

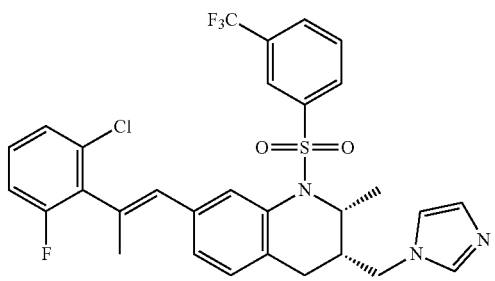 [SMILES: C/C(=C\c1ccc2c(c1)N(S(=O)(=O)c1cccc(C(F)(F)F)c1)[C@H](C)[C@H](Cn1ccnc1)C2)c1c(F)cccc1Cl]

To a solution of imidazole (20 mg, 0.29 mmol) in DMF (1.5 mL) at room temperature was added 60% sodium hydride in mineral oil (10 mg, 0.26 mmol). The mixture was stirred for fifteen minutes, and ((2R,3R)-7-((E)-2-(2-chloro-6-fluorophenyl)prop-1-en-1-yl)-2-methyl-1-((3-(trifluoromethyl)phenyl)sulfonyl)-1,2,3,4-tetrahydroquinolin-3-yl)methyl methanesulfonate (100 mg, 0.16 mmol) was added. The mixture was heated at 60° C. overnight, then cooled and partitioned between ethyl acetate and water. The organic layer was washed with brine, dried (Na$_2$SO$_4$) and concentrated. The resulting residue was purified by MPLC, eluting with a gradient of 0-10% methanol in dichloromethane to afford (2R,3S)-3-((1H-imidazol-1-yl)methyl)-7-((E)-2-(2-chloro-6-fluorophenyl)prop-1-en-1-yl)-2-methyl-1-((3-(trifluoromethyl)phenyl)sulfonyl)-1,2,3,4-tetrahydroquinoline (25 mg, 25%). $^1$H-NMR (400 MHz, DMSO-d$_6$) δ 8.08 (d, 1H), 7.79 (m, 4H), 7.58 (s, 1H), 7.38 (m, 2H), 7.28 (m, 1H), 7.16 (s, 2H), 6.96 (s, 1H), 6.90 (s, 1H), 6.41 (s, 1H), 5.73 (s, 1H), 4.35 (m, 1H), 4.08 (m, 1H), 3.92 (m, 2H), 3.15 (d, 3H), 2.40 (m, 1H), 2.12 (s, 3H), 1.77 (m, 1H), 1.05 (d, 3H). (ES, m/z): (M+H)$^+$ 604.33.

Example 6—Synthesis of (S,E)-3-(2-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)ethyl)-1,2,4-oxadiazol-5(4H)-one

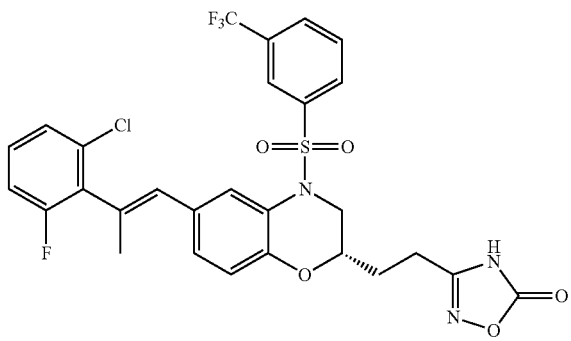 [SMILES: C/C(=C\c1ccc2c(c1)N(S(=O)(=O)c1cccc(C(F)(F)F)c1)C[C@H](CCc1noc(=O)[nH]1)O2)c1c(F)cccc1Cl]

To a solution of (S,E)-3-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)propanenitrile (70 mg, 0.124 mmol) in methanol (3 mL) was added hydroxylamine (164 mg, 2.48 mmol). The mixture was heated at 60° C. overnight, then cooled and concentrated. The resulting residue was dissolved in THF (5 mL) then cooled to 0° C. Next, diisopropylethylamine (48 mg, 372 mmol) was added, followed by triphosgene (55 mg, 186 mmol). The resulting mixture was warmed to room temperature and stirred for two hours. Then, the mixture was partitioned between ethyl acetate and water. The organic layer was washed with brine, dried (Na$_2$SO$_4$), and concentrated. The resulting residue was purified by MPLC eluting with a gradient of ethyl acetate in hexanes to afford (S,E)-3-(2-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)ethyl)-1,2,4-oxadiazol-5(4H)-one (22 mg, 27%). $^1$H-NMR (400 MHz, DMSO-d$_6$) δ 12.08 (s, 1H), 8.1 (m, 2H), 7.97 (s, 1H), 7.84 (d, 1H), 7.68 (m, 1H), 7.38 (m, 2H), 7.25 (m, 1H), 7.15 (m, 1H), 6.86 (m, 1H), 6.4 (s, 1H), 4.40 (m, 1H), 3.62 (m, 1H), 3.48 (m, 1H), 2.62 (m, 2H), 2.1 (s, 3H), 1.98 (m, 1H), 1.85 (m, 1H). (ES, m/z): (M+Na)$^+$ 646.27, 648.23.

Example 7—Synthesis of (S,E)-2-(2-(1H-imidazol-1-yl)ethyl)-6-(2-(2-chloro-6-fluorophenyl)prop-1-en-1-yl)-4-((3-(trifluoromethyl)phenyl)sulfonyl)-3,4-dihydro-2H-benzo[b][1,4]oxazine

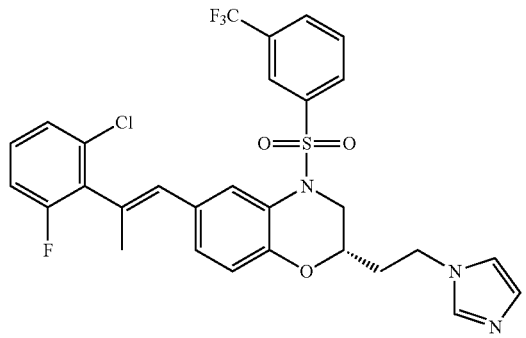 [SMILES: C/C(=C\c1ccc2c(c1)N(S(=O)(=O)c1cccc(C(F)(F)F)c1)C[C@H](CCn1ccnc1)O2)c1c(F)cccc1Cl]

Part I—Synthesis of (S)-6-bromo-2-(2-((tert-butyldimethylsilyl)oxy)ethyl)-4-((3-(trifluoromethyl)phenyl)sulfonyl)-3,4-dihydro-2H-benzo[b][1,4]oxazine

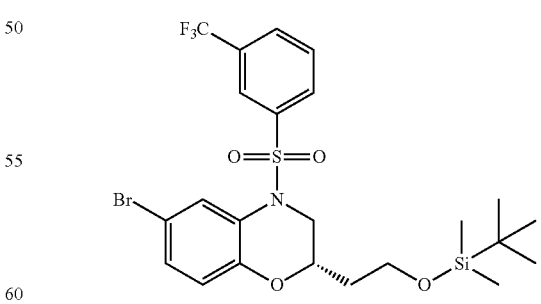

To a solution of (S)-6-bromo-2-(2-((tert-butyldimethylsilyl)oxy)ethyl)-3,4-dihydro-2H-benzo[b][1,4]oxazine (1.60 g, 4.30 mmol) in pyridine (15 mL) was added 3-(trifluoromethyl)benzenesulfonyl chloride (1.26 g, 5.15 mmol). The mixture was stirred at 50° C. for two hours, then cooled and partitioned between ethyl acetate and 1N HCl. The organic layer was washed three times with 1N HCl, brine, and dried (Na₂SO₄). Charcoal was added to the resulting mixture, and the mixture was slurried, then filtered through celite. The filtrate was concentrated and the resulting residue was purified by MPLC eluting with a gradient of ethyl acetate in hexanes to afford (S)-6-bromo-2-(2-((tert-butyldimethylsilyl)oxy)ethyl)-4-((3-(trifluoromethyl)phenyl)sulfonyl)-3,4-dihydro-2H-benzo[b][1,4]oxazine (2.40 g, 100%).

Part II—Synthesis of (S,E)-2-(2-((tert-butyldimethylsilyl)oxy)ethyl)-6-(2-(2-chloro-6-fluorophenyl)prop-1-en-1-yl)-4-((3-(trifluoromethyl)phenyl)sulfonyl)-3,4-dihydro-2H-benzo[b][1,4]oxazine

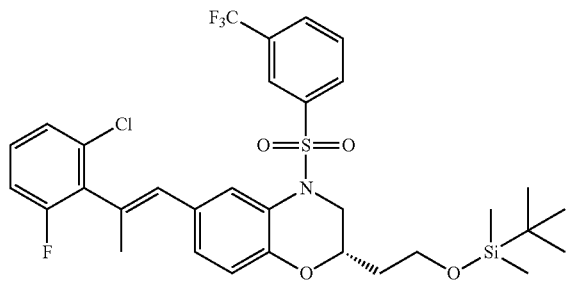 [SMILES: C/C(=C\c1ccc2c(c1)N(S(=O)(=O)c1cccc(C(F)(F)F)c1)C[C@H](CCO[Si](C)(C)C(C)(C)C)O2)c1c(F)cccc1Cl]

To a degassed mixture of (S)-6-bromo-2-(2-((tert-butyldimethylsilyl)oxy)ethyl)-4-((3-(trifluoromethyl)phenyl)sulfonyl)-3,4-dihydro-2H-benzo[b][1,4]oxazine (1.78 g, 6.03 mmol), potassium carbonate (833 mg, 6.03 mmol), (E)-2-(2-(2-chloro-6-fluorophenyl)prop-1-en-1-yl)-4,4,5,5-tetramethyl-1,3,2-dioxaborolane (1.788 g, 6.03 mmol), dioxane (25 mL) and water (5 mL) was added [1,1'-bis(diphenylphosphino)ferrocene]dichloropalladium(II), complex with dichloromethane (0.328 g, 0.431 mmol). The mixture was heated to 70° C. for five hours. Then, the mixture was cooled, and partitioned between ethyl acetate and saturated aqueous ammonium chloride. The organic layer was washed with brine, dried (Na₂SO₄), and concentrated. The resulting residue was purified by MPLC eluting with a gradient of 0-50% ethyl acetate in hexanes to afford (S,E)-2-(2-((tert-butyldimethylsilyl)oxy)ethyl)-6-(2-(2-chloro-6-fluorophenyl)prop-1-en-1-yl)-4-((3-(trifluoromethyl)phenyl)sulfonyl)-3,4-dihydro-2H-benzo[b][1,4]oxazine (2.40 g, 83%).

Part III—Synthesis of (S,E)-2-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)ethanol

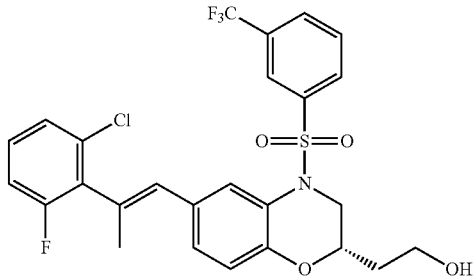 [SMILES: C/C(=C\c1ccc2c(c1)N(S(=O)(=O)c1cccc(C(F)(F)F)c1)C[C@H](CCO)O2)c1c(F)cccc1Cl]

To a solution of (S,E)-2-(2-((tert-butyldimethylsilyl)oxy)ethyl)-6-(2-(2-chloro-6-fluorophenyl)prop-1-en-1-yl)-4-((3-(trifluoromethyl)phenyl)sulfonyl)-3,4-dihydro-2H-benzo[b][1,4]oxazine (2.40 g, 3.58 mmol) in THF (24 mL) was added a 1M solution of tetrabutylammonium fluoride (1.40 g, 5.37 mmol) in THF (5.37 mL). The mixture was stirred for 1 hour, then concentrated onto a small amount of silica gel. The residue was purified by MPLC eluting with a gradient of 0-100% ethyl acetate in hexanes to afford (S,E)-2-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)ethanol (1.55 g, 78%).

Part IV—Synthesis of (S,E)-2-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)ethyl methanesulfonate

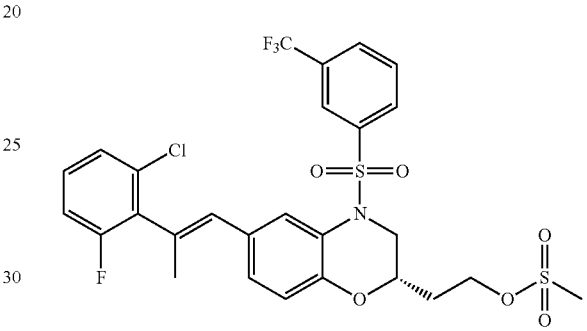

Methanesulfonic anhydride (211 mg, 1.21 mmol) was added to a solution of (S,E)-2-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)ethanol (0.45 g, 0.81 mmol) and diisopropylethylamine (0.21 g, 1.62 mmol) in dichloromethane (10 mL) at 0° C. The mixture was stirred at room temperature for two hours, then partitioned between dichloromethane and 1N HCl. The organic layer was dried (Na₂SO₄) and concentrated to afford (S,E)-2-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)ethyl methanesulfonate (0.48 g, 94%).

Part V—Synthesis of (S,E)-2-(2-(1H-imidazol-1-yl)ethyl)-6-(2-(2-chloro-6-fluorophenyl)prop-1-en-1-yl)-4-((3-(trifluoromethyl)phenyl)sulfonyl)-3,4-dihydro-2H-benzo[b][1,4]oxazine

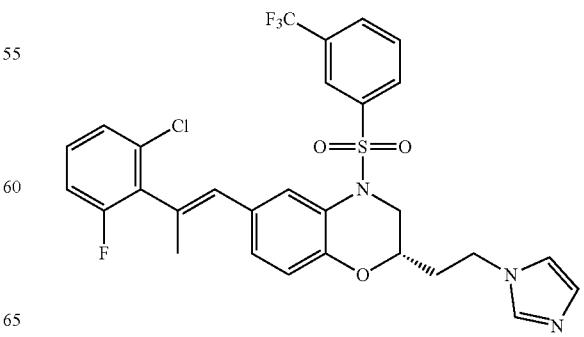

Imidazole (21.5 mg, 0.315 mmol) was added to a solution of (S,E)-2-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)ethyl methanesulfonate (50 mg, 0.079 mmol) in DMF (0.5 mL). The mixture was stirred at 70° C. overnight, then cooled and subsequently concentrated. The resulting residue was purified by MPLC eluting with a gradient of 0-5% methanol in dichloromethane to afford (S,E)-2-(2-(1H-imidazol-1-yl)ethyl)-6-(2-(2-chloro-6-fluorophenyl)prop-1-en-1-yl)-4-((3-(trifluoromethyl)phenyl)sulfonyl)-3,4-dihydro-2H-benzo[b][1,4]oxazine (26 mg, 54%). $^1$H-NMR (400 MHz, CDCl$_3$) δ 7.82 (m, 3H), 7.75 (m, 1H), 7.58 (m, 1H). 7.40 (m, 1H), 7.25-7.15 (m, 3H), 7.05 (m, 2H), 6.88 (m, 1H), 6.82 (m, 1H), 6.38 (s, 1H), 4.20-4.08 (m, 3H), 3.22 (m, 2H), 2.08 (s, 3H), 1.96 (m, 2H). (ES, m/z): (M+H)$^+$ 606.13, 608.15.

Example 8—Synthesis of (S,E)-2-(3-(1H-imidazol-1-yl)propyl)-6-(2-(2-chloro-6-fluorophenyl)prop-1-en-1-yl)-4-((3-(trifluoromethyl)phenyl)sulfonyl)-3,4-dihydro-2H-benzo[b][1,4]oxazine

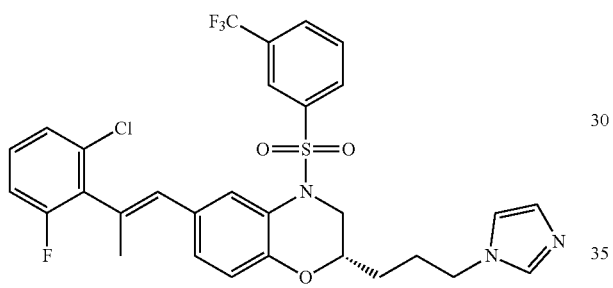

Part I—Synthesis of (S)-3-(6-bromo-3,4-dihydro-2H-benzo[b][1,4]oxazin-2-yl)propan-1-ol

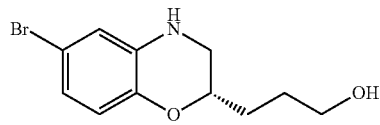 [SMILES: OCCC[C@H]1CNc2cc(Br)ccc2O1]

To (S)-3-(6-bromo-3-oxo-3,4-dihydro-2H-benzo[b][1,4]oxazin-2-yl)propanoate (6.4 g, 20.4 mmol) in anhydrous tetrahydrofuran (60 mL) was added borane-methyl sulfide complex (8.2 mL, 82 mmol) and the mixture was heated to 50° C. for 2 hours. Then, the reaction mixture was cooled to ambient temperature, and then carefully quenched by adding methanol (25 mL) and heating to 60° C. for 20 minutes. The resulting mixture was concentrated, then redissolved in ethyl acetate, washed with water, then brine, dried with sodium sulfate, filtered and concentrated to an oil. The oil was purified by column chromatography eluting with a gradient of 5-100% ethyl acetate in hexanes. Fractions containing (S)-3-(6-bromo-3,4-dihydro-2H-benzo[b][1,4]oxazin-2-yl)propan-1-ol were combined and concentrated to give a solid. (2.77 g, 50%).

Part II—Synthesis of (S)-6-bromo-2-(3-((tert-butyldimethylsilyl)oxy)propyl)-3,4-dihydro-2H-benzo[b][1,4]oxazine

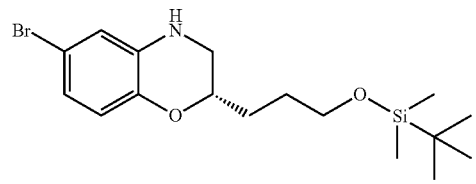 [SMILES: CC(C)(C)[Si](C)(C)OCCC[C@H]1CNc2cc(Br)ccc2O1]

To a solution of (S)-3-(6-bromo-3,4-dihydro-2H-benzo[b][1,4]oxazin-2-yl)propan-1-ol (3.50 g, 12.9 mmol) in dichloromethane (40 mL) was added diisopropylethylamine (2.49 g, 19.3 mmol), tert-butyldimethylchlorosilane (2.33 g, 15.4 mmol), and 4-dimethylaminopyridine (0.157 g, 1.29 mmol). The mixture was stirred at room temperature overnight. Then, the mixture was washed with aqueous 10% citric acid. The organic layer was dried (Na$_2$SO$_4$), and concentrated. The resulting residue was purified via MPLC eluting with a gradient of ethyl acetate in hexanes to afford (S)-6-bromo-2-(3-((tert-butyldimethylsilyl)oxy)propyl)-3,4-dihydro-2H-benzo[b][1,4]oxazine (3.80 g, 76%).

Part III—Synthesis of (S)-6-bromo-2-(3-((tert-butyldimethylsilyl)oxy)propyl)-4-((3-(trifluoromethyl)phenyl)sulfonyl)-3,4-dihydro-2H-benzo[b][1,4]oxazine

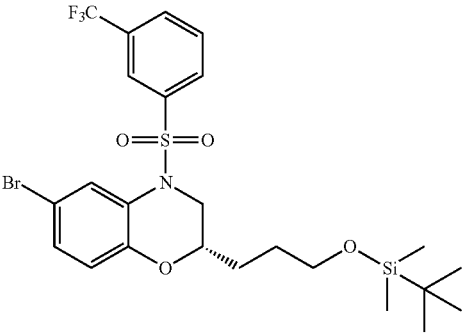 [SMILES: CC(C)(C)[Si](C)(C)OCCC[C@H]1CN(S(=O)(=O)c2cccc(C(F)(F)F)c2)c2cc(Br)ccc2O1]

To a solution of (S)-6-bromo-2-(3-((tert-butyldimethylsilyl)oxy)propyl)-3,4-dihydro-2H-benzo[b][1,4]oxazine (1.80 g, 4.67 mmol) in pyridine (15 mL) was added 3-(trifluoromethyl)benzenesulfonyl chloride (1.37 g, 5.59 mmol). The mixture was stirred at 50° C. for two hours, then cooled and partitioned between ethyl acetate and 1N HCl. The organic layer was washed three times with 1N HCl, then brine, and dried (Na$_2$SO$_4$). Charcoal was added to the resulting mixture, which was slurried and then filtered through celite. The filtrate was concentrated and the residue was purified by MPLC eluting with a gradient of ethyl acetate in hexanes to afford (S)-6-bromo-2-(3-((tert-butyldimethylsilyl)oxy)ethyl)-4-((3-(trifluoromethyl)phenyl)sulfonyl)-3,4-dihydro-2H-benzo[b][1,4]oxazine (2.45 g, 88%).

Part IV—Synthesis of (S,E)-2-(3-((tert-butyldimethylsilyl)oxy)propyl)-6-(2-(2-chloro-6-fluorophenyl)prop-1-en-1-yl)-4-((3-(trifluoromethyl)phenyl)sulfonyl)-3,4-dihydro-2H-benzo[b][1,4]oxazine

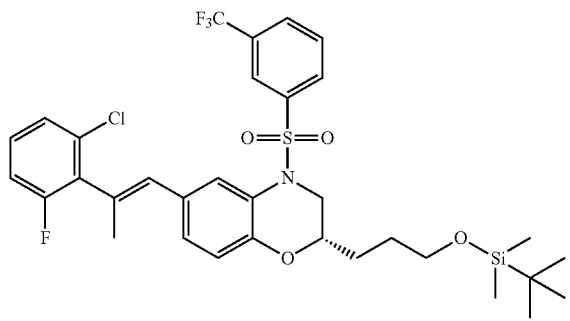 [SMILES: C/C(=C\c1ccc2c(c1)N(S(=O)(=O)c1cccc(C(F)(F)F)c1)C[C@H](CCCO[Si](C)(C)C(C)(C)C)O2)c1c(F)cccc1Cl]

To a degassed mixture of (S)-6-bromo-2-(3-((tert-butyldimethylsilyl)oxy)ethyl)-4-((3-(trifluoromethyl)phenyl)sulfonyl)-3,4-dihydro-2H-benzo[b][1,4]oxazine (2.45 g, 4.12 mmol), potassium carbonate (800 mg, 5.77 mmol), (E)-2-(2-(2-chloro-6-fluorophenyl)prop-1-en-1-yl)-4,4,5,5-tetramethyl-1,3,2-dioxaborolane (1.71 g, 5.77 mmol), dioxane (30 mL) and water (5 mL) was added [1,1'-bis(diphenylphosphino)ferrocene]dichloropalladium(II), complex with dichloromethane (0.31 g, 0.41 mmol). The mixture was heated to 70° C. for five hours. Then, the reaction mixture was cooled and subsequently partitioned between ethyl acetate and saturated aqueous ammonium chloride. The organic layer was washed with brine, dried (Na$_2$SO$_4$), and then concentrated. The resulting residue was purified by MPLC eluting with a gradient of 0-50% ethyl acetate in hexanes to afford (S,E)-2-(3-((tert-butyldimethylsilyl)oxy)propyl)-6-(2-(2-chloro-6-fluorophenyl)prop-1-en-1-yl)-4-((3-(trifluoromethyl)phenyl)sulfonyl)-3,4-dihydro-2H-benzo[b][1,4]oxazine (2.47 g, 88%).

Part V—Synthesis of (S,E)-3-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)propan-1-ol

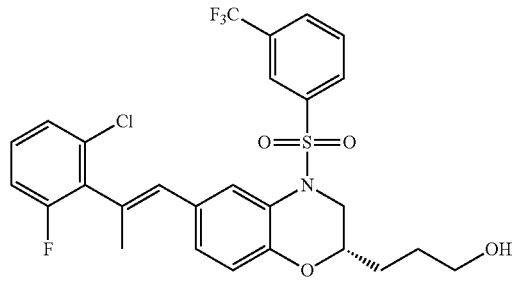 [SMILES: C/C(=C\c1ccc2c(c1)N(S(=O)(=O)c1cccc(C(F)(F)F)c1)C[C@H](CCCO)O2)c1c(F)cccc1Cl]

To a solution of (S,E)-2-(3-((tert-butyldimethylsilyl)oxy)propyl)-6-(2-(2-chloro-6-fluorophenyl)prop-1-en-1-yl)-4-((3-(trifluoromethyl)phenyl)sulfonyl)-3,4-dihydro-2H-benzo[b][1,4]oxazine (2.47 g, 3.61 mmol) in THF (24 mL) was added a 1M solution of tetrabutylammonium fluoride (1.42 g, 5.41 mmol) in THF (5.41 mL). The mixture was stirred for one hour, and then concentrated onto a small amount of silica gel. The residue was purified by MPLC eluting with a gradient of 0-100% ethyl acetate in hexanes to afford (S,E)-3-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)propan-1-ol (1.75 g, 85%).

Part VI—Synthesis of (S,E)-3-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)propyl methanesulfonate

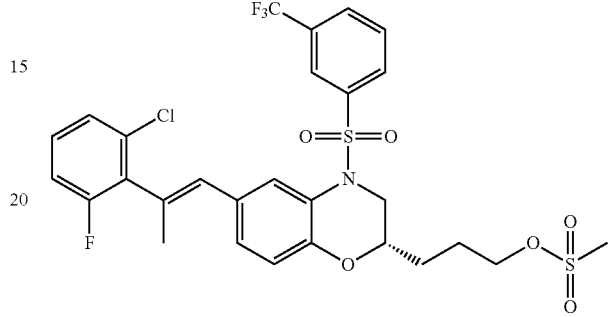

Methanesulfonic anhydride (240 mg, 1.39 mmol) was added to a solution of (S,E)-3-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)propan-1-ol (0.53 g, 0.93 mmol) and diisopropylethylamine (0.24 g, 1.86 mmol) in dichloromethane (10 mL) at 0° C. The mixture was stirred at room temperature for two hours, and then partitioned between dichloromethane and 1N HCl. The organic layer was dried (Na$_2$SO$_4$) and concentrated to afford (S,E)-3-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)propyl methanesulfonate (0.58 g, 96%).

Part VII—Synthesis of (S,E)-2-(3-(1H-imidazol-1-yl)propyl)-6-(2-(2-chloro-6-fluorophenyl)prop-1-en-1-yl)-4-((3-(trifluoromethyl)phenyl)sulfonyl)-3,4-dihydro-2H-benzo[b][1,4]oxazine

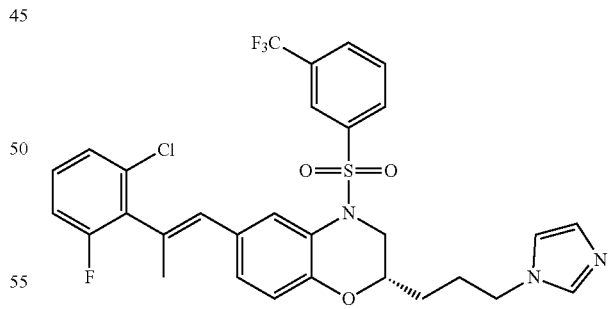

Imidazole (26.3 mg, 0.386 mmol) was added to a solution of (S,E)-3-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)propyl methanesulfonate (50 mg, 0.077 mmol) in DMF (0.5 mL). The mixture was stirred at 70° C. overnight, then cooled and concentrated. The resulting residue was purified by MPLC eluting with a gradient of 0-5% methanol in dichloromethane to afford (S,E)-2-(3-(1H-imidazol-1-yl)propyl)-6-(2-(2-chloro-6-fluorophenyl)prop-1-en-1-yl)-4-((3-(trifluoromethyl)phenyl)sulfonyl)-3, 4-dihydro-2H-benzo[b][1,4]oxazine (28 mg, 56%). ¹H-NMR (400 MHz, CDCl₃) δ 8.02 (s, 1H), 7.82 (m, 2H), 7.78 (m, 1H), 7.64 (m, 1H). 7.48 (m, 1H), 7.25-7.15 (m, 2H), 7.1 (m, 2H), 7.02 (m, 1H), 6.90 (m, 1H), 6.82 (m, 1H), 6.38 (s, 1H), 4.24 (m, 1H), 3.98 (m, 2H), 3.48 (m, 1H), 3.22 (m, 1H), 2.08 (s, 3H), 1.98 (m, 1H), 1.85 (m, 1H), 1.55 (m, 2H). (ES, m/z): (M+H)⁺ 620.31, 622.33.

Example 9—Synthesis of (S,E)-2-(2-(1H-1,2,3-triazol-1-yl)ethyl)-6-(2-(2-chloro-6-fluorophenyl)prop-1-en-1-yl)-4-((3-(trifluoromethyl)phenyl)sulfonyl)-3,4-dihydro-2H-benzo[b][1,4]oxazine

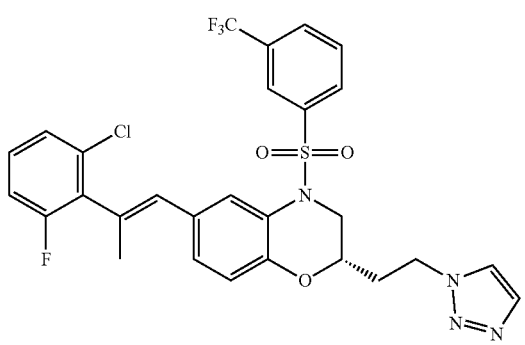 [SMILES: C/C(=C\c1ccc2c(c1)N(S(=O)(=O)c1cccc(C(F)(F)F)c1)C[C@H](CCn1ccnn1)O2)c1c(F)cccc1Cl]

Part I—Synthesis of (S,E)-2-(2-azidoethyl)-6-(2-(2-chloro-6-fluorophenyl)prop-1-en-1-yl)-4-((3-(trifluoromethyl)phenyl)sulfonyl)-3,4-dihydro-2H-benzo[b][1,4]oxazine

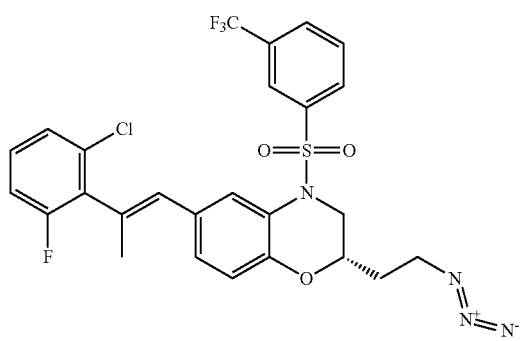 [SMILES: C/C(=C\c1ccc2c(c1)N(S(=O)(=O)c1cccc(C(F)(F)F)c1)C[C@H](CCN=[N+]=[N-])O2)c1c(F)cccc1Cl]

A mixture of (S,E)-2-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)ethyl methanesulfonate (0.50 g, 0.79 mmol) and sodium azide (0.21 g, 3.15 mmol) in DMF (5 mL) was heated to 60° C. for two hours. Then, the mixture was cooled, and partitioned between ethyl acetate and water. The organic layer was washed with water, then brine, dried (Na₂SO₄) and concentrated to afford (S,E)-2-(2-azidoethyl)-6-(2-(2-chloro-6-fluorophenyl)prop-1-en-1-yl)-4-((3-(trifluoromethyl)phenyl)sulfonyl)-3,4-dihydro-2H-benzo[b][1,4]oxazine (0.43 g, 94%).

Part II—Synthesis of (S,E)-6-(2-(2-chloro-6-fluorophenyl)prop-1-en-1-yl)-4-((3-(trifluoromethyl)phenyl)sulfonyl)-2-(2-(4-(trimethylsilyl)-1H-1,2,3-triazol-1-yl)ethyl)-3,4-dihydro-2H-benzo[b][1,4]oxazine

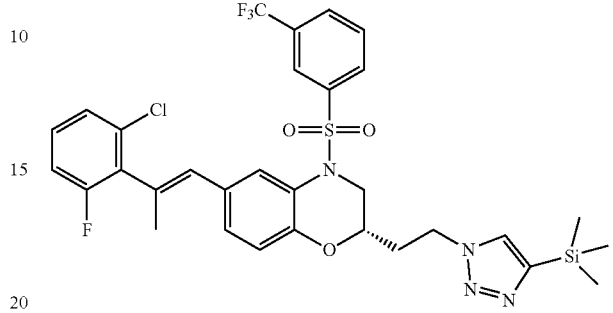

A mixture of (S,E)-2-(2-azidoethyl)-6-(2-(2-chloro-6-fluorophenyl)prop-1-en-1-yl)-4-((3-(trifluoromethyl)phenyl)sulfonyl)-3,4-dihydro-2H-benzo[b][1,4]oxazine (200 mg, 0.344 mmol), trimethylsilylacetylene (50 mg, 0.516 mmol), and copper (I) iodide (10 mg, 0.068 mmol) in acetonitrile (3 mL) was heated to 70° C. overnight. Then, the mixture was concentrated and the residue was purified via MPLC eluting with a gradient of ethyl acetate in hexanes to afford (S,E)-6-(2-(2-chloro-6-fluorophenyl)prop-1-en-1-yl)-4-((3-(trifluoromethyl)phenyl)sulfonyl)-2-(2-(4-(trimethylsilyl)-1H-1,2,3-triazol-1-yl)ethyl)-3,4-dihydro-2H-benzo[b][1,4]oxazine (210 mg, 90%).

Part III—Synthesis of (S,E)-2-(2-(1H-1,2,3-triazol-1-yl)ethyl)-6-(2-(2-chloro-6-fluorophenyl)prop-1-en-1-yl)-4-((3-(trifluoromethyl)phenyl)sulfonyl)-3,4-dihydro-2H-benzo[b][1,4]oxazine

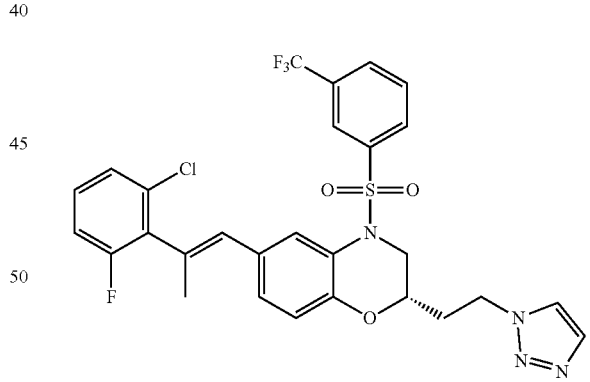

To a solution of (S,E)-6-(2-(2-chloro-6-fluorophenyl)prop-1-en-1-yl)-4-((3-(trifluoromethyl)phenyl)sulfonyl)-2-(2-(4-(trimethylsilyl)-1H-1,2,3-triazol-1-yl)ethyl)-3,4-dihydro-2H-benzo[b][1,4]oxazine (210 mg, 0.31 mmol) in THF (4 mL) was added a 1M solution of tetrabutylammonium fluoride (0.16 g, 0.62 mmol) in THF (0.62 mL). The mixture was stirred at room temperature overnight then concentrated. The resulting residue was purified via MPLC eluting with a gradient of ethyl acetate in hexanes to afford (S,E)-2-(2-(1H-1,2,3-triazol-1-yl)ethyl)-6-(2-(2-chloro-6-fluorophenyl)prop-1-en-1-yl)-4-((3-(trifluoromethyl)phenyl)sulfonyl)-3,4-dihydro-2H-benzo[b][1,4]oxazine (94 mg, 50%). $^1$H-NMR (400 MHz, DMSO-d$_6$) δ 8.06 (m, 2H), 8.00 (m, 1H), 7.91 (s, 1H), 7.81 (m, 1H), 7.71 (m, 2H), 7.38 (m, 2H), 7.27 (m, 1H), 7.14 (m, 1H), 6.89 (m, 1H), 6.38 (s, 1H), 4.52 (m, 2H), 4.39 (m, 1H), 3.43 (m, 2H), 2.23 (m, 1H), 2.09 (m, 4H). (ES, m/z): (M+Na)$^+$ 629.09, 631.11.

Example 10—Synthesis of (S,E)-1-(2-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)ethyl)-1H-1,2,3-triazole-4-carboxylic acid

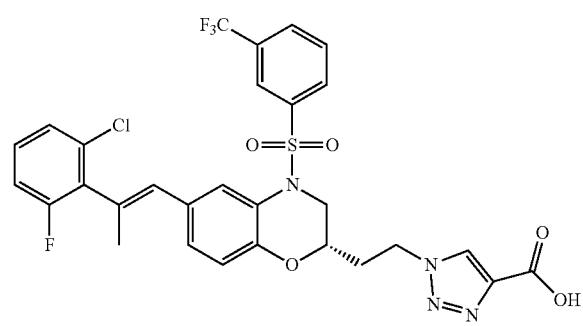 [SMILES: C/C(=C\c1ccc2c(c1)N(S(=O)(=O)c1cccc(C(F)(F)F)c1)C[C@H](CCn1cc(C(=O)O)nn1)O2)c1c(F)cccc1Cl]

Part I—Synthesis of (S,E)-methyl 1-(2-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)ethyl)-1H-1,2,3-triazole-4-carboxylate

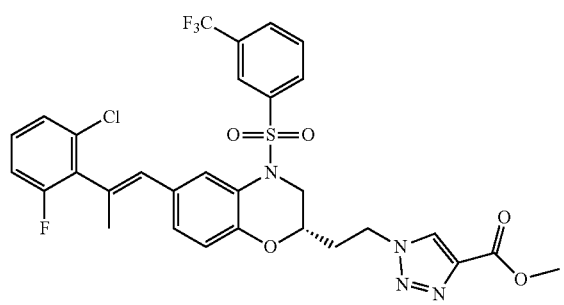 [SMILES: COC(=O)c1cn(CC[C@H]2CN(S(=O)(=O)c3cccc(C(F)(F)F)c3)c3cc(/C=C(\C)c4c(F)cccc4Cl)ccc3O2)nn1]

A mixture of (S,E)-2-(2-azidoethyl)-6-(2-(2-chloro-6-fluorophenyl)prop-1-en-1-yl)-4-((3-(trifluoromethyl)phenyl)sulfonyl)-3,4-dihydro-2H-benzo[b][1,4]oxazine (0.100 mg, 0.17 mmol), methyl propiolate (14 mg, 0.17 mmol), copper (II) sulfate pentahydrate (10 mg, 0.040 mmol) and sodium L-ascorbate (10 mg, 0.051 mmol) in tert-butanol (2 mL) and water (1 mL) was stirred at room temperature overnight. Then, the mixture was partitioned between ethyl acetate and water. The organic layer was washed with water, then brine, dried (Na$_2$SO$_4$) and concentrated. The resulting residue was purified by MPLC eluting with a gradient of ethyl acetate in hexanes to afford (S,E)-methyl 1-(2-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)ethyl)-1H-1,2,3-triazole-4-carboxylate (110 mg, 96%).

Part II—Synthesis of (S,E)-1-(2-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)ethyl)-1H-1,2,3-triazole-4-carboxylic acid

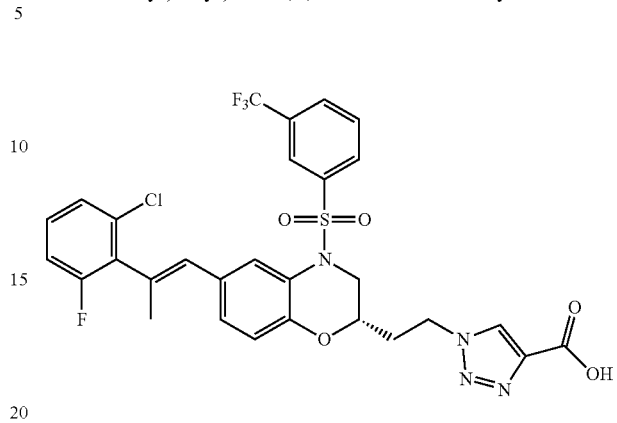

A mixture of (S,E)-methyl 1-(2-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)ethyl)-1H-1,2,3-triazole-4-carboxylate (110 mg, 0.16 mmol) and sodium hydroxide (20 mg, 0.50 mmol) was stirred at room temperature overnight. Then, the mixture was concentrated and the residue was partitioned between ethyl acetate and 1N HCl. The organic layer was washed with brine, dried (Na$_2$SO$_4$), and concentrated. The resulting residue was purified by MPLC, eluting with a gradient of 0-10% methanol in dichloromethane to afford (S,E)-1-(2-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)ethyl)-1H-1,2,3-triazole-4-carboxylic (15 mg, 14%). $^1$H-NMR (400 MHz, DMSO-d$_6$) δ 13.09 (s, 1H), 8.63 (s, 1H), 8.01 (m, 2H), 7.90 (s, 1H), 7.77 (m, 1H), 7.68 (m, 1H), 7.38 (m, 2H), 7.27 (m, 1H), 7.13 (m, 1H), 6.86 (m, 1H), 6.38 (s, 1H), 4.55 (m, 2H), 4.39 (m, 1H), 3.44 (m, 2H), 2.26 (m, 1H), 2.08 (m, 4H). (ES, m/z): (M+Na)$^+$ 673.16, 675.16.

Example 11—Synthesis of (S,E)-5-(2-(6-(2-chloro-6-(trifluoromethyl)styryl)-4-((3-(trifluoromethyl)phenyl)sulfonyl)-3,4-dihydro-2H-benzo[b][1,4]oxazin-2-yl)ethyl)-1,3,4-oxadiazol-2(3H)-one

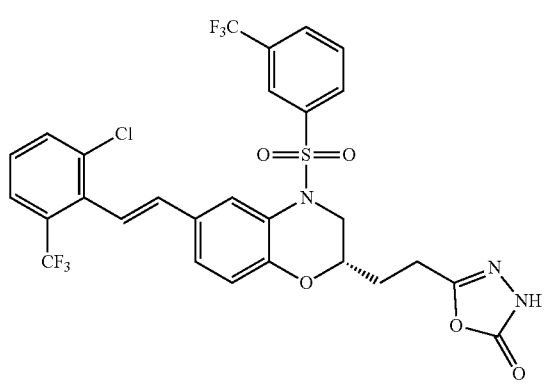 [SMILES: O=c1[nH]nc(CC[C@H]2CN(S(=O)(=O)c3cccc(C(F)(F)F)c3)c3cc(/C=C/c4c(Cl)cccc4C(F)(F)F)ccc3O2)o1]

Part I—Synthesis of
1-chloro-2-ethynyl-3-(trifluoromethyl)benzene

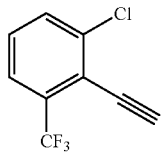

To a solution of 2-chloro-6-(trifluoromethyl)benzaldehyde (10.0 g, 47.9 mmol) in methanol (100 mL) was added dimethyl (diazomethyl)phosphonate (11.05 g, 57.5 mmol). The mixture was cooled to 0° C., and potassium carbonate (16.6 g, 119 mmol) was added. The reaction mixture was stirred at room temperature overnight. The crude mixture was diluted with ether, washed with water, washed with brine, dried (MgSO$_4$), and concentrated to afford 1-chloro-2-ethynyl-3-(trifluoromethyl)benzene (9.17 g, 93%).

Part II—Synthesis of (E)-2-(2-chloro-6-(trifluoromethyl)styryl)-4,4,5,5-tetramethyl-1,3,2-dioxaborolane

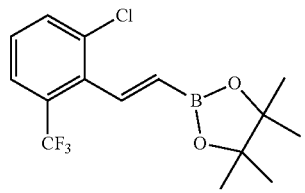 [SMILES: CC1(C)OB(/C=C/c2c(Cl)cccc2C(F)(F)F)OC1(C)C]

To [2,3-bis(1-adamantyl)imidazolidin-2-yl]-chloro-copper (0.99 g, 2.23 mmol) and sodium tert-butoxide (0.215 g, 2.23 mmol) suspended in THF (40 mL) was added bis (pinacolato)diboron (11.36 g, 44.7 mmol). The mixture was stirred for 30 minutes, and a solution of 1-chloro-2-ethynyl-3-(trifluoromethyl)benzene (9.15 g, 44.7 mmol) in THF (40 mL) and methanol (1.58 g, 49.2 mmol) was added. The mixture was stirred overnight, then filtered through celite. The filtrate was concentrated and the residue was purified via MPLC eluting with a gradient of 0-10% ethyl acetate in hexanes to afford (E)-2-(2-chloro-6-(trifluoromethyl)styryl)-4,4,5,5-tetramethyl-1,3,2-dioxaborolane (11.23 g, 76%).

Part III—Synthesis of (S,E)-methyl 3-(6-(2-chloro-6-(trifluoromethyl)styryl)-4-((3-(trifluoromethyl)phenyl)sulfonyl)-3,4-dihydro-2H-benzo[b][1,4]oxazin-2-yl)propanoate

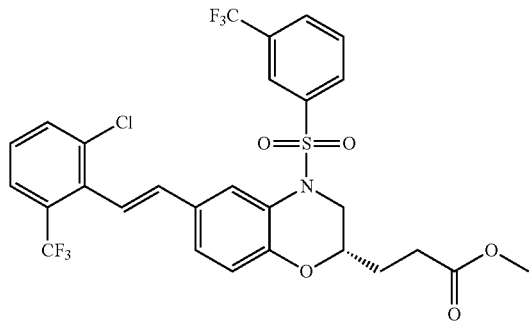 [SMILES: COC(=O)CC[C@H]1CN(S(=O)(=O)c2cccc(C(F)(F)F)c2)c2cc(/C=C/c3c(Cl)cccc3C(F)(F)F)ccc2O1]

A mixture of (S)-methyl 3-(6-bromo-4-((3-(trifluoromethyl)phenyl)sulfonyl)-3,4-dihydro-2H-benzo[b][1,4]oxazin-2-yl)propanoate (2.00 g, 3.93 mmol), (E)-2-(2-chloro-6-(trifluoromethyl)styryl)-4,4,5,5-tetramethyl-1,3,2-dioxaborolane (1.83 g, 5.51 mmol), potassium carbonate (0.65 g, 4.72 mmol) in dioxane (40 mL) and water (6 mL) was degassed and placed under an atomsphere of nitrogen. [1,1'-Bis(diphenylphosphino)ferrocene]-dichloropalladium (II), complex with dichloromethane (0.30 g, 0.39 mmol) was added and the reaction mixture heated to 70° C. overnight. Then, the reaction mixture was cooled, and subsequently partitioned between ethyl acetate and water. The organic layer was washed with brine, dried (Na$_2$SO$_4$) and concentrated onto a small amount of silica. The residue was purified by MPLC eluting with a gradient of 0-30% ethyl acetate in hexanes to afford (S,E)-methyl 3-(6-(2-chloro-6-(trifluoromethyl)styryl)-4-((3-(trifluoromethyl)phenyl)sulfonyl)-3,4-dihydro-2H-benzo[b][1,4]oxazin-2-yl)propanoate (2.0 g, 80%).

Part IV—Synthesis of (S,E)-5-(2-(6-(2-chloro-6-(trifluoromethyl)styryl)-4-((3-(trifluoromethyl)phenyl)sulfonyl)-3,4-dihydro-2H-benzo[b][1,4]oxazin-2-yl)ethyl)-1,3,4-oxadiazol-2(3H)-one

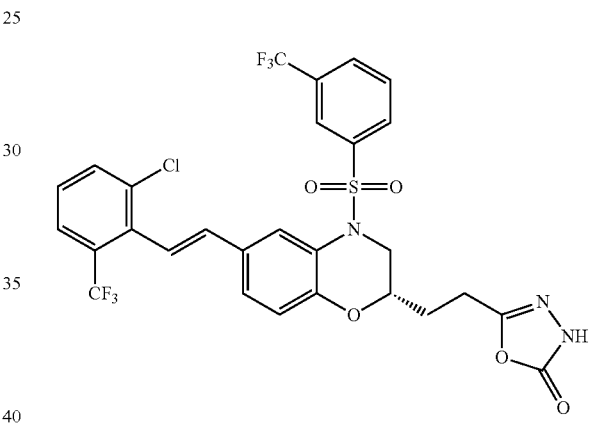

A solution of (S,E)-methyl 3-(6-(2-chloro-6-(trifluoromethyl)styryl)-4-((3-(trifluoromethyl)phenyl)sulfonyl)-3,4-dihydro-2H-benzo[b][1,4]oxazin-2-yl)propanoate (270 mg, 0.426 mmol) and hydrazine (140 mg, 4.26 mmol) in methanol (5 mL) was heated to 50° C. for five hours. Then, the reaction mixture was cooled and concentrated to afford (S,E)-3-(6-(2-chloro-6-(trifluoromethyl)styryl)-4-((3-(trifluoromethyl)phenyl)sulfonyl)-3,4-dihydro-2H-benzo[b][1,4]oxazin-2-yl)propanehydrazide, which was used without purification. To a solution of this hydrazide in THF (5 mL) at 0° C. was added diisopropylethylamine (170 mg, 1.28 mmol) followed by triphosgene (190 mg, 0.64 mmol). The mixture was stirred at 0° C. for ten minutes, and at room temperature for one hour. It then was partitioned between ethyl acetate and water, washed with brine, dried (Na$_2$SO$_4$), and concentrated onto silica gel. The residue was purified by MPLC eluting with a gradient of 20-60% ethyl acetate in hexanes to afford (S,E)-5-(2-(6-(2-chloro-6-(trifluoromethyl)styryl)-4-((3-(trifluoromethyl)phenyl)sulfonyl)-3,4-dihydro-2H-benzo[b][1,4]oxazin-2-yl)ethyl)-1,3,4-oxadiazol-2(3H)-one (140 mg, 37%) as a white solid. $^1$H-NMR (400 MHz, DMSO-d$_6$) δ 12.04 (s, 1H), 8.1 (m, 2H), 7.98 (s, 1H), 7.84 (m, 2H), 7.78 (m, 2H), 7.55 (m, 1H), 7.38 (m, 1H), 6.98 (m, 1H), 6.86 (m, 1H), 6.80 (m, 1H), 4.41 (m, 1H), 3.64 (m, 1H), 3.42 (m, 1H), 2.68 (m, 2H), 1.98 (m, 1H), 1.82 (m, 1H). (ES, m/z): (M+Na)$^+$ 682.15, 684.13.

Example 12—Synthesis of 1-((2R,3R)-7-((E)-2-fluoro-6-(trifluoromethyl)styryl)-2-methyl-1-((3-(trifluoromethyl)phenyl)sulfonyl)-1,2,3,4-tetrahydroquinolin-3-yl)-1H-imidazol-2(3H)-one

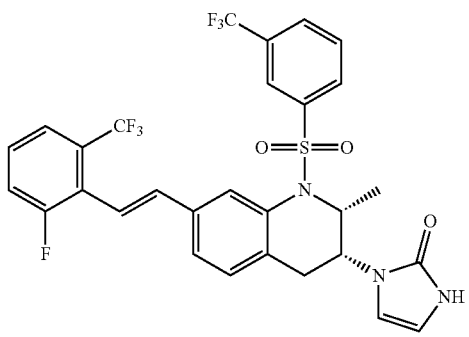 [SMILES: C[C@@H]1[C@H](n2cc[nH]c2=O)Cc2ccc(/C=C/c3c(F)cccc3C(F)(F)F)cc2N1S(=O)(=O)c1cccc(C(F)(F)F)c1]

Part I—Synthesis of (E)-2-(2-fluoro-6-(trifluoromethyl)styryl)-4,4,5,5-tetramethyl-1,3,2-dioxaborolane

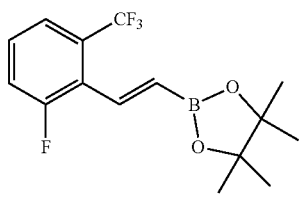

To [2,3-bis(1-adamatyl)imidazolidin-2-yl]-chloro-copper (0.21 g, 0.49 mmol) and sodium tert-butoxide (0.47 g, 0.49 mmol) suspended in THF (40 mL) was added bis(pinacolato)diboron (2.50 g, 9.83 mmol). The mixture was stirred for 30 minutes, and a solution of 1-chloro-2-ethynyl-3-(trifluoromethyl)benzene (9.15 g, 44.7 mmol) in THF (40 mL) and methanol (0.35 g, 11 mmol) was added. The mixture was stirred overnight, then filtered through celite. The filtrate was concentrated and the residue was purified by MPLC eluting with a gradient of 0-10% ethyl acetate in hexanes to afford (E)-2-(2-fluoro-6-(trifluoromethyl)styryl)-4,4,5,5-tetramethyl-1,3,2-dioxaborolane (1.55 g, 50%). $^1$H-NMR (400 MHz, DMSO-$d_6$) δ 7.58 (m, 4H), 7.23 (d, 1H), 6.13 (d, 1H), 1.22 (s, 12H).

Part II—Synthesis of (2R,3R)-methyl 7-((E)-2-fluoro-6-(trifluoromethyl)styryl)-2-methyl-1-((3-(trifluoromethyl)phenyl)sulfonyl)-1,2,3,4-tetrahydroquinoline-3-carboxylate

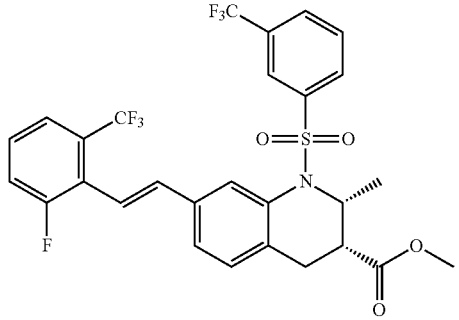 [SMILES: COC(=O)[C@@H]1Cc2ccc(/C=C/c3c(F)cccc3C(F)(F)F)cc2N(S(=O)(=O)c2cccc(C(F)(F)F)c2)[C@@H]1C]

A mixture of methyl (2R,3R)-6-bromo-3-methyl-4-((3-(trifluoromethyl)phenyl)sulfonyl)-3,4-dihydro-2H-benzo[b][1,4]oxazine-2-carboxylate, (E)-2-(2-fluoro-6-(trifluoromethyl)styryl)-4,4,5,5-tetramethyl-1,3,2-dioxaborolane (1.55 g, 4.91 mmol), potassium carbonate (0.93 g, 6.7 mmol) in dioxane (36 mL) and water (9 mL) was degassed and was placed under an atomsphere of nitrogen. [1,1'-Bis(diphenylphosphino)ferrocene]-dichloropalladium(II), complex with dichloromethane (0.37 g, 0.45 mmol) was added and the mixture was heated to 70° C. overnight. After allowing the mixture to cool, the mixture was partitioned between ethyl acetate and water. The organic layer was isolated and washed with brine, dried (Na$_2$SO$_4$) and concentrated onto a small amount of silica gel. The residue was purified by MPLC eluting with a gradient of 0-30% ethyl acetate in hexanes to afford (2R,3R)-methyl 7-((E)-2-fluoro-6-(trifluoromethyl)styryl)-2-methyl-1-((3-(trifluoromethyl)phenyl)sulfonyl)-1,2,3,4-tetrahydroquinoline-3-carboxylate (2.0 g, 74%). $^1$H-NMR (400 MHz, DMSO-$d_6$) δ 8.10 (m, 1H), 7.87 (m, 4H), 7.63 (m, 2H), 7.56 (m, 1H), 7.39 (m, 1H), 7.23 (m, 2H), 7.02 (d, 1H), 4.80 (m, 1H), 3.63 (d, 3H), 2.80 (m, 2H), 2.35 (m, 1H), 0.95 (m, 3H). (ES, m/z): (M+Na)$^+$ 624.38.

Part IV—Synthesis of (2R,3R)-7-((E)-2-fluoro-6-(trifluoromethyl)styryl)-2-methyl-1-((3-(trifluoromethyl)phenyl)sulfonyl)-1,2,3,4-tetrahydroquinoline-3-carboxylic acid

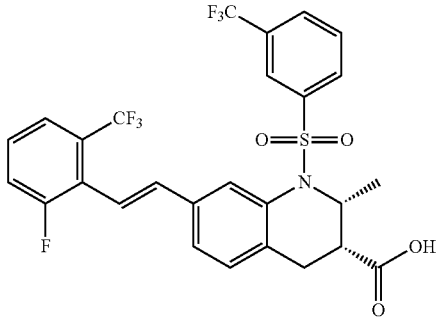 [SMILES: C[C@@H]1[C@H](C(=O)O)Cc2ccc(/C=C/c3c(F)cccc3C(F)(F)F)cc2N1S(=O)(=O)c1cccc(C(F)(F)F)c1]

A mixture of (2R,3R)-methyl 7-((E)-2-fluoro-6-(trifluoromethyl)styryl)-2-methyl-1-((3-(trifluoromethyl)phenyl)sulfonyl)-1,2,3,4-tetrahydroquinoline-3-carboxylate (2.0 g, 3.32 mmol), sodium hydroxide (0.27 g, 6.65 mmol), water (11 mL), and THF (22 mL) was stirred at room temperature overnight. Then, the reaction mixture was acidified to pH 2 with 1N HCl, and then extracted with ethyl acetate. The organic layer was dried (Na$_2$SO$_4$) and concentrated. The resulting residue was purified by MPLC, eluting with a gradient of 0-10% methanol in dichloromethane to afford (2R,3R)-7-((E)-2-fluoro-6-(trifluoromethyl)styryl)-2-methyl-1-((3-(trifluoromethyl)phenyl)sulfonyl)-1,2,3,4-tetrahydroquinoline-3-carboxylic acid (1.77 g, 82%). $^1$H-NMR (400 MHz, DMSO-$d_6$) δ 12.85 (bs, 1H), 8.10 (m, 1H), 7.95 (t, 1H), 7.84 (m, 3H), 7.64 (m, 1H), 7.54 (m, 1H), 7.38 (m, 1H), 7.22 (m, 2H), 7.05 (m, 1H), 4.56 (m, 1H), 3.57 (m, 1H), 2.75 (m, 2H), 2.22 (m, 1H), 1.73 (m, 1H), 0.96 (m, 3H). (MS, m/z): (M+Na)$^+$ 610.29.

187

Part IV—Synthesis of 1-((2R,3R)-7-((E)-2-fluoro-6-(trifluoromethyl)styryl)-2-methyl-1-((3-(trifluoromethyl)phenyl)sulfonyl)-1,2,3,4-tetrahydroquinolin-3-yl)-1H-imidazol-2(3H)-one

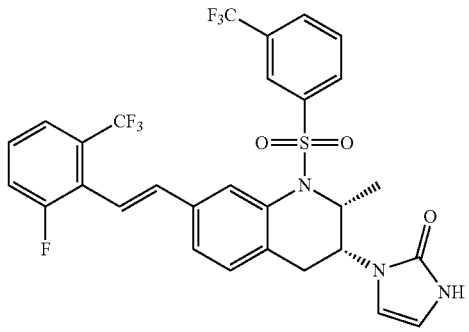 [SMILES: C[C@@H]1[C@H](n2cc[nH]c2=O)Cc2ccc(/C=C/c3c(F)cccc3C(F)(F)F)cc2N1S(=O)(=O)c1cccc(C(F)(F)F)c1]

A solution of (2R,3R)-7-((E)-2-fluoro-6-(trifluoromethyl)styryl)-2-methyl-1-((3-(trifluoromethyl)phenyl)sulfonyl)-1,2,3,4-tetrahydroquinoline-3-carboxylic acid (100 mg, 0.17 mmol), diphenylphosphonic azide (51 mg, 0.187 mmol), triethylamine (20 mg, 0.20 mmol), toluene (2 mL) and molecular sieves was heated to 95° C. for two hours. After allowing the reaction mixture to cool, aminoacetaldehyde diethyl acetal (30 mg, 0.23 mmol) was added and the mixture was heated at 70° C. overnight. Then, the mixture was cooled and subsequently partitioned between ethyl acetate and 2N HCl. The organic phase was dried (Na$_2$SO$_4$) and concentrated. The resulting residue was dissolved in acetonitrile (5 mL), water (2 mL) and trifluoroacetic acid (2 mL) and stirred at room temperature overnight. Then, the mixture was concentrated and the resulting residue was purified by MPLC eluting with a gradient of ethyl acetate in hexanes to afford 1-((2R,3R)-7-((E)-2-fluoro-6-(trifluoromethyl)styryl)-2-methyl-1-((3-(trifluoromethyl)phenyl)sulfonyl)-1,2,3,4-tetrahydroquinolin-3-yl)-1H-imidazol-2(3H)-one (10 mg, 9%) as a white solid. $^1$H-NMR (400 MHz, $^1$H-NMR (400 MHz, DMSO-d$_6$) δ 10.14 (s, 1H), 8.00 (m, 4H), 7.77 (t, 1H), 7.66 (m, 2H), 7.55 (m, 1H), 7.43 (d, 1H), 7.23 (m, 2H), 7.10 (d, 1H), 6.50 (t, 1H), 6.37 (t, 1H), 4.85 (m, 1H), 3.88 (m, 1H), 3.22 (m, 2H), 2.71 (m, 1H), 0.96 (d, 3H). (ES, m/z): (M+H)$^+$ 626.11.

Example 13—Synthesis of (S,E)-5-((6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)methyl)-1,3,4-oxadiazol-2(3H)-one

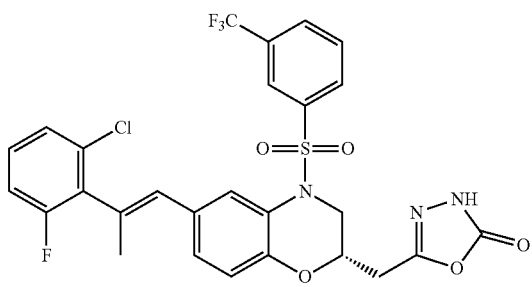 [SMILES: C/C(=C\c1ccc2c(c1)N(S(=O)(=O)c1cccc(C(F)(F)F)c1)C[C@H](Cc1n[nH]c(=O)o1)O2)c1c(F)cccc1Cl]

188

Part I—Synthesis of (S,E)-2-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)acetic acid

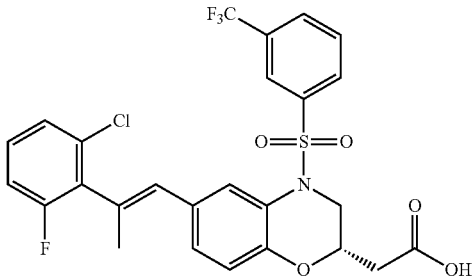 [SMILES: C/C(=C\c1ccc2c(c1)N(S(=O)(=O)c1cccc(C(F)(F)F)c1)C[C@H](CC(=O)O)O2)c1c(F)cccc1Cl]

To a solution of (S,E)-2-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)ethanol (0.45 g, 0.81 mmol) in acetone (20 mL) was added Jones' reagent dropwise until a red color persisted. The reaction mixture was held at room temperature for an additional thirty minutes. Then, isopropanol (1 mL) was added and the mixture was filtered through celite. The filtrate was concentrated, and the residue was partitioned between ethyl acetate and 1M HCl. The organic layer was washed with brine, dried (Na$_2$SO$_4$) and concentrated to afford (S,E)-2-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)acetic acid (440 mg, 95%).

Part II—Synthesis of (S,E)-methyl 2-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)acetate

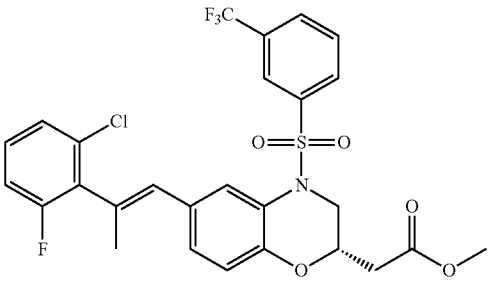 [SMILES: COC(=O)C[C@H]1CN(S(=O)(=O)c2cccc(C(F)(F)F)c2)c2cc(/C=C(\C)c3c(F)cccc3Cl)ccc2O1]

A mixture of (S,E)-2-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)acetic acid (380 mg, 0.67 mmol), potassium carbonate (180 mg, 1.33 mmol) and iodomethane (280 mg, 2.00 mmol) was stirred at room temperature for three hours. Then, the mixture was partitioned between ethyl acetate and water. The organic layer was washed with water, then brine, dried (Na$_2$SO$_4$), and concentrated to afford (S,E)-methyl 2-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)acetate (300 mg, 77%).

189

Part III—Synthesis of (S,E)-5-((6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)methyl)-1,3,4-oxadiazol-2(3H)-one

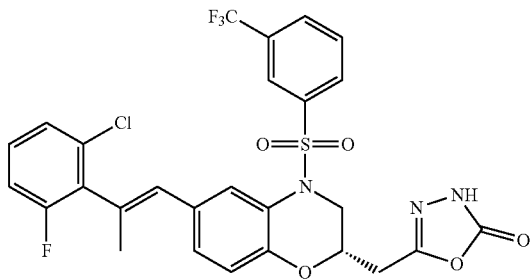 [SMILES: C/C(=C\c1ccc2c(c1)N(S(=O)(=O)c1cccc(C(F)(F)F)c1)C[C@H](Cc1n[nH]c(=O)o1)O2)c1c(F)cccc1Cl]

A solution of (S,E)-methyl 2-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)acetate (100 mg, 0.17 mmol) and hydrazine (50 mg, 1.6 mmol) in methanol (3 mL) was heated to 60° C. overnight. The mixture was cooled then concentrated to afford (S,E)-2-(6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)acetohydrazide, which was used without purification. To a solution of this hydrazide in THF (2 mL) at 0° C. was added triethylamine (50 mg, 0.50 mmol) followed by triphosgene (50 mg, 0.17 mmol). This mixture was stirred at 0° C. for ten minutes, and at room temperature for two hours. The resulting mixture was partitioned between ethyl acetate and water, washed with brine, dried (Na$_2$SO$_4$), and concentrated onto silica gel. The crude product was purified by MPLC eluting with a gradient of ethyl acetate in hexanes to afford (S,E)-5-((6-(2-(2-chloro-6-fluorophenyl)prop-1-en-1-yl)-4-((3-(trifluoromethyl)phenyl)sulfonyl)-3,4-dihydro-2H-benzo[b][1,4]oxazin-2-yl)methyl)-1,3,4-oxadiazol-2(3H)-one (32 mg, 29%) as a white solid. $^1$H-NMR (400 MHz, DMSO-d$_6$) δ 12.20 (s, 1H), 8.12 (m, 1H), 8.03 (m, 2H), 7.87 (m, 1H), 7.71 (m, 1H), 7.37 (m, 2H), 7.27 (m, 1H), 7.13 (m, 1H), 6.88 (m, 1H), 6.39 (s, 1H), 4.57 (m, 1H), 3.81 (m, 1H), 3.52 (m, 1H), 3.08 (m, 1H), 2.88 (m, 1H), 2.09 (s, 3H). (ES, m/z): (M+Na)$^+$ 632.28, 634.29.

Example 14—Synthesis of (S,E)-5-(2-(6-(2-(3-chloropyridin-2-yl)vinyl)-4-((3-(trifluoromethyl)phenyl)sulfonyl)-3,4-dihydro-2H-benzo[b][1,4]oxazin-2-yl)ethyl)-1,3,4-oxadiazol-2(3H)-one

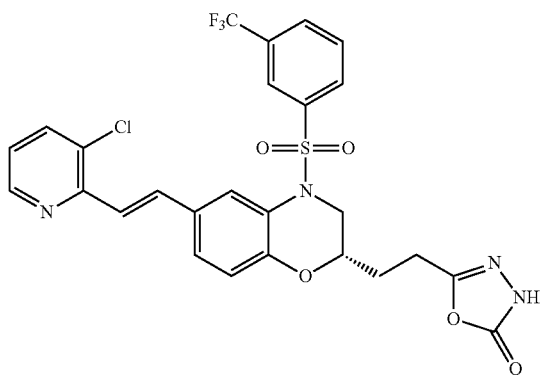 [SMILES: O=c1[nH]nc(CC[C@H]2CN(S(=O)(=O)c3cccc(C(F)(F)F)c3)c3cc(/C=C/c4ncccc4Cl)ccc3O2)o1]

190

Part I—Synthesis of methyl 3-((2S)-4-((3-(trifluoromethyl)phenyl)sulfonyl)-6-((E)-2-(4,4,6-trimethyl-1,3,2-dioxaborinan-2-yl)vinyl)-3,4-dihydro-2H-benzo[b][1,4]oxazin-2-yl)propanoate

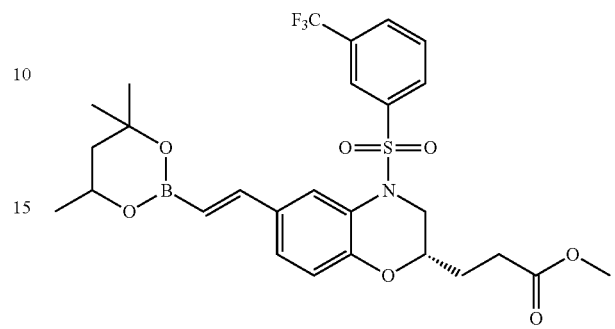

A mixture of (S)-methyl 3-(6-bromo-4-((3-(trifluoromethyl)phenyl)sulfonyl)-3,4-dihydro-2H-benzo[b][1,4]oxazin-2-yl)propanoate (15.35 g, 30.2 mmol), triethylamine (6.11 g, 60.4 mmol), and 4,4,5-trimethyl-2-vinyl-1,3,2-dioxaborinane (6.20 g, 36.2 mmol) in toluene (300 mL) was degassed and was placed under an atmosphere of nitrogen. Bis-(tri-tert-butyl)phosphine palladium (0.77 g, 1.51 mmol) was added and the reaction was heated to 80° C. overnight. Then, the mixture was cooled and subsequently partitioned between ethyl acetate and water. The organic layer was dried (Na$_2$SO$_4$), and concentrated onto a small amount of silica gel. The residue was purified by MPLC eluting with a gradient of ethyl acetate in hexanes. The fractions containing the major UV active component were concentrated to afford methyl 3-((2S)-4-((3-(trifluoromethyl)phenyl)sulfonyl)-6-((E)-2-(4,4,6-trimethyl-1,3,2-dioxaborinan-2-yl)vinyl)-3,4-dihydro-2H-benzo[b][1,4]oxazin-2-yl)propanoate (14.52 g, 82.7%) as a thick amber oil. $^1$H-NMR (400 MHz, DMSO-d$_6$) δ 8.08 (d, 1H), 7.93 (m, 2H), 7.81 (t, 1H), 7.72 (s, 1H), 7.27 (d, 1H), 7.08 (d, 1H), 6.76 (d, 1H), 5.83 (d, 1H), 4.33 (d, 1H), 4.25 (m, 1H), 3.54 (s, 3H), 3.39 (m, 2H), 2.39 (m, 2H), 1.90 (m, 2H), 1.73 (m, 1H), 1.45 (m, 1H), 1.27 (s, 6H), 1.22 (d, 3H).

Part II—Synthesis of (S,E)-methyl 3-(6-(2-(3-chloropyridin-2-yl)vinyl)-4-((3-(trifluoromethyl)phenyl)sulfonyl)-3,4-dihydro-2H-benzo[b][1,4]oxazin-2-yl)propanoate

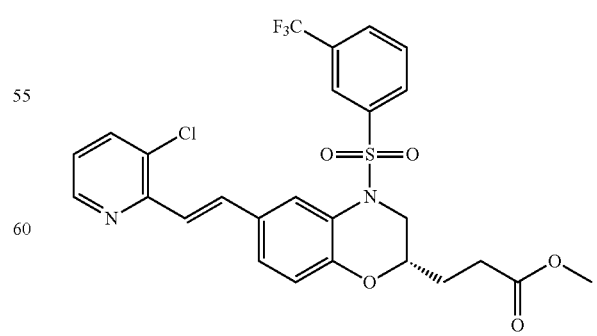

A mixture of methyl 3-((2S)-4-((3-(trifluoromethyl)phenyl)sulfonyl)-6-((E)-2-(4,4,6-trimethyl-1,3,2-dioxaborinan- 2-yl)vinyl)-3,4-dihydro-2H-benzo[b][1,4]oxazin-2-yl)propanoate (1.68 g, 2.89 mmol), 2-bromo-3-chloropyridine (0.83 g, 4.33 mmol), and potassium carbonate (1.60 g, 11.5 mmol) in toluene (1.5 mL), ethanol (0.4 mL) and water (0.5 mL) was degassed and was placed under an atomosphere of nitrogen. Tetrakistriphenylphosphine palladium (0) (0.33 g, 0.289 mmol) was added and the reaction mixture was heated to 90° C. overnight. Then, the mixture was cooled and subsequently partitioned between ethyl acetate and water. The organic layer was dried (Na$_2$SO$_4$), and concentrated onto a small amount of silica gel. The residue was purified by MPLC eluting with a gradient of 9:1 to 7:3 hexane:ethyl acetate. The fractions containing the major UV active component were concentrated to afford (S,E)-methyl 3-(6-(2-(3-chloropyridin-2-yl)vinyl)-4-((3-(trifluoromethyl)phenyl)sulfonyl)-3,4-dihydro-2H-benzo[b][1,4]oxazin-2-yl)propanoate (0.66 g, 40%). $^1$H-NMR (400 MHz, DMSO-d$_6$) δ 8.52 (s, 1H), 8.11 (m, 1H), 8.02 (m, 2H), 7.82 (m, 4H), 7.49 (m, 1H), 7.39 (d, 1H), 7.30 (m, 1H), 6.88 (d, 1H), 4.38 (d, 1H), 3.59 (s, 3H), 3.48 (m, 1H), 3.40 (m, 1H), 2.40 (m, 1H), 1.89 (m, 1H), 1.75 (m, 1H).

Part III—Synthesis of (S,E)-5-(2-(6-(2-(3-chloropyridin-2-yl)vinyl)-4-((3-(trifluoromethyl)phenyl)sulfonyl)-3,4-dihydro-2H-benzo[b][1,4]oxazin-2-yl)ethyl)-1,3,4-oxadiazol-2(3H)-one

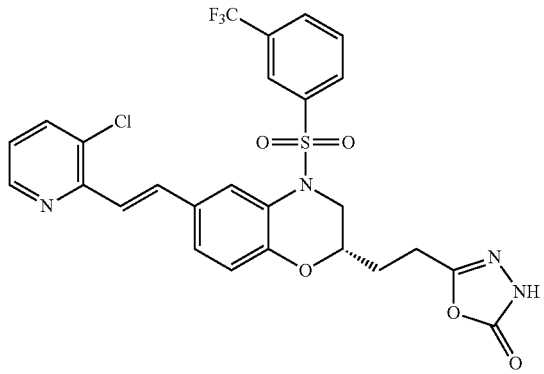 [SMILES: O=c1[nH]nc(CC[C@H]2CN(S(=O)(=O)c3cccc(C(F)(F)F)c3)c3cc(/C=C/c4ncccc4Cl)ccc3O2)o1]

A solution of (S,E)-methyl 3-(6-(2-(3-chloropyridin-2-yl)vinyl)-4-((3-(trifluoromethyl)phenyl)sulfonyl)-3,4-dihydro-2H-benzo[b][1,4]oxazin-2-yl)propanoate (330 mg, 0.58 mmol) and hydrazine (190 mg, 5.8 mmol) in methanol (6 mL) was heated to 50° C. for two hours. After allowing the reaction mixture to cool, the mixture was concentrated to afford (S,E)-3-(6-(2-(3-chloropyridin-2-yl)vinyl)-4-((3-(trifluoromethyl)phenyl)sulfonyl)-3,4-dihydro-2H-benzo[b][1,4]oxazin-2-yl)propanehydrazide, which was used without purification. To a solution of this hydrazide in THF (6 mL) at 0° C. was added diisopropylethylamine (150 mg, 1.16 mmol) followed by triphosgene (90 mg, 0.29 mmol). This mixture was stirred at 0° C. for ten minutes, and at room temperature for one hour. The resulting mixture was partitioned between ethyl acetate and water, washed with brine, dried (Na$_2$SO$_4$), and concentrated onto silica gel. The residue was purified by MPLC eluting with a gradient of ethyl acetate in hexanes to afford (S,E)-5-(2-(6-(2-(3-chloropyridin-2-yl)vinyl)-4-((3-(trifluoromethyl)phenyl)sulfonyl)-3,4-dihydro-2H-benzo[b][1,4]oxazin-2-yl)ethyl)-1,3,4-oxadiazol-2(3H)-one (203 mg, 56%) as a yellow solid. $^1$H-NMR (400 MHz, $^1$H-NMR (400 MHz, DMSO-d$_6$) δ 11.97 (s, 1H), 8.50 (s, 1H), 8.05 (d, 2H), 8.00 (s, 1H), 7.80 (m, 4H), 7.48 (d, 1H), 7.40 (d, 1H), 7.27 (dd, 1H), 6.81 (d, 1H), 4.42 (d, 1H), 3.47 (m, 2H), 2.60 (m, 2H), 1.98 (m, 1H), 1.78 (m, 1H). (MS, m/z): (M+H)$^+$ 593.13.

Example 15—Preparation of Additional 1,3,4-oxadiazol-2(3H)-ones

Compounds in Table 3 were prepared based on experimental procedures described in Example 1 and the detailed description.

TABLE 3

| Compd No. | Structure | Name | Observed m/z |
|---|---|---|---|
| 15A | 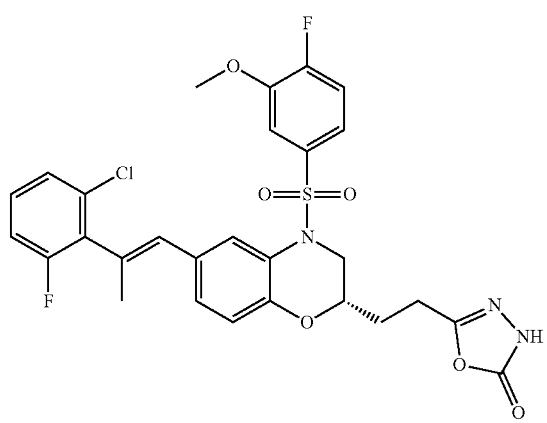 [SMILES: COc1cc(S(=O)(=O)N2C[C@H](CCc3n[nH]c(=O)o3)Oc3ccc(/C=C(\C)c4c(F)cccc4Cl)cc32)ccc1F] | (S,E)-5-(2-(6-(2-(2-chloro-6-fluorophenyl)prop-1-en-1-yl)-4-((4-fluoro-3-methoxyphenyl)sulfonyl)-3,4-dihydro-2H-benzo[b][1,4]oxazin-2-yl)ethyl)-1,3,4-oxadiazol-2(3H)-one | 604 (M + H)$^+$ |

TABLE 3-continued

| Compd No. | Structure | Name | Observed m/z |
|---|---|---|---|
| 15B | 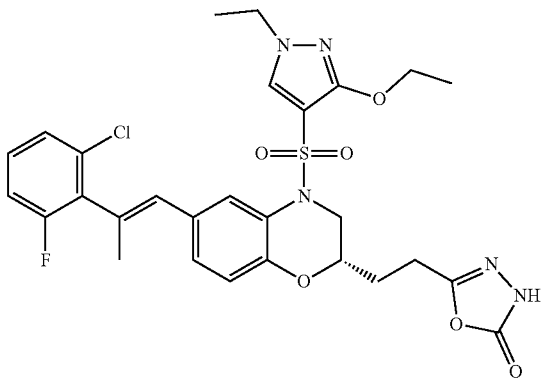 [SMILES: CCOc1nn(CC)cc1S(=O)(=O)N1C[C@H](CCc2n[nH]c(=O)o2)Oc2ccc(/C=C(\C)c3c(F)cccc3Cl)cc21] | (S,E)5-(2-(6-(2-(2-chloro-6-fluorophenyl)prop-1-en-1-yl)-4-((3-ethoxy-1-ethyl-1H-pyrazol-4-yl)sulfonyl)-3,4-dihydro-2H-benzo[b][1,4]oxazin-2-yl)ethyl)-1,3,4-oxadiazol-2(3H)-one | 618 (M + H)+ |
| 15C | 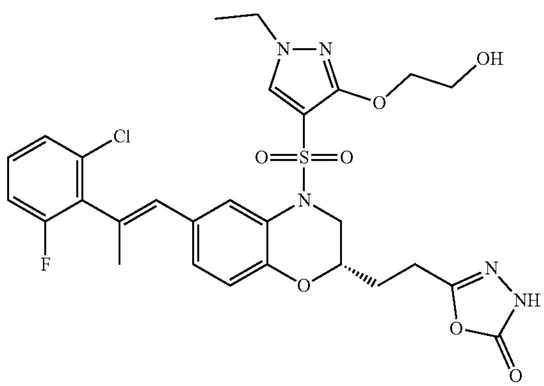 [SMILES: CCn1cc(S(=O)(=O)N2C[C@H](CCc3n[nH]c(=O)o3)Oc3ccc(/C=C(\C)c4c(F)cccc4Cl)cc32)c(OCCO)n1] | (S,E)-5-(2-(6-(2-(2-chloro-6-fluorophenyl)prop-1-en-1-yl)-4-((1-ethyl-3-(2-hydroxyethoxy)-1H-pyrazol-4-yl)sulfonyl)-3,4-dihydro-2H-benzo[b][1,4]oxazin-2-yl)ethyl)-1,3,4-oxadiazol-2(3H)-one | 634 (M + H)+ |
| 15D | 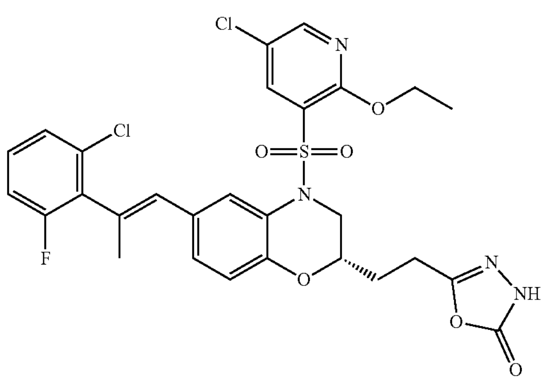 [SMILES: CCOc1ncc(Cl)cc1S(=O)(=O)N1C[C@H](CCc2n[nH]c(=O)o2)Oc2ccc(/C=C(\C)c3c(F)cccc3Cl)cc21] | (S,E)-5-(2-(4-((5-chloro-2-ethoxypyridin-3-yl)sulfonyl)-6-(2-(2-chloro-6-fluorophenyl)prop-1-en-1-yl)-3,4-dihydro-2H-benzo[b][1,4]oxazin-2-yl)ethyl)-1,3,4-oxadiazol-2(3H)-one | 635 (M + H)+ |
| 15E | 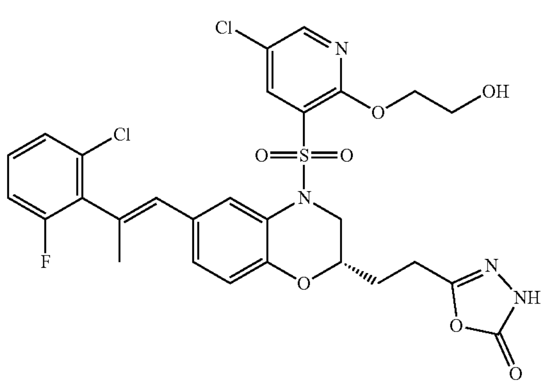 [SMILES: C/C(=C\c1ccc2c(c1)N(S(=O)(=O)c1cc(Cl)cnc1OCCO)C[C@H](CCc1n[nH]c(=O)o1)O2)c1c(F)cccc1Cl] | (S,E)-5-(2-(4-((5-chloro-2-(2-hydroxyethoxy)pyridin-3-yl)sulfonyl)-6-(2-(2-chloro-6-fluorophenyl)prop-1-en-1-yl)-3,4-dihydro-2H-benzo[b][1,4]oxazin-2-yl)ethyl)-1,3,4-oxadiazol-2(3H)-one | 651 (M + H)+ |

TABLE 3-continued

| Compd No. | Structure | Name | Observed m/z |
|---|---|---|---|
| 15F | 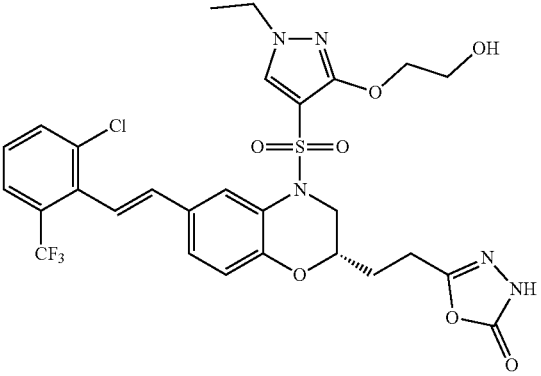 [SMILES: CCn1cc(S(=O)(=O)N2C[C@H](CCc3n[nH]c(=O)o3)Oc3ccc(/C=C/c4c(Cl)cccc4C(F)(F)F)cc32)c(OCCO)n1] | (S,E)-5-(2-(6-(2-chloro-6-(trifluoromethyl)styryl)-4-((1-ethyl-3-(2-hydroxyethoxy)-1H-pyrazol-4-yl)sulfonyl)-3,4-dihydro-2H-benzo[b][1,4]oxazin-2-yl)ethyl)-1,3,4-oxadiazol-2(3H)-one | 670 (M + H)+ |
| 15G | 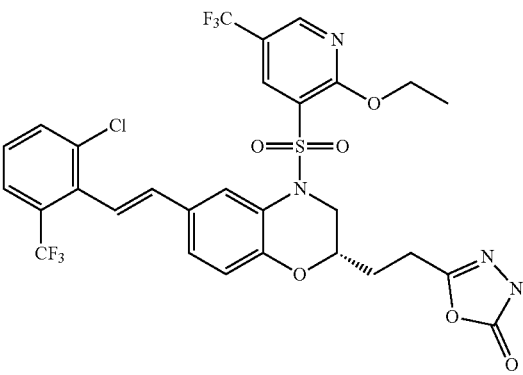 | (S,E)-5-(2-(6-(2-chloro-6-(trifluoromethyl)styryl)-4-((2-ethoxy-5-(trifluoromethyl)pyridin-3-yl)sulfonyl)-3,4-dihydro-2H-benzo[b][1,4]oxazin-2-yl)ethyl)-1,3,4-oxadiazol-2(3H)-one | 705 (M + H)+ |
| 15H | 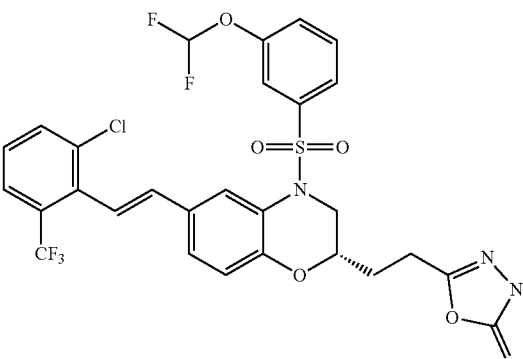 | (S,E)-5-(2-(6-(2-chloro-6-(trifluoromethyl)styryl)-4-((3-(difluoromethoxy)-phenyl)-sulfonyl)-3,4-dihydro-2H-benzo[b][1,4]-oxazin-2-yl)ethyl)-1,3,4-oxadiazol-2(3H)-one | 658 (M + H)+ |
| 15I | 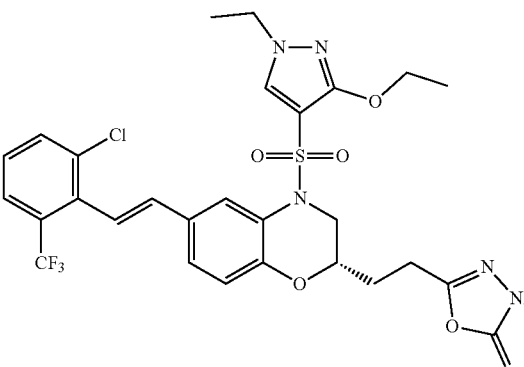 | (S,E)-5-(2-(6-(2-chloro-6-(trifluoromethyl)styryl)-4-((3-ethoxy-1-ethyl-1H-pyrazol-4-yl)sulfonyl)-3,4-dihydro-2H-benzo[b][1,4]-oxazin-2-yl)ethyl)-1,3,4-oxadiazol-2(3H)-one | 654 (M + H)+ |

TABLE 3-continued

| Compd No. | Structure | Name | Observed m/z |
|---|---|---|---|
| 15J | 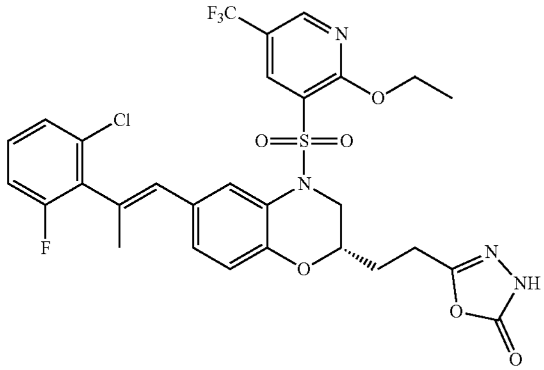 [SMILES: CCOc1ncc(C(F)(F)F)cc1S(=O)(=O)N1C[C@H](CCc2n[nH]c(=O)o2)Oc2ccc(/C=C(\C)c3c(F)cccc3Cl)cc21] | (S,E)-5-(2-(6-(2-(2-chloro-6-fluorophenyl)prop-1-en-1-yl)-4-((2-ethoxy-5-(trifluoromethyl)pyridin-3-yl)sulfonyl)-3,4-dihydro-2H-benzo[b][1,4]oxazin-2-yl)ethyl)-1,3,4-oxadiazol-2(3H)-one | 669 (M + H)+ |
| 15K | 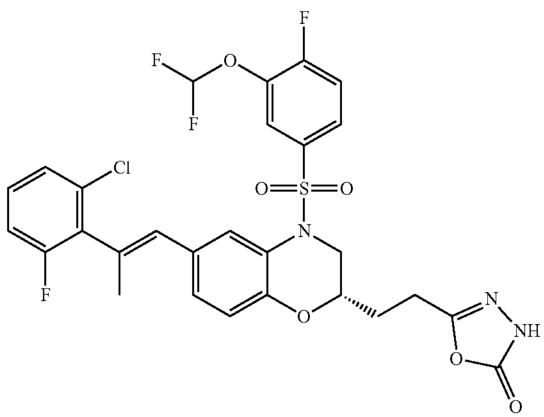 [SMILES: C/C(=C\c1ccc2c(c1)N(S(=O)(=O)c1ccc(F)c(OC(F)F)c1)C[C@H](CCc1n[nH]c(=O)o1)O2)c1c(F)cccc1Cl] | (S,E)-5-(2-(6-(2-(2-chloro-6-fluorophenyl)prop-1-en-1-yl)-4-((3-(difluoromethoxy)-4-fluorophenyl)sulfonyl)-3,4-dihydro-2H-benzo[b][1,4]oxazin-2-yl)ethyl)-1,3,4-oxadiazol-2(3H)-one | 640 (M + H)+ |

Example 16—Preparation of Additional Oxygen-Linked 1,2,4-Oxadiazol-5(4H)-ones

Compounds in Table 4 were prepared based on experimental procedures described in Example 3 and the detailed description.

TABLE 4

| Compd No. | Structure | Name | Observed m/z |
|---|---|---|---|
| 16A | 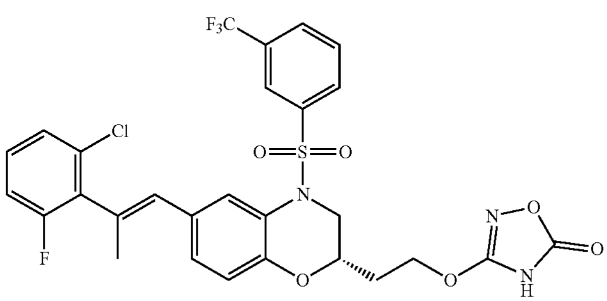 [SMILES: C/C(=C\c1ccc2c(c1)N(S(=O)(=O)c1cccc(C(F)(F)F)c1)C[C@H](CCOc1noc(=O)[nH]1)O2)c1c(F)cccc1Cl] | (S,E)-3-(2-(6-(2-(2-chloro-6-fluorophenyl)prop-1-en-1-yl)-4-((3-(trifluoromethyl)-phenyl)sulfonyl)-3,4-dihydro-2H-benzo[b][1,4]-oxazin-2-yl)ethoxy)-1,2,4-oxadiazol-5(4H)-one | 640 (M + H)+ |

TABLE 4-continued

| Compd No. | Structure | Name | Observed m/z |
|---|---|---|---|
| 16B | 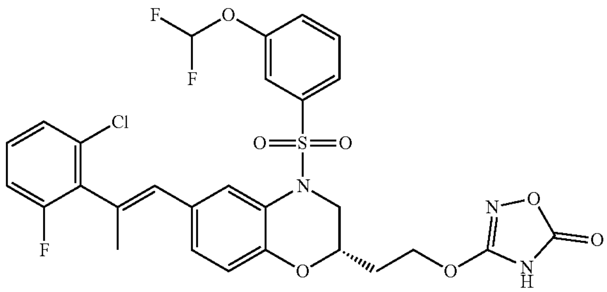 [SMILES: C/C(=C\c1ccc2c(c1)N(S(=O)(=O)c1cccc(OC(F)F)c1)C[C@H](CCOc1noc(=O)[nH]1)O2)c1c(F)cccc1Cl] | (S,E)-3-(2-(6-(2-(2-chloro-6-fluorophenyl)prop-1-en-1-yl)-4-((3-(difluoromethoxy)phenyl)sulfonyl)-3,4-dihydro-2H-benzo[b][1,4]-oxazin-2-yl)ethoxy)-1,2,4-oxadiazol-5(4H)-one | 638 (M + H)⁺ |
| 16C | 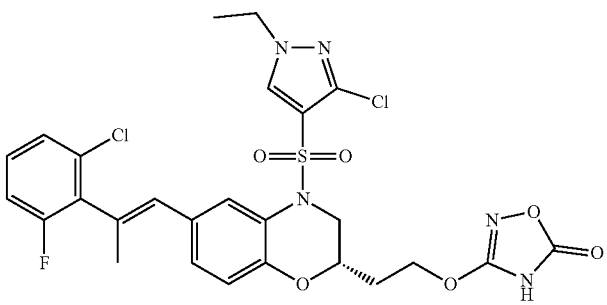 [SMILES: CCn1cc(S(=O)(=O)N2C[C@H](CCOc3noc(=O)[nH]3)Oc3ccc(/C=C(\C)c4c(F)cccc4Cl)cc32)c(Cl)n1] | (S,E)-3-(2-(4-((3-chloro-1-ethyl-1H-pyrazol-4-yl)sulfonyl)-6-(2-(2-chloro-6-fluorophenyl)prop-1-en-1-yl)-3,4-dihydro-2H-benzo[b][1,4]oxazin-2-yl)ethoxy)-1,2,4-oxadiazol-5(4H)-one | 624 (M + H)⁺ |
| 16D | 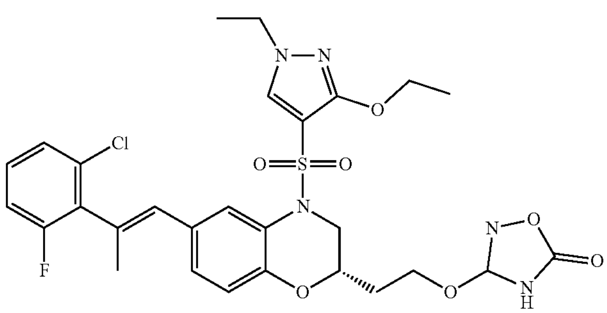 [SMILES: CCOc1nn(CC)cc1S(=O)(=O)N1C[C@H](CCOC2NOC(=O)N2)Oc2ccc(/C=C(\C)c3c(F)cccc3Cl)cc21] | (S,E)-3-(2-(6-(2-(2-chloro-6-fluorophenyl)prop-1-en-1-yl)-4-((3-ethoxy-1-ethyl-1H-pyrazol-4-yl)sulfonyl)-3,4-dihydro-2H-benzo[b][1,4]-oxazin-2-yl)ethoxy)-1,2,4-oxadiazol-5(4H)-one | 634 (M + H)⁺ |
| 16E | 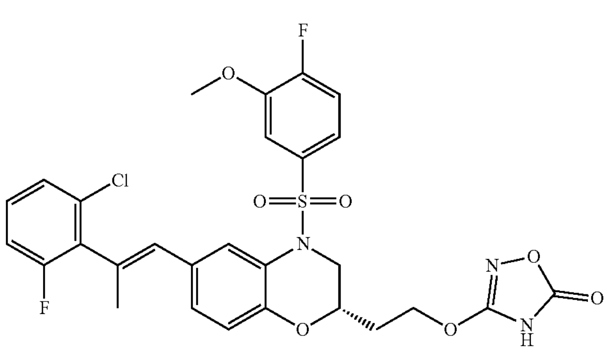 [SMILES: COc1cc(S(=O)(=O)N2C[C@H](CCOc3noc(=O)[nH]3)Oc3ccc(/C=C(\C)c4c(F)cccc4Cl)cc32)ccc1F] | ((S,E)-3-(2-(6-(2-(2-chloro-6-fluorophenyl)prop-1-en-1-yl)-4-((4-fluoro-3-methoxyphenyl)sulfonyl)-3,4-dihydro-2H-benzo[b][1,4]oxazin-2-yl)ethoxy)-1,2,4-oxadiazol-5(4H)-one | 620 (M + H)⁺ |

TABLE 4-continued

| Compd No. | Structure | Name | Observed m/z |
|---|---|---|---|
| 16F | 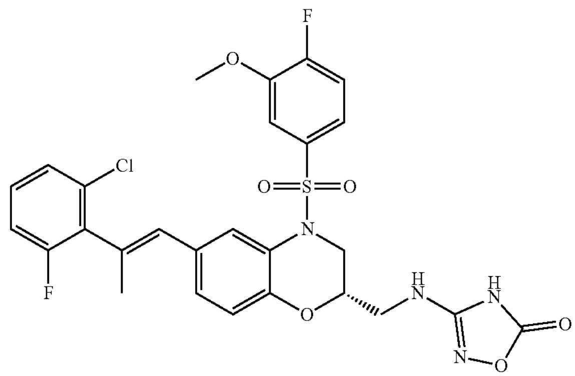 [SMILES: COc1cc(S(=O)(=O)N2C[C@H](CNc3noc(=O)[nH]3)Oc3ccc(/C=C(\C)c4c(F)cccc4Cl)cc32)ccc1F] | (S,E)-3-(((6-(2-(2-chloro-6-fluorophenyl)prop-1-en-1-yl)-4-((4-fluoro-3-methoxy-phenyl)sulfonyl)-3,4-dihydro-2H-benzo[b][1,4]-oxazin-2-yl)methyl)amino)-1,2,4-oxadiazol-5(4H)-one | 605 (M + H)+ |

Example 17—Preparation of Additional N-linked Azoles

Compounds in Table 5 were prepared based on experimental procedures described in Examples 5, 7, 8, 9, and 10 and the detailed description.

TABLE 5

| Compd No. | Structure | Name | Observed m/z |
|---|---|---|---|
| 17A | 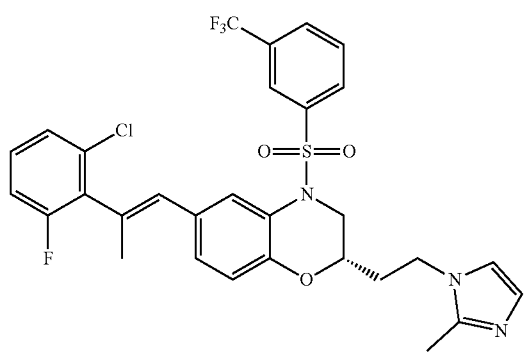 [SMILES: C/C(=C\c1ccc2c(c1)N(S(=O)(=O)c1cccc(C(F)(F)F)c1)C[C@H](CCn1ccnc1C)O2)c1c(F)cccc1Cl] | (S,E)-6-(2-(2-chloro-6-fluorophenyl)prop-1-en-1-yl)-2-(2-(2-methyl-1H-imidazol-1-yl)ethyl)-4-((3-(trifluoromethyl)-phenyl)sulfonyl)-3,4-dihydro-2H-benzo[b][1,4]oxazine | 620 (M + H)+ |
| 17B | 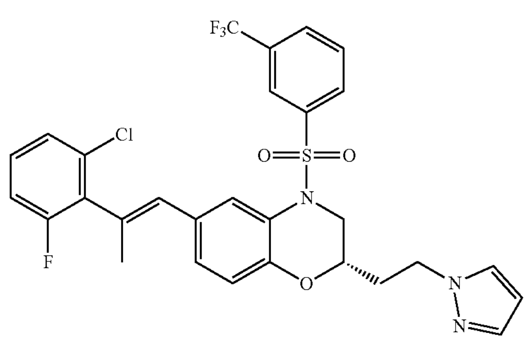 [SMILES: C/C(=C\c1ccc2c(c1)N(S(=O)(=O)c1cccc(C(F)(F)F)c1)C[C@H](CCn1cccn1)O2)c1c(F)cccc1Cl] | (S,E)-2-(2-(1H-pyrazol-1-yl)ethyl)-6-(2-(2-chloro-6-fluorophenyl)prop-1-en-1-yl)-4-((3-(trifluoromethyl)phenyl)-sulfonyl)-3,4-dihydro-2H-benzo[b][1,4]oxazine | 606 (M + H)+ |

TABLE 5-continued

| Compd No. | Name | Observed m/z |
|---|---|---|
| 17C | (S,E)-1-(3-(6-(2-(2-chloro-6-fluorophenyl)prop-1-en-1-yl)-4-((3-(trifluoro-methyl)-phenyl)sulfonyl)-3,4-dihydro-2H-benzo-[b][1,4]oxazin-2-yl)-propyl)-1H-1,2,3-triazole-4-carboxylic acid | 665 (M + H)+ |
| 17D | (S,E)-2-(3-(1H-1,2,3-triazol-1-yl)propyl)-6-(2-(2-chloro-6-fluorophenyl)prop-1-en-1-yl)-4-((3-(trifluoromethyl)phenyl)-sulfonyl)-3,4-dihydro-2H-benzo[b][1,4]oxazine | 621 (M + H)+ |
| 17E | (S,E)-2-(3-(1H-pyrazol-1-yl)propyl)-6-(2-(2-chloro-6-fluorophenyl)prop-1-en-1-yl)-4-((3-(trifluoromethyl)phenyl)-sulfonyl)-3,4-dihydro-2H-benzo[b][1,4]oxazine | 620 (M + H)+ |
| 17F | (2R,3S)-3-((1H-pyrazol-1-yl)methyl)-7-((E)-2-(2-chloro-6-fluorophenyl)prop-1-en-1-yl)-2-methyl-1-((3-(trifluoromethyl)phenyl)sulfonyl)-1,2,3,4-tetrahydroquinoline | 604 (M + H)+ |
| 17G | (2R,3S)-3-((1H-1,2,3-triazol-1-yl)methyl)-7-((E)-2-(2-chloro-6-fluorophenyl)prop-1-en-1-yl)-2-methyl-1-((3-(trifluoro-methyl)phenyl)sulfonyl)-1,2,3,4-tetrahydroquinoline | 605 (M + H)+ |

Example 18—Preparation of an Additional 1,2,4-Oxadiazol-5(4H)-one Compound

The compound in Table 6 was prepared based on experimental procedures described in Example 6 and the detailed description.

TABLE 6

| Compd No. | Structure | Name | Observed m/z |
|---|---|---|---|
| 18A | (structure) | (S,E)-3-(3-(6-(2-(2-chloro-6-fluorophenyl)prop-1-en-1-yl)-4-((3-(trifluoromethyl)phenyl)-sulfonyl)-3,4-dihydro-2H-benzo-[b][1,4]oxazin-2-yl)-propyl)-1,2,4-oxadiazol-5(4H)-one | 638 (M + H)+ |

Example 19—Preparation of an Additional Tetrazole Compound

The compound in Table 7 was prepared based on experimental procedures described in Example 2 and the detailed description.

TABLE 7

| Compd No. | Structure | Name | Observed m/z |
|---|---|---|---|
| 19A | (structure) | (S,E)-2-(3-(2H-tetrazol-5-yl)propyl)-6-(2-(2-chloro-6-fluorophenyl)prop-1-en-1-yl)-4-((3-(trifluoromethyl)-phenyl)-sulfonyl)-3,4-dihydro-2H-benzo[b][1,4]-oxazine | 622 (M + H)+ |

Example 20—Biological Assays for Agonist Activity Towards RORγ

Exemplary compounds from the above Examples were tested for ability to increase RORγ activity using (i) a RORγ-Ligand Binding Domain (LBD) TR-FRET Assay, and (ii) a Gal4-RORγ Luciferase Reporter Assay in HEK-293T Cells. Assay procedures and results are described below.

Part I—Procedures for RORγ-Ligand Binding Domain TR-FRET Assay

HIS-tagged RORγ-LBD protein was expressed in SF9 cells using a baculovirus expression system. The lysate was diluted in assay buffer (50 mM Tris pH 7.0, 50 mM KCl, 1 mM EDTA, 0.1 mM DTT, 0.01% BSA) to obtain RORγ-LBD final concentration of ~3 nM in a 384-well assay plate (need to titrate for each batch of protein).

A stock of biotinylated-LXXLL peptide from coactivator SRC1 (Biotin-CPSSHSSLTERHKILHRLLQEGSPS) was prepared in assay buffer and added to each well (200 nM final concentration). A solution of Europium tagged anti-HIS antibody (0.6 nM final concentration) and APC-conjugated streptavidin (30 nM final concentration) were also added to each well. RORγ antagonist ursolic acid was also included at a final concentration of 2 μM. Compounds were diluted in DMSO and further diluted in assay buffer with a final DMSO concentration at 1%.

The final assay mixture was incubated overnight at 4° C. or 2 hours at room temperature, and the fluorescence signal was measured on an Envision plate reader: (Excitation filter=340 nm; APC emission=665 nm; Europium emission=615 nm; dichroic mirror=D400/D630; delay time=100 μs, integration time=200 μs). 50% Effective concentration ($EC_{50}$) values for test compounds were calculated from the quotient of the fluorescence signal at 665 nm divided by the fluorescence signal at 615 nm. The quotient of the fluorescence signals in the absence of ursolic acid or test compound is set as 100. Max Response is defined as the upper plateau in the signal as determined by line-fit using a 4-parameter logistic model in PRISM (GraphPad).

Part II—Procedures for Gal4-RORγ Luciferase Reporter Assay in HEK-293T Cells Transfection of HEK-293 Cells In the following protocol, HEK-293 cells were transfected with a construct comprising the Gal4 DNA binding domain fused to the ligand binding domain of RORγ (Gal4-RORγ-LBD) in a pcDNA3.1neo plasmid, and also with a reporter construct comprising pGL4.31 Gal4-luciferase (Promega). Control cells were prepared similarly using empty pcDNA3.1neo and pGL4.31 vectors.

Trans-IT reagent (Mirus, 60 µL) at room temperature was added drop wise to OptiMEM (Invitrogen, 1.5 ml). This reagent mixture was mixed by inversion then incubated for 5 to 30 minutes at room temperature. It then was added to a solution of both expression vectors (5 µg each), mixed, and incubated at room temperature for about 20 minutes. HEK-293 cells were harvested from incubation flasks by removing the media, treating with TrypLE Express (Invitrogen), and incubating until the cells detached from the bottom of the flask (approximately 2-5 minutes). 10 Million cells were collected by centrifugation and re-suspended in 10 mL of Dulbecco's Modified Eagle Medium, High Glucose (DMEM, Invitrogen) containing 10% Fetal Bovine Serum and 100 IU each of penicillin and streptomycin. The re-suspended cells and the transfection mixture were added to a T75 flask, mixed and incubated overnight at 37° C. and 5% $CO_2$.

Assay for RORγ Activity

The cells were harvested as described above, counted, and centrifuged to obtain the desired number of cells, then re-suspended in complete growth media at $0.75 \times 10^6$ cells/mL. The RORγ antagonist, ursolic acid, was added to the cells at a final concentration of 2 µM. Cells were plated at 20 µL of cell suspension/well (10,000-15,000 cells/well) in white tissue culture treated 384 well plates. Test compounds were dissolved at 10 mM in DMSO then diluted into complete growth medium to 5× the final intended test concentration. These drug stock solutions, 5 µL/well were added to the tissue culture plate. The final DMSO concentration was 0.2%. The plates were briefly centrifuged then incubated overnight at 37° C. and 5% $CO_2$. To conduct the assay, the tissue culture plates were allowed to equilibrate to room temperature and One-Glo luciferase reagent (Promega, 25 µL/well) was added. The plates were briefly centrifuged then incubated at room temperature for 10 minutes. The luciferase intensity was read on an Envision plate reader (Perkin Elmer). RORγ activity was determined relative to controls and plotted as a function of test compound concentration using PRISM (GraphPad) to determine a 50% effective concentration ($EC_{50}$). The luciferase signal in the absence of ursolic acid or test compound is defined at 100. The Max Response is the upper plateau in the signal as determined by line-fit using a 4-parameter logistic model in PRISM (GraphPad).

Part III—Results

Experimental results are provided in Table 8 below. The symbol "++++" indicates an $EC_{50}$ less than 0.1 µM. The symbol "+++" indicates an $EC_{50}$ in the range of 0.1 µM to 5 µM. The symbol "++" indicates an $EC_{50}$ in the range of greater than 5 µM to 10 µM. The symbol "+" indicates an $EC_{50}$ greater than 10 µM. The symbol "N/A" indicates that no data was available. The symbol "**" indicates a value greater than 200. The symbol "*" indicates a value in the range of greater than 150 to 200. The symbol "**" indicates a value in the range of greater than 90 to 150. The symbol "*" indicates a value in the range of 40 to 90.

TABLE 8

Assay Results for Sulfonamido Compounds.

| Compound Structure | TR-FRET Assay | | Gal4-RORγ Assay | |
|---|---|---|---|---|
| | $EC_{50}$ | Max Response | $EC_{50}$ | Max Response |
| [structure] | ++++ | ** | +++ | ** |
| [structure] | ++++ | *** | +++ | *** |

TABLE 8-continued

Assay Results for Sulfonamido Compounds.

| Compound Structure | TR-FRET Assay | | Gal4-RORγ Assay | |
|---|---|---|---|---|
| | EC$_{50}$ | Max Response | EC$_{50}$ | Max Response |
| (structure 1) | +++ | *** | +++ | ** |
| (structure 2) | ++++ | *** | ++ | ** |
| (structure 3) | ++++ | *** | +++ | ** |
| (structure 4) | ++++ | *** | +++ | *** |

TABLE 8-continued

Assay Results for Sulfonamido Compounds.

| Compound Structure | TR-FRET Assay | | Ga14-RORγ Assay | |
|---|---|---|---|---|
| | EC$_{50}$ | Max Response | EC$_{50}$ | Max Response |
| (structure: 2-chloro-6-fluorophenyl propenyl benzoxazine, 3-CF$_3$-phenylsulfonyl, ethyl-1,2,4-triazole) | ++++ | *** | +++ | ** |
| (structure: 2-chloro-6-fluorophenyl propenyl benzoxazine, 3-CF$_3$-phenylsulfonyl, propyl-imidazole) | ++++ | *** | +++ | ** |
| (structure: 2-chloro-6-fluorophenyl propenyl benzoxazine, 3-CF$_3$-phenylsulfonyl, ethyl-1,2,3-triazole) | ++++ | *** | +++ | ** |
| (structure: 2-chloro-6-fluorophenyl propenyl benzoxazine, 3-CF$_3$-phenylsulfonyl, ethyl-triazole-carboxylic acid) | ++++ | *** | +++ | *** |

TABLE 8-continued

Assay Results for Sulfonamido Compounds.

| Compound Structure | TR-FRET Assay | | Gal4-RORγ Assay | |
|---|---|---|---|---|
| | EC$_{50}$ | Max Response | EC$_{50}$ | Max Response |
| [structure: 2-chloro-6-CF3 phenyl vinyl benzoxazine, N-sulfonyl-3-CF3-phenyl, with oxadiazolone ethyl] | ++++ | *** | +++ | ** |
| [structure: 2-fluoro-6-CF3 phenyl vinyl tetrahydroquinoline, N-sulfonyl-3-CF3-phenyl, with methyl and imidazolone] | +++ | *** | +++ | ** |
| [structure: 2-fluoro-6-chloro phenyl (methyl)vinyl benzoxazine, N-sulfonyl-3-CF3-phenyl, with oxadiazolone methyl] | ++++ | *** | +++ | * |
| [structure: 3-CF3-pyridyl vinyl benzoxazine, N-sulfonyl-3-CF3-phenyl, with oxadiazolone ethyl] | ++++ | *** | +++ | ** |

TABLE 8-continued

Assay Results for Sulfonamido Compounds.

| Compound Structure | TR-FRET Assay | | Gal4-RORγ Assay | |
|---|---|---|---|---|
| | EC$_{50}$ | Max Response | EC$_{50}$ | Max Response |
| (structure with 4-fluoro-3-methoxyphenyl sulfonyl) | ++++ | ** | +++ | ** |
| (structure with 1-ethyl-3-ethoxypyrazol-4-yl sulfonyl) | ++++ | *** | +++ | *** |
| (structure with 3-trifluoromethylphenyl sulfonyl, oxadiazolone ether) | ++++ | *** | +++ | ** |
| (structure with 3-difluoromethoxyphenyl sulfonyl, oxadiazolone ether) | ++++ | *** | +++ | ** |

TABLE 8-continued

Assay Results for Sulfonamido Compounds.

| Compound Structure | TR-FRET Assay | | Ga14-RORγ Assay | |
| --- | --- | --- | --- | --- |
| | EC$_{50}$ | Max Response | EC$_{50}$ | Max Response |
| [structure] | ++++ | *** | +++ | *** |
| [structure] | ++++ | *** | +++ | ** |
| [structure] | ++++ | *** | +++ | **** |
| [structure] | ++++ | *** | +++ | ** |

TABLE 8-continued

Assay Results for Sulfonamido Compounds.

| Compound Structure | TR-FRET Assay | | Gal4-RORγ Assay | |
|---|---|---|---|---|
| | EC$_{50}$ | Max Response | EC$_{50}$ | Max Response |
| (structure) | ++++ | *** | +++ | ** |
| (structure) | ++++ | *** | +++ | ** |
| (structure) | ++++ | *** | +++ | ** |
| (structure) | ++++ | *** | +++ | ** |
| (structure) | ++++ | *** | +++ | ** |

TABLE 8-continued

Assay Results for Sulfonamido Compounds.

| Compound Structure | TR-FRET Assay | | Gal4-RORγ Assay | |
| --- | --- | --- | --- | --- |
| | EC$_{50}$ | Max Response | EC$_{50}$ | Max Response |
| (structure) | ++++ | *** | + | * |
| (structure) | +++ | *** | +++ | ** |
| (structure) | +++ | *** | +++ | ** |
| (structure) | ++++ | **** | +++ | ** |

TABLE 8-continued

Assay Results for Sulfonamido Compounds.

| Compound Structure | TR-FRET Assay | | Ga14-RORγ Assay | |
|---|---|---|---|---|
| | EC$_{50}$ | Max Response | EC$_{50}$ | Max Response |
| (structure) | ++++ | *** | +++ | ** |
| (structure) | ++++ | **** | +++ | ** |
| (structure) | ++++ | **** | +++ | ** |
| (structure) | +++ | **** | +++ | ** |

TABLE 8-continued

Assay Results for Sulfonamido Compounds.

| Compound Structure | TR-FRET Assay | | Ga14-RORγ Assay | |
|---|---|---|---|---|
| | EC$_{50}$ | Max Response | EC$_{50}$ | Max Response |
| (structure) | ++++ | **** | +++ | ** |
| (structure) | ++++ | **** | +++ | ** |
| (structure) | ++++ | **** | +++ | ** |

TABLE 8-continued

Assay Results for Sulfonamido Compounds.

| Compound Structure | TR-FRET Assay | | Gal4-RORγ Assay | |
|---|---|---|---|---|
| | $EC_{50}$ | Max Response | $EC_{50}$ | Max Response |
| 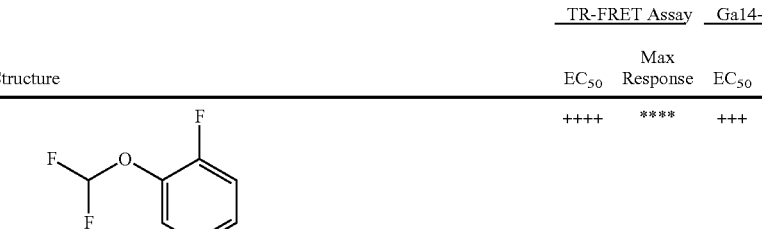 | ++++ | ** | +++ |  |

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

What is claimed is:
1. A compound represented by Formula I:

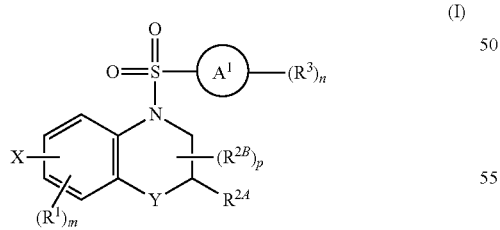

(I)

or a pharmaceutically acceptable salt thereof; wherein:
$A^1$ is phenylene, 5-6 membered heteroarylene, or $C_{3-6}$ heterocycloalkylene;
$R^1$ represents independently for each occurrence halogen, $C_{1-6}$ alkyl, $C_{1-6}$ haloalkyl, or $C_{3-6}$ cycloalkyl;
$R^{2A}$ is —($C_{1-6}$ alkylene)-$A^2$, -(2-6 membered heteroalkylene)-$A^2$, —($C_{0-3}$ alkylene)-($C_{3-6}$ cycloalkylene)-($C_{0-3}$ alkylene)-$A^2$, —O-$A^2$, —N($R^8$)-$A^2$, or -$A^2$; wherein $A^2$ is one of the following:

a 5-6 membered heterocyclic group containing at least one ring carbon atom substituted by oxo and the heterocyclic group being optionally substituted by 1 or 2 substituents independently selected from the group consisting of $C_{1-6}$ alkyl, $C_{1-6}$ haloalkyl, $C_{3-6}$ cycloalkyl, halogen, $C_{1-6}$ alkoxy, $C_{1-6}$ haloalkoxy, oxo, —C(O)$R^9$, —CO$_2R^8$, —N($R^4$)C(O)($R^9$), and —N($R^4$)($R^5$); or a 5-6 membered heteroaromatic group comprising at least two ring nitrogen atoms, at least one unsaturated carbon atom in the ring, and the heteroaromatic group being optionally substituted by 1 or 2 substituents independently selected from the group consisting of $C_{1-6}$ alkyl $C_{1-6}$ haloalkyl, $C_{3-6}$ cycloalkyl, halogen, $C_{1-6}$ alkoxy, $C_{1-6}$ haloalkoxy, —C(O)$R^9$, —CO$_2R^8$, —N($R^4$)C(O)($R^9$), and —N($R^4$)($R^5$);

$R^{2B}$ represents independently for each occurrence $C_{1-6}$ alkyl or $C_{1-3}$ haloalkyl;

$R^3$ represents independently for each occurrence hydrogen, $C_{1-6}$ haloalkyl, halogen, hydroxyl, $C_{1-6}$ alkyl, $C_{3-6}$ cycloalkyl, $C_{1-6}$ alkoxy, $C_{1-6}$ haloalkoxy, —O—($C_{1-6}$ alkylene)-OH, or —O—($C_{1-6}$ alkylene)-CO$_2R^4$; or two vicinal occurrences of $R^3$ are taken together with intervening atoms to form a 4-6 membered ring;

$R^4$ and $R^5$ each represent independently for each occurrence hydrogen, $C_{1-6}$ alkyl, or $C_{3-6}$ cycloalkyl; or an occurrence of $R^4$ and $R^5$ attached to the same nitrogen atom are taken together with the nitrogen atom to which they are attached to form a 3-7 membered heterocyclic ring;

$R^6$ and $R^7$ each represent independently for each occurrence hydrogen or $C_{1-6}$ alkyl, or $R^6$ and $R^7$ are taken together with the carbon atom to which they are attached to form a 3-6 membered carbocyclic ring; or $R^6$ and $R^{2A}$ are taken together to form a bond;

$R^8$ represents independently for each occurrence hydrogen, $C_{1-6}$ alkyl, $C_{3-6}$ cycloalkyl, or aralkyl;

$R^9$ represents independently for each occurrence $C_{1-6}$ alkyl, $C_{3-6}$ cycloalkyl, or aralkyl;

X is one of the following:
(i) —(C$_{2-6}$ alkenylene)-phenyl, —(C$_{2-6}$ alkenylene)-heteroaryl, —(C$_{1-6}$ alkylene)-phenyl, —(C$_{1-6}$ alkylene)-heteroaryl, —(C$_{1-6}$ alkylene)-(partially unsaturated bicyclic heterocyclyl), —(C$_{1-6}$ alkylene)-(partially unsaturated bicyclic oxo-heterocyclyl), -(5-6 membered heterocycloalkylene)-phenyl, or —(C$_{3-6}$ cycloalkylene)-phenyl, each of which is optionally substituted with 1, 2, or 3 substituents independently selected from the group consisting of halogen, C$_{1-6}$ haloalkyl, C$_{1-6}$ alkyl, C$_{3-6}$ cycloalkyl, C$_{1-6}$ alkoxy, C$_{1-6}$ haloalkoxy, hydroxyl, and cyano;
(ii) —(C$_{2-6}$ alkenylene)-(C$_{3-6}$ cycloalkyl),

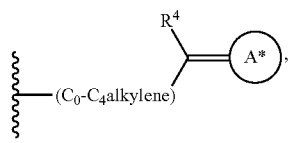

or an 8-10 membered, bicyclic partially saturated carbocyclyl, each of which is optionally substituted with 1, 2, or 3 substituents independently selected from the group consisting of halogen, C$_{1-6}$ haloalkyl, C$_{1-6}$ alkyl, C$_{3-6}$ cycloalkyl, C$_{1-6}$ alkoxy, C$_{1-6}$ haloalkoxy, hydroxyl, and cyano, wherein A* is a 5-8 membered, partially saturated carbocyclic or heterocyclic ring;
(iii) —(C$_{1-6}$ alkylene)-Z$^1$ or —(C$_{2-6}$ alkenylene)-Z$^1$, wherein Z$^1$ is —O-aralkyl, —O-heteroaralkyl, —O-phenyl, —O-heteroaryl, —O-(partially unsaturated bicyclic carbocyclyl), —O—(C$_{1-6}$ alkylene)-(C$_{3-6}$ cycloalkyl), —O—(C$_{3-6}$ cycloalkyl), —N(R$^4$)-aralkyl, —N(R$^4$)-phenyl, —N(R$^4$)-(partially unsaturated bicyclic carbocyclyl), or —N(R$^4$)-(C$_{1-6}$ alkylene)-(C$_{3-6}$ cycloalkyl), each of which is optionally substituted with 1, 2, or 3 substituents independently selected from the group consisting of halogen, C$_{1-6}$ haloalkyl, C$_{1-6}$ alkyl, C$_{3-6}$ cycloalkyl, C$_{1-6}$ alkoxy, C$_{1-6}$ haloalkoxy, hydroxyl, and cyano; or
(iv) —O-aralkyl, —O-heteroaralkyl, —O-phenyl, —O-heteroaryl, —O-(partially unsaturated bicyclic carbocyclyl), —O—(C$_{1-6}$ alkylene)-(C$_{3-6}$ cycloalkyl), —O—(C$_{3-6}$ cycloalkyl), —N(R$^4$)-aralkyl, —N(R$^4$)-phenyl, —N(R$^4$)-(partially unsaturated bicyclic carbocyclyl), or —N(R$^4$)—(C$_{1-6}$ alkylene)-(C$_{3-6}$ cycloalkyl), each of which is optionally substituted with 1, 2, or 3 substituents independently selected from the group consisting of halogen, C$_{1-6}$ haloalkyl, C$_{1-6}$ alkyl, C$_{3-6}$ cycloalkyl, C$_{1-6}$ alkoxy, C$_{1-6}$ haloalkoxy, hydroxyl, and cyano;
Y is —C(R$^6$)(R$^7$)—, —O—, —C(O)—, or —S(O)$_p$—;
m and p each represent independently for each occurrence 0, 1, or 2; and
n is 1, 2, or 3.

2. The compound of claim 1, wherein the compound is represented by Formula I-A:

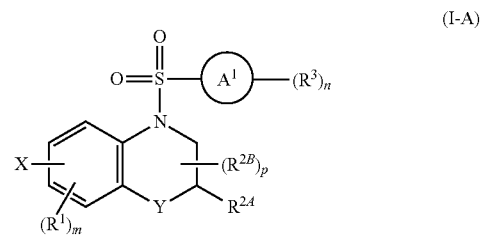

or a pharmaceutically acceptable salt thereof; wherein:
A$^1$ is phenylene or a 5-6 membered heteroarylene;
R$^1$ represents independently for each occurrence halogen, C$_{1-6}$ alkyl, or C$_{3-6}$ cycloalkyl;
R$^{2A}$ is —(C$_{1-6}$ alkylene)-A$^2$, -(2-6 membered heteroalkylene)-A$^2$, or —O-A$^2$; wherein A$^2$ is one of the following:
a 5-6 membered heterocyclic group containing at least one ring carbon atom substituted by oxo and the heterocyclic group being optionally substituted by 1 or 2 substituents independently selected from the group consisting of C$_{1-6}$ alkyl, C$_{1-6}$ haloalkyl, C$_{3-6}$ cycloalkyl, halogen, C$_{1-6}$ alkoxy, C$_{1-6}$ haloalkoxy, oxo, —C(O)R$^9$, —CO$_2$R$^8$, —N(R$^4$)C(O)(R$^9$), and —N(R$^4$)(R$^5$); or
a 5-6 membered heteroaromatic group comprising at least two ring nitrogen atoms, at least one unsaturated carbon atom in the ring, and the heteroaromatic group being optionally substituted by 1 or 2 substituents independently selected from the group consisting of C$_{1-6}$ alkyl, C$_{1-6}$ haloalkyl, C$_{3-6}$ cycloalkyl, halogen, C$_{1-6}$ alkoxy, C$_{1-6}$ haloalkoxy, —C(O)R$^9$, —CO$_2$R$^8$, —N(R$^4$)C(O)(R$^9$), and —N(R$^4$)(R$^5$);
R$^{2B}$ represents independently for each occurrence C$_{1-6}$ alkyl or C$_{1-3}$ haloalkyl;
R$^3$ represents independently for each occurrence hydrogen, C$_{1-6}$ haloalkyl, halogen, hydroxyl, C$_{1-6}$ alkyl, C$_{3-6}$ cycloalkyl, C$_{1-6}$ alkoxy, C$_{1-6}$ haloalkoxy, or —O—(C$_{1-6}$ alkylene)-OH; or two vicinal occurrences of R$^3$ are taken together with intervening atoms to form a 4-6 membered ring;
R$^4$ and R$^5$ each represent independently for each occurrence hydrogen, C$_{1-6}$ alkyl, or C$_{3-6}$ cycloalkyl; or an occurrence of R$^4$ and R$^5$ attached to the same nitrogen atom are taken together with the nitrogen atom to which they are attached to form a 3-7 membered heterocyclic ring;
R$^6$ and R$^7$ each represent independently for each occurrence hydrogen or C$_{1-6}$ alkyl, or R$^6$ and R$^7$ are taken together with the carbon atom to which they are attached to form a 3-6 membered carbocyclic ring;
R$^8$ represents independently for each occurrence hydrogen, C$_{1-6}$ alkyl, C$_{3-6}$ cycloalkyl, or aralkyl;
R$^9$ represents independently for each occurrence C$_{1-6}$ alkyl, C$_{3-6}$ cycloalkyl, or aralkyl;
X is one of the following:
(i) —(C$_{2-6}$ alkenylene)-phenyl, —(C$_{2-6}$ alkenylene)-heteroaryl, —(C$_{1-6}$ alkylene)-phenyl, —(C$_{1-6}$ alkylene)-heteroaryl, —(C$_{1-6}$ alkylene)-(partially unsaturated bicyclic heterocyclyl), —(C$_{1-6}$ alkylene)-(partially unsaturated bicyclic oxo-heterocyclyl), or -(5-6 membered heterocycloalkylene)-phenyl, each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, and $C_{1-6}$ haloalkoxy;

(ii) —($C_{1-6}$ alkylene)-$Z^1$ or —($C_{2-6}$ alkenylene)-$Z^1$, wherein $Z^1$ is —O-aralkyl, —O— heteroaralkyl, —O-phenyl, —O-heteroaryl, —O-(partially unsaturated bicyclic carbocyclyl), —O—($C_{1-6}$alkylene)-($C_{3-6}$ cycloalkyl), —O—($C_{3-6}$ cycloalkyl), —N($R^4$)-aralkyl, —N($R^4$)-phenyl, —N($R^4$)-(partially unsaturated bicyclic carbocyclyl), or —N($R^4$)—($C_{1-6}$ alkylene)-($C_{3-6}$ cycloalkyl), each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, and $C_{1-6}$ haloalkoxy; or (iii) —O-aralkyl, —O-heteroaralkyl, —O-phenyl, —O-heteroaryl, —O-(partially unsaturated bicyclic carbocyclyl), —O—($C_{1-6}$ alkylene)-($C_{3-6}$ cycloalkyl), —N($R^4$)-aralkyl, —N($R^4$)—phenyl, —N($R^4$)-(partially unsaturated bicyclic carbocyclyl), or —N($R^4$)—($C_{1-6}$ alkylene)-($C_{3-6}$ cycloalkyl), each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, and $C_{1-6}$ haloalkoxy;

Y is —C($R^6$)($R^7$)—, —O—, or —C(O)—;
m and p are independently 0, 1, or 2; and
n is 1, 2, or 3.

3. The compound of claim 2, wherein $A^1$ is phenylene.
4. The compound of claim 3, wherein n is 1.
5. The compound of claim 4, wherein $R^3$ is trifluoromethyl, fluoro, chloro, or methoxy.
6. The compound of claim 2, wherein -$A^1$-($R^3$)$_n$ is

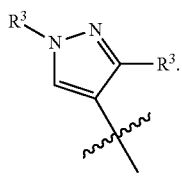

7. The compound of claim 2, wherein $R^{2A}$ is —($C_{1-6}$ alkylene)-$A^2$.
8. The compound of claim 2, wherein $R^{2A}$ is -(2-6 membered heteroalkylene)-$A^2$.
9. The compound of claim 8, wherein $A^2$ is a 5-6 membered heterocyclic group containing at least one ring carbon atom substituted by oxo and the heterocyclic group being optionally substituted by 1 or 2 substituents independently selected from the group consisting of $C_{1-6}$ alkyl, $C_{1-6}$ haloalkyl, $C_{3-6}$ cycloalkyl, halogen, $C_{1-6}$ alkoxy, $C_{1-6}$ haloalkoxy, oxo, —C(O)$R^9$, —CO$_2$$R^8$, —N($R^4$)C(O)($R^9$), and —N($R^4$)($R^5$).
10. The compound of claim 2, wherein $A^2$ is imidazolyl; pyrazolyl; 1,2,3-triazolyl; tetrazolyl; 1,2,4-oxadiazol-5(4H)-onyl; 1,3,4-oxadiazol-2(3H)-onyl; 1,3-dihydro-2H-imidazol-2-onyl; or 2,4-dihydro-3H-1,2,4-triazol-3-onyl; each of which is optionally substituted by 1 or 2 substituents independently selected from the group consisting of $C_{1-6}$ alkyl, $C_{1-6}$ haloalkyl, $C_{3-6}$ cycloalkyl, halogen, $C_{1-6}$ alkoxy, $C_{1-6}$ haloalkoxy, —C(O)$R^9$, —CO$_2$$R^8$, —N($R^4$)C(O)($R^9$), and —N($R^4$)($R^5$).
11. The compound of claim 8, wherein $A^2$ is one of the following:

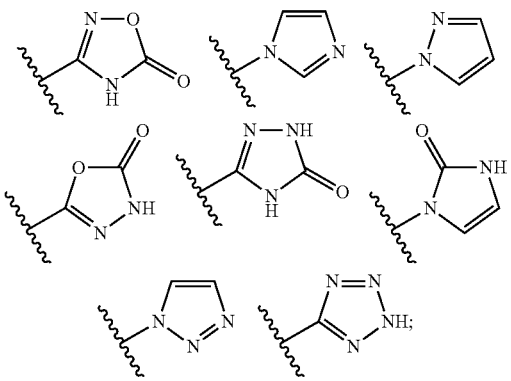

each of which is optionally substituted by 1 or 2 substituents independently selected from the group consisting of $C_{1-6}$ alkyl, $C_{1-6}$ haloalkyl, $C_{3-6}$ cycloalkyl, halogen, $C_{1-6}$ alkoxy, $C_{1-6}$ haloalkoxy, —C(O)$R^9$, and —CO$_2$$R^8$.

12. The compound of claim 2, wherein X is —($C_{2-6}$ alkenylene)-phenyl, —($C_{2-6}$ alkenylene)-heteroaryl, —($C_{1-6}$ alkylene)-phenyl, —($C_{1-6}$ alkylene)-heteroaryl, —($C_{1-6}$ alkylene)-(partially unsaturated bicyclic heterocyclyl), —($C_{1-6}$ alkylene)-(partially unsaturated bicyclic oxo-heterocyclyl), or -(5-6 membered heterocycloalkylene)-phenyl, each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, and $C_{1-6}$ haloalkoxy.

13. The compound of claim 2, wherein X is —($C_{2-6}$ alkenylene)-phenyl optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, and $C_{1-6}$ haloalkoxy.

14. The compound of claim 2, wherein Y is —C($R^6$)($R^7$)—, $R^6$ and $R^7$ are independently hydrogen or methyl, and X is attached at the 7-position of the 1,2,3,4-tetrahydroquinolinyl ring.

15. The compound of claim 2, wherein Y is —O—, and X is attached at the 6-position of the 3,4-dihydro-2H-benzo[b][1,4]oxazinyl ring.

16. The compound of claim 9, wherein p is 0, and m is 0.
17. A compound represented by Formula II:

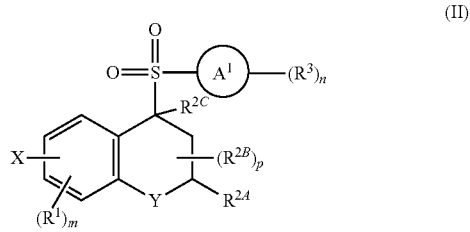

or a pharmaceutically acceptable salt thereof; wherein:
$A^1$ is phenyl, 5-6 membered heteroaryl, or $C_{3-6}$ heterocycloalkyl;
$R^1$ represents independently for each occurrence halogen, $C_{1-6}$ alkyl, $C_{1-6}$ haloalkyl, or $C_{3-6}$ cycloalkyl;
$R^{2A}$ is —($C_{1-6}$ alkylene)-$A^2$, -(2-6 membered heteroalkylene)-$A^2$, —($C_{0-3}$ alkylene)-($C_{3-6}$ cycloalkylene)-($C_{0-3}$ alkylene)-$A^2$, —O-$A^2$, —N($R^8$)-$A^2$, or -$A^2$; wherein $A^2$ is one of the following:

a 5-6 membered heterocyclic group containing at least one ring carbon atom substituted by oxo and the heterocyclic group being optionally substituted by 1 or 2 substituents independently selected from the group consisting of $C_{1-6}$ alkyl, $C_{1-6}$ haloalkyl, $C_{3-6}$ cycloalkyl, halogen, $C_{1-6}$ alkoxy, $C_{1-6}$ haloalkoxy, oxo, —C(O)$R^9$, —CO$_2R^8$, —N($R^4$)C(O)($R^9$), and —N($R^4$)($R^5$); or a 5-6 membered heteroaromatic group comprising at least two ring nitrogen atoms, at least one unsaturated carbon atom in the ring, and the heteroaromatic group being optionally substituted by 1 or 2 substituents independently selected from the group consisting of $C_{1-6}$ alkyl, $C_{1-6}$ haloalkyl, $C_{3-6}$ cycloalkyl, halogen, $C_{1-6}$ alkoxy $C_{1-6}$ haloalkoxy, —C(O)$R^9$, —CO$_2R^8$, —N($R^4$)C(O)($R^9$), and —N($R^4$)($R^5$);

$R^{2B}$ represents independently for each occurrence $C_{1-6}$ alkyl or $C_{1-3}$ haloalkyl;

$R^{2C}$ is hydrogen or $C_{1-6}$ alkyl;

$R^3$ represents independently for each occurrence hydrogen, $C_{1-6}$ haloalkyl, halogen, hydroxyl, $C_{1-6}$ alkyl, $C_{3-6}$ cycloalkyl, $C_{1-6}$ alkoxy, $C_{1-6}$ haloalkoxy, —O—($C_{1-6}$ alkylene)-OH, or —O—($C_{1-6}$ alkylene)-CO$_2R^4$; or two vicinal occurrences of $R^3$ are taken together with intervening atoms to form a 4-6 membered ring;

$R^4$ and $R^5$ each represent independently for each occurrence hydrogen, $C_{1-6}$ alkyl, or $C_{3-6}$ cycloalkyl; or an occurrence of $R^4$ and $R^5$ attached to the same nitrogen atom are taken together with the nitrogen atom to which they are attached to form a 3-7 membered heterocyclic ring;

$R^6$ and $R^7$ each represent independently for each occurrence hydrogen or $C_{1-6}$ alkyl, or $R^6$ and $R^7$ are taken together with the carbon atom to which they are attached to form a 3-6 membered carbocyclic ring; or $R^6$ and $R^{2A}$ are taken together to form a bond;

$R^8$ represents independently for each occurrence hydrogen, $C_{1-6}$ alkyl, $C_{3-6}$ cycloalkyl, or aralkyl;

$R^9$ represents independently for each occurrence $C_{1-6}$ alkyl, $C_{3-6}$ cycloalkyl, or aralkyl;

X is one of the following:
(i) —($C_{2-6}$ alkenylene)-phenyl, —($C_{2-6}$ alkenylene)-heteroaryl, —($C_{1-6}$ alkylene)-phenyl, —($C_{1-6}$ alkylene)-heteroaryl, —($C_{1-6}$ alkylene)-(partially unsaturated bicyclic heterocyclyl), —($C_{1-6}$ alkylene)-(partially unsaturated bicyclic oxo-heterocyclyl), -(5-6 membered heterocycloalkylene)-phenyl, or —($C_{3-6}$ cycloalkylene)-phenyl, each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, $C_{1-6}$ haloalkoxy, hydroxyl, and cyano;
(ii) —($C_{2-6}$ alkenylene)-($C_{3-6}$ cycloalkyl),

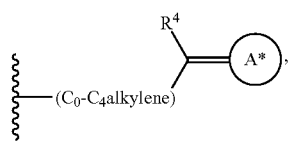

or an 8-10 membered, bicyclic partially saturated carbocyclyl, each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, $C_{1-6}$ haloalkoxy, hydroxyl, and cyano, wherein A* is a 5-8 membered, partially saturated carbocyclic or heterocyclic ring;

(iii) —($C_{1-6}$ alkylene)-$Z^1$ or —($C_{2-6}$ alkenylene)-$Z^1$, wherein $Z^1$ is —O-aralkyl, —O— heteroaralkyl, —O-phenyl, —O-heteroaryl, —O-(partially unsaturated bicyclic carbocyclyl), —O—($C_{1-6}$ alkylene)-($C_{3-6}$ cycloalkyl), —O—($C_{3-6}$ cycloalkyl), —N($R^4$)-aralkyl, —N($R^4$)-phenyl, —N($R^4$)-(partially unsaturated bicyclic carbocyclyl), or —N($R^4$)—($C_{1-6}$ alkylene)-($C_{3-6}$ cycloalkyl), each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, $C_{1-6}$ haloalkoxy, hydroxyl, and cyano; or (iv) —O-aralkyl, —O-heteroaralkyl, —O-phenyl, —O-heteroaryl, —O-(partially unsaturated bicyclic carbocyclyl), —O—($C_{1-6}$ alkylene)-($C_{3-6}$ cycloalkyl), —O—($C_{3-6}$ cycloalkyl), —N($R^4$)-aralkyl, —N($R^4$)-phenyl, —N($R^4$)-(partially unsaturated bicyclic carbocyclyl), or —N($R^4$)—($C_{1-6}$ alkylene)-($C_{3-6}$ cycloalkyl), each of which is optionally substituted with 1, 2, or 3 substituents independently selected from the group consisting of halogen, $C_{1-6}$ haloalkyl, $C_{1-6}$ alkyl, $C_{3-6}$ cycloalkyl, $C_{1-6}$ alkoxy, $C_{1-6}$ haloalkoxy, hydroxyl, and cyano;

Y is —C($R^6$)($R^7$)—, —O—, —C(O)—, or —S(O)$_p$—;

m and p each represent independently for each occurrence 0, 1, or 2; and n is 0, 1, 2, or 3.

18. A compound represented by Formula I-C:

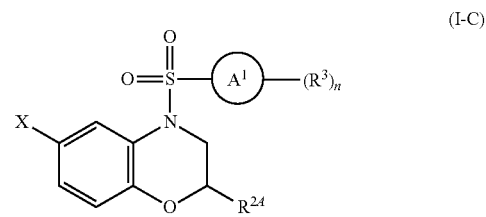

(I-C)

or a pharmaceutically acceptable salt thereof; wherein:

$A^1$ is phenylene or pyrazolylene;

$R^{2A}$ is -(2-6 membered heteroalkylene)-$A^2$; wherein $A^2$ is a 5-6 membered heterocyclic group containing at least one unsaturated carbon atom and the heterocyclic group being optionally substituted with 1, 2, or 3 substituents independently selected from the group consisting of $C_{1-3}$ alkyl, $C_{1-3}$ fluoroalkyl, chloro, fluoro, and oxo;

$R^3$ represents independently for each occurrence $C_{1-2}$ fluoroalkyl, chloro, fluoro, cyclopropyl, $C_{1-3}$ alkyl, $C_{1-2}$ alkoxy, or $C_{1-2}$ fluoroalkoxy;

X is —($C_{2-6}$ alkenylene)-phenyl wherein the phenyl is substituted with 1, 2, or 3 substituents independently selected from the group consisting of chloro, fluoro, $C_1$-2 fluoroalkyl, $C_{1-2}$ alkoxy, and $C_{1-2}$ fluoroalkoxy;

n is 1 or 2.

19. The compound of claim 18, wherein $A^1$ is phenylene; and $R^3$ represents independently for each occurrence $C_{1-2}$ fluoroalkyl, chloro, fluoro, $C_{1-2}$ alkoxy, or $C_{1-2}$ fluoroalkoxy.

20. The compound of claim 19, wherein $A^2$ is

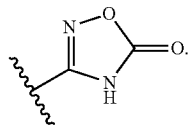 [SMILES: *c1noc(=O)[nH]1]

21. The compound of claim 18, wherein X is —(C(H)=C(CH$_3$))-phenyl substituted with 1 or 2 substituents independently selected from the group consisting of chloro, fluoro, and trifluoromethyl, and said substituents are located at the ortho positions of the phenyl group.

22. A compound in any one of Tables 1-8 herein or a pharmaceutically acceptable salt thereof.

23. A pharmaceutical composition comprising a compound of claim 1 and a pharmaceutically acceptable carrier.

24. A method of treating cancer by promoting the activity of RORγ, comprising administering a therapeutically effective amount of a compound of claim 1 to a subject in need thereof to treat the cancer, wherein the cancer is colon cancer, pancreatic, cancer, breast cancer, ovarian cancer, prostate cancer, squamous cell carcinoma, lung cancer leukemia bladder cancer, stomach cancer, skin cancer, or esophagus cancer.

25. The method of claim 4, wherein the subject is a human.

26. A method of promoting the activity of RORγ, comprising exposing a RORγ to an effective amount of a compound of claim 1 to promote the activity of said RORγ.

* * * * *